US012622874B2

(12) United States Patent (10) Patent No.: US 12,622,874 B2

Niyikiza et al. (45) Date of Patent: May 12, 2026

(54) TRANS-CROCETIN COMPOSITIONS AND TREATMENT REGIMENS

(71) Applicant: L.E.A.F. HOLDINGS GROUP LLC, Gulph Mills, PA (US)

(72) Inventors: Clet Niyikiza, Gulph Mills, PA (US); Victor Mandla Moyo, Ringoes, NJ (US)

(73) Assignee: L.E.A.F. HOLDINGS GROUP LLC, Gulph Mills, PA (US)

( * ) Notice: Subject to any disclaimer, the term of this patent is extended or adjusted under 35 U.S.C. 154(b) by 652 days.

(21) Appl. No.: 17/917,908

(22) PCT Filed: Apr. 9, 2021

(86) PCT No.: PCT/US2021/026704

§ 371 (c)(1),
(2) Date: Oct. 7, 2022

(87) PCT Pub. No.: WO2021/207690

PCT Pub. Date: Oct. 14, 2021

(65) Prior Publication Data

US 2023/0132805 A1 May 4, 2023

Related U.S. Application Data

(60) Provisional application No. 63/125,908, filed on Dec. 15, 2020, provisional application No. 63/077,986, filed on Sep. 14, 2020, provisional application No. 63/077,989, filed on Sep. 14, 2020, provisional application No. 63/064,281, filed on Aug. 11, 2020, provisional application No. 63/063,809, filed on Aug. 10, 2020, provisional application No. 63/057,208, filed on Jul. 27, 2020, provisional application No. 63/029,536, filed on May 24, 2020, provisional application No. 63/029,362, filed on May 22, 2020, provisional application No. 63/007,884, filed on Apr. 9, 2020.

(51) Int. Cl.
| | |
|---|---|
| *A61K 9/1271* | (2025.01) |
| *A61K 31/202* | (2006.01) |
| *A61K 45/06* | (2006.01) |
| *A61P 11/00* | (2006.01) |
| *A61P 31/14* | (2006.01) |
| *A61P 37/06* | (2006.01) |

(52) U.S. Cl.
CPC .......... *A61K 9/1271* (2013.01); *A61K 31/202* (2013.01); *A61K 45/06* (2013.01); *A61P 11/00* (2018.01); *A61P 31/14* (2018.01); *A61P 37/06* (2018.01)

(58) Field of Classification Search
CPC .... A61K 9/1271; A61K 31/202; A61K 45/06; A61K 9/127; A61P 11/00; A61P 31/14; A61P 37/06; A61P 9/10; A61P 9/00; A61P 31/04; Y02A 50/30
See application file for complete search history.

(56) References Cited

U.S. PATENT DOCUMENTS

| | | | |
|---|---|---|---|
| 5,939,096 A * | 8/1999 | Clerc | A61K 9/1278 424/450 |
| 6,060,511 A | 5/2000 | Gainer | |
| 6,656,498 B1 | 12/2003 | Gao | |
| 7,048,943 B2 | 5/2006 | Barenholz et al. | |
| 7,351,844 B2 | 4/2008 | Gainer et al. | |
| 7,759,506 B2 | 7/2010 | Gainer et al. | |
| 8,017,653 B2 | 9/2011 | Gainer et al. | |
| 8,632,832 B2 | 1/2014 | Leigh et al. | |
| 8,691,555 B2 | 4/2014 | Bailey et al. | |
| 10,842,805 B2 | 11/2020 | Gao | |
| 10,851,129 B2 | 12/2020 | Yao et al. | |
| 12,458,597 B2 | 11/2025 | Niyikiza et al. | |
| 2003/0059462 A1 | 3/2003 | Barenholz et al. | |
| 2004/0014725 A1* | 1/2004 | Gainer | A61P 9/10 558/24 |
| 2004/0076683 A1 | 4/2004 | Hoarau et al. | |
| 2004/0162329 A1 | 8/2004 | Lockwood et al. | |

(Continued)

FOREIGN PATENT DOCUMENTS

| | | |
|---|---|---|
| CN | 101811956 A | 8/2010 |
| CN | 103183603 A | 7/2013 |

(Continued)

OTHER PUBLICATIONS

International Search Report for PCT/US2021/026704 dated Jul. 8, 2021, 3 pages.
Written Opinion of the ISA for PCT/US2021/026704 dated Jul. 8, 2021, 10 pages.
Abdullaev et al., Biomedical properties of saffron and its potential use in cancer therapy and chemoprevention trials Cancer Detection and Prevention 28:426-432 (2004).
Focsan et al., "Photo Protection of Haematococcus pluvialis Algae by Astaxanthin: Unique Properties of Astaxanthin Deduced by EPR, Optical and Electrochemical Studies," Antioxidants 6, 80; (2017).

(Continued)

*Primary Examiner* — Robert A Wax
*Assistant Examiner* — John Seungjai Kwon
(74) *Attorney, Agent, or Firm* — Nixon & Vanderhye, PC

(57) ABSTRACT

Liposomal trans-crocetin pharmaceutical compositions, dosing regimens and methods of treating or preventing disorders and conditions associated with, but not limited to, infection, ischemia, hypoxia, ARDS, inflammation, sepsis, shock, stroke, traumatic injury, and proliferative disorders such as cancer are provided. Methods of using the provided trans-crocetin pharmaceutical compositions and dosing regimens to treat cardiovascular, renal, liver, inflammatory, metabolic, pulmonary, neurological, and other disorders and conditions are also provided, as are methods of increasing the delivery of oxygen and increasing the efficacy of a therapeutic agent using the provided compositions and dosing regimens.

26 Claims, 16 Drawing Sheets

(56) References Cited

U.S. PATENT DOCUMENTS

Figure 1C:
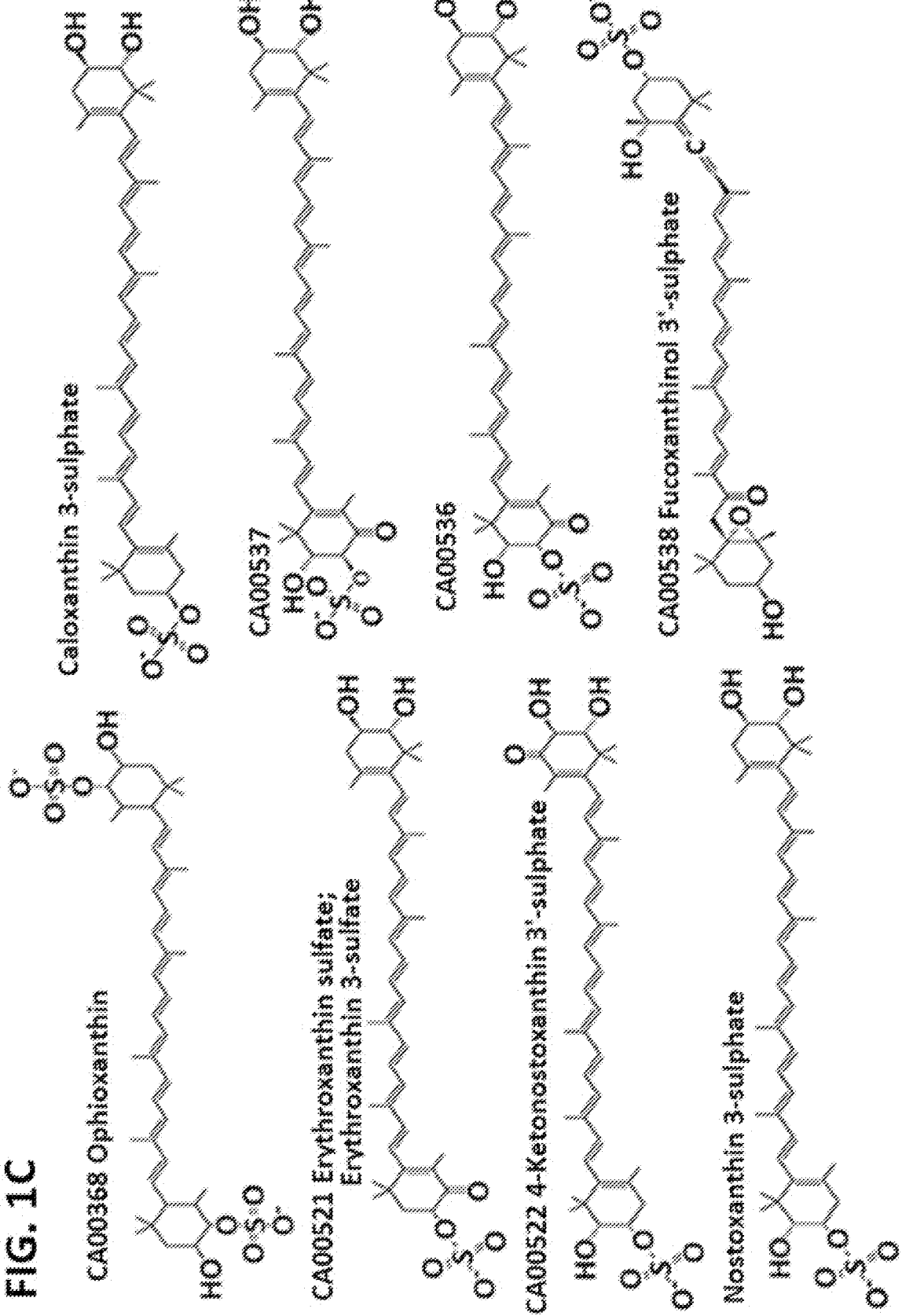
Figure 1D:
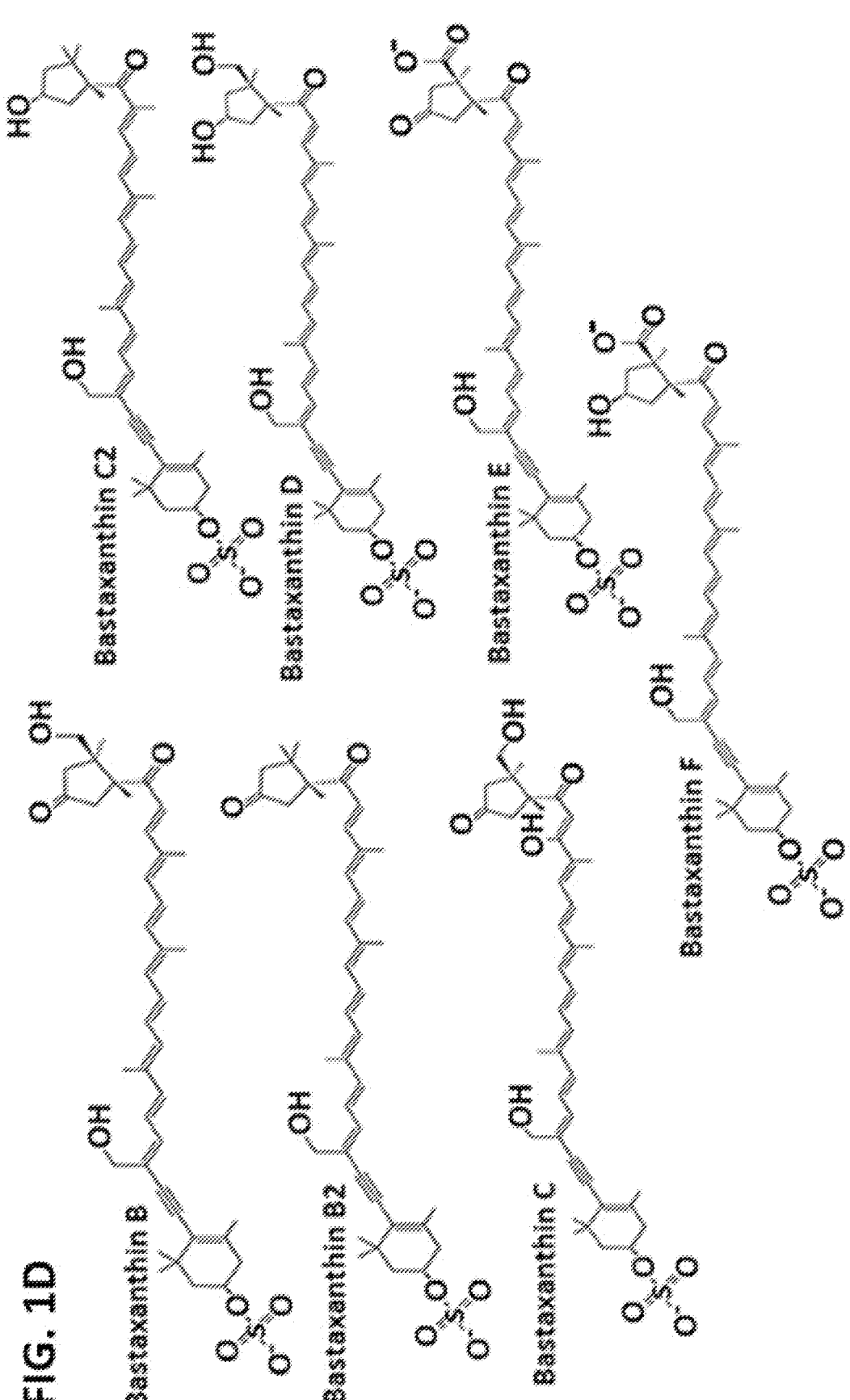

| | | | |
|---|---|---|---|
| 2006/0160751 A1 | 7/2006 | McGuire | |
| 2007/0015735 A1 | 1/2007 | Lockwood et al. | |
| 2008/0025929 A1 | 1/2008 | Burton et al. | |
| 2008/0213324 A1 | 9/2008 | Zhou et al. | |
| 2008/0221377 A1 | 9/2008 | Lockwood et al. | |
| 2010/0291053 A1 | 11/2010 | Clayton et al. | |
| 2013/0337068 A1 | 12/2013 | Petyaev | |
| 2014/0141082 A1* | 5/2014 | Gao | A23L 2/52 |
| | | | 424/774 |
| 2015/0147276 A1 | 5/2015 | Ingber et al. | |
| 2016/0199398 A1 | 7/2016 | Gao | |
| 2016/0199490 A1 | 7/2016 | Gainer et al. | |
| 2017/0049893 A1 | 2/2017 | Petyaev | |
| 2018/0289651 A1 | 10/2018 | LaFont et al. | |
| 2019/0008349 A1 | 1/2019 | Strutt et al. | |
| 2019/0015379 A1 | 1/2019 | Bacha et al. | |
| 2020/0016184 A9 | 1/2020 | Gao | |
| 2021/0283055 A1 | 9/2021 | Niyikiza et al. | |
| 2021/0283086 A1 | 9/2021 | Xu et al. | |
| 2022/0409565 A1 | 12/2022 | Niyikiza et al. | |
| 2023/0132805 A1 | 5/2023 | Niyikiza et al. | |
| 2023/0134835 A1 | 5/2023 | Niyikiza et al. | |
| 2023/0210803 A1 | 7/2023 | Niyikiza et al. | |
| 2023/0270706 A1 | 8/2023 | Niyikiza | |
| 2023/0277494 A1 | 9/2023 | Niyikiza | |
| 2024/0350446 A1 | 10/2024 | Niyikiza et al. | |
| 2025/0064768 A1 | 2/2025 | Niyikiza et al. | |

FOREIGN PATENT DOCUMENTS

| | | | | |
|---|---|---|---|---|
| CN | 107753427 A | 3/2018 | | |
| FR | 2840532 A1 | 12/2003 | | |
| JP | 2004518707 A | 6/2004 | | |
| JP | 2008273939 A | 11/2008 | | |
| JP | 2009179628 A | 8/2009 | | |
| WO | 2002064110 A1 | 8/2002 | | |
| WO | 2003101164 A1 | 12/2003 | | |
| WO | 2003101184 A2 | 12/2003 | | |
| WO | 2005028411 A1 | 3/2005 | | |
| WO | 2006102576 A1 | 9/2006 | | |
| WO | 2011152869 A1 | 12/2011 | | |
| WO | 2014194053 A3 | 12/2014 | | |
| WO | WO-2019182441 A1 * | 9/2019 | | A61K 38/05 |
| WO | 2019/213538 | 11/2019 | | |
| WO | WO-2019213538 A1 * | 11/2019 | | A61K 31/01 |
| WO | 2021091862 A1 | 5/2021 | | |
| WO | 2021207566 A1 | 10/2021 | | |
| WO | 2021207650 A1 | 10/2021 | | |
| WO | 2021207676 A1 | 10/2021 | | |
| WO | 2021207690 A1 | 10/2021 | | |
| WO | 2022025997 A1 | 2/2022 | | |
| WO | 2022025998 A1 | 2/2022 | | |
| WO | 2022240626 A1 | 11/2022 | | |

OTHER PUBLICATIONS

Fontaine et al., "Norbixin Protects Retinal Pigmented Epithelium Cells and Photoreceptors against A2E-Mediated Phototoxicity In Vitro and In Vivo." PLoS One 11 (12): e0167793 (2016). https://doi.org/10.1371/journal.pone.0167793.

Gainer, "Trans-sodium crocetinate for treating hypoxia/ischemia," Expert Opinion on Investigational Drugs 17(6): 917-924 (2008).

Gainer, "Effect of increasing the plasma oxygen diffusivity on experimental cryogenic edema," J. Neurosurg. 45(5): 535-538 (1976); Doi.org/10.3171/jns.1976.45.5.0535.

Giassi et al., "Trans-Sodium Crocetinate Restores Blood Pressure, Heart Rate, and Plasma Lactate after Hemorrhagic Shock," The Journal of TRAUMA Injury, Infection, and Critical Care, 51(5): 932-938 (2001).

Hada et al., "Hydrophilic carotenoids; recent progress": Molecules, 17:5003-5012 (2012).

Krishnaswamy et al., "Effect of short-term oral supplementation of crocin on age-related oxidative stress, cholinergic, and mitochondrial dysfunction in rat cerebral cortex, Life Sciences, 263:118545" 1-10 (2020). Doi.org/10.1016/j.lfs.2020.118545.

Kopec et al., "Recent advances in the bioaccessibility and bioavailability of carotenoids and effects of other dietary lipophiles", Journal of Food Composition and Analysis, Elsevier, Amsterdam, NL, vol. 68, Jul. 1, 2017 (Jul. 1, 2017), pp. 16-30, XP085382150.

Nco4378920: "A Study of Liposomal Trans Crocetin, LEAF-4L6715, in Patients With Acute Respiratory Distress Syndrome Due to COVID-19, Sepsis, and Other Causes", Dec. 16, 2021 (Dec. 16, 2021), XP093144684, Retrieved from the Internet: URL:https://clinicaltrials.gov/study/NCT04 378920?tab=history&a=2 [retrieved on Mar. 22, 2024.

Mertes et al., "Liposomal encapsulation of trans-crocetin enhances oxygenation in patients with COVID-19-related ARDS receiving mechanical ventilation" J. Controlled Release 336:252-261 (2021).

Puglia et al., "Nanotechnology approach to increase the antioxidant and cytotoxic efficacy of crocin and crocetin," Planta Med 85:258-265 (2019).

Rastgoo et al., "Antitumor activity of PEGylated nanoliposomes containing crocin in mice bearing C26 colon carcinoma," Planta Medica 79:447-451 (2013).

Rostamabadi et al., "Nanoencapsulation of carotenoids within lipid-based nanocarriers", Journal of Controlled Release, vol. 298, Mar. 1, 2019 (Mar. 1, 2019), pp. 38-67, XP093096469.

Wiesyaw et al., "Carotenoids as modulators of lipid membrane physical properties" Biochimica et Biophysica Acta, 1740:108-115 (2005).

U.S. Appl. No. 19/339,809, filed Sep. 25, 2025, NIYIKIZA et al.

U.S. Appl. No. 19/333,941, filed Sep. 19, 2025, NIYIKIZA et al.

* cited by examiner

Figure 1A:
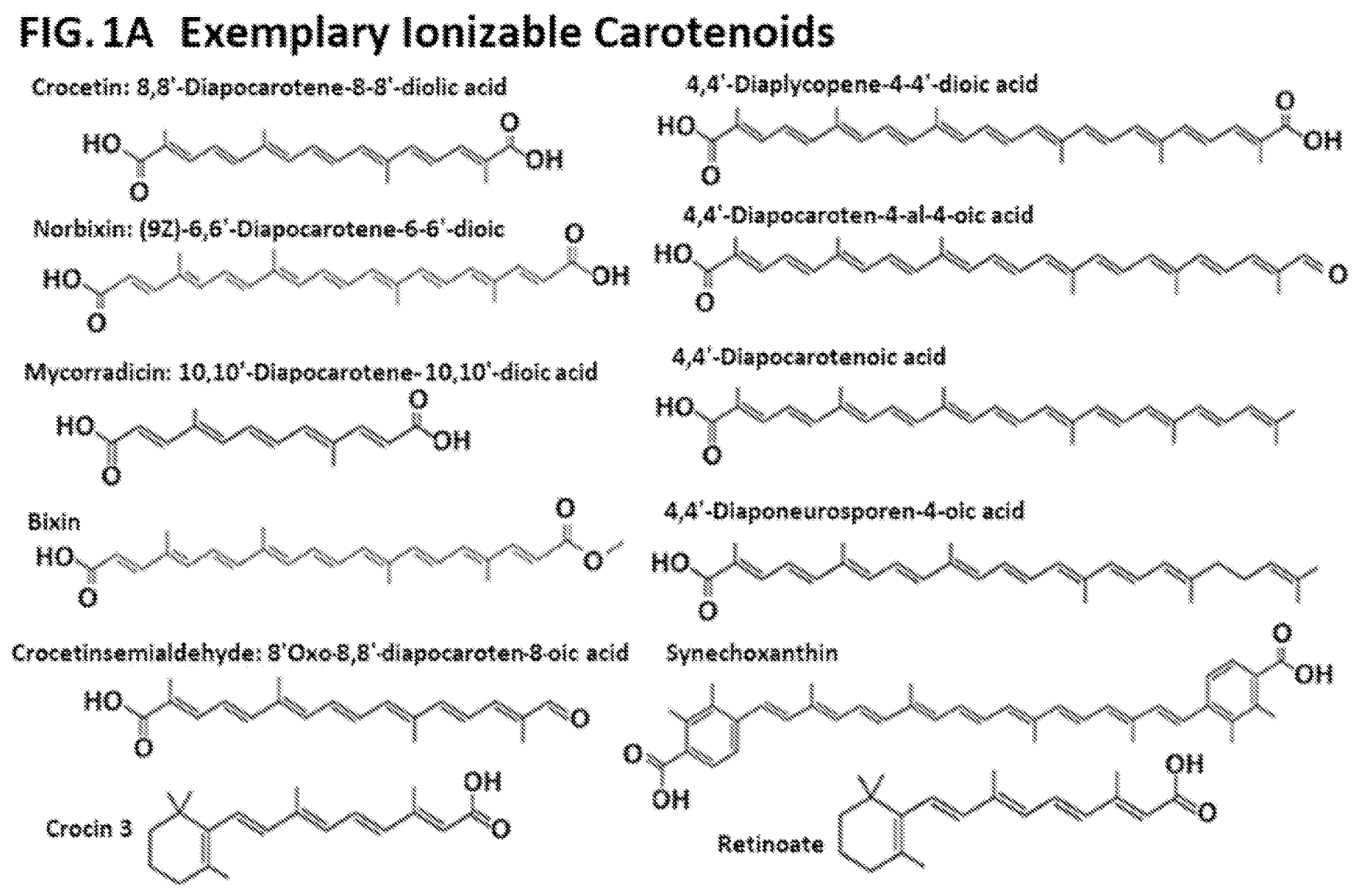

FIG. 1A Exemplary Ionizable Carotenoids

Crocetin: 8,8'-Diapocarotene-8-8'-diolic acid

Norbixin: (9Z)-6,6'-Diapocarotene-6-6'-dioic

Mycorradicin: 10,10'-Diapocarotene-10,10'-dioic acid

Bixin

Crocetinsemialdehyde: 8'Oxo-8,8'-diapocaroten-8-oic acid 4,4'-Diaplycopene-4-4'-dioic acid 4,4'-Diapocaroten-4-al-4-oic acid 4,4'-Diapocarotenoic acid 4,4'-Diaponeurosporen-4-oic acid Synechoxanthin Retinoate Crocin 3

FIG. 1B

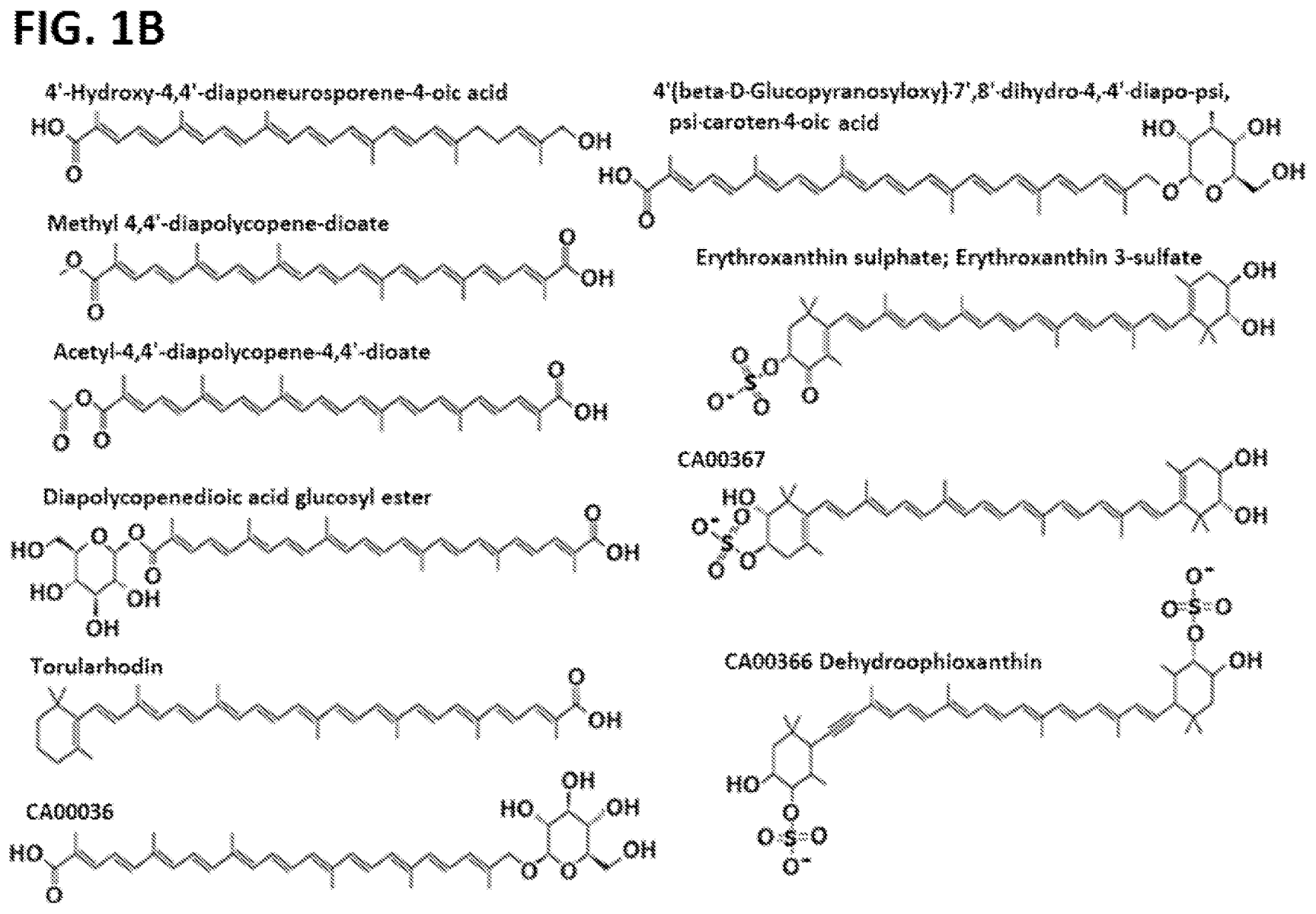

4'-Hydroxy-4,4'-diaponeurosporene-4-oic acid

Methyl 4,4'-diapolycopene-dioate

Acetyl-4,4'-diapolycopene-4,4'-dioate

Diapolycopenedioic acid glucosyl ester

Torularhodin

CA00036

4'-(beta-D-Glucopyranosyloxy)-7',8'-dihydro-4,4'-diapo-psi,psi-caroten-4-oic acid Erythroxanthin sulphate; Erythroxanthin 3-sulfate

CA00367

CA00366 Dehydroophioxanthin

Bastaxanthin C2

Bastaxanthin D

Bastaxanthin E

Bastaxanthin F

Bastaxanthin B

Bastaxanthin B2

Bastaxanthin C

FIG. 3A   CTC Liposome Stability
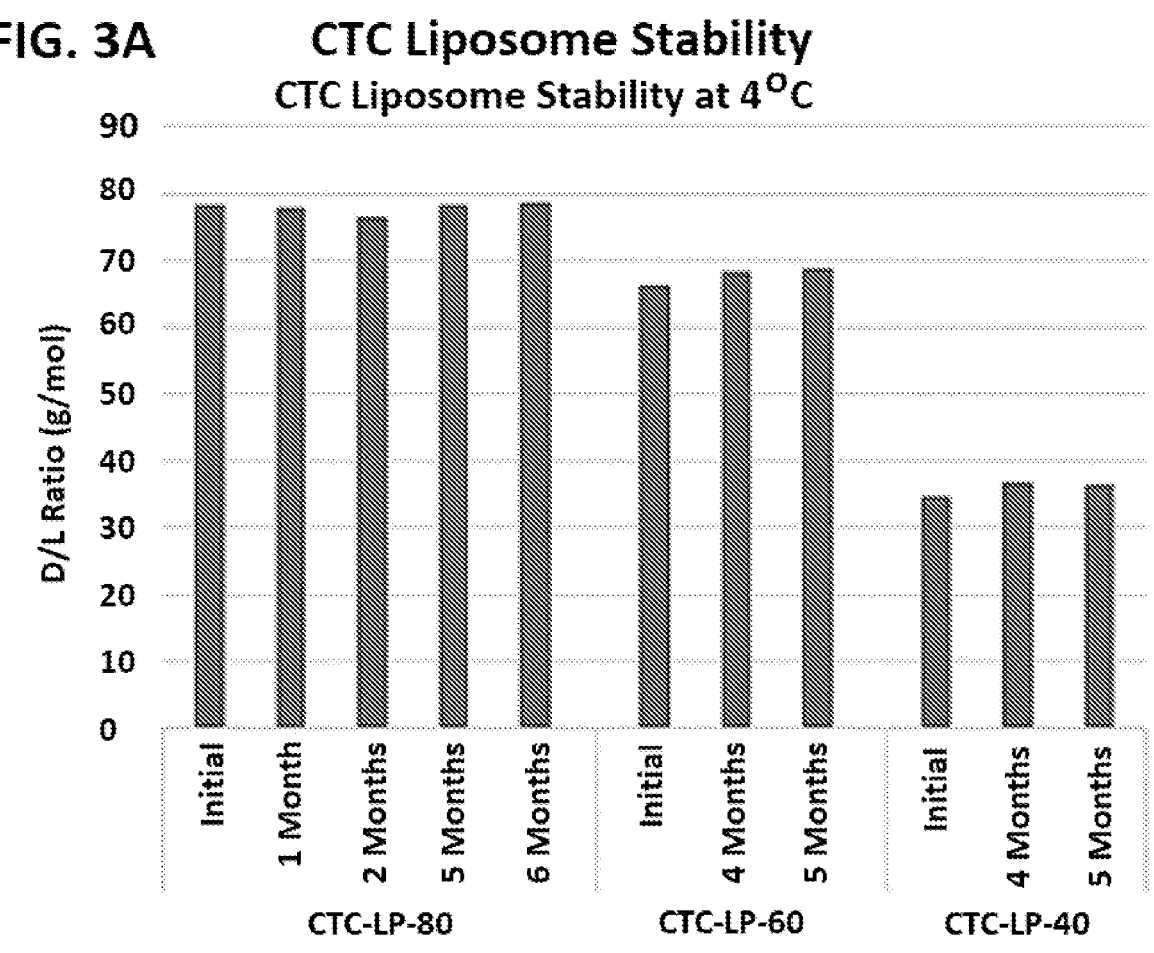
FIG. 3B   Liposomal CTC Batch Reproducibility
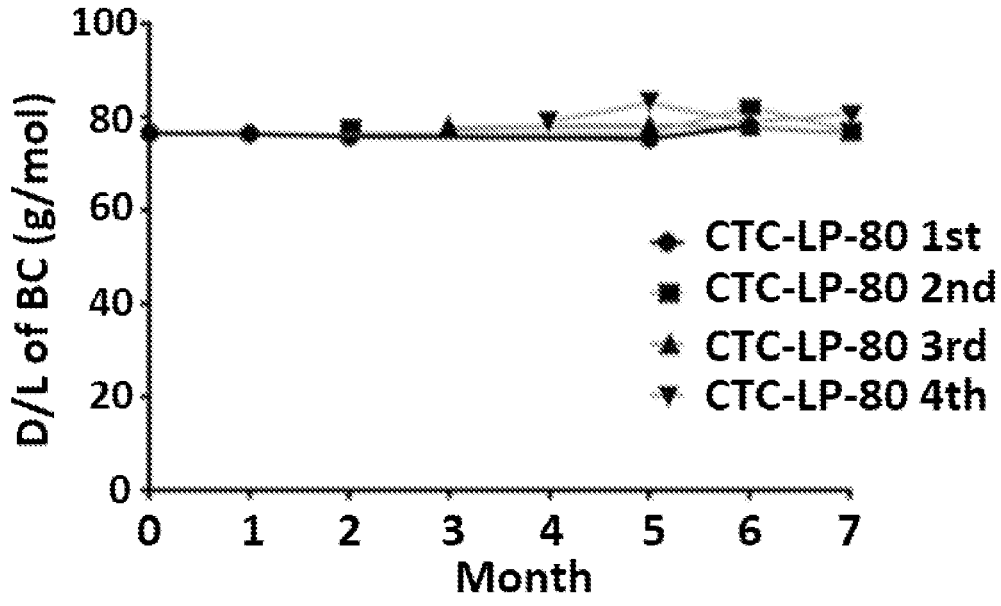

FIG. 4     MTC Liposome Stability
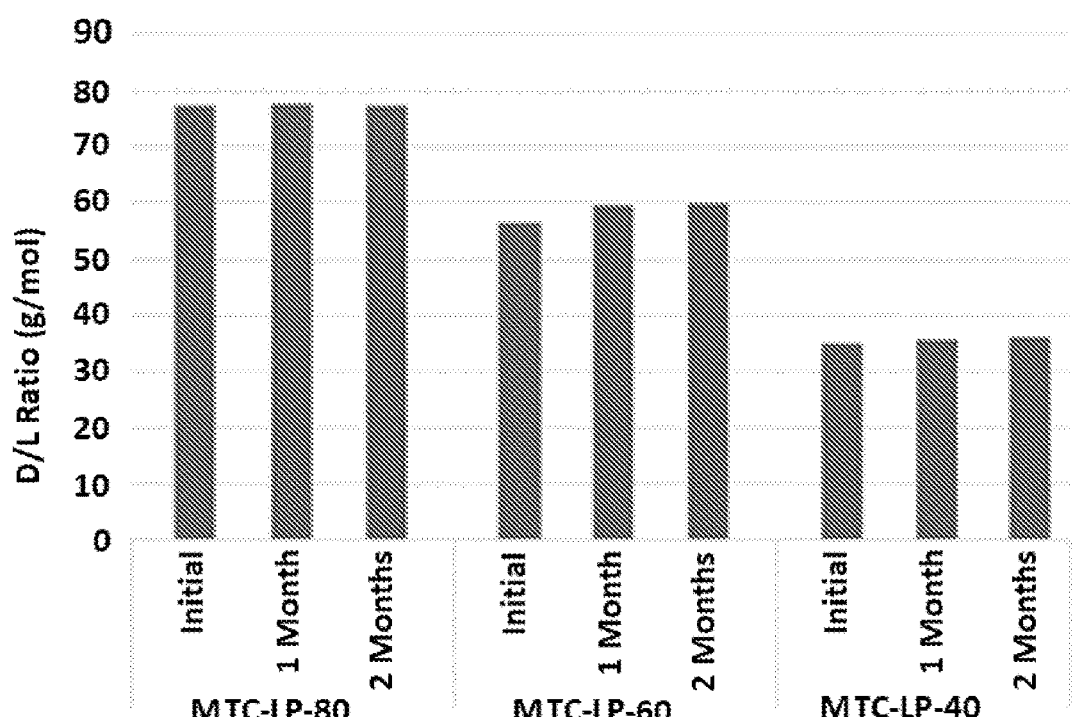
MTC Liposome Stability at 4°C
FIG. 5   Survival Study 1 (Study Number: TP-936)
Overall Survival
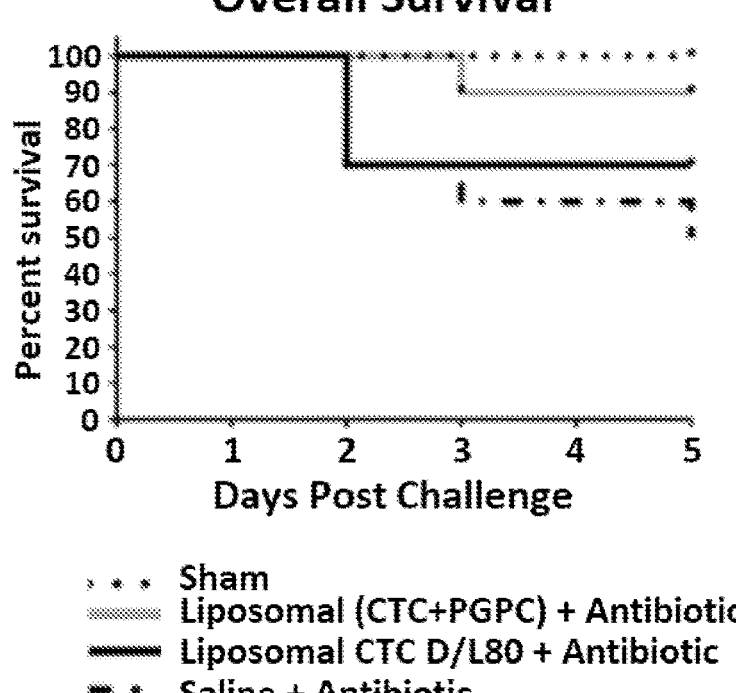

FIG. 6   Survival Study 1 (Study Number: TP-96⁊

Overall Survival

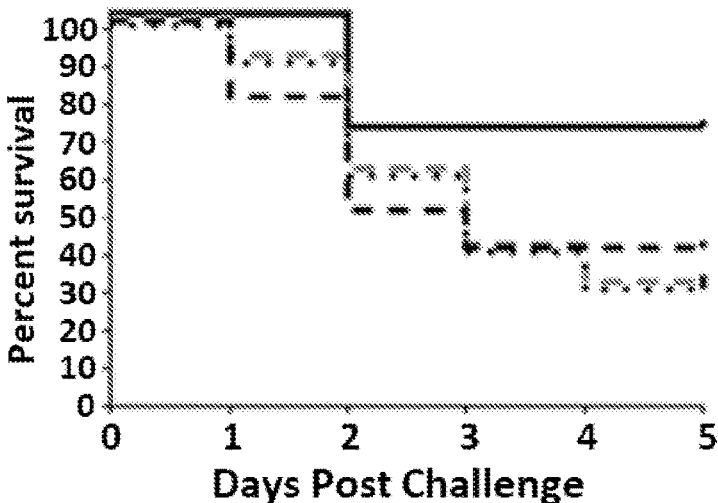

Days Post Challenge

· · · ·  Saline + Antibiotic
─ ─  Liposomal PGPC + Antibiotic
⚻ ⚻  Liposomal (PGPC + CTC)D/L80 + Antibiotic
─────  Liposomal CTC D/L80 + Antibiotic FIG. 7  Survival Study 3 (Study Number: TP-986)

Overall Survival

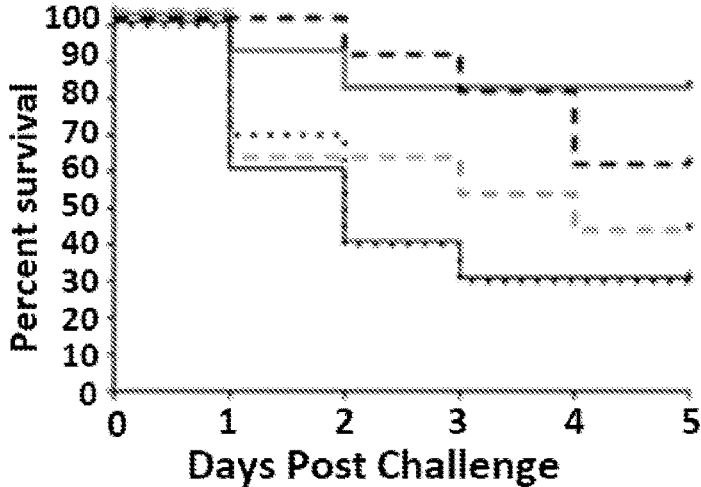

Days Post Challenge

· · · ·  Saline + Antibiotic
─────  Liposomal CTC D/L80 (25 mg/kg) + Antibiotic
⚻ ⚻ ⚻  Liposomal CTC D/L80 (50 mg/kg) + Antibiotic
─────  Liposomal CTC D/L80 (5 mg/kg) + Antibiotic
⚻ ⚻ ⚻  Liposomal CTC D/L80 (1 mg/kg) + Antibiotic

| Cohort | | 1 | 2 | 3 | 4 | total |
|---|---|---|---|---|---|---|
| | N | 6 | 6 | 4 | 2 | 18 |
| Patients (%) with >25% increase PaO2/FiO2 ratio | 24h | 2 (33%) | 1 (17%) | 3 (75%) | 1 (50%) | 7 (39%) |
| | 48h | 3 (50%) | 3 (50%) | 3 (75%) | 1 (50%) | 10 (55%) |
| | 72h | 3 (50%) | 6 (100%) | 3 (75%) | 1 (50%) | 13 (72%) |
| Any time in treatment period | | 3 (50%) | 6 (100%) | 4 (100%) | 1 (50%) | 14 (78%) |
| 28 day survival rate n (%) | | 5 (83%) | 6 (100%) | 4 (100%) | 0 (0%) | 15 (83%) |

| Inclusion time (hours) | -72 | -48 | -24 | 0 | 24 | 48 | 72 |
|---|---|---|---|---|---|---|---|
| PEP (median{quartile}) | 10.0 (8.0-11.0) | 10.0 (8.0-12.0) | 9.0 (7.0-12.0) | 10.0 (6.5-12.0) | 10.0 (5.5-12.0) | 8.0 (6.5-11.5) | 8.0 (6.5-10.0) |
| PaCO2 (median{quartile}) | 44.9 (40.6-57.7) | 42.7 (39.7-52.3) | 44 (37.2-49.2) | 46.3 (39.4-52.3) | 43.3 (38.7-52.4) | 44.7 (38.9-49.6) | 43.2 (37.5-47.8) |
| noradrenaline (%) | 50.0 | 43.8 | 55.6 | 72.2 | 61.1 | 55.5 | 27.8 |
| Position (% supine) | 26.6 | 18.8 | 59.0 | 22.2 | 11.1 | 77.7 | 94.4 |
| Mechanical respiration (%) | 91.6 | 94.1 | 94.4 | 100.0 | 100.0 | 77.7 | 94.4 |

TRANS-CROCETIN COMPOSITIONS AND TREATMENT REGIMENS

CROSS-REFERENCE TO RELATED APPLICATIONS

This application is the U.S. national phase of International Application No. PCT/US2021/026704 filed Apr. 9, 2021 which designated the U.S. and claims priority to U.S. Provisional Patent Application No. 63/077,989 filed Sep. 14, 2020, 63/125,908 filed Dec. 15, 2020, 63/007,884 filed Apr. 9, 2020, 63/029,362 filed May 22, 2020, 63/029,536 filed May 24, 2020, 63/057,208 filed Jul. 27, 2020, 63/063,809 filed Aug. 10, 2020, 63/064,281 filed Aug. 11, 2020, and 63/077,986 filed Sep. 14, 2020, the entire contents of each of which are hereby incorporated by reference.

BACKGROUND

Crocetin is a carotenoid with antioxidative properties that is sparingly soluble in water. Chemically, crocetin is a 20-carbon apocarotenoid molecule containing seven double bonds and a carboxylic acid group at each end. The administration of trans-crocetin (free acid), and its salt sodium trans-crocetinate in free form (e.g., unencapsulated) pharmaceutical formulations has been reported to offer promise in treatment for conditions caused by hypoxia, ischemia, and other medical conditions. However, neither has demonstrated sufficient impactful clinical therapeutic efficacy to warrant approval. This is partly due to the fact that formulations of trans-crocetin and its salt are limited by poor solubility, instability, low bioavailability and short half-life. For example, trans-crocetinate monovalent metal salt compositions such as sodium trans-crocetin (TSC), were presumably designed in an effort to overcome pharmacokinetic (PK) and pharmacodynamic (PD) issues associated with the low solubility and short half-life of crocetin (free acid), but the half-life of TSC is only about 30 minutes, which in a clinical setting leads to brief and transient therapeutic effect that limits the clinical development of this class of drugs.

In view of the potential health benefits conferred by trans-crocetin and the low bioavailability outlined above, there is a need for providing trans-crocetin pharmaceutical compositions and dosing regimens that provide improved bioavailability and stability. The compositions and methods including dosing regimens provided herein, address the shortcomings that have limited the therapeutic use and applications of trans-crocetin. The provided compositions and methods will further help overcome the limitations of current therapeutic approaches to disease states linked to ischemia, acute respiratory distress syndrome (ARDS), pneumonia, sepsis, endotoxemia and hypoxia, and many other unmet medical needs. The provided compositions, methods and dosing regimens have applications as single agents and in combination with other therapies and therapeutic agents.

BRIEF SUMMARY

The disclosure provides pharmaceutical compositions comprising trans-crocetin and methods of using the compositions to treat or prevent disorders and conditions associated with, but not limited to, infection, ischemia, hypoxia, ARDS, inflammation, sepsis, shock, stroke, traumatic injury, and proliferative disorders such as cancer, that comprises administering one or more dose(s) of trans-crocetin to a subject in an amount effective to treat the disorder or condition.

In some embodiments, the disclosure provides a method of treating a disorder or condition associated with ischemia that comprises administering one or more dose(s) of trans-crocetin to a subject in an amount effective to treat the disorder or condition. In some embodiments, the disclosure provides a method of treating a disorder or condition associated with acute respiratory distress syndrome (ARDS) caused by a viral infection (e.g., influenza or COVID-19) that comprises administering one or more dose(s) of trans-crocetin to a subject in an amount effective to treat the disorder or condition. Methods of using one or more dose(s) of trans-crocetin to treat a cardiovascular, renal, liver, inflammatory, metabolic, pulmonary, and/or neurological disorder or condition are also provided, as are methods of increasing the delivery of oxygen and increasing the efficacy of a therapeutic agent wherein the method comprises administering one or more dose(s) of trans-crocetin.

In one embodiment, the disclosure provides a method of treating a disorder or condition in a subject that comprises a dosing regimen wherein at least one dose of 0.05 mg/kg to 10 mg/kg (e.g., 0.5 mg/kg to 7.5 mg/kg, and 1 mg/kg to 5 mg/kg) liposomal trans-crocetin is administered to the subject. In some embodiments, two or more doses of liposomal trans-crocetin are administered to the subject once every 1, 2, 3, 6, 12 hours (+/−3 hours), 24 hours (+/−6 hours), or 48 hours (+/−12 hours).

In one embodiment, the disclosure provides a method of treating a disorder or condition in a subject that comprises a dosing regimen wherein at least one dose of 0.05 mg/kg to 2.5 mg/kg, 0.2 mg/kg to 2 mg/kg, 0.75 mg/kg to 2 mg/kg, or 0.15 to 0.5 mg/kg, liposomal trans-crocetin is administered to the subject. In some embodiments, two or more doses of liposomal trans-crocetin are administered to the subject once every 1, 2, 3, 6, 12 hours (+/−3 hours), 24 hours (+/−6 hours), or 48 hours (+/−12 hours).

In a preferred embodiment, the disclosure provides a method of treating a disorder or condition in a subject that comprises a dosing regimen wherein at least one dose of 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), liposomal trans-crocetin is administered to the subject. In some embodiments, one or more doses of liposomal trans-crocetin are administered to the subject once every 12 hours (+/−3 hours), once every 24 hours (+/−6 hours), or once every 48 hours (+/−12 hours).

In another preferred embodiment, the disclosure provides a method of treating a disorder or condition in a subject that comprises a dosing regimen wherein at least one dose of 2.5 mg/kg to 7.5 mg/kg, or 2.5 mg/kg to 5 mg/kg (e.g., 2.5 mg/kg, 5 mg/kg, or 7.5 mg/kg), liposomal trans-crocetin is administered to the subject. In some embodiments, one or more doses of liposomal trans-crocetin are administered to the subject once every 12 hours (+/−3 hours), once every 24 hours (+/−6 hours), or once every 48 hours (+/−12 hours).

The disclosure also provides an article of manufacture comprising at least 1 vial containing a 1.5 mg-250 mg, 1.5 mg-70 mg, 3 mg-150 mg, or 5 mg-240 mg, or any range therein between, of trans-crocetin.

In one embodiment, the disclosure provides an article of manufacture comprising at least 1 vial containing 25 mg-900 mg, 60 mg-600 mg, 150 mg-600 mg, 70 mg-580 mg, 150 mg-550 mg, 80 mg-350 mg, 75 mg-260 mg, or 25 mg-250 mg, or any range therein between, of liposomal trans-crocetin).

The provided pharmaceutical compositions and dosing regimens have uses in treating disorders and conditions associated with, but not limited to, infection, pneumonia, endotoxemia, inflammation, acute respiratory distress syndrome (ARDS), sepsis, ischemia, hypoxia, anemia, trauma, injury, stroke, shock, diabetes, wound healing, injury (e.g., reperfusion injury, neural injury, renal injury, livery injury and lung injury), and hyperproliferative disorders such as cancer, as well as conditions associated with the treatment of these disorders (e.g., anemia, neutropenia and immunosuppression). In particular embodiments, the pharmaceutical compositions and dosing regimens have uses in treating disorders and/or conditions associated with ischemia. In particular embodiments, the pharmaceutical compositions and dosing regimens have uses in treating disorders and/or conditions associated with traumatic injury (e.g., hemorrhaging associated with a car crash, other accident, or combat), or wherein the subject has undergone, will undergo, or is undergoing surgery. In particular embodiments, the pharmaceutical compositions and dosing regimens have uses in treating disorders and/or conditions associated with ARDS. In an additional embodiment, the provided pharmaceutical compositions and dosing regimens have uses in treating disorders and conditions associated with ARDS caused by an infection. In an additional embodiment, the provided pharmaceutical compositions and dosing regimens have uses in treating disorders and conditions associated with ARDS caused by a viral infection, e.g., influenza or COVID-19. Methods of making, delivering, and using the compositions are also provided.

In some embodiments, the disclosure provides:

[1] a method of increasing the delivery of oxygen in a subject, which comprises administering an effective amount of one or more dose(s) of liposomal trans-crocetin to the subject;

[2] a method of increasing the delivery of oxygen in a subject, which comprises administering one or more loading dose(s) of liposomal trans-crocetin to a subject, followed by administering a plurality of maintenance doses of liposomal trans-crocetin in a maintenance phase, wherein the one or more loading doses and/or the plurality of maintenance doses is effective to increase the delivery of oxygen in the subject;

[3] a method of treating an ischemic or hypoxic condition which comprises administering one or more dose(s) of liposomal trans-crocetin to a subject in need thereof

[4] a method of treating an ischemic or hypoxic condition which comprises administering one or more loading dose(s) of liposomal trans-crocetin to a subject in need thereof, followed by administering a plurality of maintenance doses of liposomal trans-crocetin to the subject in a maintenance phase;

[5] a method of treating blood loss in a subject which comprises administering to a subject who has experienced, is experiencing, will experience, or is at risk of experiencing blood loss, one or more dose(s) of liposomal trans-crocetin;

[6] a method of treating blood loss in a subject which comprises administering to a subject who has experienced, is experiencing, or will experience, or is at risk of experiencing, blood loss, one or more loading dose (s) of liposomal trans-crocetin, followed by administering a plurality of maintenance doses of liposomal trans-crocetin in a maintenance phase;

[7] a method of treating acute respiratory distress syndrome (ARDS), which comprises administering one or more dose(s) of liposomal trans-crocetin to a subject in need thereof;

[8] a method of treating ARDS, which comprises administering one or more loading dose(s) of liposomal trans-crocetin to a subject in need thereof, followed by administering a plurality of maintenance doses of liposomal trans-crocetin to the subject in a maintenance phase;

[9] a method of treating sepsis which comprises administering one or more dose(s) of liposomal trans-crocetin to a subject in need thereof;

[10] a method of treating sepsis which comprises administering one or more loading dose(s) of liposomal trans-crocetin to a subject in need thereof, followed by administering a plurality of maintenance doses of liposomal trans-crocetin in a maintenance phase to the subject;

[11] a method of treating pneumonia, which comprises administering one or more dose(s) of liposomal trans-crocetin to a subject in need thereof;

[12] a method of treating pneumonia which comprises administering one or more loading dose(s) of liposomal trans-crocetin to a subject in need thereof, followed by administering a plurality of maintenance doses of liposomal trans-crocetin to the subject in a maintenance phase;

[13] the method of [11] or [12], wherein the pneumonia results from an infection of lung tissue;

[14] the method according to any one of [1] to [13], wherein the pneumonia results from a bacterial infection (e.g., caused by an Enterobacteriaceae species (spp.), *Streptococcus pneumoniae, Staphylococcus aureus, Bacillus anthracis, Haemophilus influenzae, Klebsiella pneumoniae, Escherichia coli*, or *Pseudomonas aeruginosa*), a viral infection (e.g., an infection caused by an influenza virus, or a coronavirus such as COVID-19), a fungal infection, a parasite infection, or an infection caused by another type of microorganism;

[15] a method of treating an infection which comprises administering one or more dose(s) of liposomal trans-crocetin to a subject in need thereof;

[16] a method of treating an infection which comprises administering one or more loading dose(s) of liposomal trans-crocetin to a subject in need thereof, followed by administering a plurality of maintenance doses of liposomal trans-crocetin to the subject in a maintenance phase;

[17] the method of [15] or [16], wherein the infection is a bacterial infection (infection (e.g., caused by an Enterobacteriaceae species (spp.), *Streptococcus pneumoniae, Staphylococcus aureus, Bacillus anthracis, Haemophilus influenzae, Klebsiella pneumoniae, Escherichia coli*, or *Pseudomonas aeruginosa*), a viral infection (e.g., an infection caused by an influenza virus, or a coronavirus such as COVID-19), a fungal infection, a parasite infection, or an infection caused by another type of microorganism;

[18] a method of treating a hyperproliferative disorder which comprises administering one or more dose(s) of liposomal trans-crocetin to a subject in need thereof;

[19] a method of treating a hyperproliferative disorder which comprises administering one or more loading dose(s) of liposomal trans-crocetin to a subject in need thereof, followed by administering a plurality of maintenance doses of liposomal trans-crocetin to the subject in a maintenance phase;

[20] the method of [18] or [19], wherein the hyperproliferative disorder is cancer;

[21] a method of treating inflammation or a condition associated with inflammation, which comprises administering one or more dose(s) of liposomal trans-crocetin to a subject in need thereof;

[22] a method of treating inflammation or a condition associated with inflammation, which comprises administering one or more loading dose(s) of liposomal trans-crocetin to a subject in need thereof, followed by administering a plurality of maintenance doses of liposomal trans-crocetin to the subject in a maintenance phase;

[23] a method of increasing the efficacy of a therapeutic agent, which comprises administering one or more dose(s) of liposomal trans-crocetin to a subject who has received, is receiving, or is scheduled to receive treatment with the therapeutic agent;

[24] a method of increasing the efficacy of a therapeutic agent, which comprises administering one or more dose(s) of liposomal trans-crocetin to a subject who has received, is receiving, or is scheduled to receive treatment with the therapeutic agent, a loading phase comprising one or more loading dose(s) of liposomal trans-crocetin, followed by administering a plurality of maintenance doses of liposomal trans-crocetin to the subject in a maintenance phase;

[25] the method of [23] or [24], wherein therapeutic agent is a transfusion, radiation, a chemotherapeutic agent, an immunotherapeutic agent, or a thrombolytic agent;

[26] the method according to any one of [23] to [25], wherein one or more doses of liposomal trans-crocetin is administered to the subject before the subject is administered the therapeutic agent (e.g., 5 minutes to 72 hours, 15 minutes to 48 hours, or 30 minutes to 24 hours before, or within 12 hours, 9 hours, 6 hours, 4 hours, 2 hours, or 1 hour before the administration of the therapeutic agent (e.g., radiation, a chemotherapeutic agent, immunotherapeutic agent, or oxygen therapy);

[27] the method according to any one of [23] to [26], wherein one or more doses of liposomal trans-crocetin is administered to the subject during administration of the therapeutic agent (e.g., radiation, a chemotherapeutic agent or oxygen therapy);

[28] the method according to any one of [1] to [27], wherein at least 2, 3, 4, 5, 6, 7, 8, 9, 10, 11, 12, 13, 14, 15, 16, 17, 18, 19, 20, 21, 22, 23, 24, or 25 doses of liposomal trans-crocetin is administered to the subject;

[29] the method according to any one of [1] to [28], wherein 1 to 50, 1 to 40, 1 to 30, 1 to 25, 1 to 20, 1 to 15, 1 to 10, or 1 to 5 doses, or any range therein between, of liposomal trans-crocetin is administered to the subject;

[30] the method according to any one of [1] to [29], wherein one or more doses of liposomal trans-crocetin is administered to the subject in an amount of:

(a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, (b) 4 mg/kg to 7.5 mg/kg (e.g., 5 mg/kg), or any range therein between, or (c) 2 mg/kg to 4 mg/kg (e.g., 2.5 mg/kg); or any range therein between;

[31] the method according to any one of [1] to [30], wherein one or more doses of liposomal trans-crocetin is administered to the subject in an amount of 2 mg/kg to 10 mg/kg, or any range therein between;

[32] the method according to any one of [1] to [31], wherein one or more doses of liposomal trans-crocetin is administered to the subject in an amount of 2.5 mg/kg to 7.5 mg/kg, or any range therein between;

[33] the method according to any one of [1] to [32], wherein one or more doses of liposomal trans-crocetin is administered to the subject in an amount of 2.5 mg/kg to 5 mg/kg (e.g., 2.5 mg/kg, 5 mg/kg, or 7.5 mg/kg), or any range therein between;

[34] the method according to any one of [1] to [33], wherein one or more doses of liposomal trans-crocetin is administered to the subject in an amount of 4 mg/kg to 7.5 mg/kg (e.g., 5 mg/kg), or any range therein between;

[35] the method according to any one of [1] to [34], wherein one or more doses of liposomal trans-crocetin is administered to the subject in an amount of 2 mg/kg to 4 mg/kg (e.g., 2.5 mg/kg); or any range therein between;

[36] the method according to any one of [1] to [35], wherein the subject is administered two or more dose(s) of liposomal trans-crocetin at (a) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between, or (b) five times a day, four times a day, three times a day, twice a day, once a day, or once every other day;

[37] the method according to any one of [1] to [36], wherein the subject is administered two or more dose(s) of liposomal trans-crocetin at 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between;

[38] the method according to any one of [1] to [37], wherein the subject is administered two or more dose(s) of liposomal trans-crocetin at five times a day, four times a day, three times a day, twice a day, once a day, or once every other day;

[39] the method according to any one of [1] to [38], wherein the subject is administered two or more dose(s) of liposomal trans-crocetin at once a day (e.g., 24 hours (+/−6 hours) apart);

[40] the method according to any one of [1] to [39], wherein trans-crocetin is administered to the subject in an amount of:

(a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, (b) 4 mg/kg to 7.5 mg/kg (e.g., 5 mg/kg), or any range therein between, or (c) 2 mg/kg to 4 mg/kg (e.g., 2.5 mg/kg); or any range therein between, and wherein the subject is administered two or more dose(s) of liposomal trans-crocetin at (a) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between, or (b) five times a day, four times a day, three times a day, twice a day, once a day, or once every other day;

[41] the method according to any one of [1] to [40], wherein trans-crocetin is administered to the subject in an amount of 2 mg/kg to 4 mg/kg (e.g., 2.5 mg/kg), or any range therein between, at five times a day, four times a day, three times a day, twice a day, once a day, or once every other day;

[42] the method according to any one of [1] to [41], wherein trans-crocetin is administered to the subject in an amount of 2 mg/kg to 4 mg/kg (e.g., 2.5 mg/kg), or any range therein between, twice a day;

[43] the method according to any one of [1] to [42], wherein trans-crocetin is administered to the subject in an amount of 2 mg/kg to 4 mg/kg (e.g., 2.5 mg/kg), or any range therein between, once a day;

[44] the method according to any one of [1] to [43], wherein trans-crocetin is administered to the subject in an amount of 2.5 mg/kg twice a day;

[45] the method according to any one of [1] to [44], wherein trans-crocetin is administered to the subject in an amount of 2.5 mg/kg once a day;

[46] the method according to any one of [1] to [45], wherein trans-crocetin is administered to the subject in an amount of 4 mg/kg to 7.5 mg/kg (e.g., 5 mg/kg), or any range therein between, at five times a day, four times a day, three times a day, twice a day, once a day, or once every other day;

[47] the method according to any one of [1] to [46], wherein trans-crocetin is administered to the subject in an amount of 4 mg/kg to 7.5 mg/kg (e.g., 5 mg/kg), or any range therein between, twice a day;

[48] the method according to any one of [1] to [47], wherein trans-crocetin is administered to the subject in an amount of 4 mg/kg to 7.5 mg/kg (e.g., 5 mg/kg), or any range therein between, once a day;

[49] the method according to any one of [1] to [48], wherein trans-crocetin is administered to the subject in an amount of 5 mg/kg twice a day;

[50] the method according to any one of [1] to [49], wherein trans-crocetin is administered to the subject in an amount of 5 mg/kg once a day;

[51] the method according to any one of [1] to [50], wherein one or more administered dose(s) of liposomal trans-crocetin comprises liposomal trans-crocetin in an aqueous solution, and wherein the one or more administered dose(s) comprises:

[a] a liposome encapsulating trans-crocetin having the formula:

$Q$-trans-crocetin-$Q$, wherein,

Q is (i) a multivalent cation counterion or (ii) a monovalent cation;

[b] the aqueous solution according of [a], wherein Q is a multivalent counterion (e.g., a multivalent cation such as a divalent metal cation or a divalent organic cation);

[c] the aqueous solution according of [b], wherein Q is at least one divalent cation selected from $Ca^{2+}$, $Mg^{2+}$, $Zn^{2+}$, $Cu^{2+}$, $Co^{2+}$, and $Fe^{2+}$, a divalent organic cation such as protonated diamine, or a trivalent cation such as $Fe^{3+}$;

[d] the aqueous solution according to [a], wherein Q is a monovalent counterion (e.g., a monovalent metal cation or a monovalent organic cation);

[e] the aqueous solution according to [d], wherein Q is at least one monovalent counterion selected from $NH_4^+$, $Na^+$, $Li^+$, and $K^+$, or a monovalent organic cation such as protonated amine;

[f] the aqueous solution according to [a], which comprises magnesium trans-crocetinate (MTC) or calcium trans-crocetinate (CTC);

[g] the aqueous solution according to any one of [a] to [f], wherein the trans-crocetin is in an amount from 1 mg to 300 mg, 1 mg to 140 mg, or 2 to 240 mg, 160 mg to 265 mg, 150 mg to 525 mg, or 275 mg to 875 mg, or 560 mg to 860 mg, or any range therein between;

[h] the aqueous solution according to any one of [a] to [g], wherein the trans-crocetin/lipid ratio is 1 to 1000 g/M, about 10 to 150 g/mol, about 20 to 100 g/mol, or any range therein between;

[i] the aqueous solution according to any one of [a] to [h], wherein the liposomes comprise at least 0.1% to 97% weight by weight (w/w) trans-crocetin, or any range therein between;

[j] the aqueous solution according to any one of [a] to [i], wherein the liposome has a diameter of 20 nm to 500 nm, 20 nm to 200 nm, or 80 nm to 120 nm, or any range therein between;

[k] the aqueous solution according to any one of [a] to [j], wherein the liposome is formed from liposomal components;

[l] the aqueous solution according to [k], wherein the liposomal components comprise at least one of an anionic lipid, a cationic lipid and a neutral lipid;

[m] the aqueous solution according to [k] or [1], wherein the liposomal components comprise at least one selected from: DSPE; DSPE-PEG; DSPE-PEG-FITC; DSPE-PEG-maleimide; HSPC; HSPC-PEG; cholesterol; cholesterol-PEG; and cholesterol-maleimide;

[n] the aqueous solution according to any one of [a] to [m], wherein the liposome comprises an oxidized phospholipid such as an OxPAPC;

[o] the aqueous solution according to [n], wherein the OxPAPC is an oxidized phospholipid containing fragmented oxygenated sn-2 residues, an oxidized phospholipid containing full length oxygenated sn-2 residues, and/or an oxidized phospholipid containing a five-carbon sn-2 residue bearing omega-aldehyde or omega-carboxyl groups;

[p] the aqueous solution according to any one of [a] or [o], wherein the liposome comprises an OxPAPC selected from HOdiA-PC, KOdiA-PC, HOOA-PC and KOOA-PC, 1-palmitoyl-2-(5,6-epoxyisoprostane E2)-sn-glycero-3-phosphocholine (5,6 PEIPC), 1-palmitoyl-2-(epoxy-cyclo-pentenone)-sn-glycero-3-phosphoryl-chol-ine (PECPC), 1-palmitoyl-2-(epoxy-isoprostane E2)-sn-glycero-4-phospho-choline (PEIPC), 1-palmitoyl-2-glutaroyl-sn-glycero-3-phosphocholine (PGPC); 1-palmitoyl-2-(9'oxo-nonanoyl)-sn-glycero-3-phosphocholine; 1-palmitoyl-2-arachinodoyl-sn-glycero-3-phosphocholine; 1-palmitoyl-2-myristoyl-sn-glycero-3-phosphocholine; 1-palmitoyl-2-hexa-decyl-sn-glycero-3-phosphocholine; 1-palmitoyl-2-azelaoyl-sn-glycero-3-phosphocholine; and 1-palmitoyl-2-acetoyl-sn-glycero-3-phospho-choline; or the OxPAPC is an epoxyisoprostane-containing phospholipid;

[q] the aqueous solution according to [p], wherein the liposome comprises PGPC;

[r] the aqueous solution according to any one of [a] to [q], wherein the liposome comprises 0% to 100%, 0.1% to 30%, 1% to 25%, 5% to 20%, or 7% to 15% OxPAPC (e.g., about 10% OxPAPC), or any range therein between;

[s] the aqueous solution according to any one of [a] to [r], wherein the liposome comprises HSPE, cholesterol, PEG-DSPE-2000, and OxPAPC at a molar ratio of 2 to 5:1 to 4:0.01 to 0.3:0.05 to 1.5;

[t] the aqueous solution according to any one of [a] to [s], wherein the liposome is pegylated;

[u] the aqueous solution according to any one of [a] to [t], wherein one or more liposomal components further comprises a steric stabilizer;

[v] the aqueous solution according to [u], wherein the steric stabilizer is at least one selected from consisting of polyethylene glycol (PEG); poly-L-lysine (PLL); monosialoganglioside (GM1); poly(vinyl pyrrolidone) (PVP); poly(acrylamide) (PAA); poly (2-methyl-2-oxazoline); poly(2-ethyl-2-oxazoline); phosphatidyl polyglycerol; poly[N-(2-hydroxypropyl) meth-acrylamide]; amphiphilic poly-N-vinylpyrrolidones; L-amino-acid-based polymer; oligoglycerol, copolymer containing polyethylene glycol and polypropylene oxide, Poloxamer 188, and polyvinyl alcohol;

[w] the aqueous solution according to [v], wherein the steric stabilizer is PEG and the PEG has a number average molecular weight (Mn) of 200 to 5000 Daltons;

[x] the aqueous solution according to any one of [a] to [w], wherein the liposome is anionic or neutral;

[y] the aqueous solution according to any one of [a] to [x], wherein the liposome has a zeta potential of –150 to 150 mV, or –50 to 50 mV, or any range therein between;

[z] the aqueous solution according to any one of [a] to [y], wherein the liposome has a zeta potential that is less than or equal to zero (e.g., –150 to 0, –50 to 0 mV, –25 to –1 mV, –15 to –1 mV, –10 to –1 mV, or –5 to –1 mV, or any range therein between);

[aa] the aqueous solution according to any one of [a] to [z], wherein the liposome has a zeta potential greater than 0 (e.g., 0.2 to 150 mV, or 1 to 50 mV, or any range therein between);

[ab] the aqueous solution according to any one of [a] to [z], or [aa], wherein the liposome is cationic;

[ac] the aqueous solution according to any one of [a] to [ab], which further comprises a pharmaceutically acceptable carrier,

[ad] the aqueous solution according to any one of [a] to [ac], which comprises a tonicity agent such as dextrose, mannitol, glycerin, potassium chloride, or sodium chloride, optionally at a concentration of greater than 0.1%, or a concentration of 0.3% to 2.5%, or any range therein between;

[ae] the aqueous solution of [ad], which comprises trehalose or dextrose;

[af] the aqueous solution of [ae], which contains 1% to 50% trehalose;

[ag] the aqueous solution of [af], which contains dextrose, optionally 1% to 50% dextrose;

[ah] the aqueous solution according to any one of [a] to [ag], which contains 5% dextrose in a HEPES buffered solution;

[ai] the aqueous solution according to any one of [a] to [ah], which comprises a buffer such as HEPES Buffered Saline (HBS) or similar, at a concentration of 1 to 200 mM and a pH of 2 to 8, or any range therein between;

[aj] the aqueous solution according to any one of [a] to [ai], which has a pH of 5-8, or a pH of 6-7, or any range therein between;

[ak] the aqueous solution according to any one of [a] to [aj], wherein the liposome comprises less than 6 million, less than 500,000, less than 200,000, less than 100,000, less than 50,000, less than 10,000, or less than 5,000, molecules of trans-crocetin;

[al] the aqueous solution according to any one of [a] to [ak], wherein the liposome comprises 10 to 100,000, 100 to 10,000, or 500 to 5,000, molecules of trans-crocetin, or any range therein between;

[am] the aqueous solution according to any one of [a] to [al], wherein the liposome comprises calcium trans-crocetinate (CTC), the trans-crocetin/lipid ratio is 20 to 120 g/mM (e.g., about 25 to 100 g/mM), or any range therein between, the liposome has a diameter of 80 nm to 120 nm (e.g., 90 to 110), or any range therein between, and the liposome has a zeta potential of –25 to 0 mV (e.g., –15 to 0 mV, –10 to –1 mV, or –5 to –1 mV), or any range therein between;

[an] the aqueous solution according to any one of [a] to [am], wherein the PDI is 0.020 to 0.075 (e.g., 0.030 to 0.050), or any range therein between; and/or

[ao] the aqueous solution according to any one of [a] to [an], wherein the administered trans-crocetin concentration is 2.0 to 10 mg/ml (e.g., 2 to 7.5 or 2.5 to 6 mg/ml), or any range therein between;

[52] the method according to any one of [1] to [51], wherein the subject is administered at least 2, 3, 4, 5, 6, 7, 8, 9, 10, 11, 12, 13, 14, 15, 16, 17, 18, 19, 20, 21, 22, 23, 24, or 25 doses of liposomal trans-crocetin;

[53] the method according to any one of [1] to [52], wherein the subject is administered 1 to 50, 1 to 40, 1 to 30, 1 to 25, 1 to 20, 1 to 15, 1 to 10, or 1 to 5 doses, or any range therein between, of liposomal trans-crocetin;

[54] the method according to any one of [51] to [53], wherein the subject is administered one or more doses of liposomal trans-crocetin in an amount of:

(a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, (b) 4 mg/kg to 7.5 mg/kg (e.g., 5 mg/kg), or any range therein between, or (c) 2 mg/kg to 4 mg/kg (e.g., 2.5 mg/kg), or any range therein between;

[55] the method according to any one of [51] to [54], wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of –15 to –1 mV (e.g., –10 to –1 mV, or –5 to –1 mV), or any range therein between;

[56] the method according to any one of [51] to [55], wherein one or more doses of liposomal trans-crocetin is administered to the subject in an amount of:

(a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, (b) 4 mg/kg to 7.5 mg/kg (e.g., 5 mg/kg), or any range therein between, or (c) 2 mg/kg to 4 mg/kg (e.g., 2.5 mg/kg), or any range therein between; and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[57] the method according to any one of [1] to [56], wherein trans-crocetin is administered to the subject in an amount of 2 mg/kg to 4 mg/kg (e.g., 2.5 mg/kg), or any range therein between, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[58] the method according to any one of [1] to [57], wherein trans-crocetin is administered to the subject in an amount of 2 mg/kg to 4 mg/kg (e.g., 2.5 mg/kg), or any range therein between, and wherein the administered liposomal trans-crocetin comprises liposomes having a diameter of 90 nm to 110 nm, or any range therein between and/or the administered liposome composition comprises liposomes having a zeta potential of −10 to −1 mV, or any range therein between;

[59] the method according to any one of [1] to [58], wherein trans-crocetin is administered to the subject in an amount of 2.5 mg/kg, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[60] the method according to any one of [1] to [59], wherein trans-crocetin is administered to the subject in an amount of 2.5 mg/kg, and wherein the administered liposomal trans-crocetin comprises liposomes having a diameter of 90 nm to 110 nm, or any range therein between and/or the administered liposome composition comprises liposomes having a zeta potential of −15 to −1 mV (e.g., −10 to −1 mV, or −5 to −1 mV), or any range therein between;

[61] the method according to any one of [1] to [60], wherein trans-crocetin is administered to the subject in an amount of 4 mg/kg to 7.5 mg/kg (e.g., 5 mg/kg), or any range therein between, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[62] the method according to any one of [1] to [61 56], wherein trans-crocetin is administered to the subject in an amount of 4 mg/kg to 7.5 mg/kg (e.g., 5 mg/kg), or any range therein between, and wherein the administered liposomal trans-crocetin comprises liposomes having a diameter of 90 nm to 110 nm, or any range therein between and/or the administered liposome composition comprises liposomes having a zeta potential of −10 to −1 mV, or any range therein between;

[63] the method according to any one of [1] to [62], wherein trans-crocetin is administered to the subject in an amount of 5 mg/kg, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[64] the method according to any one of [1] to [63], wherein trans-crocetin is administered to the subject in an amount of 5 mg/kg, and wherein the administered liposomal trans-crocetin comprises liposomes having a diameter 90 nm to 110 nm, or any range therein between and/or the administered liposome composition comprises liposomes having a zeta potential of −10 to −1 mV, or any range therein between;

[65] the method according to any one of [61] to [64], wherein the subject is administered two or more dose(s) of liposomal trans-crocetin at
  (a) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between, or
  (b) five times a day, four times a day, three times a day, twice a day, once a day, or once every other day;

[66] the method according to any one of [61] to [65], wherein liposomal trans-crocetin is administered to the subject in an amount of:
  (a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between,
  (b) 4 mg/kg to 7.5 mg/kg (e.g., 5 mg/kg), or any range therein between, or
  (c) 2 mg/kg to 4 mg/kg (e.g., 2.5 mg/kg), or any range therein between, and
  wherein the subject is administered two or more dose(s) of liposomal trans-crocetin at
  (a) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between, or
  (b) three times a day, twice a day, once a day, or once every other day;

[67] the method according to any one of [61] to [66], wherein liposomal trans-crocetin is administered to the subject in an amount of:
  (a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between,
  (b) 4 mg/kg to 7.5 mg/kg (e.g., 5 mg/kg), or any range therein between, or
  (c) 2 mg/kg to 4 mg/kg (e.g., 2.5 mg/kg), or any range therein between,
  wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between; and wherein the subject is administered two or more dose(s) of liposomal trans-crocetin at
  (a) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between, or
  (b) three times a day, twice a day, once a day, or once every other day;

[68] the method according to any one of [1] to [67], wherein trans-crocetin is administered to the subject in an amount of 2 mg/kg to 4 mg/kg (e.g., 2.5 mg/kg), or any range therein between, at five times a day, four times a day, three times a day, twice a day, once a day, or once every other day, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[69] the method according to any one of [1] to [68], wherein trans-crocetin is administered to the subject in an amount of 2 mg/kg to 4 mg/kg (e.g., 2.5 mg/kg), or any range therein between, twice a day, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[70] the method according to any one of [1] to [69], wherein trans-crocetin is administered to the subject in an amount of 2 mg/kg to 4 mg/kg (e.g., 2.5 mg/kg), or any range therein between, once a day, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[71] the method according to any one of [1] to [70], wherein trans-crocetin is administered to the subject in an amount of 2.5 mg/kg twice a day, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[72] the method according to any one of [1] to [71], wherein trans-crocetin is administered to the subject in an amount of 2.5 mg/kg once a day, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[73] the method according to any one of [1] to [72], wherein trans-crocetin is administered to the subject in an amount of 4 mg/kg to 7.5 mg/kg (e.g., 5 mg/kg), or any range therein between, at five times a day, four times a day, three times a day, twice a day, once a day, or once every other day, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[74] the method according to any one of [1] to [73], wherein trans-crocetin is administered to the subject in an amount of 4 mg/kg to 7.5 mg/kg (e.g., 5 mg/kg), or any range therein between, twice a day, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[75] the method according to any one of [1] to [74], wherein trans-crocetin is administered to the subject in an amount of 4 mg/kg to 7.5 mg/kg (e.g., 5 mg/kg), or any range therein between, once a day, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[76] the method according to any one of [1] to [75], wherein trans-crocetin is administered to the subject in an amount of 5 mg/kg twice a day, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[77] the method according to any one of [1] to [76], wherein trans-crocetin is administered to the subject in an amount of 5 mg/kg once a day, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[78] the method according to any one of [1] to [77], wherein the subject is administered one or more (e.g., 1, 2, 3, 4, 5, or 6) loading dose(s) of liposomal trans-crocetin;

[79] the method according to any one of [1] to [78], wherein the subject is administered one or more loading dose(s) of liposomal trans-crocetin at 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between;

[80] the method according to any one of [1] to [79], wherein the subject is administered one or more loading dose(s) of liposomal trans-crocetin at 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, at
  (a) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between, or
  (b) four times a day, three times a day, two times a day, once a day, or once every other day;

[81] the method according to any [1] to [80], wherein the subject is administered (a) at least 2, 3, 4, 5, 6, 7, 8, 9, 10, 11, 12, 13, 14, 15, 16, 17, 18, 19, 20, 21, 22, 23, 24, or 25, or (b) 1 to 50, 1 to 40, 1 to 30, 1 to 25, 1 to 20, 1 to 15, 1 to 10, or 1 to 5, or any range therein between, maintenance doses of liposomal trans-crocetin;

[82] the method according to any one of [1] to [81], wherein the subject is administered one or more maintenance dose(s) of liposomal trans-crocetin at 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between;

[83] the method according to any one of [1] to [82], wherein the subject is administered two or more maintenance dose(s) of liposomal trans-crocetin at 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, of trans-crocetin, at (a) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between, or (b) four times a day, three times a day, two times a day, once a day, or once every other day;

[84] the method according to any one of [1] to [83], wherein the subject is administered one or more (e.g., 1, 2, 3, 4, 5, or 6) loading dose(s) of liposomal trans-crocetin at 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, at (a) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between, or (b) four times a day, three times a day, two times a day, once a day, or once every other day;

and wherein the subject is administered at least 2, 3, 4, 5, 6, 7, 8, 9, 10, 11, 12, 13, 14, 15, 16, 17, 18, 19, 20, 21, 22, 23, 24, or 25, or 1 to 50, 1 to 40, 1 to 30, 1 to 25, 1 to 20, 1 to 15, 1 to 10, or 1 to 5, or any range therein between, maintenance doses of liposomal trans-crocetin at 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), trans-crocetin, or any range therein between, at (a) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between, or (b) four times a day, three times a day, two times a day, once a day, or once every other day;

[85] the method according to any one of [1] to [84], wherein the subject is administered one or more (e.g., 1, 2, 3, 4, 5, or 6) loading dose(s) of liposomal trans-crocetin;

[86] the method according to any one of [1] to [85], wherein the subject is administered one or more loading dose(s) of liposomal trans-crocetin at (a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, or (b) 4 mg/kg to 7.5 mg/kg (e.g., 5 mg/kg), or any range therein between;

[87] the method according to any one of [1] to [86], wherein one or more administered loading dose(s) of liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[88] the method according to any one of [1] to [87], wherein one or more loading doses of liposomal trans crocetin is administered to the subject in an amount of:

(a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, or (b) 4 mg/kg to 7.5 mg/kg (e.g., 5 mg/kg), or any range therein between, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[89] the method according to any one of [1] to [88], wherein the subject is administered a loading dose of liposomal trans-crocetin in an amount of:

(a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, or (b) 4 mg/kg to 7.5 mg/kg (e.g., 5 mg/kg), or any range therein between;

[90] the method according to any one of [1] to [89], wherein the subject is administered a loading dose of liposomal trans-crocetin in an amount of 4 mg/kg to 10 mg/kg);

[91] the method according to any one of [1] to [90], wherein the subject is administered a loading dose of liposomal trans-crocetin in an amount of 5 mg/kg;

[92] the method according to any one of [1] to [91], wherein the subject is administered a loading dose of liposomal trans-crocetin in an amount of 5 mg/kg, optionally followed by a maintenance dose comprising liposomal trans-crocetin 24 hours (+/−9 hours) thereafter;

[93] the method according to any one of [1] to [92], wherein the subject is administered a loading dose of liposomal trans-crocetin in an amount of:

(a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, or (b) 4 mg/kg to 7.5 mg/kg (e.g., 5 mg/kg), or any range therein between, wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[94] the method according to any one of [1] to [93], wherein the subject is administered a loading dose of liposomal trans-crocetin in an amount of 4 mg/kg to 10 mg/kg), and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[95] the method according to any one of [1] to [94], wherein the subject is administered a loading dose of liposomal trans-crocetin in an amount of 5 mg/kg, and wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[96] the method according to any one of [1] to [95], wherein the subject is administered one loading dose of liposomal trans-crocetin followed by a maintenance dose comprising liposomal trans-crocetin 24 hours (+/−9 hours) thereafter; or two or more loading dose(s) of liposomal trans-crocetin at
  (i) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between, or
  (ii) five times a day, four times a day, three times a day, twice a day, once a day, or once every other day;

[97] the method according to any one of [1] to [96], wherein liposomal trans-crocetin is administered to the subject in an amount of:
  (a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between,
  (b) 4 mg/kg to 7.5 mg/kg (e.g., 5 mg/kg), or any range therein between, or
  (c) 2 mg/kg to 4 mg/kg (e.g., 2.5 mg/kg), or any range therein between, and wherein the subject is administered one loading dose of liposomal trans-crocetin followed by a maintenance dose comprising liposomal trans-crocetin 24 hours (+/−9 hours) thereafter; or two or more (e.g., 2, 3, or 4) loading dose(s) of liposomal trans-crocetin at
  (i) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between, or
  (ii) three times a day, twice a day, once a day, or once every other day;

[98] the method according to any one of [1] to [97], wherein liposomal trans-crocetin is administered to the subject in a loading dose of:
  (a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, or
  (b) 4 mg/kg to 7.5 mg/kg (e.g., 5 mg/kg), or any range therein between, wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between, and wherein the subject is administered one loading dose of liposomal trans-crocetin followed by a maintenance dose comprising liposomal trans-crocetin 24 hours (+/−9 hours) thereafter; or two or more (e.g., 2, 3, or 4) loading dose(s) of liposomal trans-crocetin at
  (i) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between, or (ii) three times a day, twice a day, once a day, or once every other day;

[99] the method according to any one of [1] to [98], wherein liposomal trans-crocetin is administered to the subject in an amount of 4 mg/kg to 7.5 mg/kg (e.g., 5 mg/kg), wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between; and wherein the subject is administered one loading dose of liposomal trans-crocetin followed by a maintenance dose comprising liposomal trans-crocetin 24 hours (+/−9 hours) thereafter;

[100] the method according to any [1] to [99], wherein the subject is administered at least 2, 3, 4, 5, 6, 7, 8, 9, 10, 11, 12, 13, 14, 15, 16, 17, 18, 19, 20, 21, 22, 23, 24, or 25 maintenance doses of liposomal trans-crocetin;

[101] the method according to any [1] to [100], wherein the subject is administered 1 to 50, 1 to 40, 1 to 30, 1 to 25, 1 to 20, 1 to 15, 1 to 10, or 1 to 5, or any range therein between, maintenance doses of liposomal trans-crocetin;

[102] the method according to any one of [1] to [101], wherein one or more maintenance doses of liposomal trans-crocetin is administered to the subject in an amount of:
  (a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, or
  (b) 2 mg/kg to 4 mg/kg (e.g., 2.5 mg/kg), or any range therein between;

[103] the method according to any one of [1] to [102], wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[104] the method according to any one of [1] to [103], wherein one or more doses of maintenance liposomal trans-crocetin is administered to the subject in an amount of:
  (a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, or
  (b) 2 mg/kg to 4 mg/kg (e.g., 2.5 mg/kg), or any range therein between; and
  wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between;

[105] the method according to any one of [1] to [104], wherein the subject is administered two or more maintenance dose(s) of liposomal trans-crocetin at
  (a) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between,
  (b) five times a day, four times a day, three times a day, twice a day, once a day, or once every other day, or
  (c) 24 hours apart (+/−9 hours);

[106] the method according to any one of [1] to [105], wherein liposomal trans-crocetin is administered to the subject in an amount of:

(a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, or (b) 2 mg/kg to 4 mg/kg (e.g., 2.5 mg/kg), or any range therein between;

wherein the subject is administered two or more maintenance dose(s) of liposomal trans-crocetin at (a) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between, (b) five times a day, four times a day, three times a day, twice a day, once a day, or once every other day, or (c) 24 hours apart (+/−9 hours);

[107] the method according to any one of [1] to [106], wherein two or more maintenance doses of liposomal trans-crocetin is administered to the subject in an amount of:

(a) 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, or (b) 2 mg/kg to 4 mg/kg (e.g., 2.5 mg/kg), or any range therein between;

wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between; and wherein the subject is administered two or more maintenance dose(s) of liposomal trans-crocetin at (a) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between, (b) five times a day, four times a day, three times a day, twice a day, once a day, or once every other day, or (c) 24 hours apart (+/−9 hours);

[108] the method according to any one of [1] to [107], wherein two or more maintenance doses of liposomal trans-crocetin is administered to the subject in an amount of 2 mg/kg to 4 mg/kg (e.g., 2.5 mg/kg), or any range therein between, wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between; and wherein the subject is administered two or more maintenance dose(s) of liposomal trans-crocetin at three times a day, twice a day, once a day, or once every other day;

[109] the method according to any one of [1] to [108], wherein two or more maintenance doses of liposomal trans-crocetin is administered to the subject in an amount of 2 mg/kg to 4 mg/kg (e.g., 2.5 mg/kg), or any range therein between, wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between; and wherein the subject is administered two or more maintenance dose(s) of liposomal trans-crocetin at 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between;

[110] the method according to any one of [1] to [109], wherein two or more maintenance doses of liposomal trans-crocetin is administered to the subject in an amount of 2 mg/kg to 4 mg/kg (e.g., 2.5 mg/kg), or any range therein between, wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between; and wherein the subject is administered two or more maintenance dose(s) of liposomal trans-crocetin at 24 hours apart (+/−9 hours);

[111] the method according to any one of [1] to [110], wherein two or more maintenance doses of liposomal trans-crocetin is administered to the subject in an amount of 2.5 mg/kg, wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between, and wherein the subject is administered two or more maintenance dose(s) of liposomal trans-crocetin at three times a day, twice a day, once a day, or once every other day;

[112] the method according to any one of [1] to [111], wherein two or more maintenance doses of liposomal trans-crocetin is administered to the subject in an amount of 2.5 mg/kg, wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between, and wherein the subject is administered two or more maintenance dose(s) of liposomal trans-crocetin at crocetin at 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between;

[113] the method according to any one of [1] to [112], wherein two or more maintenance doses of liposomal trans-crocetin is administered to the subject in an amount of 2.5 mg/kg, wherein the administered liposomal trans-crocetin comprises liposomes having a diameter of 80 nm to 120 nm (e.g., 90 nm to 110 nm, or, 95 nm to 109 nm), or any range therein between and/or the administered liposome composition comprises liposomes having a zeta potential of −15 to −1 mV (e.g., −10 to −1 mV, or −5 to −1 mV), or any range therein between, and wherein the subject is administered two or more maintenance dose(s) of liposomal trans-crocetin at once a day (e.g., 24 hours apart (+/−9 hours));

[114] the method of [88] or [113] wherein and wherein the subject is administered at least 2, 3, 4, 5, 6, 7, 8, 9, 10, 11, 12, 13, 14, 15, 16, 17, 18, 19, 20, 21, 22, 23, 24, or 25, or 1 to 50, 1 to 40, 1 to 30, 1 to 25, 1 to 20, 1 to 15, 1 to 10, or 1 to 5, or any range therein between, maintenance doses of liposomal trans-crocetin

[115] the method according to any one of [1] to [114], wherein the subject is administered one or more (e.g., 1, 2, 3 or 4) loading dose(s) of liposomal trans-crocetin at 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, at
  (a) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between,
  (b) five times a day, four times a day, three times a day, twice a day, once a day, or once every other day, or
  (c) 24 hours apart (+/−9 hours),
  and wherein the subject is administered at least 2, 3, 4, 5, 6, 7, 8, 9, 10, 11, 12, 13, 14, 15, 16, 17, 18, 19, 20, 21, 22, 23, 24, or 25, or 1 to 50, 1 to 40, 1 to 30, 1 to 25, 1 to 20, 1 to 15, 1 to 10, or 1 to 5, or any range therein between, maintenance doses of liposomal trans-crocetin at 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg), or any range therein between, at
  (a) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between,
  (b) five times a day, four times a day, three times a day, twice a day, once a day, or once every other day, or
  (c) 24 hours apart (+/−9 hours);

[116] the method according to any one of [1] to [115], wherein the subject is administered one or more (e.g., 1, 2, 3 or 4) loading dose(s) of liposomal trans-crocetin at 4 mg/kg to 7.5 mg/kg, (e.g., 5 mg/kg or 7.5 mg/kg), or any range therein between, three times a day, twice a day, once a day, or once every other day, and wherein the subject is administered one or more maintenance doses of liposomal trans-crocetin at
  (a) 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between,
  (b) five times a day, four times a day, three times a day, twice a day, once a day, or once every other day, or
  (c) 24 hours apart (+/−9 hours);

[117] the method according to any one of [1] to [116], wherein the subject is administered one or more (e.g., 1, 2, 3 or 4) loading dose(s) of liposomal trans-crocetin at 4 mg/kg to 10 mg/kg, or any range therein between, three times a day, twice a day, once a day, or once every other day, and wherein the subject is administered one or more maintenance doses of liposomal trans-crocetin at 2 mg/kg to 5 mg/kg (e.g., 2.5 mg/kg), or any range therein between, three times a day, twice a day, once a day, or once every other day;

[118] the method according to any one of [1] to [117], wherein the subject is administered one or more (e.g., 1, 2, 3 or 4) loading dose(s) of liposomal trans-crocetin at 4 mg/kg to 10 mg/kg (e.g., 5 mg/kg or 7.5 mg/kg), or any range therein between, three times a day, twice a day, once a day, or once every other day, and wherein the subject is administered one or more maintenance doses of liposomal trans-crocetin at 2 mg/kg to 5 mg/kg (e.g., 2.5 mg/kg), or any range therein between, three times a day, twice a day, once a day, or once every other day;

[119] the method according to any one of [1] to [118], wherein the subject is administered 1 or 2 loading dose(s) of liposomal trans-crocetin at 4 mg/kg to 7.5 mg/kg, (e.g., 5 mg/kg or 7.5 mg/kg), or any range therein between, twice a day or once a day, and wherein the subject is administered one or more maintenance doses of liposomal trans-crocetin at 2 mg/kg to 5 mg/kg (e.g., 2.5 mg/kg), or any range therein between, twice a day or once a day starting 24 hours (+/−6 hours thereafter) after the 1 or 2 loading dose(s);

[120] the method according to any one of [1] to [119], wherein the subject is administered 1 loading dose of liposomal trans-crocetin at 5 mg/kg (Day 1), followed by daily administration (daily administration from Day 2 onward) of one or more maintenance doses of liposomal trans-crocetin at 2.5 mg/kg;

[121] the method of [113] or [114] wherein and wherein the subject is administered at least 2, 3, 4, 5, 6, 7, 8, 9, 10, 11, 12, 13, 14, 15, 16, 17, 18, 19, 20, 21, 22, 23, 24, or 25, or 1 to 50, 1 to 40, 1 to 30, 1 to 25, 1 to 20, 1 to 15, 1 to 10, or 1 to 5, or any range therein between, maintenance doses of liposomal trans-crocetin;

[122] the method according to any one of [1] to [121], wherein at least one dose of the administered trans-crocetin is based on the age of the subject;

[123] the method according to any one of [1] to [122], wherein at least one dose of the administered trans-crocetin is based on the sex of the subject;

[124] the method according to any one of [1] to [123], wherein at least one dose of the administered trans-crocetin is based on the age and sex of the subject;

[125] the method according to any one of [1] to [124], wherein at least one dose of the administered trans-crocetin is based on the weight of the subject;

[126] the method according to any one of [1] to [125], wherein at least one dose of the administered trans-crocetin is not a fixed dose and is specifically formulated based on the particular body weight or body mass of the subject;

[127] the method according to any one of [1] to [126], wherein a dose of 1 mg/kg to 15 mg/kg (e.g., 2 mg/kg to 8 mg/kg, or 2 mg/kg to 6 mg/kg, of liposomal trans-crocetin is administered to the subject;

[128] the method according to any one of [1] to [127], wherein a dose of 2.5 mg/kg, 3.0 mg/kg, 3.5 mg/kg, 4 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, or 10 mg/kg of liposomal trans-crocetin is administered to the subject;

[129] the method according to any one of [1] to [128], wherein the subject is administered at least 2, 3, 4, 5, 6, 7, 8, 9, 10, 15, or more than 15 doses of liposomal trans-crocetin;

[130] the method according to any one of [1] to [129], wherein the doses are administered in an amount and over a time interval sufficient to maintain a serum trans-crocetin concentration of at least 0.4 ug/ml or 1.0 ug/ml (e.g., 12 ug/ml to 49.2 ug/ml, 15 to ug/ml to 49.2 ug/ml, or 20 to ug/ml to 49.2 ug/ml), or any range therein between, to the subject;

[131] the method according to any one of [1] to [130], wherein a maintenance dose of 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg) of trans-crocetin is administered 3 to 24 hours, 9 to 18 hours, or 10 to 14 hours (e.g., 12 hours (+/−3 hours)) after the last loading dose;

[132] the method according to any one of [1] to [131], wherein the subject administered the trans-crocetin has a >25% improvement in Partial Pressure of arterial oxygen/Fraction of inspired oxygen (PaO2/FiO2) ratio at 24 hours, 48 hours, or 96 hours after administration of the trans-crocetin;

[133] the method according to any one of [1] to [132], wherein the subject has or is at risk of developing acute respiratory distress syndrome (ARDS);

[134] the method according to any one of [7], [8], or [132], wherein the ARDS comprises acute respiratory failure (ARF);

[135] the method of according to any one of [7], [8], or [132], wherein, the ARDS is associated with sepsis, pneumonia, ventilation induced pneumonia, trauma, damage to the brain, a blood transfusion, babesiosis, lung contusion, lung transplant, aspiration of stomach contents, drug abuse or overdose, a burn, pancreatitis, near drowning, inhalation of chemical fumes, or administration of fluid during post-trauma resuscitation, or infection (e.g., of lung tissue such as alveolar lung tissue);

[136] the method according to any one of [1] to [135], wherein the method comprises treating a subject presenting one or more symptoms selected from: mild, moderate or severe hypoxemia as determined by Partial Pressure of arterial oxygen/Fraction of inspired oxygen (PaO2/FiO2) or positive end-expiratory pressure (PEEP), bilateral opacities, respiratory failure, shortness of breath, labored breathing, cough, fever, increased heart rate, low blood pressure, confusion, extreme tiredness, rapid breathing, organ failure, chest pain, bluish coloring of nails or lips, elevated or depressed levels of one or more biomarker such as inflammatory markers, or need for mechanical ventilation;

[137] the method of [136], wherein the one or more inflammatory markers is selected from the group consisting of TNF-alpha, IL6, C5a, DAMPs, ERK, NF-kappaB, IL10, and a serine protease;

[138] the method of [137], wherein the one or more biomarkers are selected from histone, histone/P alpha 1 complexes, histone/l alpha 1 complexes, histone/l alpha 1/P alpha 1 complexes, TNF-alpha, IL6, IL10, IL1, IL1ra, IL1B, IL8, MCP1, MIP2, CRP, PCT, cytokine-induced neutrophil chemoattractant/KC, UTI, a complement component (e.g., of C1, C2, C3, C3a, C3b, C4, C4b, C5, C5a, C5b, C6, C7, C8, C9, membrane attack complex, Factor B, Factor D, MASP1, and MASP2), or fragments thereof;

[139] the method according to any one of [1] to [138], wherein the subject has respiratory failure;

[140] the method according to any one of [1] to [139], wherein the subject requires ventilator-assisted breathing;

[141] the method of [140], wherein the ventilator-assisted breathing is mechanical ventilator-assisted breathing (e.g., invasive or non-invasive mechanical ventilator-assisted breathing);

[142] the method of [141], wherein the mechanical ventilator-assisted breathing is pressure-limited or volume-limited;

[143] the method according to any one of [1] to [142], wherein the subject has one or more organ failures or organ impairments;

[144] the method according to any one of [1] to [143], wherein the subject has two or more organ failures or organ impairments;

[145] the method according to any one of [1] to [144], wherein the subject has a failure or impairment of the liver, kidney, intestine, heart, or brain;

[146] the method of [145], wherein the subject has kidney (renal) impairment;

[147] the method according to [145] or [146], wherein the subject has a condition associated with a liver disease (e.g., cirrhosis, nonalcoholic fatty liver disease (NAFLD), non-alcoholic steatohepatitis (NASH); alcoholic liver disease, acute liver injury, and cirrhosis of the liver);

[148] the method according to any one of [1] or [147], wherein the subject has a cardiovascular disease or condition (e.g., coronary artery disease such as myocardial infarction, sudden cardiac death, cardiorespiratory arrest, hypertension, pulmonary arterial hypertension, atherosclerosis, occlusive arterial disease, Raynaud's disease, peripheral vascular disease, other vasculopathies such as Buerger's disease, Takayasu's arthritis, and post-cardiac arrest syndrome (PCAS), chronic venous insufficiency, heart disease, congestive heart failure, chronic skin ulcers);

[149] the method according to any one of [1] to [148], wherein the subject has experienced, is experiencing, or is at risk of experiencing a heart attack or stroke, or a condition associated with a heart attack or stroke (e.g., ischemic and hemorrhagic stroke); or the method according to any one of [1] to [147], wherein the subject has experienced or is experiencing a heart attack or stroke, or a condition associated with a heart attack or stroke (e.g., ischemic and hemorrhagic stroke); and trans-crocetin is administered within 1 hour or within 4, 12, 18 or 24 hours, or 48 hours of the onset of stroke or heart attack symptoms or associated conditions;

[150] the method according to any one of [1] to [149], wherein the subject has experienced, is experiencing, or is at risk of experiencing shock or a condition associated with shock (e.g., cardiogenic shock, hypovolemic shock, septic shock, neurogenic shock, and anaphylactic shock); or the method according to any one of [1] to [149], wherein the subject has experienced or is experiencing shock or a condition associated with shock (e.g., cardiogenic shock, hypovolemic shock, septic shock, neurogenic shock, and anaphylactic shock) and trans-crocetin is administered within 1 hour or within 4, 12, 18 or 24 hours, or 48 hours of the onset of shock or a condition associated with shock;

[151] the method according to any one of [1] to [150], wherein the subject has experienced, is experiencing, or is at risk of experiencing a condition associated with nitric oxide deficiency (e.g., sickle cell disease, paroxysmal nocturnal hemoglobinuria (PNH), a hemolytic anemia, a thalassemia, another red blood cell disorder, a purpura such as thrombotic thrombocytic purpura (TTP), hemolytic uremic syndrome (HUS), idiopathic thrombocytopenia (ITP), another platelet disorder, a coagulation abnormality such as disseminated intravascular coagulopathy (DIC), purpura fulminans, heparin induced thrombocytopenia (HIT), hyperleukocytosis, and hyper viscosity syndrome, or a condition associated therewith);

[152] the method according to any one of [1] to [151], wherein the subject has a lung disease or condition (e.g., acute respiratory distress syndrome (ARDS), pulmonary fibrosis, pulmonary hemorrhage, lung injury, lung cancer, chronic obstructive pulmonary disease (COPD) and other respiratory disorders);

[153] the method according to any one of [1] to [152], wherein the subject has a kidney disease or condition (e.g., lipopolysaccharide medication or toxin induced acute kidney injury (AKI) and end stage kidney disease);

[154] the method according to any one of [1] to [153], wherein the subject has an ischemic or hypoxic condition selected from: tissue hypoperfusion, ischemic-reperfusion injury, transient cerebral ischemia, cerebral ischemia-reperfusion, ischemic stroke, hemorrhagic stroke, traumatic brain injury, migraine (e.g., a chronic migraine or severe migraine disorder), gastrointestinal ischemia, kidney disease, pulmonary embolism, acute respiratory failure, neonatal respiratory distress syndrome, an obstetric emergency to reduce perinatal comorbidity (such as, pre/eclampsia and conditions that lead to cerebral palsy), myocardial infarction, acute limb or mesenteric ischemia, cardiac cirrhosis, chronic peripheral vascular disease, congestive heart failure, atherosclerotic stenosis, anemia, thrombosis, or embolism;

[155] the method according to any one of [1] to [154], wherein the subject has experienced a traumatic injury (e.g., hemorrhaging associated with a car crash or combat), or wherein the subject has undergone, will undergo, or is undergoing surgery;

[156] the method according to any one of [1] to [155], wherein the subject has an infection;

[157] the method according to any one of [1] to [156], wherein the subject has a condition associated with an infection, such as endotoxemia, bacteremia, hypoxia, tissue hypoperfusion, ischemia, ARDS, or sepsis;

[158] the method of [157], wherein the subject has endotoxemia or a condition associated with endotoxemia, including endotoxemia associated with conditions such as periodontal disease (e.g., periodontitis or inflammation of the gums), chronic alcoholism, chronic smoking, transplantation, neonatal necrotizing enterocolitis, or neonatal ear infection;

[159] the method of [158], wherein the treatment reduces systemic levels of LPS, endotoxin and/or another trigger of systemic inflammation in the subject;

[160] the method according to any one of [156] to [159], wherein the infection is a bacterial infection such as an *P. aeruginosa* infection, an *S. aureus* infection (e.g., MRSA) or a condition associated therewith (e.g., endotoxemia), or an enterococcal infection (e.g., VRE), a fungal infection (e.g., a candidiasis infection (e.g., invasive candidiasis) or a condition associated therewith, or a parasitic infection or a condition associated therewith such as malaria (or an associated condition such as cerebral malaria, severe anemia, acidosis, acute kidney failure and ARDS), Schistosomiasis, and human African trypanosomiasis, and conditions associated therewith; a viral infection or a condition associated therewith such as Ebola, Dengue and Marburg (or an associated condition such as influenza, measles, and a viral hemorrhagic fever);

[161] the method according to any one of [156] to [160], wherein the method treats a condition associated with a bacterial infection (e.g., an *P. aeruginosa* infection, *S. aureus* infection (e.g., MRSA), or an enterococcal infection (e.g., VRE), such as endotoxemia, bacteremia, hypoxia, tissue hypoperfusion, ischemia, and sepsis);

[162] the method according to any one of [156] to [160], wherein the method treats a condition associated with a viral infection (e.g., hypoxia, tissue hypoperfusion, ischemia, sepsis, and ARDS);

[163] the method of [162], wherein the method treats a condition associated with a coronavirus infection (e.g., COVID-19 and ARDS);

[164] the method of [160], wherein the method treats a condition associated with an Ebola, Dengue or Marburg infection (e.g., influenza, measles, and a viral hemorrhagic fever);

[165] the method according to any one of [156] to [160], wherein the method treats a condition associated with a fungal infection (e.g., a candidiasis infection such as invasive candidiasis);

[166] the method according to any one of [156] to [160], wherein the method treats a condition associated with a parasitic infection such as malaria (e.g., cerebral malaria, severe anemia, acidosis, acute kidney failure, ischemia, tissue hypoperfusion and ARDS), Schistosomiasis, and human African trypanosomiasis;

[167] the method according to any one of [1] to [166], wherein the subject has an inflammatory disease or condition (e.g., systemic inflammation, systemic inflammatory response syndrome (SIRS), low-grade inflammation, acute inflammation, or a chronic inflammatory disease); inflammatory bowel disease (e.g., Crohn's disease);

[168] the method according to any one of [1] to [167], wherein the subject has an autoimmune disease or condition associated with an autoimmune disease (e.g., psoriasis, cystic fibrosis, and rheumatoid arthritis);

[169] the method according to any one of [1] to [168], wherein the subject has a metabolic disease or a condition associated with a metabolic disease, such as insulin resistance or diabetes or an associated condition (e.g., gangrene, diabetic necrosis, diabetic neuropathy, diabetic vascular disease (e.g., microvascular disease such as retinopathy and nephropathy, and diabetic ulcers)); type 2 diabetes or a condition associated with type 2 diabetes;

[170] the method according to any one of [1] to [169], wherein the subject has a low grade endotoxemic disease;

[171] the method according to any one of [1] to [170], wherein the subject has sepsis;

[172] the method according to any one of [1] to [171], wherein the subject is at risk of developing sepsis;

[173] the method according to any one of [1] to [172], wherein the trans-crocetin is administered in combination with another therapeutic agent;

[174] the method according to any one of [23] to [27], or [173], wherein the therapeutic agent is an alkylating agent (e.g., carboplatin, cisplatin, melphalan, oxaliplatin, procarbazine, temozolomide, or thiotepa), an antimetabolite (e.g., 5-Fluorouracil, gemcitabine, methotrexate, or pemetrexed), an antibiotic (e.g., actinomycin D, bleomycin, doxorubicin, or Streptonigrin), or a plant alkaloid (e.g., docetaxel, etoposide, vincristine, irinotecan, or VP16) or a multikinase (e.g., Sorafenib);

[175] the method according to any one [23] to [27], [173], or [174], wherein the therapeutic agent is a chemotherapeutic agent;

[176] the method according to any one [23] to [27] or [173] to [175], wherein the therapeutic agent is immunotherapeutic agent (e.g., CAR-immune cell therapy, or an antibody or other inhibitor of a checkpoint protein such as PD1, PDL1, CTLA4, PDL2, LAG3, TIM3, 2B4, A2aR, B7-H3, B7-H4, BTLA, HVEM, GAL9, VISTA, TIGIT, KIR, CD160, CGEN15049, CHK1, CHK2, or a B-7 family ligand);

[177] the method according to any one of [23] to [27] or [173] to [176], wherein the therapeutic agent is radiation therapy and/or a radiosensitizing agent;

[178] the method according to any one of [23] to [27] or [173] to [177], wherein the therapeutic agent is oxygen and/or intravenous fluids to maintain/increase blood oxygen levels and/or blood pressure or hyperbaric therapy;

[179] the method according to any one of [23] to [27] or [173] to [178], wherein the therapeutic agent is another ionizable carotenoid or a carotenoid comprising at least one polar group or monocyclic group (e.g., an ionizable carotenoid depicted in FIGS. 1A-1D);

[180] the method according to any one of [23] to [27] or [173] to [179], wherein the therapeutic agent is an anesthetic agent, anti-inflammatory agent (e.g., an NSAID, corticosteroid, TNFR-Fc (e.g., etanercept), or an anti-TNF alpha, anti-IL6 receptor antibody or anti-IL6 antibody), thrombolytic agent (e.g., tissue plasminogen activator (tPA), a vasopressor agent, an antioxidant, or a corticosteroid (e.g., a glucocorticoid or mineralocorticoid such as fludrocortisonel);

[181] the method according to any one [23] to [27] or [173] to [180], wherein the therapeutic agent is a standard of care treatment for the disorder or condition to be treated;

[182] the method according to any one of [23] to [27] or [173] to [181], wherein the therapeutic agent is an antimicrobial agent;

[183] the method of [182], wherein the antimicrobial agent is an antiviral agent (e.g., remdesivir), antibacterial agent, antifungal agent or an antiparasite agent;

[184] the method according to any one of [1] to [183], wherein the subject is immunocompromised;

[185] the method according to any one of [1] to [184], wherein the subject has or will receive chemotherapy and/or is immune-suppressed (e.g., a febrile neutropenic subject);

[186] the method according to any one of [1] to [185], wherein the subject is elderly; and/or

[187] the method according any one of [1] to [186], wherein the subject is critically ill.

In some embodiments, the disclosure provides methods and dosing regimens in which the provided trans-crocetin compositions are administered in combination therapy with another therapeutic agent.

Still other features and advantages of the compositions and methods described herein will become more apparent from the following detailed description when read in conjunction with the accompanying drawings.

BRIEF DESCRIPTION OF THE DRAWINGS/FIGURES

FIGS. 1A-1D depict trans-crocetin and other exemplary ionizable Polyene Carotenoids that may be administered in combination with the liposomal trans-crocetin compositions provided herein.

Figures 2A, 2B, 2C, 2D, 2E, 2F, 2G, 2H, 2I:
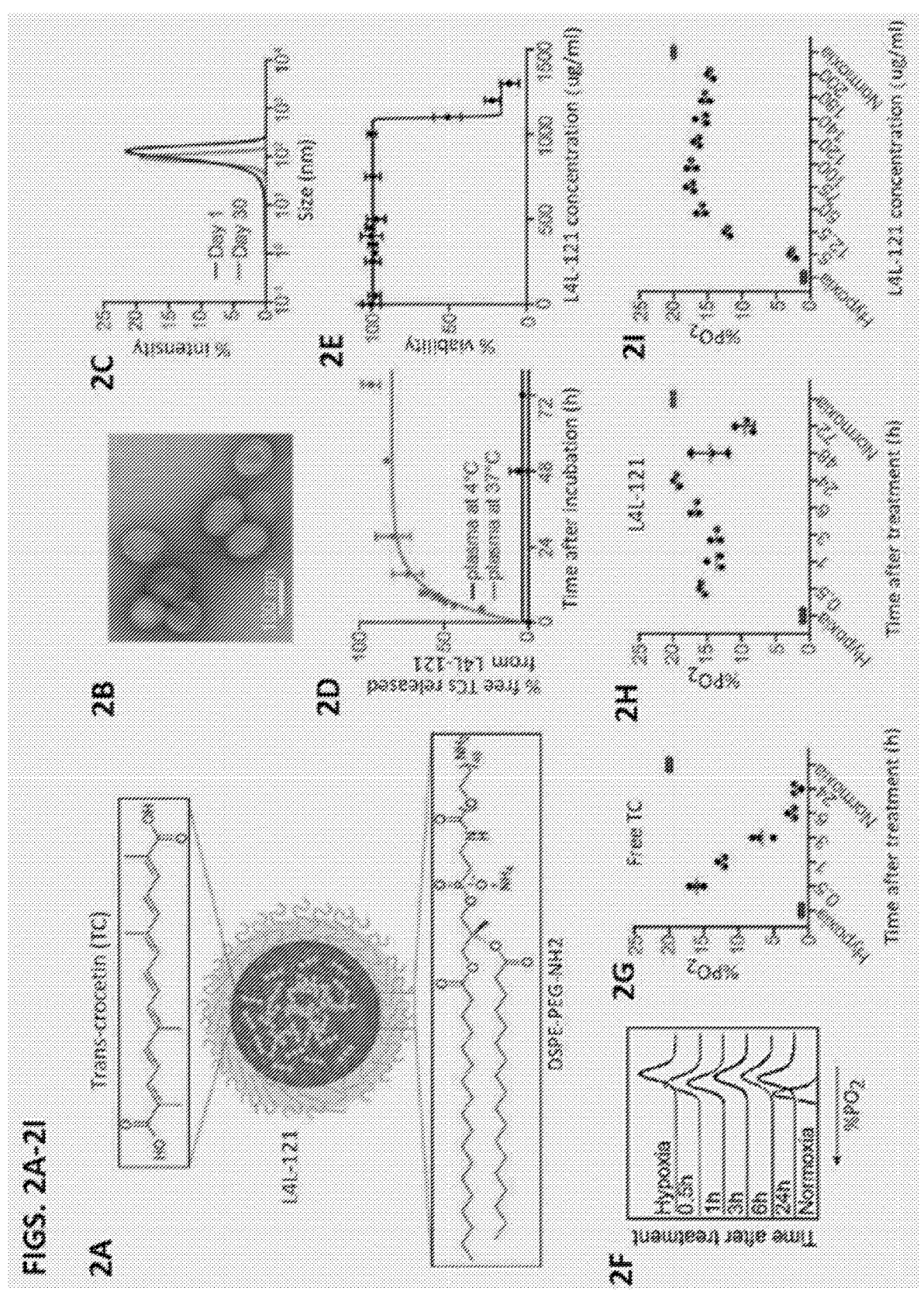

FIGS. 2A-2I: FIG. 2A: Schematic representation of L4L-121, a liposomal nanoparticle encapsulating TC. FIG. 2B: Transmission electron microscopy of L4L121). FIG. 2C: DLS measurements of L4L-121 at day 1 and day 30 after treatment confirmed its stability over time at 4° C. FIG. 2D: Release measurements of TC from L4L-121 in the plasma demonstrated sustained release over time, with a plateau 30 h after incubation at 37° C. No release was observed at 4° C. FIG. 2E: Cell viability assays (CellTiter-Glo®) performed 72 h after treatment of HUVECs with various concentrations of L4L-121. FIG. 2F: Flow cytometric analysis of HUVECs incubated with 2 µg/mL free TC over time. FIG. 2G: The % $PO_2$ was assessed based on the readout of the BioTracker 520 green hypoxia dye. FIG. 2H: Quantification of % $PO_2$ based on the flow cytometric data. FIG. 2I: Quantification of % $PO_2$ based on the flow cytometric data of HUVECs incubated with 120 µg/mL L4L-121 over time and (FIG. 2H) as a function of various concentrations of L4L-121 at 24 h.

FIGS. 3A-3B. Calcium trans-crocetinate liposome (CTC-LP) stability at 4° C. over 6 months—the CTC-LP test articles contain drug/lipid (D/L) ratios of 80, 60, and 40 (FIG. 3A). Each CTC-LP test article showed negligible leaching (change in D/L ratio) over the 6-month evaluation period. 3. Liposomal CTC batch reproducibility—four batches of liposomal CTC were reproducible and stable at 4° C., up to at least 7 months (FIG. 3B).

FIG. 4. Magnesium trans-crocetinate liposome (MTC-LP) stability at 4° C. over 6 months. The MTC-LP test articles contain drug/lipid (D/L) ratios of 80, 60, and 40. Each MTC-LP test article showed negligible leaching (change in D/L ratio) over the 2 month evaluation period.

FIG. 5 presents the percent survival at Day 5 after treatment with L4L-121 plus imipenem vs saline plus imipenem in a CLP model (L4L-121 Efficacy Study 1).

FIG. 6 presents a survival at Day 5 after treatment with L4L-121 plus imipenem vs saline plus imipenem in a CLP model (L4L-121 Efficacy Study 2).

FIG. 7 presents the treatment effect of L4L-121 vs saline on aspartate aminotransferase, creatinine, blood urea nitrogen, alanine aminotransferase, bilirubin, albumin and alkaline phosphatase (L4L-121 Efficacy Study 2). The horizontal dotted lines represent the upper and lower ranges of normal.

Figure 8:
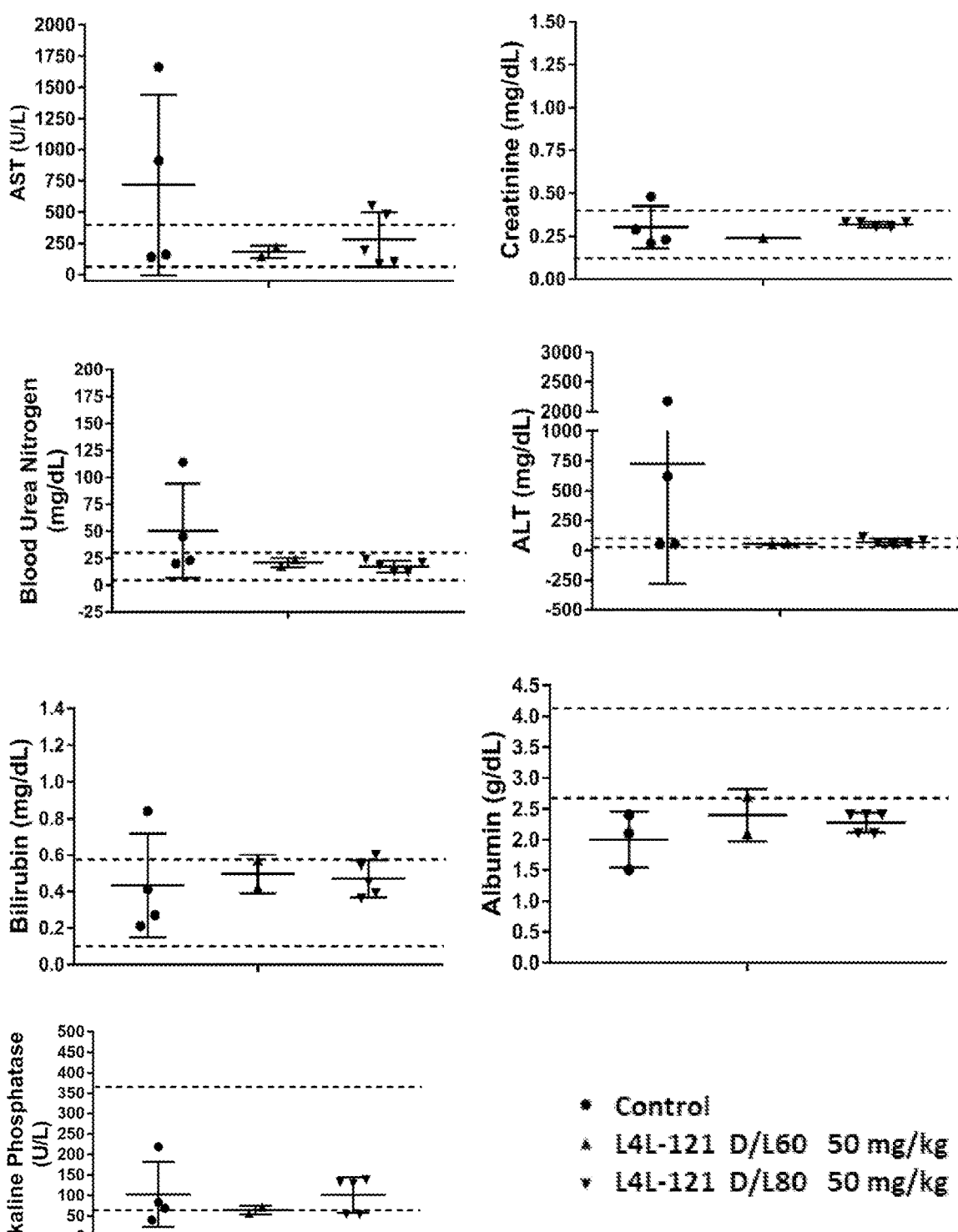

FIG. 8 presents the percent survival at Day 5 after treatment with L4L-121 plus imipenem vs saline plus imipenem in a CLP model (L4L-121 Efficacy Study 3).

Figure 9:
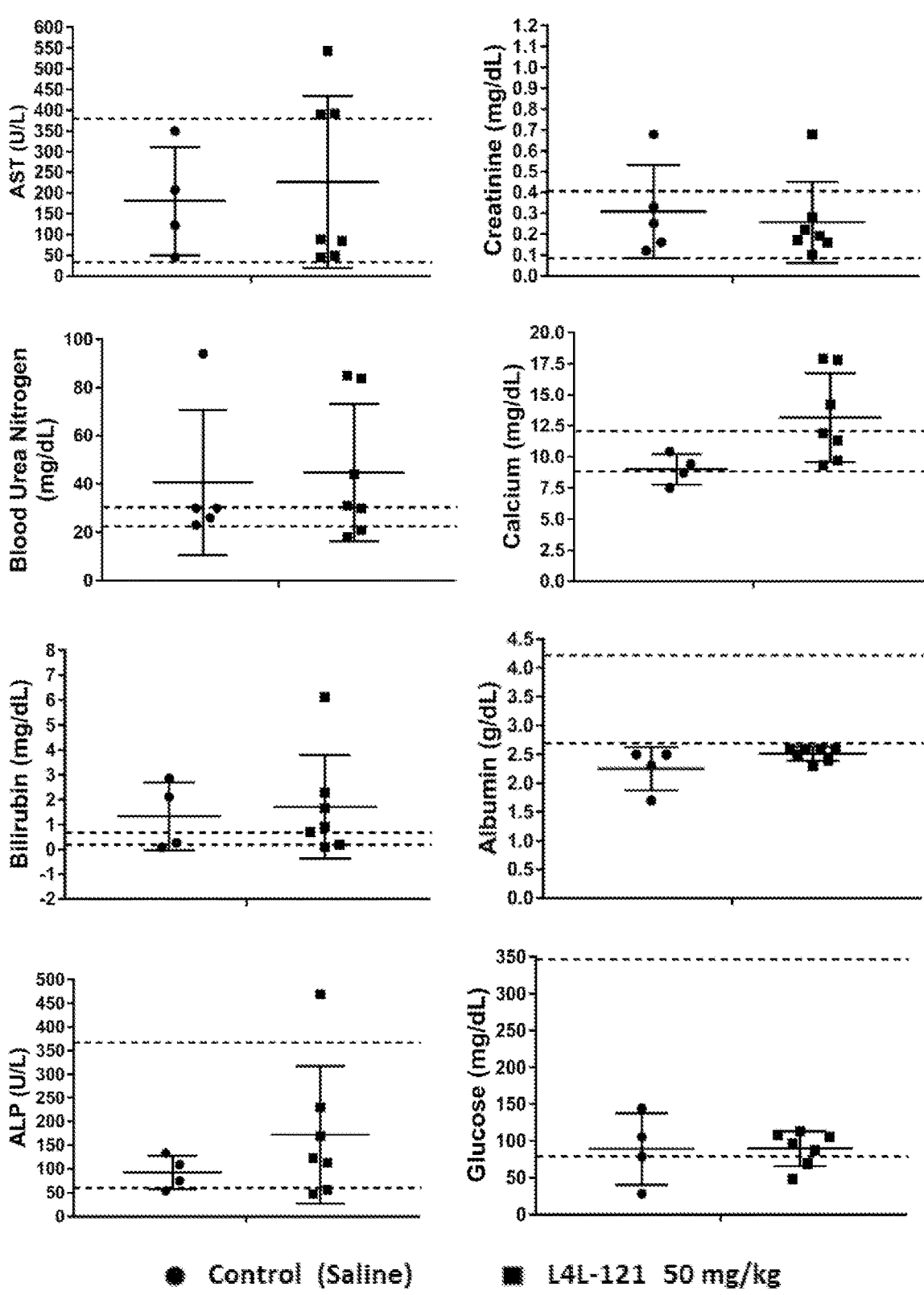

FIG. 9 presents Treatment effect of L4L-121 vs saline on aspartate aminotransferase, creatinine, blood urea nitrogen, calcium, bilirubin, albumin, alkaline phosphatase and glucose. The horizontal dotted lines represent the upper and lower ranges of normal (L4L-121 Efficacy Study 3).

Figure 10:
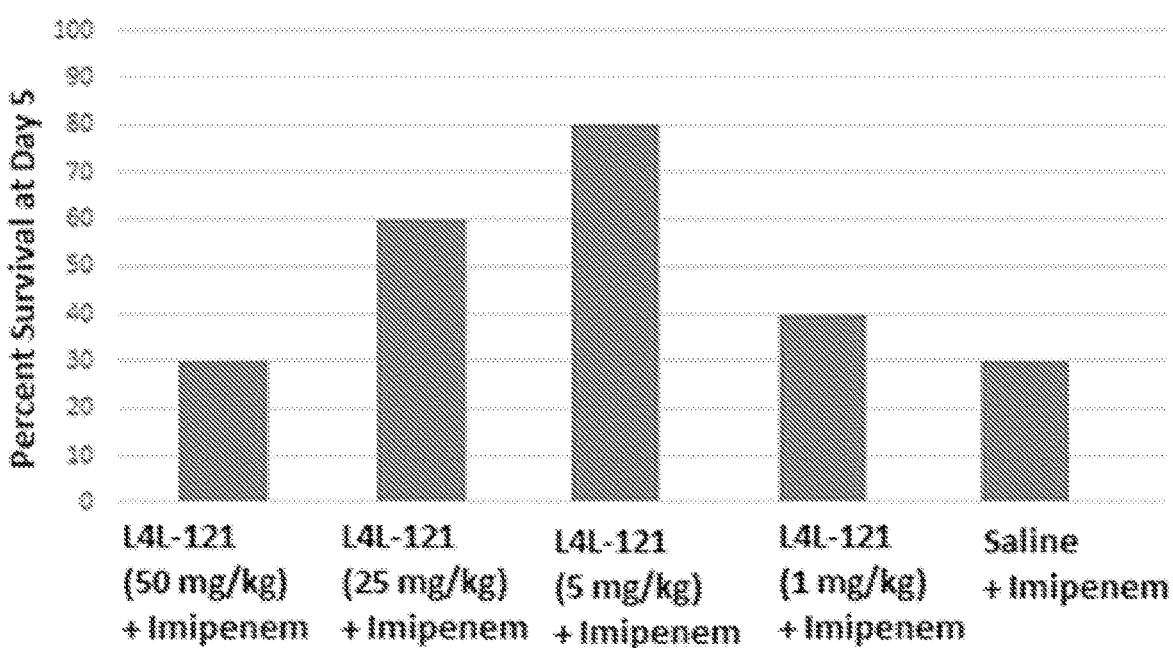

FIG. 10 presents the percent survival at Day 5 after treatment with L4L-121 plus imipenem vs saline plus imipenem in a CLP model (L4L-121 Efficacy Study 4).

Figure 11:
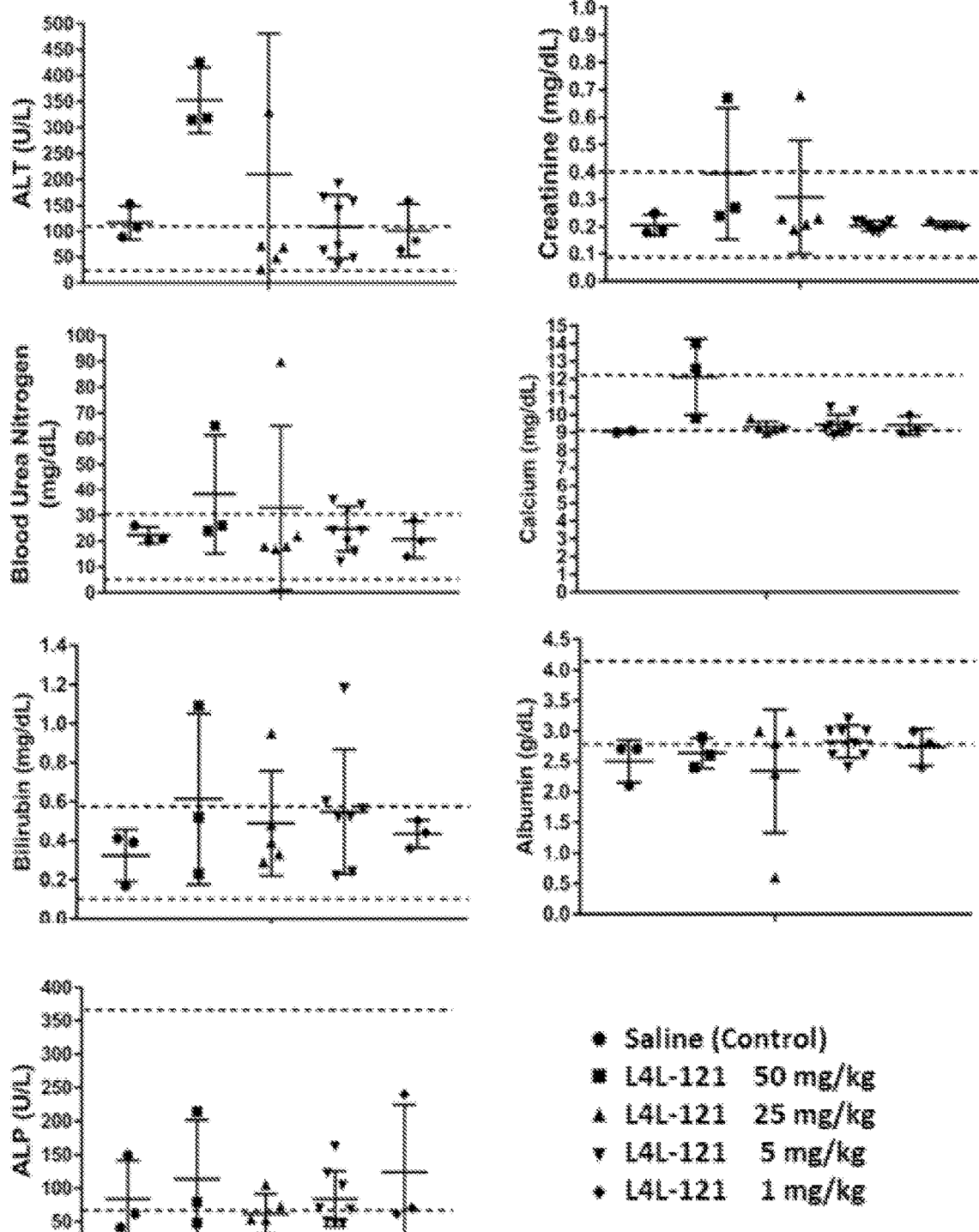

FIG. 11 presents the treatment effect of different doses of L4L-121 on alanine aminotransferase, creatinine, blood urea nitrogen, calcium, bilirubin, albumin and alkaline phosphatase (L4L-121 Efficacy Study 4). The horizontal dotted lines represent the upper and lower ranges of normal.

Figure 12:
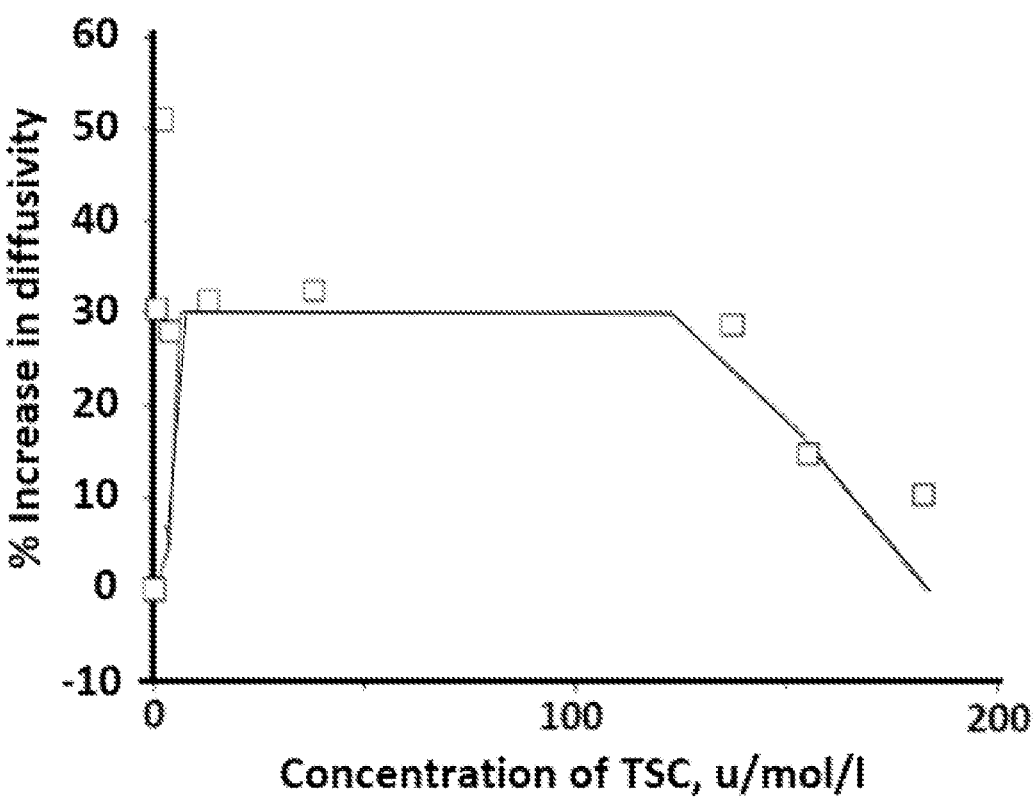

FIG. 12. The effect of trans-crocetin on the diffusivity of oxygen (line) and glucose (open squares) through water or plasma. Gainer et al., J Neurosurg, 126(2): 460-466 (2017).

Figure 13:
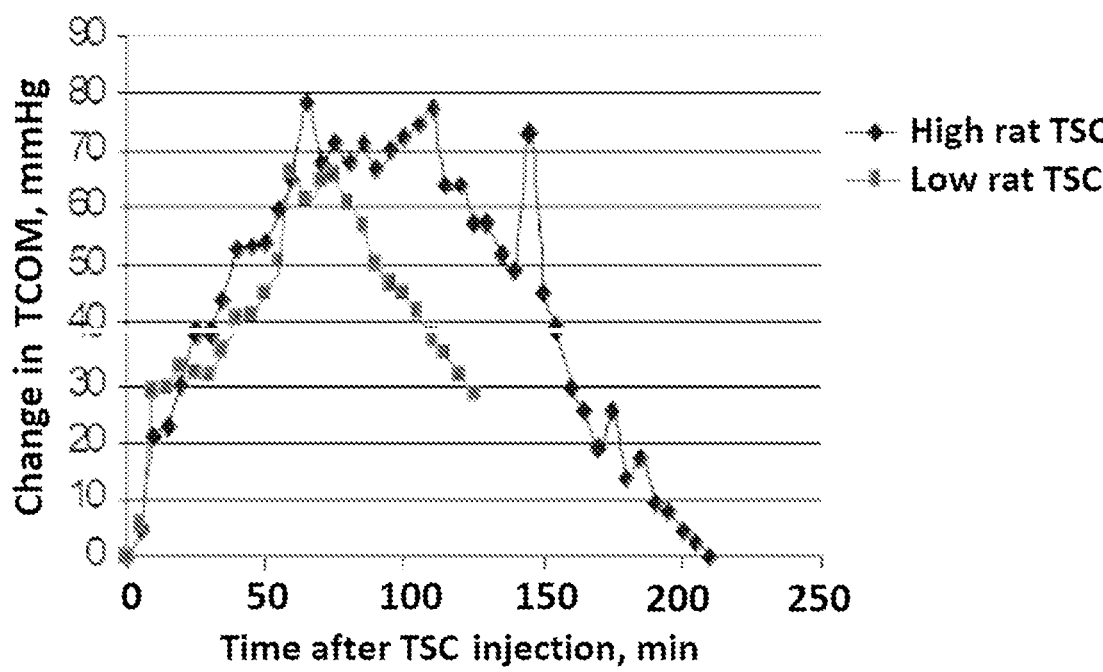

FIG. 13. Oxygen levels in rats after injection of a low and a high dose of TSC.

Figure 14:
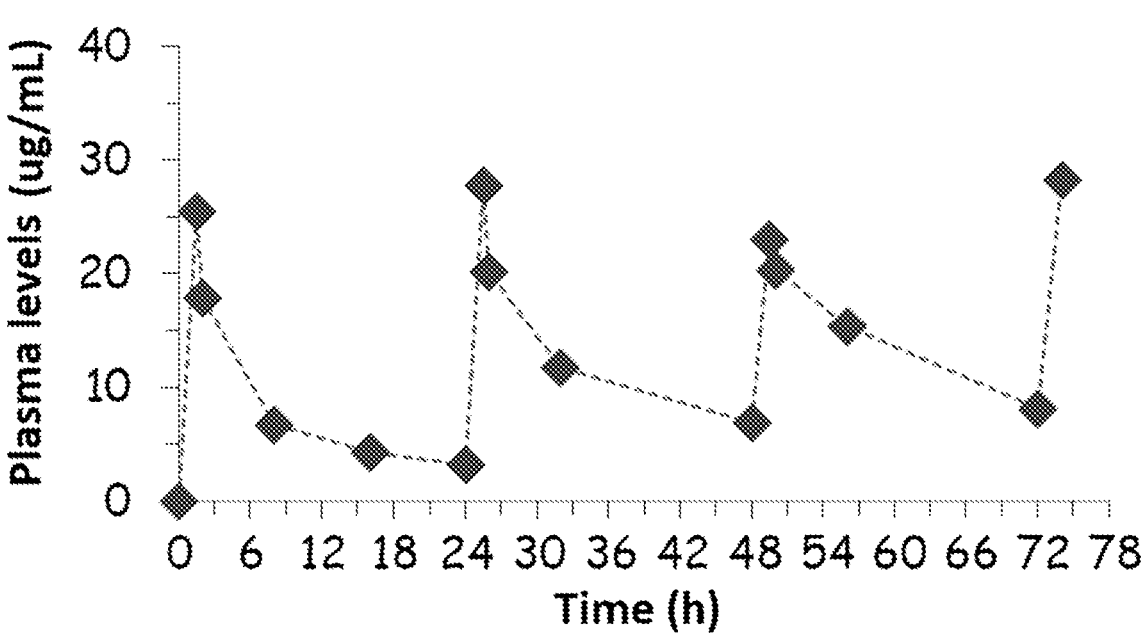

FIG. 14. Total drug in Cohort 1.

Figure 15:
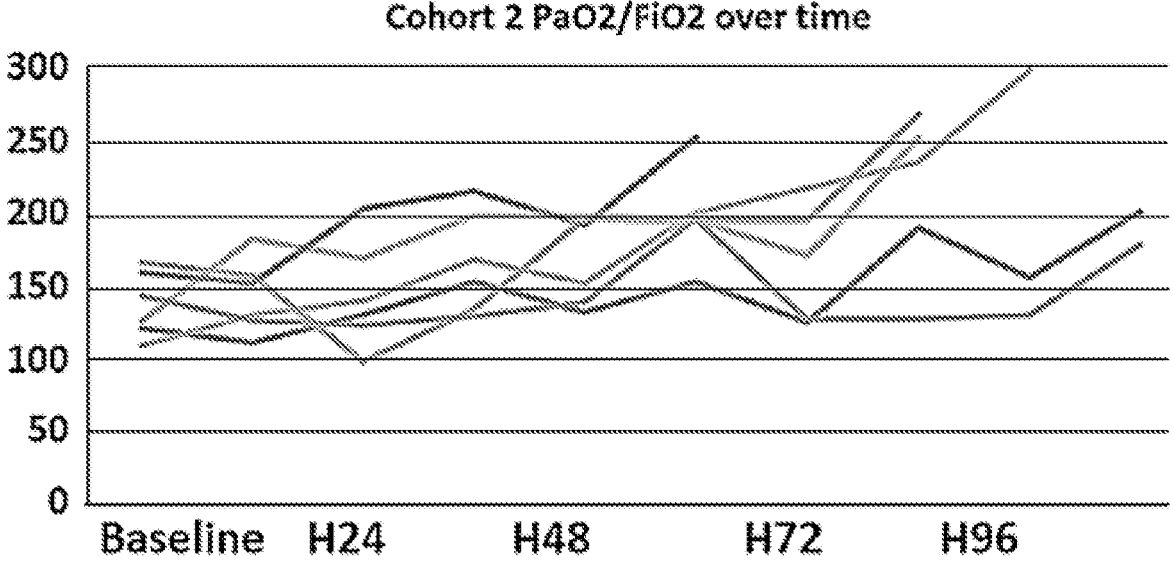

FIG. 15. Evolution of PaO2/FiO2 ratio over time in the Cohort 2.

Figures 16, 17A, 17B:
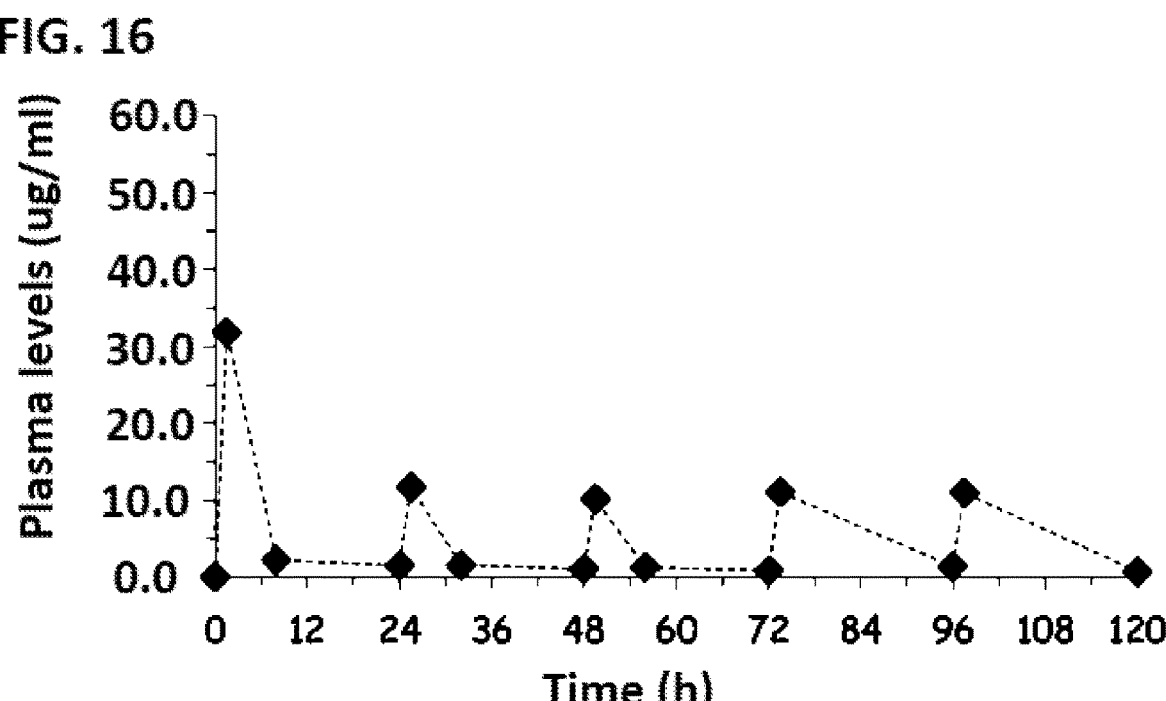

FIG. 16. PK profile of free drug in Cohort 2 that informed the dose changes for Cohort 4.

Figure 17C:
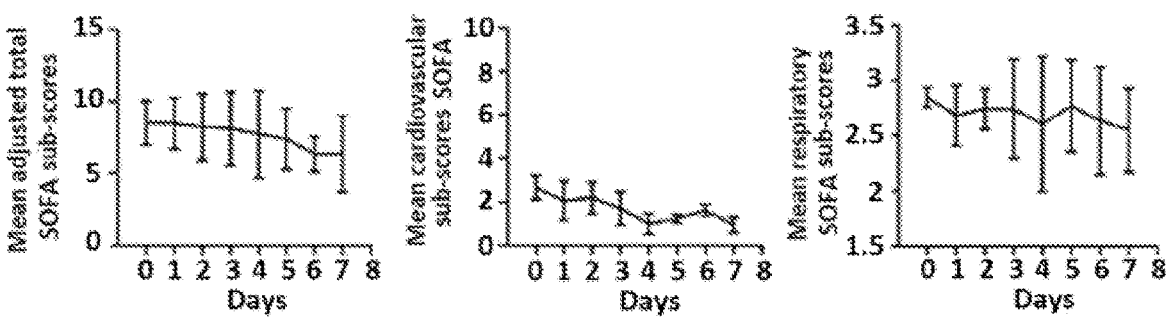
Figure 17D:
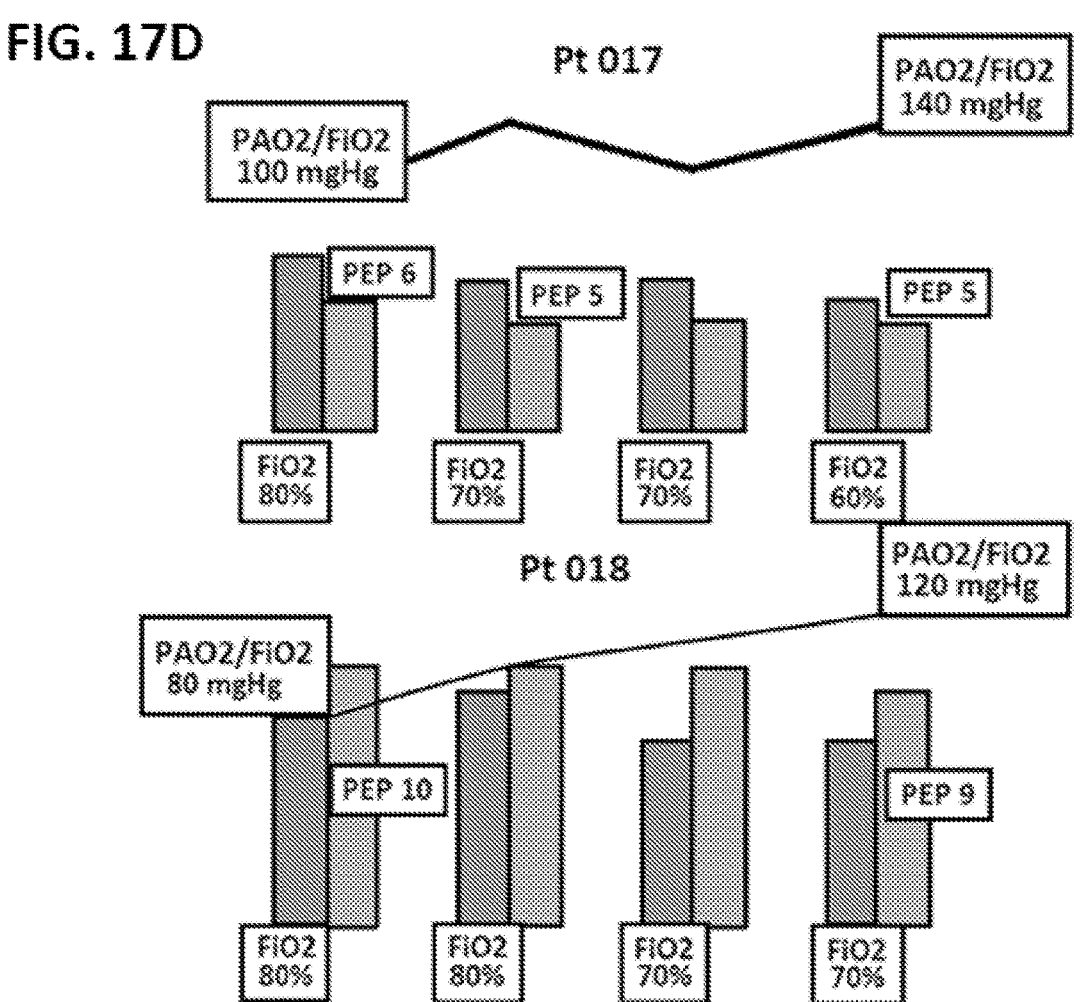

FIGS. 17A-17D. FIG. 17A: The effect of trans-crocetin treatment on PaO2/FiO2 (mmHg), positive expiratory pressure (PEP; cmH2O), and FIO2 (the concentration of oxygen that the subject inhales) in Cohort 2 over time. FIG. 17B: L4L-121 efficiently improved the oxygenation of COVID-19 patients. FIG. 17C: Validation of the major endpoint criteria of the study. FIG. 17D: PaO2/FiO2 ratio, PEP, PaCO2, noradrenaline status, position of the patients, and mechanical respiration status 3 days before and 3 days after the first injection of L4L-121. Mean adjusted SOFA score, as well as cardiovascular and respiratory SOFA subscores.

DETAILED DESCRIPTION

The Applicants have surprisingly discovered that liposomal trans-crocetin pharmaceutical compositions comprising multivalent trans-crocetin salts containing multivalent counterions substantially improves the pharmacokinetics (e.g., half-life, stability, and bioavailability) and dramatically increases drug exposure via a sustained release of the trans-crocetin when compared to for example, trans-crocetin free acids and trans-crocetin salts containing monovalent counterions.

Definitions

Unless otherwise defined, all technical and scientific terms used herein have the same meaning as commonly understood by one of ordinary skill in the art to which this disclosure pertains. Although methods and materials similar or equivalent to those described herein can be used in the practice or testing of the provided compositions, suitable methods and materials are described below. Each publication, patent application, patent, and other reference mentioned herein is herein incorporated by reference in its entirety. In case of conflict, the present specification, including definitions, will control. In addition, the materials, methods, and examples are illustrative only and are not intended to be limiting.

Other features and advantages of the disclosed compositions and methods will be apparent from the following disclosure, drawings, and claims.

It is understood that wherever embodiments, are described herein with the language "comprising" otherwise analogous embodiments, described in terms of "containing" "consisting of" and/or "consisting essentially of" are also provided. However, when used in the claims as transitional phrases, each should be interpreted separately and in the appropriate legal and factual context (e.g., in claims, the transitional phrase "comprising" is considered more of an open-ended phrase while "consisting of" is more exclusive and "consisting essentially of" achieves a middle ground).

As used herein, the singular form "a", "an", and "the", include plural forms unless it is expressly stated or is unambiguously clear from the context that such is not intended. The singular form "a", "an", and "the" also includes the statistical mean composition, characteristics, or size of the particles in a population of particles (e.g., mean liposome diameter, mean liposome zeta potential, mean number of targeting moieties on liposomes in a liposomal solution, mean number of encapsulated trans-crocetin molecules). The mean particle size and zeta potential of liposomes in a pharmaceutical composition can routinely be measured using methods known in the art, such as dynamic light scattering. The mean amount of a therapeutic agent in a nanoparticle composition may routinely be measured for example, using absorption spectroscopy (e.g., ultraviolet-visible spectroscopy).

As used herein, the terms "approximately" and "about," as applied to one or more values of interest, refer to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). For example, when used in the context of an amount of a given compound in a lipid component of a nanoparticle composition, "about" may mean+/−10% of the recited value. For instance, a nanoparticle composition including a lipid component having about 40% of a given compound may include 30-50% of the compound.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Where embodiments, of the disclosure are described in terms of a Markush group or other grouping of alternatives, the disclosed composition or method encompasses not only the entire group listed as a whole, but also each member of the group individually and all possible subgroups of the main group, and also the main group absent one or more of the group members. The disclosed compositions and methods also envisage the explicit exclusion of one or more of any of the group members in the disclosed compositions or methods.

The term "encapsulated" as used herein refers to the location of a biomacromolecule agent (e.g., trans-crocetin) that is enclosed or completely contained within the inside of a polymer such as a liposome.

The term "liposome" refers to a closed vesicle having an internal phase (i.e., interior space (internal solution)) enclosed by lipid bilayer. A liposome can be a small single-membrane liposome such as a small unilamellar vesicle (SUV), large single-membrane liposome such as a large unilamellar vesicle (LUV), a still larger single-membrane liposome such as a giant unilamellar vesicle (GUV), a multilayer liposome having multiple concentric membranes (e.g., 2, 3, 4, 5, 6, 7, 8, 9, or 10), such as a multilamellar vesicle (MLV), or a liposome having multiple membranes that are irregular and not concentric such as a multivesicular vesicle (MVV). Liposomes and liposome formulations are well known in the art. Lipids which are capable of forming liposomes include all substances having fatty or fat-like properties. Lipids which can make up the lipids in the liposomes include without limitation, glycerides, glycerophospholipids, glycerophosphinolipids, glycerophosphonolipids, sulfo-lipids, sphingolipids, phospholipids, isoprenolides, steroids, stearines, sterols, archeolipids, synthetic cationic lipids and carbohydrate containing lipids.

A "liposome composition" is a prepared composition comprising a liposome and the contents within the liposome, particularly including the lipids which form the liposome bilayer(s), compounds other than the lipids within the bi-layer(s) of the liposome, compounds within and associated with the aqueous interior(s) of the liposome, and compounds bound to or associated with the outer layer of the liposome.

Thus, in addition to the lipids of the liposome, a liposome composition described herein suitably may include, but is not limited to, therapeutic agents, immunostimulating agents, vaccine antigens and adjuvants, excipients, carriers and buffering agents. In a preferred embodiment, such compounds are complementary to and/or are not significantly detrimental to the stability or AGP-incorporation efficiency of the liposome composition.

The terms liposome "internal phase", "interior space", and "internal core" are used interchangeably to refer to an aqueous region enclosed within (i.e., encapsulated by) the lipid bilayer of the liposome. The solution of the liposomal internal phase is referred to as the "internal solution." By contrast, the term "liposome external phase" refers to the region not enclosed by the lipid bilayer of the liposome, such as the region apart from the internal phase and the lipid bilayer in the case where the liposome is dispersed in liquid.

The term "counterion" refers to an anionic or cationic counterion.

A "cationic counterion" is a positively charged atom or group associated with an anionic atom or group in order to maintain electronic neutrality. Exemplary cationic counterions include inorganic cations (e.g., metal cations (e.g., alkali metal cations, alkaline earth metal cations, and transition metal cations)) and organic cations (e.g., ammonium cations, sulfonium cations, phosphonium cations, and pyridinium cations). An "anionic counterion" is a negatively charged atom or group associated with a cationic atom or group in order to maintain electronic neutrality. Exemplary anionic counterions include halide anions (e.g., F—, Cl—, Br—, and I—), NO3-, ClO4-OH—, H2PO4-2, HSO4-, sulfonate anions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate anions (e.g., acetate, ethanoate, propanoate, benzoate, glycerate, lactate, tartrate, and glycolate). A counterion may be monovalent or multivalent (e.g., divalent, trivalent, tetravalent, etc.).

The term "ionizable" refers to a compound containing at least one functional group that (a) bears a positive or negative charge (i.e., is "ionized") and is therefore associated with a counterion of opposite charge, or (b) is electronically neutral but ionized at a higher or lower pH. Thus, ionizable compounds include quaternary ammonium salts as well as uncharged amines, and carboxylate moieties as well as uncharged carboxyl groups.

The term "naturally occurring" refers to a compound or composition that occurs in nature, regardless of whether the compound or composition has been isolated from a natural source or chemically synthesized. Examples of naturally occurring carotenoid mono- and di-carboxylic acids include crocetin, norbixin, azafrin and neurosporaxanthin.

An "apocarotenoid" is a carotenoid degradation product in which the normal structure (e.g., C40) has been shortened by the removal of fragments from one or both ends. Examples of naturally occurring apocarotenoids include crocetin (C20), bixin (C25), Vitamin A, abscisic acid, mycorradicin and blumenin.

As used herein an "effective amount" refers to a dosage of an agent sufficient to provide a medically desirable result. The effective amount will vary with the desired outcome, the particular disease or condition being treated or prevented, the age and physical condition of the subject being treated, the severity of the condition, the duration of the treatment, the nature of the concurrent or combination therapy (if any), the specific route of administration and like factors within the knowledge and expertise of the health practitioner. An "effective amount" can be determined empirically and in a routine manner, in relation to the stated purpose.

In the case of a pulmonary disorder such as ARDS, COPD, sepsis or pulmonary inflammation, an effective amount of an agent may for example, stabilize or improve lung function, such as demonstrated by physical examination and respiratory rate normalization, improving pAO2/FiO2 ratio (P/F ratio, e.g., show an increase of at least 15%, 20%, 25% PaO2/FiO2 ratio increase or a PaO2/FiO2 ratio increase above 200 mm Hg within 24 hours after administration), normalization of pCO2, preventing need for intubation and mechanical ventilation, (for those mechanically ventilated) decreased number of ventilator days, decreased hospital length of stay, decreased intensive care unit length of stay, or a combination thereof.

In the case of cancer, the effective amount of an agent may for example, reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, duration of progression free survival (PFS), the response rates (RR), duration of response, and/or quality of life.

As used herein, the phrase "a subject in need thereof" means a subject (e.g., human or non-human mammal that exhibits one or more symptoms or indications of, or has been identified as having a disorder or condition and thereby having a need for the particular method or treatment. In some embodiments, the diagnosis can be by any means of diagnosis. In any of the methods and treatment regimens described herein, the subject can be in need thereof.

The terms "hyperproliferative disorder", "proliferative disease", and "proliferative disorder", are used interchangeably herein to pertain to an unwanted or uncontrolled cellular proliferation of excessive or abnormal cells which is undesired, such as, neoplastic or hyperplastic growth, whether in vitro or in vivo. In some embodiments, the proliferative disease is cancer or tumor disease (including benign or cancerous) and/or any metastases, wherever the cancer, tumor and/or the metastasis is located. In some embodiments, the proliferative disease is a benign or malignant tumor. In some embodiments, the proliferative disease is a non-cancerous disease. In some embodiments, the proliferative disease is a hyperproliferative condition such as hyperplasias, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty.

"Cancer," "tumor," or "malignancy" are used as synonymous terms and refer to any of a number of disorders that are characterized by uncontrolled, abnormal proliferation of cells, the ability of affected cells to spread locally or through the bloodstream and lymphatic system to other parts of the body (metastasize) as well as any of a number of characteristic structural and/or molecular features. "Tumor," as used herein refers to all neoplastic cell growth and proliferation, whether malignant or benign, and all pre-cancerous and cancerous cells and tissues. A "cancerous tumor," or "malignant cell" is understood as a cell having specific structural properties, lacking differentiation and being capable of invasion and metastasis. A cancer that can be treated using a liposomal trans-crocetin pharmaceutical composition and/or dosing regimen provided herein includes without limitation, a non-hematologic malignancy including such as for example, lung cancer, pancreatic cancer, breast cancer, ovarian cancer, prostate cancer, head and neck cancer, gastric cancer, gastrointestinal cancer, colorectal cancer, esophageal cancer, cervical cancer, liver cancer, kidney cancer, biliary duct cancer, gallbladder cancer, bladder cancer, sarcoma (e.g., osteosarcoma), brain cancer, central nervous system cancer, and melanoma; and a hematologic malignancy such as for example, a leukemia, a lymphoma and other B cell malignancies, myeloma and other plasma cell dysplasias or dyscrasias. Other types of cancer and tumors that may be treated using a liposomal trans-crocetin composition are described herein or otherwise known in the art. The terms "cancer," "cancerous," "cell proliferative disorder," "proliferative disorder," and "tumor" are not mutually exclusive as referred to herein.

"Ischemia" relates to a restriction in blood supply to tissues or organs (tissue hypoperfusion) causing a shortage of oxygen needed for cellular metabolism. The term "ischemia injury", as used herein, relates to the damage due to a shortage of oxygen needed for cellular metabolism and to conditions associated with ischemia, including, but not limited to ischemic stroke, peripheral vascular disease, cerebral vascular disease, kidney disease and ischemia associated renal pathologies, reperfusion, reperfusion injury, ischemia associated with wounds, tissue hypoperfusion, ischemic-reperfusion injury, transient cerebral ischemia, cerebral ischemia-reperfusion, ischemic stroke, hemorrhagic stroke, traumatic brain injury, gastrointestinal ischemia, pulmonary embolism, acute respiratory failure, neonatal respiratory distress syndrome, an obstetric emergency to reduce perinatal comorbidity (such as, pre/eclampsia and conditions that lead to cerebral palsy), myocardial infarction, acute limb or mesenteric ischemia, coronary artery disease, cardiac cirrhosis, chronic congestive heart failure, atherosclerotic stenosis, anemia, thrombosis, embolism, or migraine (e.g., a chronic migraine or severe migraine disorder).

"Reperfusion" refers to the restoration of blood flow to ischemic tissue.

The term "ischemia/reperfusion injury", also known as "ischemia/reperfusion damage" relates to organ or tissue damage caused when blood supply returns to the organ or tissue after a period of ischemia. The absence of oxygen and nutrients from blood during the ischemic period creates a condition in which the restoration of circulation results in inflammation and oxidative damage through the induction of oxidative stress rather than restoration of normal function. Oxidative stress associated with reperfusion may cause damage to the affected tissues or organs. Ischemia/reperfusion injury is characterized biochemically by a depletion of oxygen during an ischemic event followed by reoxygenation and the concomitant generation of reactive oxygen species during reperfusion. Examples of ischemia injury or ischemia/reperfusion injury include organ dysfunction (in the ischemic organ or in any other organ), infarct, inflammation (in the damaged organ or tissue), oxidative damage, mitochondrial membrane potential damage, apoptosis, reperfusion-related arrhythmia, cardiac stunning, cardiac lipotoxicity, ischemia-derived scar formation, and combinations thereof. In some embodiments, ischemia/reperfusion injury is assessed by using oxidative stress biochemical markers such as malondialdehyde (MDA), high-sensitivity troponin T (hs-TnT), high-sensitivity troponin T (hs-TnI), creatin kinase myocardial band (CK-MB), and the inflammatory cytokines TNF-alpha IL1 beta, IL6, and IL10.

Organ "impairment" or dysfunction" refers to a condition wherein a particular organ does not perform its expected function. An organ dysfunction develops into organ failure if the normal homeostasis cannot be maintained without external clinical intervention. Methods to determine organ dysfunction are known in the art and include without limitation, monitorization and scores including sequential organ failure assessment (SOFA) score, multiple organ dysfunction (MOD) score and logistic organ dysfunction (LOD) score.

Terms such as "treating," or "treatment," or "to treat" refer to both (a) therapeutic measures that cure, slow down, attenuate, lessen symptoms of, and/or halt progression of a diagnosed pathologic disorder or condition and (b) prophylactic or preventative measures that prevent and/or slow the development of a targeted disorder or condition. The desirable effects of the treatment include, but are not limited to, the prevention of the development or recurrence of a disorder or condition, the alleviation of symptoms associated with the disorder or conditions, the attenuation of any direct or indirect pathological influence of the disorder or condition, the prevention of metastasis, reduction in the rate of progression of the disorder or condition, recovery from or alleviation of a disorder or condition, and/or ameliorated or improved prognosis. Thus, subjects in need of treatment include for example, those already with pneumonia, ARDS, hypoxia, sepsis, an ischemic condition, an infection, cancer, or another disorder condition, those at risk of having the disorder or condition, and those in whom the disorder or condition is to be prevented. Subjects are identified as "having or at risk of having" a disorder or condition such as, ischemia, ARDS, an infection, pneumonia, sepsis, an infectious disease, a disorder of the immune system, a metabolic disorder (e.g., diabetes), a hyperproliferative disease, or another disorder or condition referred to herein using well-known medical and diagnostic techniques. In certain embodiments, a subject is successfully "treated" according to the methods provided herein if the subject shows, e.g., total, partial, or transient amelioration or elimination of a symptom associated with the disease or condition (e.g., pneumonia, ARDS, sepsis, cancer and arthritis such as rheumatoid arthritis). In specific embodiments, the terms "treating," or "treatment," or "to treat" refer to the amelioration of at least one measurable physical parameter of a proliferative disorder, such as growth of a tumor, not necessarily discernible by the patient. In other embodiments, the terms "treating," or "treatment," or "to treat" refer to the inhibition of the progression of a proliferative disorder, either physically by, e.g., stabilization of a discernible symptom, physiologically by, e.g., stabilization of a physical parameter, or both. In other embodiments, the terms "treating," or "treatment," or "to treat" refer to the reduction or stabilization of tumor size, tumor cell proliferation or survival, or cancerous cell count. Treatment can be with a provided pharmaceutical composition disclosed herein (e.g., a liposomal trans-crocetinate) alone, or in combination with an additional therapeutic agent.

The terms "subject" and "patient," and "animal" are used interchangeably and refer to mammals such as human patients and non-human primates, as well as experimental animals such as rabbits, rats, and mice, and other animals. Animals include all vertebrates, e.g., mammals and non-mammals, such as chickens, amphibians, and reptiles. "Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and other members of the class Mammalia known in the art. In a particular embodiment, the patient is a human.

The term "elderly" refers to an aged subject, who has passed middle age. In one embodiment, an elderly mammalian subject is a subject that has survived more than two-thirds of the normal lifespan for that mammalian species. In a further embodiment, for humans, an aged or elderly subject is more than 65 years of age, such as a subject of more than 70, more than 75, more than 80 years of age. In yet another embodiment, for mice, an elderly mouse is from about 14 to about 18 months of age.

A "loading dose" refers to an amount of a therapeutic agent such as liposomal trans-crocetin, administered to a subject during the initial stages of the treatment. The purpose of a loading dose is to more rapidly achieve therapeutic levels of the therapeutic agent in the subject than that which would have been reached with maintenance dosing only. In addition, the loading dose can also achieve sufficient levels of the therapeutic agent (e.g., trans-crocetin) to enable therapeutic levels to be maintained once the switch to maintenance dosing is made. Furthermore, the loading dose allows a relatively constant therapeutic level of the therapeutic agent to be achieved in which the therapeutic agent is in a steady-state. The steady state of the therapeutic agent may be regarded as a state in which the overall intake of the therapeutic agent is in dynamic equilibrium with its elimination. Once the therapeutic levels of the therapeutic agent are reached, the loading doses may be followed by a plurality of maintenance doses. Increasing the loading dose concentration may allow the time intervals between the loading doses to be extended. In some embodiments, loading doses of trans-crocetin are administered once, twice, three times a day, or more, for a total of 1, 2, 3, 4, or more doses. In particular embodiments, a total of one loading dose of liposomal trans-crocetin is administered. In other particular embodiments, a total of two loading doses of liposomal trans-crocetin are administered to the subject. In other particular embodiments, a total of three loading doses of liposomal trans-crocetin are administered to the subject. In other particular embodiments, a total of four loading doses of liposomal trans-crocetin are administered to the subject.

A "maintenance dose" refers to an amount of therapeutic agent such as liposomal trans-crocetin administered to a subject over a treatment period in order to maintain therapeutic levels of therapeutic agent in the subject. Such therapeutic levels of the therapeutic agent are achieved and maintained more rapidly by providing the subject with one or more loading doses as described herein prior to providing the maintenance dose(s). Usually, the maintenance doses are administered at spaced treatment intervals. In some embodiments, maintenance doses of trans-crocetin are administered once, twice, three times a day, or once, twice or three times a week, for a total of 2 to 20 doses, or more. In particular embodiments, one maintenance dose of liposomal trans-crocetin is administered once a day (e.g., every 24 hours (+/−9 hours), for a total of 2 to 20 days, or more. In other particular embodiments, two maintenance doses of liposomal trans-crocetin are administered twice a day (e.g., every 12 hours+/−3 hours) for a total of 2 to 20 days, or more.

The term "pharmaceutically acceptable carrier" refers to an ingredient in a pharmaceutical formulation, other than an active ingredient, which is nontoxic to a subject. A pharmaceutically acceptable carrier includes, but is not limited to, a buffer, carrier, excipient, stabilizer, diluent, or preservative. Pharmaceutically acceptable carriers can include for example, one or more compatible solid or liquid filler, diluents or encapsulating substances which are suitable for administration to a human or other subject.

The term "therapeutic agent" is used herein in its broadest sense to include any agent capable of providing a desired or beneficial effect on a subject. Thus, the term includes both prophylactic and therapeutic agents, as well as any other category of agent having such desired effects. The therapeutic agent or therapeutic agents used in combination therapy with trans-crocetin according to the disclosed compositions and methods can include any agent directed to treat a condition in a subject. In some embodiments, the therapeutic agent is a chemotherapeutic agent, an alkylating agent (e.g., carboplatin, cisplatin, melphalan, oxaliplatin, procarbazine, temozolomide, or thiotepa), an antimetabolite (e.g., 5-Fluorouracil, gemcitabine, methotrexate, or pemetrexed), an antibiotic (e.g., actinomycin D, bleomycin, doxorubicin, or Streptonigrin), or a plant alkaloid (e.g., docetaxel, etoposide, vincristine, irinotecan, or VP-16) or a multikinase (e.g., Sorafenib), an immunotherapeutic agent (e.g., CAR-immune cell therapy, or an antibody or other inhibitor of a checkpoint protein such as PD1, PDL1, CTLA4, PDL2, LAG3, TIM3, 2B4, A2aR, B7-H3, B7-H4, BTLA, HVEM, GAL9, VISTA, TIGIT, KIR, CD160, CGEN-15049, CHK1, CHK2, or a B-7 family ligand), an anesthetic agent, anti-inflammatory agent (e.g., an NSAID, corticosteroid, TNFR-Fc (e.g., etanercept), or an anti-TNF alpha, anti-IL6 receptor antibody or anti-IL6 antibody), thrombolytic agent (e.g., tissue plasminogen activator (tPA) tenecteplase, anistreplase, streptokinase, urokinase), a vasopressor agent, an antioxidant, or a corticosteroid (e.g., a glucocorticoid or mineralocorticoid such as fludrocortisonel). In some embodiments, the therapeutic agent is another ionizable carotenoid or a carotenoid comprising at least one polar group or monocyclic group (e.g., an ionizable carotenoid depicted in FIGS. 1A-1D). In some embodiments, the therapeutic agent is a standard of care treatment for the disorder or condition to be treated. In some embodiments, the therapeutic agent is an antimicrobial agent such as, an antiviral agent (e.g., remdesivir), antibacterial agent, antifungal agent or an antiparasite agent. In some embodiments, the therapeutic agent is radiation therapy and/or a radiosensitizing agent. In additional embodiments, the therapeutic agent enhances the oxygen level in the blood and/or a hypoxic tissue (e.g., at the macrocirculatory level or microcirculatory level). In additional embodiments, the therapeutic agent is oxygen and/or intravenous fluids to maintain/increase blood oxygen levels and/or blood pressure or hyperbaric therapy.

Examples of therapeutic agents that may be suitable for use in accordance with the disclosed methods include vitamin C, thiamine, hydrocortisone or another corticosteroid (e.g., a glucocorticoid such as, cortisone, ethamethasoneb, prednisone, prednisolone, triamcinolone, dexamethasone and methylprednisolone; and mineralocorticoids such as fludrocortisonel), astaxanthin, abscisic acid, vitamin A, angiotensin II (e.g., GIAPREZA™), tissue plasminogen activator (tPA), an antimicrobial (e.g., antibiotic) and an anti-inflammatory.

Additional examples of therapeutic agents that may be suitable for use in accordance with the disclosed methods include, without limitation, anti-restenosis, pro- or anti-proliferative, anti-neoplastic, antimitotic, anti-platelet, anti-coagulant, antifibrin, antithrombin, cytostatic, antibiotic and other anti-infective agents, anti-enzymatic, anti-metabolic, angiogenic, cytoprotective, angiotensin converting enzyme (ACE) inhibiting, angiotensin II receptor antagonizing and/or cardioprotective agents. In general, any therapeutic agent known in the art can be used, including without limitation agents listed in the United States Pharmacopeia (U.S.P.), Goodman and Gilman's The Pharmacological Basis of Therapeutics, 10th Ed., McGraw Hill, 2001; Katzung, Ed., Basic and Clinical Pharmacology, McGraw-Hill/Appleton & Lange, 8th ed., Sep. 21, 2000; Physician's Desk Reference (Thomson Publishing; and/or The Merck Manual of Diagnosis and Therapy, 18th ed., 2006, Beers and Berkow, Eds., Merck Publishing Group; or, in the case of animals, The Merck Veterinary Manual, 9th ed., Kahn Ed., Merck Publishing Group, 2005; all of which are incorporated herein by reference used herein to refer to an agent or a derivative thereof that can interact with a hyperproliferative cell such as a cancer cell or an immune cell, thereby reducing the proliferative status of the cell and/or killing the cell. Examples of therapeutic agents include, but are not limited to, chemotherapeutic agents, cytotoxic agents, platinum-based agents (e.g., cisplatin, carboplatin, oxaliplatin), taxanes (e.g., Taxol), etoposide, alkylating agents (e.g., cyclophosphamide, ifosamide), metabolic antagonists (e.g., methotrexate (MTX), 5-fluorouracil, gemcitabine, pemetrexed, or derivatives thereof), antitumor antibiotics (e.g., mitomycin, doxorubicin), plant-derived antitumor agents (e.g., vincristine, vindesine, Taxol). Such agents may further include, but are not limited to, the anticancer agents trimetrexate, TEMOZOLOMIDE™, RALTRITREXED™, S-(4-Nitrobenzyl)-6-thioinosine (NBMPR), 6-benzyguanidine (6-BG), bis-chloronitrosourea (BCNU) and CAMPTOTHECIN™, or a therapeutic derivative of any thereof.

"Therapeutic agents" also refer to salts, acids, and free based forms of the above agents.

The term "kit" refers to a set of one or more components necessary for employing the methods and compositions provided herein. Kit components can include, but are not limited to, liposomal trans-crocetin formulations disclosed herein, reagents, buffers, containers and/or equipment.

The term "radiosensitizing agent" means a compound that makes tumor cells more sensitive to radiation therapy. Examples of radiosensitizing agents include misonidazole, metronidazole, tirapazamine, and trans-crocetin.

Articles of Manufacture

In an additional embodiment, the disclosure provides an article of manufacture comprising materials useful for the treatment of a disorder or condition described herein (e.g., ischemia, ARDS, sepsis, infection, pneumonia, blood loss, cancer, and other disorders and conditions described herein). The article of manufacture comprises a vial containing trans-crocetin and optionally a package insert. The vial may be formed from a variety of materials, such as glass or plastic, and may be sealed by a syringe with a stopper that can be punctured. In further embodiments, the article of manufacture may contain other materials desirable from a commercial and user standpoint, including other buffers, diluents, filters, needles, syringes, and the like. In one embodiment, the article of manufacture comprises a vial containing liposomal trans-crocetin. In some embodiments, the article of manufacture comprises one or more vials containing approximately 100 mg-300 mg of trans-crocetin.

In some embodiments, the article of manufacture further comprises a package insert. The package inserts may provide instructions for administering trans-crocetin pharmaceutical composition and/or for administering compositions according to the dosing regimens provided herein. The package inserts may also provide drug preparation and/or dosing instructions for treating disorders and conditions such as ischemia, ARDS, sepsis, infection, pneumonia, blood loss, cancer, and other disorders and conditions described herein.

In one embodiment, the article of manufacture comprises two vials, where the first vial contains a dose of approximately 75 mg-175 mg trans-crocetin and the second vial contains a constant dose of approximately 200 mg-300 mg trans-crocetin.

The article of manufacture preferably further comprises a package insert. The package insert may provide instructions to administer the dose of trans-crocetin to a subject, including but not limited to a patient with ischemia, ARDS, sepsis, infection, pneumonia, blood loss, cancer, and other disorders and conditions described herein.

Pharmaceutical Compositions

The term "pharmaceutical composition" as used herein usually refers to a drug for the treatment or prevention of a disease or condition, or for examination or diagnosis. The provided pharmaceutical compositions can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith et al., March's Advanced Organic Chemistry. Reactions, Mechanisms, and Structure, 5th edition, John Wiley & Sons: New York, 2001; Greene, T. W., Wuts, P. G. M., Protective Groups in Organic Synthesis, 3rd edition, John Wiley & Sons: New York, 1999; R. Larock, Comprehensive Organic Transformations, VCH Publishers (1989); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present disclosure.

In some embodiments, the pharmaceutical composition comprises a trans-crocetin having the formula: Q-trans-crocetin-Q wherein, Q is a multivalent cation counterion. In some embodiments, the pharmaceutical composition administered according to the provided methods is liposomal trans-crocetin.

In some embodiments, Q is a multivalent metal cation. In further embodiments, Q is a multivalent transition metal cation. In some embodiments, Q is a divalent cation counterion. In further embodiments, Q is a divalent metal cation. In some embodiments, Q is at least one member selected from Ca2+, Mg2+, Zn2+, Cu2+, Co2+, and Fe2+. In further embodiments, Q is Ca2+ or Mg2+. In some embodiments, Q is Ca2+. In some embodiments, Q is Mg2+. In other embodiments, Q is a trivalent cation counterion such as Fe3+. In some embodiments, Q is a multivalent organic cation. In further embodiments, Q is a divalent organic cation such as a protonated diamine. Liposomes comprising the trans-crocetin compositions and pharmaceutical compositions (e.g., liposome compositions) comprising the liposomes are also provided herein.

In some embodiments, the disclosure provides a pharmaceutical composition comprising calcium trans-crocetin (CTC). The CTC can exist in linear and/or cyclic form (shown below)

Liposomes comprising the CTC compositions and pharmaceutical compositions (e.g., liposome compositions) comprising the liposomes are also provided herein. In some embodiments, the pharmaceutical composition administered according to the provided methods is liposomal CTC.

In some embodiments, the disclosure provides a pharmaceutical composition comprising magnesium trans-crocetin (MTC). The MTC can exist in linear and/or cyclic form (shown below).

Liposomes comprising the MTC compositions and pharmaceutical compositions (e.g., liposome compositions) comprising the liposomes are also provided herein. In some embodiments, the pharmaceutical composition administered according to the provided methods comprises liposomal MTC.

The lipids and other components of the liposomes contained in the liposome compositions can be any lipid, lipid combination and ratio, or combination of lipids and other liposome components and their respective ratios known in the art. However, it will be understood by one skilled in the art that liposomal encapsulation of any particular drug, such as, and without limitation, the liposomal trans-crocetin compositions discussed herein, may involve substantial routine experimentation to achieve a useful and functional liposomal formulation. In general, the provided liposomes may have any liposome structure, e.g., structures having an inner space sequestered from the outer medium by one or more lipid bilayers, or any microcapsule that has a semi-permeable membrane with a lipophilic central part where the membrane sequesters an interior. The lipid bilayer can be any arrangement of amphiphilic molecules characterized by a hydrophilic part (hydrophilic moiety) and a hydrophobic part (hydrophobic moiety). Usually amphiphilic molecules in a bilayer are arranged into two dimensional sheets in which hydrophobic moieties are oriented inward the sheet while hydrophilic moieties are oriented outward. Amphiphilic molecules forming the provided liposomes can be any known or later discovered amphiphilic molecules, e.g., lipids of synthetic or natural origin or biocompatible lipids. The liposomes can also be formed by amphiphilic polymers and surfactants, e.g., polymerosomes and niosomes. For the purpose of this disclosure, without limitation, these liposome-forming materials also are referred to as "lipids".

The liposome composition formulations provided herein can be in liquid or dry form such as a dry powder or dry cake. The dry powder or dry cake may have undergone primary drying under, for example, lyophilization conditions or optionally, the dry cake or dry powder may have undergone both primary drying only or both primary drying and secondary drying. In the dry form, the powder or cake may, for example, have between 1% to 6% moisture, for example, such as between 2% to 5% moisture or between 2% to 4% moisture. One example method of drying is lyophilization (also called freeze-drying, or cryodessication). Any of the compositions and methods of the disclosure may include liposomes, lyophilized liposomes or liposomes reconstituted from lyophilized liposomes. In some embodiments, the compositions and methods include one or more lyoprotectants or cryoprotectants. These protectants are typically polyhydroxy compounds such as sugars (mono-, di-, and polysaccharides), polyalcohols, and their derivatives, glycerol, or polyethyleneglycol, trehalose, maltose, sucrose, glucose, lactose, dextran, glycerol, or aminoglycosides. In further embodiments, the lyoprotectants or cryoprotectants comprise up to 10% or up to 20% of a solution outside the liposome, inside the liposome, or both outside and inside the liposome.

The properties of liposomes are influenced by the nature of lipids used to make the liposomes. A wide variety of lipids have been used to make liposomes. These include cationic, anionic and neutral lipids. In some embodiments, the liposomes comprising the trans-crocetin compositions (e.g., CTC and MTC) are anionic or neutral. In other embodiments, the provided liposomes are cationic. The determination of the charge (e.g., anionic, neutral or cationic) can routinely be determined by measuring the zeta potential of the liposome. The zeta potential of the liposome can be positive, zero or negative. In some embodiments, the zeta potential of the liposome is −150 to 150 mV, or −50 to 50 mV, or any range therein between. In some embodiments, the zeta potential of the liposome is less than or equal to zero. In some embodiments, the zeta potential of the liposome is −150 to 0, −50 to 0 mV, −40 to 0 mV, −30 to 0 mV, −25 to 0 mV, −20 to 0 mV, −10 to 0 mV, −9 to 0 mV, −8 to 0 mV, −7 to 0 mV, −6 to 0 mV, −5 to 0 mV, −4 to 0 mV, −3 to 0 mV, −2 to 0 mV, −1 to 0 mV, or −8 to 2 mV, or any range therein between. In other embodiments, the zeta potential of the liposome is more than zero. In some embodiments, the liposome has a zeta potential that is 0.2 to 150 mV, 1 to 50 mV, 1 to 40 mV, 1 to 30 mV, 1 to 25 mV, 1 to 20 mV, 1 to 15 mV, 1 to 10 mV, 1 to 5 mV, 2 to 10 mV, 3 to 10 mV, 4 to 10 mV, or 5 to 10 mV, or any range therein between.

Depending on the desired application, the particle size (diameter) of the liposome can be regulated. For example, when it is intended to deliver the liposome to cancerous tissue or inflamed tissue by the Enhanced Permeability and Retention (EPR) effect as an injection product or the like, it is preferable that liposome diameter is 20-500 nm, 30-175 nm, or 50-150 nm, or any range therein between. In the case where the intention is to transmit liposome to macrophage, it is preferable that liposome diameter is 30 to 1000 nm, or 80 to 400 nm, or any range therein between. In the case where liposome composition is to be used as an oral preparation or transdermal preparation, the particle size of liposome can be set at several microns. It should be noted that in normal tissue, vascular walls serve as barriers (because the vascular walls are densely constituted by vascular endothelial cells), and microparticles such as supermolecules and liposome of specified size cannot be distributed within the tissue. However, in diseased tissue, vascular walls are loose (because interstices exist between vascular endothelial cells), increasing vascular permeability, and supermolecules and microparticles can be distributed to extravascular tissue (enhanced permeability). Moreover, the lymphatic system is well developed in normal tissue, but it is known that the lymphatic system is not developed in diseased tissue, and that supermolecules or microparticles, once incorporated, are not recycled through the general system, and are retained in the diseased tissue (enhanced retention), which forms the basis of the EPR effect (Wang et al., Ann. Rev. Med. 63:185-198 (2012); Peer et al., Nat. Nanotech. 2:751-760 (2007); Gubernator, Exp. Opin. Drug Deliv. 8:565-580 (2011); Huwyler et al., Int. J. Nanomed. 3:21-29 (2008); Maruyama et al. Adv. Drug Deliv. Rev. 63:161-169 (2011); Musacchio and Torchilin Front. Biosci. 16:1388-1412 (2011); Baryshnikov Vest. Ross. Akad. Med. Nauk. 23-31 (2012); and Torchilin Nat. Rev. Drug Disc. 4:145-160 (2005)). Thus, it is possible to control liposome pharmacokinetics by adjusting liposome particle size (diameter).

In some embodiments, cationic lipids are used to make cationic liposomes which are commonly used as gene transfection agents. The positive charge on cationic liposomes enables interaction with the negative charge on cell surfaces. Following binding of the cationic liposomes to the cell, the liposome is transported inside the cell through endocytosis.

In some preferred embodiments, a neutral to anionic liposome is used. In a preferred embodiment, an anionic liposome is used. Using a mixture of, for example, neutral lipids such as HSPC and anionic lipids such as PEG-DSPE results in the formation of anionic liposomes which are less likely to non-specifically bind to normal cells. Specific binding to tumor cells can be achieved by using a tumor targeting antibody such as, for example, a folate receptor antibody, including, for example, folate receptor alpha antibody, folate receptor beta antibody and/or folate receptor delta antibody.

As an example, at least one (or some) of the lipids is/are amphipathic lipids, defined as having a hydrophilic and a hydrophobic portion (typically a hydrophilic head and a hydrophobic tail). The hydrophobic portion typically orients into a hydrophobic phase (e.g., within the bilayer), while the hydrophilic portion typically orients toward the aqueous phase (e.g., outside the bilayer). The hydrophilic portion can comprise polar or charged groups such as carbohydrates, phosphate, carboxylic, sulfate, amino, sulfhydryl, nitro, hydroxy and other like groups. The hydrophobic portion can comprise apolar groups that include without limitation long chain saturated and unsaturated aliphatic hydrocarbon groups and groups substituted by one or more aromatic, cyclo-aliphatic or heterocyclic group(s). Examples of amphipathic compounds include, but are not limited to, phospholipids, aminolipids and sphingolipids.

Typically, for example, the lipids are phospholipids. Phospholipids include without limitation phosphatidylcholine, phosphatidylethanolamine, phosphatidylglycerol, phosphatidylinositol, phosphatidylserine, and the like. It is to be understood that other lipid membrane components, such as cholesterol, sphingomyelin, and cardiolipin, can be used.

The lipids comprising the liposomes provided herein can be anionic and neutral (including zwitterionic and polar) lipids including anionic and neutral phospholipids. Neutral lipids exist in an uncharged or neutral zwitterionic form at a selected pH. At physiological pH, such lipids include, for example, dioleoylphosphatidylglycerol (DOPG), diacylphosphatidylcholine, diacylphos-phatidylethanolamine, ceramide, sphingomyelin, cephalin, cholesterol, cerebrosides and diacylglycerols. Examples of zwitterionic lipids include without limitation dioleoylphosphatidylcholine (DOPC), dimyristoylphos-phatidylcholine (DMPC), and dioleoylphosphatidylserine (DOPS). Anionic lipids are negatively charged at physiological pH. These lipids include without limitation phosphatidylglycerol, cardiolipin, diacylphosphatidylserine, diacyl-phosphatidic acid, N-dodecanoyl phosphatidylethanolamines, N-succinyl phospha-tidylethanolamines, N-glutaryl-phosphatidylethanolamines, lysylphosphatidyl-glycerols, palmitoyloleyolphosphatidylglycerol (POPG), and other anionic modifying groups joined to neutral lipids.

Collectively, anionic and neutral lipids are referred to herein as non-cationic lipids. Such lipids may contain phosphorus but they are not so limited. Examples of non-cationic lipids include lecithin, lysolecithin, phosphatidylethanolamine, lysophosphatidyl-ethanolamine, dioleoylphos-phatidylethanolamine (DOPE), dipalmitoyl phosphatidyl ethanolamine (DPPE), dimyristoylphosphoethanolamine (DMPE), distearoylphosphatidy 1-ethanolamine (DSPE), palmitoyloleoylphosphatidylethan-olamine (POPE) palmitoyl-oleoylphosphatidylcholine (POPC), egg phosphatidylcholine (EPC), distearoylphospha-tidylcholine (DSPC), dioleoylphosphatidylcholine (DOPC), dipalmitoylphosphatidyl-choline (DPPC), dioleoylphosphatidylglycerol (DOPG), dipal-mitoylphosphatidyl-glycerol (DPPG), palmitoyloleyol-phosphatidylglycerol (POPG), 16-0-monomethyl PE, 16-0-dimethyl PE, 18-1-trans-PE, palmitoyloleoylphosphatidyl-ethanolamine (POPE), 1-stearoyl-2-oleoylphosphatidylethanolamine (SOPE), phosphatidylserine, phosphatidyl-inositol, sphingomyelin, cephalin, cardiolipin, phosphatidic acid, cerebrosides, dicetylphosphate, and cholesterol.

The liposomes may be assembled using any liposomal assembly method using liposomal components (also referred to as liposome components) known in the art. Liposomal components include, for example, lipids such as DSPE, HSPC, cholesterol and derivatives of these components. Other suitable lipids are commercially available for example, by Avanti Polar Lipids, Inc. (Alabaster, Alabama, USA). A partial listing of available negatively or neutrally charged lipids suitable for making anionic liposomes, can be, for example, at least one of the following: DLPC, DMPC, DPPC, DSPC, DOPC, DMPE, DPPE, DOPE, DMPA•Na, DPPA•Na, DOPA•Na, DMPG•Na, DPPG•Na, DOPG•Na, DMPS•Na, DPPS•Na, DOPS•Na, DOPE-Glutaryl•(Na)2, tetramyristoyl cardiolipine•(Na)2, DSPE-mPEG-2000•Na, DSPE-mPEG-5000•Na, and DSPE-maleimide PEG-2000•Na.

In some embodiments, the provided compositions are formulated in a liposome comprising a cationic lipid. In one embodiment, the cationic lipid is selected from, but not limited to, a cationic lipid described in Intl. Publ. Nos.

WO2012/040184, WO2011/153120, WO2011/149733, WO2011/090965, WO2011/043913, WO2011/022460, WO2012/061259, WO2012/054365, WO2012/044638, WO2010/080724, WO2010/21865 and WO2008/103276, U.S. Pat. Nos. 7,893,302, 7,404,969 and 8,283,333, and U.S. Appl. Publ. Nos. US20100036115 and US20120202871; each of which is herein incorporated by reference in its entirety. In another embodiment, the cationic lipid may be selected from, but not limited to, formula A described in Intl. Appl. Publ. Nos. WO2012/040184, WO2011/153120, WO201/1149733, WO2011/090965, WO2011/043913, WO2011/022460, WO2012/061259, WO2012/054365 and WO2012/044638; each of which is herein incorporated by reference in its entirety. In yet another embodiment, the cationic lipid may be selected from, but not limited to, formula CLI-CLXXIX of International Publication No. WO2008103276, formula CLI-CLXXIX of U.S. Pat. No. 7,893,302, formula CLI-CLXXXII of U.S. Pat. No. 7,404, 969 and formula I-VI of US Publ. No. US20100036115; each of which is herein incorporated by reference in its entirety. As a non-limiting example, the cationic lipid may be selected from (20Z,23Z)-N,N-dimethylnonacosa-20,23-dien-10-amine, (17Z,20Z)-N,N-dimemylhexacosa-17,20-dien-9-amine, (1Z,19Z)-N5N-dimethyl-pentacosa-16,19-dien-8-amine, (13Z,16Z)-N,N-dimethyldocosa-13,16-dien-5-amine, (12Z,15Z)-N,N-dimethyl-henicosa-12,15-dien-4-amine, (14Z,17Z)-N,N-dimethyltricosa-14,17-dien-6-amine, (15Z,18Z)-N,N-dimethyltetracosa-15,18-dien-7-amine, (18Z,21Z)-N,N-dimethylhept-acosa-18,21-dien-10-amine, (15Z,18Z)-N,N-dimethyltetracosa-15,18-dien-5-amine, (14Z,17Z)-N,N-dimethyl-tricosa-14,17-dien-4-amine, (19Z,22Z)-N,N-dimeihyloctacosa-19,22-dien-9-amine, (18Z,21Z)-N,N-dimethylheptacosa-18,21-dien-8-amine, (17Z,20Z)-N,N-dimethylhexacosa-17,20-dien-7-amine, (16Z,19Z)-N,N-dimethylpenta-cosa-16,19-dien-6-amine, (22Z,25Z)-N,N-dimethylhentriaconta-22,25-dien-10-amine, (21Z,24Z)-N,N-dimethyl-triaconta-21,24-dien-9-amine, (18Z)-N,N-dimetylheptacos-18-en-10-amine, (17Z)-N,N-dimethylhexacos-17-en-9-amine, (19Z,22Z)-N,N-dimethyloctacosa-19,22-dien-7-amine, N,N-dimethylheptacos-an-10-amine, (20Z,23Z)-N-ethyl-N-methyl-nonacosa-20,23-dien-10-amine, 1-[(11Z,14Z)-1-nonylicosa-11,14-dien-1-yl] pyrrolidine, (20Z)-N,N-dimethyl-heptacos-20-en-10-amine, (15Z)-N,N-dimethyl eptacos-15-en-10-amine, (14Z)-N,N-dimethylnonacos-14-en-10-amine, (17Z)-N,N-dimethylnonacos-17-en-10-amine, (24Z)-N,N-dimethyltritriacont-24-en-10-amine, (20Z)-N,N-di-methylnona-cos-20-en-10-amine, (22Z)-N,N-dimethyl-hen-triacont-22-en-10-amine, (16Z)-N,N-dimethylpenta-cos-16-en-8-amine, (12Z,15Z)-N,N-dimethyl-2-nonylhenicosa-12,15-dien-1-amine, (13Z,16Z)-N,N-dimethyl-3-nonyldocosa-13,16-dien-1-amine, N,N-dimethyl-1-[(1S,2R)-2-octylcyclo-propyl]eptadec-an-8-amine, 1-[(1S,2R)-2-hexylcyclo-propyl]-N,N-dimethylnonadecan-10-amine, N,N-dimethyl-1-[(1S,2R)-2-octylcyclo-propyl]nonadecan-10-amine, N,N-dimethyl-21-[R1S,2R)-2-octylcyclopropyl]henicosan-10-amine, N,N-dimethyl-1-[(1S,2S)-2-{[(1R,2R)-2-pentylcyclopropyl] methyl} cyclo-propyl]nonadecan-10-amine, N,N-dimethyl-1-[(1S,2R)-2-octylcyclopropyl]hexadecan-8-amine, N,N-dimethyl-[(1R,2S)-2-undecyl-cyclopropyl] tetradecan-5-amine, N,N-dimethyl-3-{7-[(1S,2R)-2-octylcyclopropyl]heptyl} dodecan-1-amine, 1-[(1R,2S)-2-heptylcyclopropyl]-N,N-dimethyloctadecan-9-amine, 1-[(1S,2R)-2-decylcyclopropyl]-N,N-dimethyl-penta-decan-6-amine, N,N-dimethyl-1-[(1S,2R)-2-octylcyclopropyl]-pentadecan-8-amine, R-N,N-dimethyl-1-[(9Z,12Z)-octadeca-9,12-dien- 1-yloxy]-3-(octyloxy)propan-2-amine, S-N,N-dimethyl-1-[(9Z,12Z)-octadeca-9,12-dien-1-yloxy]-3-(octyloxy) propan-2-amine, 1-{2-[(9Z,12Z)-octadeca-9,12-dien-1-yloxy]-1-[(octyloxy)-methyl]ethyl}pyrrolidine, (2S)-N,N-dimethyl-1-[(9Z,12Z)-octadeca-9,12-dien-1-yloxy]-3-[(5Z-)-oct-5-en-1-yloxy]propan-2-amine, 1-{2-[(9Z,12Z)-octadeca-9,12-dien-1-yloxy]-1-[(octyloxy)methyl] ethyl}azetidine, (2S)-1-(hexyloxy)-N,N-dimethyl-3-[(9Z, 12Z)-octadeca-9,12-dien-1-yloxy]propan-2-amine, (2S)-1-(heptyloxy)-N,N-di-methyl-3-[(9Z,12Z)-octadeca-9,12-dien-1-yloxy]propan-2-amine, N,N-dimethyl-1-(non-yloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-amine; (2S)-N,N-dimethyl-1-[(6Z,9Z, 12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl 1-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13, 16-dien-1-yloxy]-3-(hexyloxy)-N,N-dimethyl-propan-2-amine, (2S)-1-[(13Z)-docos-13-en-1-yloxy]-3-(hexyloxy)-N,N-dimethyl propan-2-amine, 1-[(13Z)-docos-13-en-1-yloxy]-N,N-dimethyl-3-(octyloxy) propan-2-amine, 1-[(9Z)-hexadec-9-en-1-yloxy]-N,N-dimethyl-3-(octyloxy) propan-2-amine, (2R)-N,N-di-methyl-H(1-metoyloctyl) oxy]-3-[(9Z,12Z)-octa-deca-9,12-dien-1-yloxy] propan-2-amine, (2R)-1-[(3,7-dimethyloctyl)-oxy]-N, N-dimethyl-3-R9Z,12Z)-octadeca-9,12-dien-1-yloxylpropan-2-amine, N,N-di-methyl-1-(octyloxy)-3-({8-[(1S,2S)-2-{[(1R,2R)-2-pentylcyclopropyl]-methyl} cyclo-propyl]octyl}oxy)pro-pan-2-amine, N,N-dimethyl-1-{[-(2-oclylcyclo-propyl)oc-tyl]oxy}-3-(octyloxy)propan-2-amine and (11E,20Z,23Z)-N,N-dimethylnonacosa-11,20,2-trien-10-amine or a pharmaceutically acceptable salt or acid or stereoisomer thereof.

In one embodiment, the lipid may be a cleavable lipid such as those described in in Intl. Publ. No. WO2012/170889, which is herein incorporated by reference in its entirety The cationic lipid can routinely be synthesized using methods known in the art (see, e.g., Intl. Publ. Nos. WO2012/040184, WO2011/153120, WO2011/149733, WO2011/090965, WO201/1043913, WO2011/022460, WO2012/061259, WO2012/054365, WO2012/044638, WO2010/080724 and WO2010/21865; each of which is herein incorporated by reference in its entirety.

Lipid derivatives can include, for example, at least, the bonding (preferably covalent bonding) of one or more steric stabilizers and/or functional groups to the liposomal component after which the steric stabilizers and/or functional groups should be considered part of the liposomal compo-nents. Functional groups comprise groups that can be used to attach a liposomal component to another moiety such as a protein. Such functional groups include, at least, maleim-ide. These steric stabilizers include at least one from the group consisting of polyethylene glycol (PEG); poly-L-lysine (PLL); monosialo-ganglioside (GM1); poly(vinyl pyrrolidone) (PVP); poly(acrylamide) (PAA); poly(2-methyl-2-oxazoline); poly(2-ethyl-2-oxazoline); phosphati-dylpoly-glycerol; poly[N-(2-hydroxy-propyl) methacrylam-ide]; amphiphilic poly-N-vinylpyrrolidones; L-amino-acid-based polymer; and polyvinyl alcohol.

In some embodiments, the provided trans-crocetin com-positions are formulated in a lipid-polycation complex. The formation of the lipid-polycation complex may be accomplished using methods known in the art and/or as described in U.S. Pub. No. 2012/0178702, herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012/013326; herein incorporated by reference in its entirety. In another embodiment, the provided trans-crocetin composition is formulated in a lipid-polycation complex which further includes a neutral lipid such as, but not limited to, cholesterol or dioleoyl phosphatidylethanolamine (DOPE).

Since the components of a liposome can include any molecule(s) (i.e., chemical/reagent/protein) that is bound to it, in some embodiments, the components of the provided liposomes include, at least, a member selected from: DSPE, DSPE-PEG, DSPE-maleimide, HSPC; HSPC-PEG; HSPC-maleimide; cholesterol; cholesterol-PEG; and cholesterol-maleimide. In some embodiments, the components of the provided liposomes include DSPE, DSPE-PEG, DSPE-maleimide, HSPC; HSPC-PEG; HSPC-maleimide; cholesterol; cholesterol-PEG; and cholesterol-maleimide. In a preferred embodiment, the liposomal components that make up the liposome comprises DSPE; DSPE-FITC; DSPE-maleimide; cholesterol; and HSPC.

In additional embodiments, the liposomes of the liposome compositions provided herein comprise oxidized phospholipids. In some embodiments, the liposomes comprise an oxidize phospholipid of a member selected from phosphatidylserines, phosphatidylinositols, phosphatidylethanolamines, phosphatidylcholines and 1-palmytoyl-2-arachidonoyl-sn-glycero-2-phosphate. In some embodiments, the phospholipids have unsaturated bonds. In some embodiments, the phospholipids are arachidonic acid containing phospholipids. In additional embodiments, the phospholipids are sn-2-oxygenated. In additional embodiments, the phospholipids are not fragmented.

In some embodiments, the liposomes of the disclosed liposome compositions comprise oxidized 1-palmitoyl-2-arachidonoyl-sn-glycero-3-phosphorylcholine (OxPAPC). The term "oxPAPC", as used herein, refers to lipids generated by the oxidation of 1-palmitoyl-2-arachidonyl-sn-glycero-3-phosphorylcholine (PAPC), which results in a mixture of oxidized phospholipids containing either fragmented or full length oxygenated sn-2 residues. Well-characterized oxidatively fragmented species contain a five-carbon sn-2 residue bearing omega-aldehyde or omega-carboxyl groups. Oxidation of arachidonic acid residue also produces phospholipids containing esterified isoprostanes. oxPAPC includes HOdiA-PC, KOdiA-PC, HOOA-PC and KOOA-PC species, among other oxidized products present in oxPAPC. In further embodiments, the oxPAPCs are epoxyisoprostane-containing phospholipids. In further embodiments, the oxPAPC is 1-palmitoyl-2-(5,6-epoxyisoprostane E2)-sn-glycero-3-phosphocholine (5,6-PEIPC), 1-palmitoyl-2-(epoxy-cyclopenten-one)-sn-glycero-3-phosphorylcholine (PECPC) and/or 1-palmitoyl-2-(epoxy-isoprostane E2)-sn-glycero-4-phosphocholine (PEIPC). In some embodiments, the phospholipids have unsaturated bonds. In some embodiments, the phospholipids are arachidonic acid containing phospholipids. In additional embodiments, the phospholipids are sn-2-oxygenated. In additional embodiments, the phospholipids are not fragmented.

In some embodiments, the liposomes of the disclosed liposome compositions comprise a lipid selected from: 1-palmitoyl-2-glutaroyl-sn-glycero-3-phosphocholine (PGPC); 1-palmitoyl-2-(9'oxo-nonanoyl)-sn-glycero-3-phospho-choline; 1-palmitoyl-2-arachinodoyl-sn-glycero-3-phosphocholine; 1-palmitoyl-2-myristoyl-sn-glycero-3-phos-phocholine; 1-palmitoyl-2-hexadec-yl-sn-glycero-3-phosphocholine; 1-palmitoyl-2-azel-aoyl-sn-glycero-3-phosphocholine; and 1-palmitoyl-2-acetoyl-sn-glycero-3-phospho-choline. In further embodiments, the liposome comprises PGPC.

In some embodiments, at least one component of the liposome lipid bilayer is functionalized (or reactive). As used herein, a functionalized component is a component that comprises a reactive group that can be used to crosslink reagents and moieties to the lipid. If the lipid is functionalized, any liposome that it forms is also functionalized. In some embodiments, the reactive group is one that will react with a crosslinker (or other moiety) to form crosslinks. The reactive group in the liposome lipid bilayer is located anywhere on the lipid that allows it to contact a crosslinker and be crosslinked to another moiety (e.g., a steric stabilizer or targeting moiety). In some embodiments, the reactive group is in the head group of the lipid, including for example a phospholipid. In some embodiments, the reactive group is a maleimide group. Maleimide groups can be crosslinked to each other in the presence of dithiol crosslinkers including but not limited to dithiothreitol (DTT).

It is to be understood that the use of other functionalized lipids, other reactive groups, and other crosslinkers beyond those described above is further contemplated. In addition to the maleimide groups, other examples of contemplated reactive groups include but are not limited to other thiol reactive groups, amino groups such as primary and secondary amines, carboxyl groups, hydroxyl groups, aldehyde groups, alkyne groups, azide groups, carbonyls, halo acetyl (e.g., iodoacetyl) groups, imidoester groups, N-hydroxysuccinimide esters, sulfhydryl groups, and pyridyl disulfide groups.

Functionalized and non-functionalized lipids are available from a number of commercial sources including Avanti Polar Lipids (Alabaster, AL) and Lipoid LLC (Newark, NJ).

In some embodiments, the liposomes include a steric stabilizer that increases their longevity in circulation. One or more steric stabilizers such as a hydrophilic polymer (polyethylene glycol (PEG)), a glycolipid (monosialo-ganglioside (GM1)) or others occupies the space immediately adjacent to the liposome surface and excludes other macromolecules from this space. Consequently, access and binding of blood plasma opsonins to the liposome surface are hindered, and thus interactions of macrophages with such liposomes, or any other clearing mechanism, are inhibited and longevity of the liposome in circulation is enhanced. In some embodiments, the steric stabilizer or the population of steric stabilizers is a PEG or a combination comprising PEG. In further embodiments, the steric stabilizer is a PEG or a combination comprising PEG with a number average molecular weight (Mn) of 200 to 5000 Daltons. These PEG(s) can be of any structure such as linear, branched, star or comb structure and are commercially available.

In some embodiments, liposomes of the provided liposomal compositions are pegylated (e.g., pegylated liposomal CTC and pegylated liposomal MTC). In some embodiments, the pegylated liposomes are water soluble. That is, the pegylated liposomes are in the form of an aqueous solution.

The diameter of the provided liposomes is not particularly limited. In some embodiments, the liposomes have a mean diameter of for example, 20 nm to 500 nm (nanometer), or 20 nm to 200 nm, or any range therein between. In some embodiments, the liposomes have a mean diameter of 80 nm to 120 nm, or any range therein between.

In some embodiments, the pH of solutions comprising the liposome composition is from pH 2 to 8, or any range therein between. In some embodiments, the pH of solutions comprising the liposome composition is from pH 5 to 8, or 6 to 7, or any range therein between. In some embodiments, the pH of solutions comprising the liposome composition is from pH 6 to 7, or any range therein between. In some embodiments, the pH of solutions comprising the liposome composition is from 6 to 7.5, from 6.5 to 7.5, from 6.7 to 7.5, or from 6.3 to 7.0, or any range therein between.

In additional embodiments, the provided liposomal composition comprises a buffer. In further embodiments, the buffer is selected from HEPES, citrate, or sodium phosphate (e.g., monobasic and/or dibasic sodium phosphate). In some embodiments, the buffer is HEPES. In some embodiments, the buffer is citrate. In some embodiments, the buffer is sodium phosphate (e.g., monobasic and/or dibasic sodium phosphate). In some embodiments, the buffer is at a concentration of 15 to 200 mM, or any range therein between. In yet further embodiments, the buffer is at a concentration of 5 to 200 mM, 15 to 200, 5 to 100 mM, 15 to 100 mM, 5 to 50 mM, 15 to 50 mM, 5 to 25 mM, 5 to 20 mM, 5 to 15 mM, or any range therein between. In some embodiments, the buffer is HEPES at a concentration of 5 to 200 mM, or any range therein between. In some embodiments, the buffer is citrate at a concentration of 5 to 200 mM, or any range therein between. In some embodiments, the buffer is sodium phosphate at a concentration of 5 to 200 mM, or any range therein between.

In additional embodiments, the liposome composition contains one or more lyoprotectants or cryoprotectants. In some embodiments, the cryoprotectant is mannitol, trehalose, sorbitol, or sucrose. In some embodiments, the lyoprotectant and/or cryoprotectant is present in the composition at 1 to 20%, or 5 to 20% weight percent, or any range therein between.

In additional embodiments, the provided liposomal composition comprises a tonicity agent. In some embodiments, the concentration (weight percent) of the tonicity agent is 0.1-20%, 1-20%, 0.5-15%, 1-15%, or 1-50%, or any range therein between. In some embodiments, the liposome composition includes a sugar (e.g., trehalose, maltose, sucrose, lactose, mannose, mannitol, glycerol, dextrose, fructose, etc.). In further embodiments, the concentration (weight percent) of the sugar is 0.1-20%, 1-20%, 0.5-15%, 1%-15%, or 1-50%, or any range therein between.

In some embodiments, the provided liposomal composition comprises trehalose. In further embodiments, the concentration weight percent of trehalose is 0.1-20%, 1-20%, 0.5-15%, 1%-15%, 5-20%, or 1-50%, or any range therein between. In yet further embodiments, the concentration (weight percent) of trehalose is 1-15%, or any range therein between. In an additional embodiment, the trehalose is present at about 5% to 20% weight percent of trehalose or any combination of one or more lyoprotectants or cryoprotectants at a total concentration of 5% to 20%. In some embodiments, the pH of the liposome composition is from 6 to 7.5, from 6.5 to 7.5, from 6.7 to 7.5, or from 6.3 to 7.0, or any range therein between.

In some embodiments, the liposome composition comprises dextrose. In some embodiments, the concentration weight percent of dextrose is 0.1-20%, 1-20%, 0.5-15%, 1-15%, 5-20%, or 1-50%, or any range therein between. In particular embodiments, the concentration (weight percent) of dextrose is 1-20%, or any range therein between. In an additional embodiment, the dextrose is present at 1 to 20% weight percent of dextrose or any combination of one or more lyoprotectants or cryoprotectants at a total concentration of 1% to 20%, or 5% to 20%, or any range therein between.

In some embodiments, the disclosure provides a liposomal composition that comprises a liposome encapsulating a trans-crocetin salt. In some embodiments, the liposome is pegylated. In some embodiments, the liposome is targeted. In some embodiments, the liposome is unpegylated and targeted. In some embodiments, the liposome is unpegylated and nontargeted. In some embodiments, the liposome contains less than 6 million, less than 500,000, less than 200,000, less than 100,000, less than 50,000, less than 10,000, or less than 5,000, molecules of trans-crocetin. In some embodiments, the liposome contains 10 to 100,000, 100 to 10,000, or 1,000 to 5,000 molecules of trans-crocetin, or any range therein between. In some embodiments, the liposome encapsulates trans-crocetin and one or more of different carotenoids. In further embodiments, the liposome encapsulates trans-crocetin and one or more different ionizable carotenoids provided in FIGS. 1A-1D).

In additional embodiments, the disclosure provides a liposome composition that comprises an unpegylated liposome encapsulating trans-crocetin salt. In some embodiments, the liposome contains less than 6 million, less than 500,000, less than 200,000, less than 100,000, less than 50,000, less than 10,000, or less than 5,000, molecules of trans-crocetin. In some embodiments, the unpegylated liposome contains 10 to 100,000, 100 to 10,000, or 1,000 to 5,000 molecules of trans-crocetin, or any range therein between. In additional embodiments, the unpegylated liposome comprises trans-crocetin and one or more different carotenoids. In further embodiments, the liposome comprises trans-crocetin and one or more different ionizable carotenoids provided in FIGS. 1A-1D).

In additional embodiments, the disclosure provides a liposome composition that comprises an unpegylated and targeted liposome encapsulating a trans-crocetin salt. In some embodiments, the unpegylated and targeted liposome contains 1 to 1000, 50 to 750, 100 to 500, or 30 to 200 targeting moieties, or any range therein between. In some embodiments, the unpegylated and targeted liposome contains 10 to 100,000, 100 to 10,000, or 1,000 to 5,000 molecules of trans-crocetin, or any range therein between. In additional embodiments, the unpegylated and targeted liposome comprises trans-crocetin and one or more different carotenoids. In further embodiments, the liposome comprises trans-crocetin and one or more different ionizable carotenoids provided in FIGS. 1A-1D).

In additional embodiments, the disclosure provides a liposome composition that comprises an unpegylated and nontargeted liposome encapsulating a trans-crocetin salt. In some embodiments, the unpegylated and nontargeted liposome contains 10 to 100,000, 100 to 10,000, or 1,000 to 5,000 molecules of trans-crocetin, or any range therein between. In additional embodiments, the unpegylated and nontargeted liposome comprises trans-crocetin and one or more different carotenoids. In further embodiments, the liposome comprises trans-crocetin and one or more different ionizable carotenoids provided in FIGS. 1A-1D).

In further embodiments, the provided liposomal compositions comprise a liposome encapsulating a trans-crocetin salt, and one or more aqueous pharmaceutically acceptable carriers. In some embodiments, the liposome solution contains trehalose. In some embodiments, the liposome solution contains 1% to 50% weight of trehalose. In some embodiments, the liposome solution contains HBS at a concentration of 1 to 200 mM and a pH of 2-8, or any range therein between. In some embodiments, liposome solution has a pH 5-8, or any range therein between. In some embodiments, liposome solution has a pH 6-7, or any range therein between. In some embodiments, the provided trans-crocetin salt is a multivalent salt (e.g., divalent, trivalent, or tetravalent). In some embodiments, the trans-crocetin salt is CTC. In some embodiments, the trans-crocetin salt is MTC.

The provided liposomes comprise an aqueous compartment enclosed by at least one lipid bilayer. When lipids that include a hydrophilic headgroup are dispersed in water they can spontaneously form bilayer membranes referred to as lamellae. The lamellae are composed of two monolayer sheets of lipid molecules with their non-polar (hydrophobic) surfaces facing each other and their polar (hydrophilic) surfaces facing the aqueous medium. The term liposome includes unilamellar vesicles which are comprised of a single lipid bilayer and generally have a diameter of about 20 to about 500 nm, about 50 to about 300 nm, about 50 to about 150 nm, about 30 to about 1000 nm, about 30 to about 175 nm, about 80 to about 400 nm, or about 80 to about 120 nm. Liposomes can also be multilamellar, which generally have a diameter 0.5 to 10 um with anywhere from two to hundreds of concentric lipid bilayers alternating with layers of an aqueous phase. In some embodiments, liposomes can include multilamellar vesicles (MLV), large unilamellar vesicles (LUV), and small unilamellar vesicles (SUV). The lipids of the liposome can be cationic, zwitterionic, neutral or anionic, or any mixture thereof.

The size of the liposomes in the provided liposomal compositions may vary from for example, 0.5 nm to 10 um, or 20 nm to 5 um, depending on the phospholipid composition, the method used for their preparation, and the intended therapeutic use of the liposomes. In some embodiments, the median diameter of the liposomes in the provided liposomal composition is 20 nm to 500 nm, 50 nm to 200 nm, or 20 nm to 200 nm, or any range therein between. In some embodiments, the liposome median diameter is 80 nm to 120 nm, or any range therein between (e.g., 85-115 nm, 90-110 nm, 95-110 nm, or 95-105 nm). In some embodiments, the median diameter of the liposomes in the provided liposomal composition is 10-250 nm, or any range therein between (e.g., 10-225 nm, 10-200 nm, 10-175 nm, 10-150 nm, 40-150 nm, 50-150 nm, 60-150 nm, 70-150 nm, 80-150 nm, 90-150 nm, 100-150 nm, 10-125 nm, 10-100 nm, 10-75 nm, 10-50 nm, 50-100 nm, 50-90 nm, 50-80 nm, 50-70 nm, 50-60 nm, 60-100 nm, 60-90 nm, 60-80 nm, 60-70 nm, 70-100 nm, 70-90 nm, 70-80 nm, 80-100 nm, 80-90 nm, or 90-100 nm). In some embodiments, the median diameter of the liposomes in the provided liposomal composition is 100-250 nm, or any range therein between (e.g., 100-225 nm, 100-200 nm, 100-175 nm, or 100-150 nm). In other embodiments, the median diameter of the liposomes in the provided liposomal composition is 10-100 nm, or any range therein between (e.g., from about 10-90 nm, 10-80 nm, 10-70 nm, 10-60 nm, or 10-50 nm). In some embodiments, the median diameter of the liposomes in the provided liposomal composition is less than, about 500 nm, 450 nm, 400 nm, 350 nm, 300 nm, 250 nm, 200 nm, 150 nm, 145 nm, 150 nm, 135 nm, 130 nm, 125 nm, 120 nm, 115 nm, 110 nm, 105 nm, 100 nm, 95 nm, 90 nm, 85 nm, 80 nm, 75 nm, 70 nm, 65 nm, 60 nm, 55 nm, or 50 nm, 45 nm, or 40 nm. Dynamic laser light scattering is a method used to measure the diameter of liposomes that is well known to those skilled in the art. The diameter of the liposomes (DLP) can routinely be determined using any techniques and equipment known in the art including for example, dynamic laser light scattering (Coulter N4 particle size analyzer), the Zetasizer Nano ZSP (Malvern, UK), and an ELS-8000 (Otsuka Electronics Co., Ltd.)).

In some embodiments, the provided liposomal compositions have a monodisperse size (diameter) distribution. "Monodisperse" and "homogeneous size distribution," are used interchangeably herein and describe a plurality of liposomal nanoparticles or microparticles where the particles have the same or nearly the same diameter. As used herein, a monodisperse distribution refers to particle distributions in which 75%, 76%, 77%, 78%, 79%, 80%, 81%, 82%, 83%, 84%, 85%, 86%, 86%, 88%, 89%, 90%, 91%, 92%, 93%, 94%, 95% or greater of the particle distribution lies within 85%, 80%, 75%, 70%, 65%, 60%, 55%, 50%, 45%, 40%, 35%, 30%, 25%, 20%, 15%, or 10% of the mass median diameter.

In some embodiments, the liposome population in the provided liposomal composition is relatively homogenous. In some embodiments, the liposome population in the provided liposomal composition is heterogeneous. A polydispersity index may be used to indicate the homogeneity of a nanoparticle composition, e.g., the particle size (diameter) distribution of the nanoparticle compositions. A small (e.g., less than 0.3) polydispersity index generally indicates a narrow particle size distribution. In some embodiments, the liposome population in the provided liposomal composition has a polydispersity index from 0 to 0.25, or 0.01 to 0.1, or any range therein between (e.g., 0.001 to 0.2, 0.005 to 0.1, 0.005 to 0, 0.005 to 0.09, 0.009 to 0.09, 0.01 to 0.08, 0.02 to 0.09, or 0.02 to 0.07, or any range therein between.

In some embodiments, liposomes in the liposome population in the provided liposomal composition differ in their lipid composition, molar ratio of lipid components, size, charge (zeta potential), targeting ligands and/or combinations thereof.

The zeta potential of a nanoparticle composition may be used to indicate the electrokinetic potential of the composition. For example, the zeta potential may describe the surface charge of a nanoparticle composition. Nanoparticle compositions with relatively low charges, positive or negative, are generally desirable, as more highly charged species may interact undesirably with cells, tissues, and other elements in the body. In some embodiments, the zeta potential of a nanoparticle composition can be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV. Liposome zeta potential can routinely be determined using techniques and equipment known in the art including for example, dynamic light scattering (Zetasizer Nano ZSP, Malvern, UK) and laser Doppler electrophoresis.

The encapsulation efficiency of a therapeutic and/or prophylactic such as trans-crocetin, describes the amount of therapeutic and/or prophylactic that is encapsulated or otherwise associated with a nanoparticle composition after preparation, relative to the initial amount provided. The encapsulation efficiency is desirably high (e.g., close to 100%). The encapsulation efficiency may be measured, for example, by comparing the amount of therapeutic and/or prophylactic in a solution containing the nanoparticle composition before and after removing the unencapsulated therapeutic and/or prophylactic drug. For the liposome compositions described herein, the encapsulation efficiency of trans-crocetin can be at least 50%, for example 60%, 70%, 80%, 85%, 90%, 91%, 92%, 93%, 94%, 95%, 96%, 97%, 98%, or 99%. In some embodiments, the encapsulation efficiency is at least 80%. In certain embodiments, the encapsulation efficiency is at least 90%. In certain embodiments, the encapsulation efficiency is at least 95%. In certain embodiments, the encapsulation efficiency is at least 98%.

In additional embodiments, the provided liposomal compositions contain liposomes encapsulating a trans-crocetin salt. In some embodiments, the trans-crocetin/lipid ratio of the provided liposomal composition is 1 to 1000 g/mol, or any range therein between. In some embodiments, the trans-crocetin/lipid ratio of the liposome composition is 10 to 200 g/mM, 10 to 150 g/mM, 10 to 100 g/mM, 20 to 200 g/mM, 20 to 150 g/mM, 20 to 100 g/mM, 30 to 200 g/mM, 30 to 150 g/mM, 30 to 100 g/mM, 40 to 200 g/mM, 40 to 150 g/mM, 40 to 100 g/mM, 50 to 200 g/mM, 50 to 150 g/mM, or 50 to 100 g/mM, or any range therein between. In some embodiments, trans-crocetin/lipid ratio is 30 to 90 g/mM, or any range therein between. In some embodiments, trans-crocetin/lipid ratio is 30 to 50 g/mM, 40 to 60 g/mM, 50 to 70 g/mM, 60 to 80 g/mM, or 70 to 90 g/mM, or any range therein between. In additional embodiments, the trans-crocetin/lipid ratio of the liposome composition is 20 to 120 g/mM (e.g., about 25 to 100 g/mM), or any range therein between.

In some embodiments, the liposome composition is buffered using a zwitterionic buffer. Suitably, the zwitterionic buffer is an aminoalkanesulfonic acid or suitable salt. Examples of aminoalkanesulfonic buffers include but are not limited to HEPES, HEPPS/EPPS, MOPS, MOBS and PIPES. Preferably, the buffer is a pharmaceutically acceptable buffer, suitable for use in humans, such as in for use in a commercial injection product. Most preferably the buffer is HEPES. The liposome composition may suitable include an AGP.

In some embodiments, the liposome composition is buffered using HEPES. In some embodiments, the liposome composition is buffered using HEPES having a pH of 7.

In some embodiments, the pharmaceutical composition is a liposome composition comprising a cationic liposome. In some embodiments, the liposome composition comprises a liposome that has a zeta potential that is more than zero. In some embodiments, the liposome has a zeta potential of 0.2 to 150 mV, 1 to 50 mV, 1 to 40 mV, 1 to 30 mV, 1 to 25 mV, 1 to 20 mV, 1 to 15 mV, 1 to 10 mV, 1 to 5 mV, 2 to 10 mV, 3 to 10 mV, 4 to 10 mV, or 5 to 10 mV, or any range therein between. In some embodiments, the liposome has a diameter of 20 nm to 500 nm, 20 nm to 200 nm, 30 nm to 175 nm, 50 nm to 200 nm, or 50 nm to 150 nm, or any range therein between. In some embodiments, the cationic liposome has a diameter of 80 nm to 120 nm, or any range therein between. In some embodiments, the liposome composition comprises at least 1%, 5%, 10%, 15%, 20%, 25%, 30%, 35%, 40%, 45%, 50%, 55%, 60%, 65%, 70%, 75%, or more than 75%, w/w of trans-crocetin. In some embodiments, during the process of preparing the liposome composition, at least 1%, 5%, 10%, 15%, 20%, 25%, 30%, 35%, 40%, 45%, 50%, 55%, 60%, 65%, 70%, 75%, 75%, 80%, 85%, 90%, 95%, or 97%, of the trans-crocetin starting material is encapsulated (entrapped) in the liposomes of the liposome composition. In additional embodiments, trans-crocetin encapsulated by the liposome is in a HEPES buffered solution within the liposome. In further embodiments, the liposome comprises at least one OxPAPC.

In some embodiments, the provided pharmaceutical composition is a liposome composition comprising an anionic or neutral liposome. In some embodiments, the liposome composition comprises a liposome that has a zeta potential that is less than or equal to zero. In some embodiments, the liposome has a zeta potential that is −150 to 0, −50 to 0 mV, −40 to 0 mV, −30 to 0 mV, −25 to 0 mV, −20 to 0 mV, −10 to 0 mV, −9 to 0 mV, −8 to 0 mV, −7 to 0 mV, −6 to 0 mV, −5 to 0 mV, −4 to 0 mV, −3 to 0 mV, −2 to 0 mV, −1 to 0 mV, or −8 to 2 mV, or any range therein between. In some embodiments, the anionic or neutral liposome has a diameter of 20 nm to 500 nm, 20 nm to 200 nm, 30 nm to 175 nm, or 50 nm to 150 nm, or any range therein between. In other embodiments, the anionic or neutral liposome has a diameter of 80 nm to 120 nm, or any range therein between. In some embodiments, the anionic liposome has a diameter of 20 nm to 500 nm, 20 nm to 200 nm, 30 nm to 175 nm, or 50 nm to 150 nm, or any range therein between. In further embodiments, the anionic liposome has a diameter of 80 nm to 120 nm, or any range therein between. In some embodiments, the neutral liposome has a diameter of 20 nm to 500 nm, 20 nm to 200 nm, 30 nm to 175 nm, or 50 nm to 150 nm, or any range therein between. In some embodiments, the neutral liposome has a diameter of 80 nm to 120 nm, or any range therein between. In some embodiments, the pharmaceutical composition comprises at least 1%, 5%, 10%, 15%, 20%, 25%, 30%, 35, 40%, 45%, 50%, 55%, 60%, 65%, 70%, 75%, or more than 75%, w/w trans-crocetin. In some embodiments, during the process of preparing the liposome composition, at least 1%, 5%, 10%, 15%, 20%, 25%, 30%, 35%, 40%, 45%, 50%, 55%, 60%, 65%, 70%, 75%, or more than 75%, of the starting material of trans-crocetin is encapsulated (entrapped) in the liposomes. In some embodiments, the liposome composition comprises at least 1%, 5%, 10%, 15%, 20%, 25%, 30%, 35, 40%, 45%, 50%, 55%, 60%, 65%, 70%, 75%, or more than 75%, w/w of the trans-crocetin. In some embodiments, the anionic or neutral liposome composition comprises at least 1%, 5%, 10%, 15%, 20%, 25%, 30%, 35, 40%, 45%, 50%, 55%, 60%, 65%, 70%, 75%, or more than 75%, w/w of the trans-crocetin. In some embodiments, liposome composition comprises at least 1%, 5%, 10%, 15%, 20%, 25%, 30%, 35, 40%, 45%, 50%, 55%, 60%, 65%, 70%, 75%, or more than 75%, w/w of the trans-crocetin. In additional embodiments, the trans-crocetin is encapsulated by the anionic or neutral liposome is in a HEPES buffered solution within the liposome. In further embodiments, the liposome comprises at least one OxPAPC.

In some embodiments, the provided pharmaceutical composition is a liposome composition comprising a liposome that comprises at least one OxPAPC. In some embodiments, the OxPAPC is an oxidized and/or phospholipid containing fragmented oxygenated sn-2 residues. In some embodiments, the OxPAPC is an oxidized phospholipid containing a five-carbon sn-2 residue bearing an omega-aldehyde or omega-carboxyl group. In some embodiments, the OxPAPC is an oxidized phospholipid selected from HOdiA-PC, KOdiA-PC, HOOA-PC and KOOA-PC. In some embodiments, the OxPAPC is an epoxyisoprostane-containing phospholipid. In some embodiments, the OxPAPC is PGPC. In some embodiments, the liposome comprises at least 0.01%, 0.1%, 1%, 5%, 10%, 15%, 20%, 25%, or at least 30%, OxPAPC. In some embodiments, the liposome composition has a cationic liposome that comprises 0.01%-35%, 0.1%-30%, 1%-25%, 3-20%, or 5-15%, OxPAPC, or any range therein between. In some embodiments, the liposome composition comprises a cationic liposome. In some embodiments, the liposome composition comprises a neutral liposome. In some embodiments, the liposome composition comprises an anionic liposome. In additional embodiments, the liposome composition comprises at least one liposome containing an OxPAPC that has a diameter of 20 nm to 500 nm, 20 nm to 200 nm, 30 nm to 175 nm, or 50 nm to 150 nm, or any range therein between. In further embodiments, the liposome composition comprises an at least one liposome containing an OxPAPC that has a diameter of 80 nm to 120 nm, or any range therein between.

In some embodiments, the provided pharmaceutical composition is a liposome composition comprising a cationic liposome that comprises at least 0.01%, 0.1%, 1%, 5%, 10%, 15%, 20%, 25%, or at least 30%, OxPAPC. In some embodiments, the liposome composition has a cationic liposome that comprises 0.01%-35%, 0.1%-30%, 10%-25%, 3-20%, or 5-15%, OxPAPC, or any range therein between. In some embodiments, the liposome comprises at least 0.01%, 0.1%, 1%, 5%, 10%, 15%, 20%, 25%, or at least 30%, OxPAPC. In some embodiments, the liposome composition has a cationic liposome that contains about 10% OxPAPC. In some embodiments, the liposome composition has a cationic liposome that comprises at least 0.01%, 0.1%, 1%, 5%, 10%, 15%, 20%, 25%, or at least 30%, PGPC. In some embodiments, the liposome comprises 0.01%-35%, 0.1%-30%, 1%-25%, 3-20%, or 5-15%, PGPC, or any range therein between. In some embodiments, the liposome composition has a cationic liposome that comprises about 10% PGPC.

In some embodiments, the pharmaceutical composition is a liposome composition comprising an anionic or neutral liposome that comprises at least 0.01%, 0.1%, 1%, 5%, 10%, 15%, 20%, 25%, or at least 30%, OxPAPC. In some embodiments, the liposomal composition has an anionic or neutral liposome that comprises 0.01%-35%, 0.1%-30%, 1%-25%, 3-20%, or 5-15%, OxPAPC, or any range therein between. In some embodiments, the liposome comprises at least 0.01%, 0.1%, 1%, 5%, 10%, 15%, 20%, 25%, or at least 30%, OxPAPC. In some embodiments, the liposomal composition has an anionic or neutral liposome that contains about 10% OxPAPC. In some embodiments, the liposomal composition comprises an anionic or neutral liposome that comprises at least 0.01%, 0.1%, 1%, 5%, 10%, 15%, 20%, 25%, or at least 30%, PGPC. In some embodiments, the liposome comprises 0.01/6-35%, 0.1%-30%, 1%-25%, 3-20%, or 5-15%, PGPC, or any range therein between. In some embodiments, the liposomal composition has an anionic or neutral liposome that contains about 10% PGPC.

In some embodiments, the pharmaceutical composition is a liposomal composition comprising a neutral liposome that comprises at least 0.01%, 0.1%, 1%, 5%, 10%, 15%, 20%, 25%, or at least 30%, OxPAPC. In some embodiments, the neutral OxPAPC containing liposomal composition comprises 0.01%-35%, 0.1%-30%, %-25%, 3-20%, or 5-15%, OxPAPC, or any range therein between. In some embodiments, the neutral OxPAPC containing liposomal composition comprises about 10% OxPAPC. In some embodiments, the neutral OxPAPC containing liposomal composition comprises at least 0.01%, 0.1%, 1%, 5%, 10%, 15%, 20%, 25%, or at least 30%, PGPC. In some embodiments, the neutral PGPC containing liposomal composition comprises 0.01%-35%, 0.1%-30%, 1%-25%, 3%-20%, or 5-15%, PGPC, or any range therein between. In some embodiments, the neutral OxPAPC containing liposomal composition comprises about 10% PGPC.

In some embodiments, the pharmaceutical composition is a liposomal composition comprising a surface active copolymer. Surface active copolymers, also termed block polymer nonionic surfactants, are surface active agents synthesized by the sequential addition of two or more alkylene oxides to a low molecular weight water soluble organic compound containing one or more active hydrogen atoms. In some embodiments, the liposomal composition comprises a surface active copolymer selected from a poloxamer, meroxapol, poloxamine, and PLURADOT™. The surface active copolymers in the liposomal composition can be encapsulated by, or integrated into or otherwise attached with the liposomes by covalent, ionic, or other binding interaction and/or the surface active copolymers may not be encapsulated by, integrated into or otherwise attached with liposomes in the liposomal composition (e.g., the surface active copolymers may be free in the liposomal composition).

In some embodiments, the liposomal composition comprises a poloxamer such as P188, and P124, P182, P188, and P234, have been reported to bind to cell membranes and markedly reduce cell permeability that has been induced by ischemic injury. The embodiments described herein also deliver increased oxygen to the organs and cells more effectively, and in a way that reduces reperfusion injury. Without wishing to be limited to any particular theory or mechanism, it is believed that this oxygen delivery reduces the intracellular injury that is attributable to mitochondrial dysfunction and/or metabolic and enzymatic abnormalities associated with poor perfusion and/or reperfusion injury. In some embodiments, the liposomal composition comprises a poloxamer with a molecular weight of between 2,000 and 20,000 Daltons. Poloxamers within this molecular weight range remain soluble in water while minimizing potential toxicity. In some embodiments, the poloxamer's hydrophobic group has a molecular weight range from approximately 950-4,000 Daltons. In such embodiments, the hydrophilic groups may constitute approximately 45-95% by weight of the poloxamer. In an exemplary embodiment, the hydrophobic group has a molecular weight of 1,750-3,500 Daltons and the hydrophilic groups constitute between 50-90% by weight of the molecule.

In some embodiments, the liposomal composition comprises at least one poloxamer selected from P108, P124, PI 38, P171, P181, P182, P185, P188, P234, P237, P288, and P407. In some embodiments, the liposomal composition comprises at least one poloxamer selected from P124, P182, P188, and P234.

In particular embodiments, the liposomal composition comprises poloxamer 188 (P188) (Pluronic F68).

In additional embodiments, a liposome in the liposomal composition is pegylated.

In some embodiments, the provided pharmaceutical composition is a non-targeted liposomal composition. That is, the liposomes in the liposomal composition do not have specific affinity towards an epitope (e.g., an epitope on a surface antigen) expressed on the surface of a target cell of interest. In further embodiments, the non-targeted liposomal composition is pegylated.

In some cases, liposome accumulation at a target site may be due to the enhanced permeability and retention characteristics of certain tissues such as cancer tissues. Accumulation in such a manner often results in part because of liposome size and may not require special targeting functionality. In other embodiments, the provided liposomes include a targeting agent. Generally, the targeting agents can associate with any target of interest, such as a target associated with an organ, tissues, cell, extracellular matrix, or intracellular region. In certain embodiments, a target can be associated with a particular disease state, such as a cancerous condition. In some embodiments, the targeting component can be specific to only one target, such as a receptor. Suitable targets can include but are not limited to a nucleic acid, such as a DNA, RNA, or modified derivatives thereof. Suitable targets can also include but are not limited to a protein, such as an extracellular protein, a receptor, a cell surface receptor, a tumor-marker, a transmembrane protein, an enzyme, or an antibody. Suitable targets can include a carbohydrate, such as a monosaccharide, disaccharide, or polysaccharide that can be, for example, present on the surface of a cell.

In certain embodiments, a targeting agent can include a target ligand (e.g., an RGD-containing peptide), a small molecule mimic of a target ligand (e.g., a peptide mimetic ligand), or an antibody or antibody fragment specific for a particular target. In some embodiments, a targeting agent can further include folic acid derivatives, B-12 derivatives, integrin RGD peptides, NGR derivatives, somatostatin derivatives or peptides that bind to the somatostatin receptor, e.g., octreotide and octreotate, and the like. In some embodiments, the targeting agents include an aptamer. Aptamers can be designed to associate with or bind to a target of interest. Aptamers can be comprised of, for example, DNA, RNA, and/or peptides, and certain aspects of aptamers are known in the art. (See, e.g., Klussman, Ed., The Aptamer Handbook, Wiley-VCH (2006); Nissenbaum, Trends in Biotech. 26(8): 442-449 (2008)).

In other embodiments, the liposomal composition comprises a targeted liposome. That is, the liposome contains a targeting moiety that has specific affinity for an epitope (e.g., a surface antigen or other molecule) on a target cell of interest. In some embodiments, the targeting moiety of the liposome is not attached to the liposome through a covalent bond. In other embodiments, the targeting moiety of the liposome is attached to one or both of a PEG and the exterior of the liposome. In further embodiments, the targeted liposome is pegylated. The functions of the targeting moiety of the targeted liposome may include but is not limited to, targeting the liposome to the target cell of interest in vivo or in vitro; interacting with the surface antigen for which the targeting moiety has specific affinity, and delivering the liposome payload (e.g., trans-crocetin) to the location of or into the cell.

Suitable targeting moieties are known in the art and include, but are not limited to, antibodies, antigen-binding antibody fragments, scaffold proteins, polypeptides, and peptides. In some embodiments, the targeting moiety is a polypeptide. In further embodiments, the targeting moiety is a polypeptide that comprises at least 3, 5, 10, 15, 20, 30, 40, 50, or 100, amino acid residues. In some embodiments, the targeting moiety is an antibody or an antigen-binding antibody fragment. In further embodiments, the targeting moiety comprises one or more of an antibody, a humanized antibody, and an antigen binding fragment of an antibody, a single chain antibody, a single-domain antibody, a bi-specific antibody, a synthetic antibody, a pegylated antibody, and a multimeric antibody. In some embodiments, the targeting moiety has specific affinity for an epitope that is preferentially expressed on a target cell such as a tumor cell, compared to normal or non-tumor cells. In some embodiments, the targeting moiety has specific affinity for an epitope on a tumor cell surface antigen that is present on a tumor cell but absent or inaccessible on a non-tumor cell. In some embodiments, the targeting moiety binds an epitope of interest with an equilibrium dissociation constant (Kd) in a range of $50 \times 10^{-12}$ to $10 \times 10^{-6}$ as determined using BIA-CORE® analysis. In further embodiments, the Kd is determined using a surface plasmon resonance technique in which an antigen containing the epitope is immobilized, the targeting moiety serves as analyte, and the following conditions are used: 10 mM MES buffer, 0.05% polyoxyethylene sorbitan monolaurate, and 150 mM NaCl at 37° C.

In additional embodiments, the liposome composition comprises one or more of an immunostimulatory agent, a detectable marker, and a maleimide, disposed on at least one of the PEG and the exterior of the liposome. In some embodiments, a liposome of the liposome composition is cationic. In other embodiments, a liposome of the liposome composition is anionic or neutral. In additional embodiments, a liposome of the liposomal composition has a diameter of 20 nm to 500 nm, or any range therein between. In further embodiments, a liposome of the liposomal composition has a diameter of 80 nm to 120 nm, or any range therein between. In some embodiments, a liposome of the liposomal composition is pegylated. In some embodiments, a liposome of the liposomal composition is targeted. In further embodiments, a liposome of the liposomal composition is pegylated and targeted.

In some embodiments, the pharmaceutical composition comprises a trans-crocetin salt having the formula: Q-trans-crocetin-Q encapsulated by a liposome, wherein, Q is a (a) multivalent counterion or (b) monovalent cation.

In some embodiments, Q is a multivalent cation counterion. In some embodiments, Q is a multivalent metal cation. In further embodiments, Q is a multivalent transition metal cation. In some embodiments, Q is a divalent cation counterion. In further embodiments, Q is a divalent metal cation. In some embodiments, Q is at least one member selected from $Ca^{2+}$, $Mg^{2+}$, $Zn^{2+}$, $Cu^{2+}$, $Co^{2+}$, and $Fe^{2+}$. In further embodiments, Q is $Ca^{2+}$ or $Mg^{2+}$. In some embodiments, Q is $Ca^{2+}$. In some embodiments, Q is $Mg^{2+}$. In some embodiments, Q is a divalent organic counterion. In other embodiments, Q is a trivalent cation counterion such as $Fe^{3+}$. In other embodiments, Q is a multivalent organic counterion. In some embodiments, Q is a divalent organic cation. In some embodiments, Q is a bivalent organic cation such as protonated diamine.

In further embodiments, Q is a monovalent cation counterion. In some embodiments, Q is a monovalent metal cation. In some embodiments, Q is at least one member selected from $Na^+$, $Li^+$, or $K^+$. In some embodiments, Q is an organic cation. In some embodiments, Q is a monovalent organic cation such as a protonated amine (e.g., a protonated diamine or a protonated polyamine). In some embodiments, Q is an organic cation such as $NH4^+$, a protonated diamine or a protonated polyamine.

In some embodiments, the liposome contains less than 6 million, less than 500,000, less than 200,000, less than 100,000, less than 50,000, or less than 10,000, molecules of trans-crocetin. In some embodiments, the liposome contains 10 to 100,000, 100 to 10,000, or 1,000 to 5,000, molecules of trans-crocetin, or any range therein between. In some embodiments, the trans-crocetin/lipid ratio of the liposomal composition is Ig/mol and about 1000 g/mol, or any range therein between. In some embodiments, the trans-crocetin/lipid ratio is 10-150 g/mol, 10-100 g/mol, 30-200 g/mol, 40-200 g/mol, or 50-200 g/mol, or any range therein between. In some embodiments, the liposome comprises at least 0.1% to 97% trans-crocetin. In some embodiments, the liposome has a diameter of 20 nm to 500 nm, or 20 nm to 200 nm, or any range therein between. In some embodiments, the liposome has a diameter of 80 nm to 120 nm, or any range therein between. In some embodiments, the liposome is formed from liposomal components. In further embodiments, the liposomal components comprise at least one of an anionic lipid and a neutral lipid. In further embodiments, the liposomal components comprise at least one selected from: DSPE; DSPE-PEG; DSPE-PEG-maleimide; HSPC; HSPC-PEG; cholesterol; cholesterol-PEG; and cholesterol-maleimide. In further embodiments, the liposomal components comprise at least one selected from: DSPE; DSPE-PEG; DSPE-PEG-FITC; DSPE-PEG-maleimide; cholesterol; and HSPC. In additional embodiments, the liposome further comprises an oxidized phospholipid such as an OxPAPC. In some embodiments, the liposome comprises an OxPAPC that is an oxidized phospholipid containing fragmented oxygenated sn-2 residues, an oxidized phospholipid containing full length oxygenated sn-2 residues, and/or an oxidized phospholipid containing a five-carbon sn-2 residue bearing omega-aldehyde or omega-carboxyl groups. In some embodiments, the liposome comprises an OxPAPC selected from HOdiA-PC, KOdiA-PC, HOOA-PC and KOOA-PC, or the OxPAPC is an epoxyisoprostane-containing phospholipid. In some embodiments, the liposome comprises an OxPAPC selected from 1-palmitoyl-2-(5,6-epoxyisoprostane E2)-sn-glycero-3-phosphocholine (5,6 PEIPC), 1-palmitoyl-2-(epoxy-cyclopentenone)-sn-glycero-3-phosphorylcholine (PECPC), 1-palmitoyl-2-(epoxyisoprostane E2)-sn-glycero-4-phosphocholine (PEIPC), 1-palmitoyl-2-glutaroyl-sn-glycero-3-phosphocholine (PGPC); 1-palmitoyl-2-(9'oxo-nonan-oyl)-sn-glycero-3-phosphocholine; 1-palmitoyl-2-ar-achinodoyl-sn-glycero-3-phosphocholine; 1-palmitoyl-2-myristoyl-sn-glycero-3-phosphocholine; 1-palmit-oyl-2-hexadecyl-sn-glycero-3-phosphocholine; 1-palmitoyl-2-azelaoyl-sn-glycero-3-phosphocholine; and 1-palmitoyl-2-acetoyl-sn-glycero-3-phosphocholine. In some embodiments, the liposome comprises PGPC. In some embodiments, the OxPAPC within the liposome lipid bilayer is 0%-100% of total lipids, or any range therein between. In some embodiments, the liposome comprises a targeting moiety having a specific affinity for a surface antigen on a target cell of interest. In some embodiments, the targeting moiety is attached to one or both of a PEG and the exterior of the liposome, optionally wherein the targeting moiety is attached to one or both of the PEG and the exterior of the liposome by a covalent bond. In some embodiments, the targeting moiety is a polypeptide. In further embodiments, the targeting moiety is an antibody or an antigen binding fragment of an antibody. In some embodiments, the liposome contains 1 to 1000, 50 to 750, 100 to 500, or 30 to 200 targeting moieties, or any range therein between. In some embodiments, the liposome further comprises an immunostimulating agent (such as 1,6-beta glucan). In some embodiments, the liposome comprises a steric stabilizer. In some embodiments, the steric stabilizer is polyethylene glycol (i.e., the liposome is pegylated). In some embodiments, the PEG has a number average molecular weight (Mn) of 200 to 5000 Daltons. In additional embodiments, the liposome is anionic or neutral. In some embodiments, the liposome has a zeta potential that is less than or equal to zero. In some embodiments, the liposome has a zeta potential that is −150 to 0, −50 to 0 mV, −40 to 0 mV, −30 to 0 mV, −25 to 0 mV, −20 to 0 mV, −10 to 0 mV, −9 to 0 mV, −8 to 0 mV, −7 to 0 mV, −6 to 0 mV, −5 to 0 mV, −4 to 0 mV, −3 to 0 mV, −2 to 0 mV, −1 to 0 mV, or −8 to 2 mV, or any range therein between. In other embodiments, the liposome is cationic. In some embodiments, the liposomal composition comprises a liposome that has a zeta potential that is more than zero. In some embodiments, the liposome has a zeta potential that is 0.2 to 150 mV, 1 to 50 mV, 1 to 40 mV, 1 to 30 mV, 1 to 25 mV, 1 to 20 mV, 1 to 15 mV, 1 to 10 mV, 1 to 5 mV, 2 to 10 mV, 3 to 10 mV, 4 to 10 mV, or 5 to 10 mV, or any range therein between.

In some embodiments, the disclosure provides a pharmaceutical composition comprising calcium trans-crocetinate (CTC) encapsulated by a liposome. The CTC can exist in linear and/or cyclic form (shown below).

In some embodiments, the pharmaceutical composition administered according to the provided methods comprises liposomal CTC.

In some embodiments, the liposome contains less than 6 million, less than 500,000, less than 200,000, less than 100,000, less than 50,000, or less than 10,000, molecules of trans-crocetin. In some embodiments, the liposome contains 10 to 100,000, 100 to 10,000, or 1,000 to 5,000, molecules of trans-crocetin, or any range therein between. In some embodiments, the trans-crocetin/lipid ratio of the liposomal composition is 1 g/mol and about 1000 g/mol, or any range therein between. In some embodiments, the trans-crocetin/lipid ratio is 10-150 g/mol, 10-100 g/mol, 30-200 g/mol, 40-200 g/mol, or 50-200 g/mol, or any range therein between. In some embodiments, the liposome comprises at least 0.1% to 97% trans-crocetin. In some embodiments, the liposome has a diameter of 20 nm to 500 nm, or 20 nm to 200 nm, or any range therein between. In some embodiments, the liposome has a diameter of 80 nm to 120 nm, or any range therein between. In some embodiments, the liposome is formed from liposomal components. In further embodiments, the liposomal components comprise at least one of an anionic lipid and a neutral lipid. In further embodiments, the liposomal components comprise at least one selected from: DSPE; DSPE-PEG; DSPE-PEG-maleimide; HSPC; HSPC-PEG; cholesterol; cholesterol-PEG; and cholesterol-maleimide. In further embodiments, the liposomal components comprise at least one selected from: DSPE; DSPE-PEG; DSPE-PEG-FITC; DSPE-PEG-maleimide; cholesterol; and HSPC. In additional embodiments, the liposome further comprises an oxidized phospholipid such as an OxPAPC. In some embodiments, the liposome comprises an OxPAPC that is an oxidized phospholipid containing fragmented oxygenated sn-2 residues, an oxidized phospholipid containing full length oxygenated sn-2 residues, and/or an oxidized phospholipid containing a five-carbon sn-2 residue bearing omega-aldehyde or omega-carboxyl groups. In some embodiments, the liposome comprises an OxPAPC selected from HOdiA-PC, KOdiA-PC, HOOA-PC and KOOA-PC, or the OxPAPC is an epoxyisoprostane-containing phospholipid. In some embodiments, the liposome comprises an OxPAPC selected from 1-palmitoyl-2-(5,6-epoxyisoprostane E2)-sn-glycero-3-phosphocholine (5,6 PEIPC), 1-palmitoyl-2-(epoxy-cyclopentenone)-sn-glycero-3-phosphorylcholine (PECPC), 1-palmitoyl-2-(epoxy-isoprostane E2)-sn-glycero-4-phos-phocholine (PEIPC), 1-palmitoyl-2-glutaroyl-sn-glycero-3-phosphocholine (PGPC); 1-palmitoyl-2-(9'oxononanoyl)-sn-glyc-ero-3-phosphocholine; 1-palmitoyl-2-arachinodoyl-sn-glycero-3-phospho-choline; 1-pa-lmitoyl-2-myristoyl-sn-glycero-3-phosphocholine; 1-palmitoyl-2-hexadecyl-sn-glycero-3-phosphocholine; 1-palmitoyl-2-azelaoyl-sn-glycero-3-phosphocholine; and 1-palmit-oyl-2-acetoyl-sn-glycero-3-phospho-choline. In some embodiments, the liposome comprises PGPC. In some embodiments, the OxPAPC within the liposome lipid bilayer is 0%-100% of total lipids, or any range therein between. In some embodi-ments, the liposome comprises a targeting moiety having a specific affinity for a surface antigen on a target cell of interest. In some embodiments, the targeting moiety is attached to one or both of a PEG and the exterior of the liposome, optionally wherein the targeting moiety is attached to one or both of the PEG and the exterior of the liposome by a covalent bond. In some embodiments, the targeting moiety is a polypeptide. In further embodiments, the targeting moiety is an antibody or an antigen binding fragment of an antibody. In some embodiments, the lipo-some contains 1 to 1000, 50 to 750, 100 to 500, or 30 to 200 targeting moieties, or any range therein between. In some embodiments, the liposome contains less than 500,000 or less than 200,000 molecules of trans-crocetin. In some embodiments, the liposome contains between 10 to 100,000 molecules of trans-crocetin, or any range therein between. In some embodiments, the liposome further comprises an immunostimulating agent (such as 1,6-beta glucan). In some embodiments, the liposome comprises a steric stabilizer. In some embodiments, the steric stabilizer is polyethylene glycol (i.e., the liposome is pegylated). In some embodi-ments, the PEG has a number average molecular weight (Mn) of 200 to 5000 Daltons. In additional embodiments, the liposome is anionic or neutral. In some embodiments, the liposome has a zeta potential that is less than or equal to zero. In some embodiments, the liposome has a zeta poten-tial that is −150 to 0, −50 to 0 mV, −40 to 0 mV, −30 to 0 mV, −25 to 0 mV, −20 to 0 mV, −10 to 0 mV, −9 to 0 mV, −8 to 0 mV, −7 to 0 mV, −6 to 0 mV, −5 to 0 mV, −4 to 0 mV, −3 to 0 mV, −2 to 0 mV, −1 to 0 mV, or −8 to 2 mV, or any range therein between. In other embodiments, the lipo-some is cationic. In some embodiments, the liposomal composition comprises a liposome that has a zeta potential that is more than zero. In some embodiments, the liposome has a zeta potential that is 0.2 to 150 mV, 1 to 50 mV, 1 to 40 mV, 1 to 30 mV, 1 to 25 mV, 1 to 20 mV, 1 to 15 mV, 1 to 10 mV, 1 to 5 mV, 2 to 10 mV, 3 to 10 mV, 4 to 10 mV, or 5 to 10 mV, or any range therein between.

In some embodiments, the disclosure provides a pharma-ceutical composition comprising magnesium trans-croceti-nate (MTC) encapsulated by a liposome. The MTC can exist in linear and/or cyclic form (shown below).

In some embodiments, the pharmaceutical composition administered according to the provided methods comprises liposomal CTC.

In some embodiments, the liposome contains less than 6 million, less than 500,000, less than 200,000, less than 100,000, less than 50,000, or less than 10,000, molecules of trans-crocetin. In some embodiments, the liposome contains 10 to 100,000, 100 to 10,000, or 500 to 5,000, molecules of trans-crocetin, or any range therein between. In some embodiments, the trans-crocetin/lipid ratio is 10-150 g/mol, 10-100 g/mol, 30-200 g/mol, 40-200 g/mol, or 50-200 g/mol, or any range therein between. In some embodiments, the liposome comprises at least 0.1% to 97% trans-crocetin. In some embodiments, the liposome has a diameter of 20 nm to 500 nm, or 20 nm to 200 nm, or any range therein between. In some embodiments, the liposome has a diameter of 80 nm to 120 nm, or any range therein between. In some embodiments, the liposome is formed from liposomal com-ponents. In further embodiments, the liposomal components comprise at least one of an anionic lipid and a neutral lipid. In further embodiments, the liposomal components com-prise at least one selected from: DSPE; DSPE-PEG; DSPE-PEG-maleimide; HSPC; HSPC-PEG; cholesterol; choles-terol-PEG; and cholesterol-maleimide. In further embodiments, the liposomal components comprise at least one selected from: DSPE; DSPE-PEG; DSPE-PEG-FITC; DSPE-PEG-maleimide; cholesterol; and HSPC. In addi-tional embodiments, the liposome further comprises an oxidized phospholipid such as an OxPAPC. In some embodiments, the liposome comprises an OxPAPC that is an oxidized phospholipid containing fragmented oxygenated sn-2 residues, an oxidized phospholipid containing full length oxygenated sn-2 residues, and/or an oxidized phos-pholipid containing a five-carbon sn-2 residue bearing omega-aldehyde or omega-carboxyl groups. In some embodiments, the liposome comprises an OxPAPC selected from HOdiA-PC, KOdiA-PC, HOOA-PC and KOOA-PC, or the OxPAPC is an epoxyisoprostane-containing phospho-lipid. In some embodiments, the liposome comprises an OxPAPC selected from 1-palmitoyl-2-(5,6-epoxyisopros-tane E2)-sn-glycero-3-phosphocholine (5,6 PEIPC), 1-palmitoyl-2-(epoxy-cyclopentenone)-sn-glycero-3-phos-phorylcholine (PECPC), 1-palmitoyl-2-(epoxyiso-prostane E2)-sn-glycero-4-phosphocholine (PEIPC), 1-palmitoyl-2-glutaroyl-sn-glycero-3-phosphocholine (PGPC); 1-palmi-toyl-2-(9'oxo-nonanoyl)-sn-glycero-3-phosphochol-ine; 1-palmitoyl-2-arachinodoyl-sn-glycero-3-phospho-choline; 1-palmitoyl-2-myristoyl-sn-glycero-3-phospho-choline; 1-palmitoyl-2-hexadecyl-sn-glycero-3-phosphocholine; 1-palmitoyl-2-azelaoyl-sn-glycero-3-phosphocholine; and 1-palmitoyl-2-acetoyl-sn-gly-cero-3-phosphocholine. In some embodiments, the liposome comprises PGPC. In some embodiments, the OxPAPC within the liposome lipid bilayer is 0%4-100% of total lipids, or any range therein between. In some embodiments, the liposome comprises a targeting moiety having a specific affinity for a surface antigen on a target cell of interest. In some embodiments, the targeting moiety is attached to one or both of a PEG and the exterior of the liposome, optionally wherein the targeting moiety is attached to one or both of the PEG and the exterior of the liposome by a covalent bond. In some embodiments, the targeting moiety is a polypeptide. In further embodiments, the targeting moiety is an antibody or an antigen binding fragment of an antibody. In some embodiments, the lipo-some contains 1 to 1000, 50 to 750, 100 to 500, or 30 to 200 targeting moieties, or any range therein between. In some embodiments, the liposome further comprises an immunostimulating agent (such as 1,6-beta glucan). In some embodiments, the liposome comprises a steric stabilizer. In some embodiments, the steric stabilizer is polyethylene glycol (i.e., the liposome is pegylated). In some embodiments, the PEG has a number average molecular weight (Mn) of 200 to 5000 Daltons. In additional embodiments, the liposome is anionic or neutral. In some embodiments, the liposome has a zeta potential that is less than or equal to zero. In some embodiments, the liposome has a zeta potential that is −150 to 0, −50 to 0 mV, −40 to 0 mV, −30 to 0 mV, −25 to 0 mV, −20 to 0 mV, −10 to 0 mV, −9 to 0 mV, −8 to 0 mV, −7 to 0 mV, −6 to 0 mV, −5 to 0 mV, −4 to 0 mV, −3 to 0 mV, −2 to 0 mV, −1 to 0 mV, or −8 to 2 mV, or any range therein between. In other embodiments, the liposome is cationic. In some embodiments, the liposomal composition comprises a liposome that has a zeta potential that is more than zero. In some embodiments, the liposome has a zeta potential that is 0.2 to 150 mV, 1 to 50 mV, 1 to 40 mV, 1 to 30 mV, 1 to 25 mV, 1 to 20 mV, 1 to 15 mV, 1 to 10 mV, 1 to 5 mV, 2 to 10 mV, 3 to 10 mV, 4 to 10 mV, or 5 to 10 mV, or any range therein between.

Formulation and Administration

The provided compositions can be formulated in whole or in part as pharmaceutical compositions. Pharmaceutical compositions may include one or more nanoparticle compositions. For example, a pharmaceutical composition may include one or more nanoparticle compositions including one or more different therapeutic and/or prophylactics. Pharmaceutical compositions may further include one or more pharmaceutically acceptable excipients or accessory ingredients such as those described herein. General guidelines for the formulation and manufacture of pharmaceutical compositions and agents are available, for example, in Remington's The Science and Practice of Pharmacy, 21st Edition, A. R. Gennaro; Lippincott, Williams & Wilkins, Baltimore, Md., 2006. Conventional excipients and accessory ingredients may be used in any pharmaceutical composition, except insofar as any conventional excipient or accessory ingredient may be incompatible with one or more components of a nanoparticle composition. An excipient or accessory ingredient may be incompatible with a component of a nanoparticle composition if its combination with the component may result in any undesirable biological effect or otherwise deleterious effect.

In some embodiments, one or more excipients or accessory ingredients may make up greater than 50% of the total mass or volume of a pharmaceutical composition including a nanoparticle composition. For example, the one or more excipients or accessory ingredients may make up 50%, 60%, 70%, 80%, 90%, or more of a pharmaceutical convention. In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Standard methods for making liposomes include, but are not limited to methods reported in Liposomes: A Practical Approach, V. P. Torchilin, Volkmar Weissig Oxford University Press, 2003 and are known in the art.

In some embodiments, the disclosure provides a trans-crocetin composition and a physiologically (i.e., pharmaceutically) acceptable carrier. As used herein, the term "carrier" refers to a typically inert substance used as a diluent or vehicle for a drug such as a therapeutic agent. The term also encompasses a typically inert substance that imparts cohesive qualities to the composition. Typically, the physiologically acceptable carriers are present in liquid form. Examples of liquid carriers include physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Since physiologically acceptable carriers are determined in part by the particular composition being administered as well as by the particular method used to administer the composition, there are a wide variety of suitable formulations of pharmaceutical compositions provided herein (See, e.g., Remington's Pharmaceutical Sciences, 17th ed., 1989).

The provided compositions may be sterilized by conventional, known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized trans-crocetin compositions. In some embodiments, the pharmaceutical composition comprises a tonicity agent at a concentration of greater than 0.1%, or a concentration of 0.3% to 2.5%, 0.5% to 2.0%, 0.5% to 1.5%, 0.5% to 1.5%, 0.6% to 1.1%, or any range therein between. In some embodiments, the pharmaceutical composition comprises a tonicity agent such as dextrose, mannitol, glycerin, potassium chloride, or sodium chloride. In further embodiments, the pharmaceutical composition comprises dextrose, mannitol, glycerin, potassium chloride, or sodium chloride at a concentration of greater than 0.1%, or a concentration of 0.3% to 2.5%, 0.5% to 2.0%, 0.5% to 1.5%, 0.5% to 1.5%, 0.6% to 1.1%, or any range therein between.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In some embodiments, the provided trans-crocetin compositions are administered, for example, by intravenous infusion, topically, intraperitoneally, intravesically, or intrathecally. In particular embodiments, the trans-crocetin compositions are parentally or intravenously administered. Preferably, the trans-crocetin compositions are administered parentally, i.e. intraarticularly, intravenously, subcutaneously, or intramuscularly. In other embodiments, the pharmaceutical preparation may be administered topically.

In some embodiments, one or more of the provided trans-crocetin compositions are administered as an intravenous infusion. In some embodiments, one or more trans-crocetin compositions is administered as an intravenous infusion over 15 minutes to 5 hours, or any range therein between. In some embodiments, one or more trans-crocetin compositions is administered as an intravenous infusion over 2 hours to 4 hours, or any range therein between. In some embodiments, the one or more trans-crocetin compositions is administered over 3 hours. In some embodiments, the trans-crocetin composition is administered as an intravenous infusion four times a day, three times a day, 2 times a day, once a day, once every other day, once every 3 days, once every 4 days, once every 5 days, once every 6 days, twice a week, once weekly, once every other week, or once a month, for 1, 2, 3, 4, 5, 6, 7, 8, 9, 10, 15, or 20 days, or more. In some embodiments, the trans-crocetin composition is administered as an intravenous infusion two times a day (e.g., every 12 hours (+/−3 hours)), for 1, 2, 3, 4, 5, 6, 7, 8, 9, 10, 15, or 20 days, or more. In some embodiments, the trans-crocetin composition is administered as an intravenous infusion once a day (e.g., every 24 hours (+/−9 hours)), for 1, 2, 3, 4, 5, 6, 7, 8, 9, 10, 15, or 20 days, or more.

In some embodiments, one or more liposomal trans-crocetin compositions is administered as an intravenous infusion. In some embodiments, the one or more liposomal trans-crocetin composition is administered as an intravenous infusion over 15 minutes to 5 hours, or any range therein between. In some embodiments, the one or more liposomal trans-crocetin composition is administered as an intravenous infusion over 2 hours to 4 hours, or any range therein between. In some embodiments, the one or more liposomal trans-crocetin composition is administered as an intravenous infusion over 3 hours. In some embodiments, the liposomal trans-crocetin composition is administered as an intravenous infusion four times a day, three times a day, 2 times a day, once a day, once every other day, once every 3 days, once every 4 days, once every 5 days, once every 6 days, twice a week, once weekly, once every other week, or once a month, for 1, 2, 3, 4, 5, 6, 7, 8, 9, 10, 15, or 20 days, or more. In some embodiments, the liposomal trans-crocetin composition is administered as an intravenous infusion two times a day (e.g., every 12 hours (+/−3 hours)), for 1, 2, 3, 4, 5, 6, 7, 8, 9, 10, 15, or 20 days, or more. In some embodiments, the liposomal trans-crocetin composition is administered as an intravenous infusion once a day (e.g., every 24 hours (+/−9 hours)), for 1, 2, 3, 4, 5, 6, 7, 8, 9, 10, 15, or 20 days, or more.

In particular embodiments, one or more liposomal trans-crocetin compositions at a dosage of 2.5 mg/kg to 7.5 mg/kg, or any range therein between, is administered as an intravenous infusion. In some embodiments, one or more liposomal trans-crocetin compositions at a dosage of 4 mg/kg to 7.5 mg/kg (e.g., 5 mg/kg), or any range therein between, is administered as an intravenous infusion. In some embodiments, one or more liposomal trans-crocetin compositions at a dosage of 2 mg/kg to 4 mg/kg (e.g., 2.5 mg/kg), or any range therein between, is administered as an intravenous infusion. In some embodiments, the one or more liposomal trans-crocetin composition is administered as an intravenous infusion over 15 minutes to 5 hours, or any range therein between. In some embodiments, the one or more liposomal trans-crocetin composition is administered as an intravenous infusion over 2 hours to 4 hours, or any range therein between. In particular embodiments, one or more liposomal trans-crocetin compositions at a dosage of 4 mg/kg to 7.5 mg/kg (e.g., 5 mg/kg), or any range therein between, is administered as an intravenous infusion over 2 hours to 4 hours, or any range therein between. In other particular embodiments, one or more liposomal trans-crocetin compositions at a dosage of 2 mg/kg to 4 mg/kg (e.g., 2.5 mg/kg), or any range therein between, is administered as an intravenous infusion over 2 hours to 4 hours, or any range therein between. In additional embodiments, one or more liposomal trans-crocetin compositions at a dosage of 4 mg/kg to 7.5 mg/kg (e.g., 5 mg/kg), or any range therein between, is administered as an intravenous infusion over 3 hours. In other particular embodiments, one or more liposomal trans-crocetin compositions at a dosage of 2 mg/kg to 4 mg/kg (e.g., 2.5 mg/kg), or any range therein between, is administered as an intravenous infusion over 3 hours. In some embodiments, the liposomal trans-crocetin composition is administered as an intravenous infusion four times a day, three times a day, 2 times a day, once a day, once every other day, once every 3 days, once every 4 days, once every 5 days, once every 6 days, twice a week, once weekly, once every other week, or once a month, for 1, 2, 3, 4, 5, 6, 7, 8, 9, 10, 15, or 20 days, or more. In some embodiments, the liposomal trans-crocetin composition is administered as an intravenous infusion two times a day (e.g., every 12 hours (+/−3 hours)), for 1, 2, 3, 4, 5, 6, 7, 8, 9, 10, 15, or 20 days, or more. In some embodiments, the liposomal trans-crocetin composition is administered as an intravenous infusion once a day (e.g., every 24 hours (+/−9 hours)), for 1, 2, 3, 4, 5, 6, 7, 8, 9, 10, 15, or 20 days, or more.

In some embodiments, one or more liposomal trans-crocetin compositions is administered as an intravenous infusion. In some embodiments, the one or more liposomal trans-crocetin composition is administered as an intravenous infusion over 15 minutes to 5 hours, or any range therein between. In some embodiments, the one or more liposomal trans-crocetin composition is administered as an intravenous infusion over 2 hours to 4 hours, or any range therein between. In some embodiments, the one or more liposomal trans-crocetin composition is administered as an intravenous infusion over 3 hours.

In some embodiments, the provided pharmaceutical compositions (e.g., liposomal compositions are presented in unit-dose or multi-dose sealed containers, such as ampoules and vials.

In some embodiments, the pharmaceutical preparations are administered in unit dosage form. In such form the preparation is subdivided into unit doses containing appropriate quantities of trans-crocetin. The unit dosage form can be a packaged preparation, the package containing discrete quantities of preparation. The composition can, if desired, also contain other compatible therapeutic agents (e.g., as described herein).

In some embodiments, the trans-crocetin pharmaceutical compositions provided herein are administered at the initial dosage of about 0.05 mg/kg to about 25 mg/kg a day. A day dose range of about 0.01 mg/kg to about 25 mg/kg, 2 mg/kg to 10 mg/kg, 2.5 mg/kg to 7.5 mg/kg, or 2.5 mg/kg to 5 mg/kg (e.g., 2.5 mg/kg, 5 mg/kg, or 7.5 mg/kg trans-crocetin). In some embodiments, two or more trans-crocetin pharmaceutical compositions are administered to a subject at 1 hour to 48 hours, 1.5 hours to 24 hours, 2 hours to 18 hours, 4 hours to 16 hours (e.g., 12 hours (+/−3 hours)), or 1 hour to 8 hours (e.g., 3 hours) apart, or any range therein between. In some embodiments, two or more pharmaceutical compositions are administered to a subject four times a day, three times a day, twice a day, once a day, or once every other day.

The dosages, however, may be varied depending upon the requirements of the patient, the severity of the condition being treated, and the trans-crocetin composition being employed. For example, dosages can be empirically determined considering the type and stage of the disorder or condition diagnosed in a particular patient. The dose administered to a patient, in the context of the provided liposomal trans-crocetin pharmaceutical compositions should be sufficient to affect a beneficial therapeutic response in the patient over time. The size of the dose will also be determined by the existence, nature, and extent of any adverse side-effects that accompany the administration of a particular liposome composition in a particular patient. Determination of the proper dosage for a particular situation is within the skill of the practitioner. Generally, treatment is initiated with smaller dosages which are less than the optimum dose of the liposome composition. Thereafter, the dosage is increased by small increments until the optimum effect under circumstances is reached. For convenience, the total a day dosage may be divided and administered in portions during the day, if desired.

In particular embodiments, the administered trans-crocetin is in a liposomal composition and is administered to a subject (e.g., human) at a dosage sufficient to achieve a trans-crocetin serum concentration of about 0.4 to ug/ml to 49.2 ug/ml or any range therein between. In some embodiments, the liposomal composition is administered at a dosage sufficient to achieve a trans-crocetin serum concentration of about 12 ug/ml to 49.2 ug/ml, 15 to ug/ml to 49.2 ug/ml, or 20 to ug/ml to 49.2 ug/ml, or any range therein between. In particular embodiments, the liposomal composition is administered to a subject (e.g., human) at a dosage of about 2 mg/kg to about 10 mg/kg. In some embodiments, the liposomal trans-crocetin is administered at a dosage of about 2.5 mg/kg to about 7.5 mg/kg, or any range therein between. In some embodiments, the liposomal trans-crocetin is administered at a dosage of about 7.5 mg/kg. In some embodiments, the liposomal trans-crocetin is administered at a dosage of about 5.0 mg/kg. In some embodiments, the liposomal trans-crocetin is administered at a dosage of about 2.5 mg/kg. In some embodiments, the liposomal trans-crocetin is administered 4 times a day, 3 times a day, 2 times a day, once a day, once every other day, once every 3 days, once every 4 days, once every 5 days, once every 6 days, twice a week, once weekly, once every other week, or once a month. In a particular embodiment, the liposomal trans-crocetin is administered to a subject twice a day (e.g., 12 hours, +/−6 hours), once every other day, or once a week. In another particular embodiment, the liposome encapsulated trans-crocetin is administered once a day (e.g., 24 hours (+/−9 hours). In a further embodiment, the liposomal trans-crocetin is administered at a dosage of about 7.5 mg/kg once a day. In another further embodiment, the liposomal trans-crocetin is administered at a dosage of about 5.0 mg/kg once a day. In another further embodiment, the liposomal trans-crocetin is administered at a dosage of about 2.5 mg/kg once a day. In yet a further embodiment, the liposomal trans-crocetin is administered to a subject at a dosage of about 5.0 mg/kg (e.g., once, or once a day) followed by the administration of liposomal trans-crocetin at a dosage of about 2.5 mg/kg within 24-36 hours after the administration of the 5.0 mg/kg dose. In some embodiments, the administered liposome composition comprises liposomes having a diameter of 80 nm to 120 nm (e.g., 90 nm to 110, 95 nm to 109 nm), or any range therein between. In some embodiments, the administered liposome composition comprises liposomes having a zeta potential of −15 to −1 mV (e.g., −10 to −1 mV, or −5 to −1 mV), or any range therein between. In some embodiments, the administered liposome composition comprises liposomes having a diameter of 80 nm to 120 nm (e.g., 90 nm to 110, 95 nm to 109 nm), or any range therein between, and liposomes having a zeta potential of −15 to −1 mV (e.g., −10 to −1 mV, or −5 to −1 mV), or any range therein between. In further embodiments, the liposome composition has a PDI of 0.020 to 0.075 (e.g., 0.030 to 0.050), or any range therein between.

In another particular embodiment, the liposome encapsulated trans-crocetin is administered twice a week. In a further particular embodiment, the liposome encapsulated trans-crocetin is administered once a month. In a particular embodiment, liposomal trans-crocetin is administered once a day. In another particular embodiment, the liposome encapsulated trans-crocetin is administered twice a week. In some embodiments, the liposome encapsulated trans-crocetin is administered once every three days. In a further particular embodiment, the liposome encapsulated trans-crocetin is administered once a month. In particular embodiments, the liposomal trans-crocetin is administered to a subject (e.g., a human) experiencing acute lung distress (e.g., presenting symptoms such as having difficulty breathing, tachypnea, mental confusion due to low oxygen levels) and/or having a PaO2/FiO2 ratio of less than 300 mm Hg. In other particular embodiments, the liposomal trans-crocetin is administered to a subject (e.g., a human) experiencing Acute Respiratory ARDS and/or having a PaO2/FiO2 ratio of less than 200 mm Hg. In other particular embodiments, the liposomal trans-crocetin is administered to a subject in order to increase the patients PaO2/FiO2 ratio. In some embodiments, the administration of the liposomal trans-crocetin increases the patient's PaO2/FiO2 ratio by at least 5%-75%, or any range therein between, after 4, 3, 2, or 1 day(s) of trans-crocetin treatment. In further embodiments, the administration of the liposomal trans-crocetin increases the patient's PaO2/FiO2 ratio by at least 5%, 10%, 15%, 20%, 25%, 30% 40% or 50%, after 4, 3, 2, or 1 day(s) of trans-crocetin treatment. In particular embodiments, the administration of the liposomal trans-crocetin increases the patient's PaO2/FiO2 ratio by at least 10%, after 4, 3, 2, or 1 day(s) of trans-crocetin treatment. In other particular embodiments, the administration of the liposomal trans-crocetin increases the patient's PaO2/FiO2 ratio by at least 25%, after 4, 3, 2, or 1 day(s) of trans-crocetin treatment. In other particular embodiments, the administration of the liposomal trans-crocetin increases the patient's PaO2/FiO2 ratio by at least 40%, after 4, 3, 2, or 1 day(s) of trans-crocetin treatment Animal toxicology studies have indicated efficacy without dose limiting toxicity at liposomal trans-crocetin doses as high as 25 mg/kg. As disclosed herein, dose limiting toxicity of liposomal trans-crocetin has not been observed in humans and liposomal trans-crocetin has been administered at doses as high as 7.5 mg/kg in humans. In particular embodiments, the administered composition comprises liposomal trans-crocetin and is administered to a subject (e.g., human) at a dosage of about 2 mg/kg to about 15 mg/kg or 2 mg/kg to about 10 mg/kg, or any range therein between. In some embodiments, the liposomal trans-crocetin is administered at a dosage of about 2.5 mg/kg to about 7.5 mg/kg, or any range therein between. In a particular embodiment, the liposomal trans-crocetin is administered at a dosage of about 2.5 mg/kg. In another particular embodiment, the liposomal trans-crocetin is administered at a dosage of about 5 mg/kg. In a further particular embodiment, the liposomal trans-crocetin is administered at a dosage of about 7.5 mg/kg. In some embodiments, liposomal trans-crocetin is administered 4 times a day, 3 times a day, 2 times a day, once a day, once every other day, once every 3 days, once every 4 days, once every 5 days, once every 6 days, twice a week, once weekly, once every other week, or once a month. In a particular embodiment, liposomal trans-crocetin is administered once or twice a day (e.g., every 24 hours, +/−9 hours), once every other day, or once a week. In one embodiment, the liposome encapsulated trans-crocetin is administered once a day. In another embodiment, the liposome encapsulated trans-crocetin is administered twice a week. In some embodiments, the liposome encapsulated trans-crocetin is administered once every three days. In a further embodiment, the liposome encapsulated trans-crocetin is administered once a week. In a particular embodiment, the liposome encapsulated trans-crocetin is administered once a day. In some embodiments, the administered liposome composition comprises liposomes having a diameter of 80 nm to 120 nm (e.g., 90 nm to 110, 95 nm to 109 nm), or any range therein between. In some embodiments, the administered liposome composition comprises liposomes having a zeta potential of −15 to −1 mV (e.g., −10 to −1 mV, or −5 to −1 mV), or any range therein between. In some embodiments, the administered liposome composition comprises liposomes having a diameter of 80 nm to 120 nm (e.g., 90 nm to 110, 95 nm to 109 nm), or any range therein between, and liposomes having a zeta potential of −15 to −1 mV (e.g., −10 to −1 mV, or −5 to −1 mV), or any range therein between. In further embodiments, the liposome composition has a PDI of 0.020 to 0.075 (e.g., 0.030 to 0.050), or any range therein between.

In some embodiments, the liposomal trans-crocetin is administered at a dosage of about 2.5 mg/kg trans-crocetin and comprises liposomes having a diameter of 80 nm to 120 nm (e.g., 90 nm to 110, 95 nm to 109 nm), or any range therein between, and liposomes having a zeta potential of −15 to −1 mV (e.g., −10 to −1 mV, or −5 to −1 mV), or any range therein between. In further embodiments, the liposome composition has a PDI of 0.020 to 0.075 (e.g., 0.030 to 0.050), or any range therein between. In some embodiments, the liposomal trans-crocetin is administered once a day (e.g., every 24 hours (+/−9 hours). In some embodiments, liposomal trans-crocetin and is administered 3 times a day, 2 times a day, once a day, once every other day, once every 3 days, once every 4 days, once every 5 days, once every 6 days, twice a weekly, once weekly, once every other week, or once a month. In a particular embodiment, liposomal trans-crocetin is administered once or twice a day (e.g., every 24 hours (+/−9 hours)), once every other day, or once a week. In a particular embodiment, the liposome encapsulated trans-crocetin is administered once a day.

In some embodiments, the liposomal trans-crocetin is administered at a dosage of about 5 mg/kg trans-crocetin and comprises liposomes having a diameter of 80 nm to 120 nm (e.g., 90 nm to 110, 95 nm to 109 nm), or any range therein between, and liposomes having a zeta potential of −15 to −1 mV (e.g., −10 to −1 mV, or −5 to −1 mV), or any range therein between. In further embodiments, the liposome composition has a PDI of 0.020 to 0.075 (e.g., 0.030 to 0.050), or any range therein between. In some embodiments, the liposomal trans-crocetin is administered once a day (e.g., every 24 hours (+/−9 hours). In some embodiments, liposomal trans-crocetin and is administered 3 times a day, 2 times a day, once a day, once every other day, once every 3 days, once every 4 days, once every 5 days, once every 6 days, twice a weekly, once weekly, once every other week, or once a month. In a particular embodiment, liposomal trans-crocetin is administered once or twice a day (e.g., every 24 hours (+/−9 hours)), once every other day, or once a week. In a particular embodiment, the liposome encapsulated trans-crocetin is administered once a day In some embodiments, the liposomal trans-crocetin is administered at a dosage of about 7.5 mg/kg trans-crocetin and comprises liposomes having a diameter of 80 nm to 120 nm (e.g., 90 nm to 110, 95 nm to 109 nm), or any range therein between, and liposomes having a zeta potential of −15 to −1 mV (e.g., −10 to −1 mV, or −5 to −1 mV), or any range therein between. In further embodiments, the liposome composition has a PDI of 0.020 to 0.075 (e.g., 0.030 to 0.050), or any range therein between. In some embodiments, the liposomal trans-crocetin is administered once a day (e.g., every 24 hours (+/−9 hours). In some embodiments, liposomal trans-crocetin and is administered 3 times a day, 2 times a day, once a day, once every other day, once every 3 days, once every 4 days, once every 5 days, once every 6 days, twice a weekly, once weekly, once every other week, or once a month. In a particular embodiment, liposomal trans-crocetin is administered once or twice a day (e.g., every 24 hours (+/−9 hours)), once every other day, or once a week. In a particular embodiment, the liposome encapsulated trans-crocetin is administered once a day In some embodiments, the administration of liposomal trans-crocetin increases the patient's PaO2/FiO2 ratio by 5%-75%, or any range therein between, after 4, 3, 2, or 1 day(s) of trans-crocetin treatment. In some embodiments, the administration of the liposomal trans-crocetin increases the patient's PaO2/FiO2 ratio by 10%-50%, or any range therein between, after 4, 3, 2, or 1 day(s) of trans-crocetin treatment. In further embodiments, the administration of the liposomal trans-crocetin increases the patient's PaO2/FiO2 ratio by at least 5%, 10%, 15%, 20%, 25%, 30% 40% or 50%, or any range therein between, after 4, 3, 2, or 1 day(s) of trans-crocetin treatment In some embodiments, the administered liposome composition comprises liposomes having a diameter of 80 nm to 120 nm (e.g., 90 nm to 110, 95 nm to 109 nm), or any range therein between. In some embodiments, the administered liposome composition comprises liposomes having a zeta potential of −15 to −1 mV (e.g., −10 to −1 mV, or −5 to −1 mV), or any range therein between. In some embodiments, the administered liposome composition comprises liposomes having a diameter of 80 nm to 120 nm (e.g., 90 nm to 110, 95 nm to 109 nm), or any range therein between, and liposomes having a zeta potential of −15 to −1 mV (e.g., −10 to −1 mV, or −5 to −1 mV), or any range therein between. In further embodiments, the liposome composition has a PDI of 0.020 to 0.075 (e.g., 0.030 to 0.050), or any range therein between.

In some embodiments, the dose of trans-crocetin administered to a patient depends on the type of disorder or condition to be treated, the severity and the course of the disease, whether the trans-crocetin is administered for preventive or therapeutic purposes, previous therapy, the patient's clinical history and response to the trans-crocetin, and the discretion of the attending physician. The dose is suitably administered to the patient at one time or over a series of treatments.

In particular embodiments, liposomal trans-crocetin is administered to a subject (e.g., a human) experiencing acute lung distress (e.g., presenting symptoms such as having difficulty breathing, tachypnea, mental confusion (e.g., due to low oxygen levels)) and/or having a PaO2/FiO2 ratio of less than 300 mm Hg or less than 250 mm Hg. In other particular embodiments, the trans-crocetin is administered to a subject (e.g., a human) experiencing ARDS and/or having a PaO2/FiO2 ratio of less than 200 mm Hg. In other particular embodiments, trans-crocetin is administered to a subject in order to increase the patients PaO2/FiO2 ratio. In some embodiments, the administration of trans-crocetin increases the patient's PaO2/FiO2 ratio by 5%-75%, or any range therein between. In some embodiments, administration of the liposomal trans-crocetin increases the patient's PaO2/FiO2 ratio by 10%-50%, or any range therein between, after 4, 3, 2, or 1 day(s) of trans-crocetin treatment. In further embodiments, the administration of the trans-crocetin increases the patient's PaO2/FiO2 ratio by at least 5%, 10%, 15%, 20%, 25%, 30% 40% or 50%, after 4, 3, 2, or 1 day(s) of trans-crocetin treatment.

In some embodiments, liposomal trans-crocetin is administered to a subject (e.g., a human) experiencing acute lung distress (e.g., presenting symptoms such as having difficulty breathing, tachypnea, mental confusion (e.g., due to low oxygen levels)) and/or having a PaO2/FiO2 ratio of less than 300 mm Hg or less than 250 mm Hg. In other embodiments, liposomal trans-crocetin is administered to a subject (e.g., a human) experiencing ARDS and/or having a PaO2/FiO2 ratio of less than 200 mm Hg. In other embodiments, liposomal trans-crocetin is administered to a subject in order to increase the patients PaO2/FiO2 ratio. In some embodiments, the administration of liposomal trans-crocetin increases the patient's PaO2/FiO2 ratio by 5%-75%, or any range therein between, after 4, 3, 2, or 1 day(s) of trans-crocetin treatment. In some embodiments, the administration of the liposomal trans-crocetin increases the patient's PaO2/FiO2 ratio by 10%-50%, or any range therein between, after 4, 3, 2, or 1 day(s) of trans-crocetin treatment. In further embodiments, the administration of the liposomal trans-crocetin increases the patient's PaO2/FiO2 ratio by at least 5%, 10%, 15%, 20%, 25%, 30% 40% or 50%, or any range therein between, after 4, 3, 2, or 1 day(s) of trans-crocetin treatment.

In some embodiments, liposomal trans-crocetin is administered at a dosage of about 2.5 mg/kg to about 7.5 mg/kg, or any range therein between, 3 times a day, 2 times a day, once a day, once every other day, once every 3 days, once every 4 days, once every 5 days, once every 6 days, twice a weekly, once weekly, once every other week, or once a month. In a particular embodiment, liposome encapsulated trans-crocetin is administered once or twice a day (e.g., every 24 hours (+/−9 hours)), once every other day, or once a week. In some embodiments, administered trans-crocetin is liposomal trans-crocetin and is administered once a day. In some embodiments, liposomal trans-crocetin is administered twice a week. In some embodiments, liposomal trans-crocetin is administered once every three days. In some embodiments, liposomal trans-crocetin is administered once a month. In particular embodiments, liposomal trans-crocetin is administered to a subject (e.g., human) experiencing acute lung distress (e.g., presenting symptoms such as having difficulty breathing, tachypnea, or mental confusion due to low oxygen levels) and/or having a PaO2/FiO2 ratio of less than 300 mm Hg or less than 250 mm Hg. In other particular embodiments, liposomal trans-crocetin is administered to a subject (e.g., human) experiencing Acute Respiratory Distress Syndrome (ARDS) and/or having a PaO2/FiO2 ratio of less than 200 mm Hg. In other particular embodiments, the liposomal trans-crocetin is administered to a subject in order to increase the patients PaO2/FiO2 ratio. In some embodiments, administration of the liposomal trans-crocetin increases the patient's PaO2/FiO2 ratio by 5%-75%, or any range therein between, after 4, 3, 2, or 1 day(s) of trans-crocetin treatment. In some embodiments, administration of the liposomal trans-crocetin increases the patient's PaO2/FiO2 ratio by 10%-50%, or any range therein between, after 4, 3, 2, or 1 day(s) of trans-crocetin treatment. In further embodiments, the administration of the liposomal trans-crocetin increases the patient's PaO2/FiO2 ratio by at least 5%, 10%, 15%, 20%, 25%, 30%40% or 50%, or any range therein between, after 4, 3, 2, or 1 day(s) of trans-crocetin treatment.

In some embodiments, liposomal trans-crocetin is administered at a dosage of 2.5 mg/kg to 7.5 mg/kg, or any range therein between, three times a day, 2 times a day, once a day, once every other day, once every 3 days, once every 4 days, once every 5 days, once every 6 days, twice a week, once weekly, once every other week, or once a month. In a particular embodiment, the liposomal trans-crocetin is administered once a day (e.g., every 24 hours (+/−9 hours)), or twice a day (e.g., every 12 hours (+/−3 hours)), once every other day, or once a week. In some embodiments, the liposomal trans-crocetin is administered twice a day. In some embodiments, the liposomal trans-crocetin is administered once a day. In some embodiments, the liposomal trans-crocetin is administered twice a week. In some embodiments, the liposomal trans-crocetin is administered once every three days. In some embodiments, the liposomal trans-crocetin is administered once a month. In particular embodiments, liposomal trans-crocetin is administered at a dosage of 2.5 mg/kg to 7.5 mg/kg, or any range therein between, once a days. In particular embodiments, liposomal trans-crocetin is administered at a dosage of 2.5 mg/kg to 7.5 mg/kg, or any range therein between, once a day for 1, 2, 3, 4, 5, 6, 7, 8, 9, 10, 15, 20, or more days In some embodiments, administration of the liposomal trans-crocetin increases the patient's PaO2/FiO2 ratio by 5%-75%, or any range therein between, after 4, 3, 2, or 1 day(s) of trans-crocetin treatment. In particular embodiments, the administration of the liposomal trans-crocetin increases the patient's PaO2/FiO2 ratio by at least 20% after 4, 3, 2, or 1 day(s) of trans-crocetin treatment. In further particular embodiments, the administration of the liposomal trans-crocetin increases the patient's PaO2/FiO2 ratio by at least 25% after 4, 3, 2, or 1 day(s) of trans-crocetin treatment. In further particular embodiments, the administration of the liposomal trans-crocetin increases the patient's PaO2/FiO2 ratio by at least 30% after 4, 3, 2, or 1 day(s) of trans-crocetin treatment.

In some embodiments, liposomal trans-crocetin is administered at a dosage of about 2.5 mg/kg, three times a day, 2 times a day, once a day, once every other day, once every 3 days, once every 4 days, once every 5 days, once every 6 days, twice a week, once weekly, once every other week, or once a month. In a particular embodiment, the liposomal trans-crocetin is administered once a day (e.g., every 24 hours (+/−9 hours)), or twice a day (e.g., every 12 hours (+/−3 hours)), once every other day, or once a week. In some embodiments, the liposomal trans-crocetin is administered twice a day. In some embodiments, the liposomal trans-crocetin is administered once a day. In some embodiments, the liposomal trans-crocetin is administered twice a week. In some embodiments, the liposomal trans-crocetin is administered once every three days. In some embodiments, the liposomal trans-crocetin is administered once a month. In particular embodiments, liposomal trans-crocetin is administered at a dosage of about 2.5 mg/kg once a day. In particular embodiments, liposomal trans-crocetin is administered at a dosage of about 2.5 mg/kg once a day for 1, 2, 3, 4, 5, 6, 7, 8, 9, 10, 15, 20, or more days In some embodiments, administration of the liposomal trans-crocetin increases the patient's PaO2/FiO2 ratio by 5%-75%, or any range therein between, after 4, 3, 2, or 1 day(s) of trans-crocetin treatment. In particular embodiments, the administration of the liposomal trans-crocetin increases the patient's PaO2/FiO2 ratio by at least 20% after 4, 3, 2, or 1 day(s) of trans-crocetin treatment. In further particular embodiments, the administration of the liposomal trans-crocetin increases the patient's PaO2/FiO2 ratio by at least 25% after 4, 3, 2, or 1 day(s) of trans-crocetin treatment. In further particular embodiments, the administration of the liposomal trans-crocetin increases the patient's PaO2/FiO2 ratio by at least 30% after 4, 3, 2, or 1 day(s) of trans-crocetin treatment.

In particular embodiments, liposomal trans-crocetin is administered at a dosage of about 2.5 mg/kg 3 times a day, 2 times a day, once a day, once every other day, once every 3 days, once every 4 days, once every 5 days, once every 6 days, twice a weekly, once weekly, once every other week, or once a month. In a particular embodiment, the liposome encapsulated trans-crocetin is administered once or twice a day (e.g., every 24 hours (+/−9 hours)), once every other day, or once a week. In some embodiments, the liposome encapsulated trans-crocetin is administered once a day. In some embodiments, the liposome encapsulated trans-crocetin is administered twice a week. In some embodiments, the liposome encapsulated trans-crocetin is administered once every three days. In some embodiments, the liposome encapsulated trans-crocetin is administered once a month. In particular embodiments, the liposomal trans-crocetin is administered once a day (e.g., every 24 hours (+/−9 hours)), or twice a day (e.g., every 12 hours (+/−3 hours)), once every other day, or once a week. In some embodiments, the liposomal trans-crocetin is administered to a subject (e.g., human) experiencing acute lung distress (e.g., presenting symptoms such as having difficulty breathing, tachypnea, or mental confusion due to low oxygen levels) and/or having a PaO2/FiO2 ratio of less than 300 mm Hg or less than 250 mm Hg. In other particular embodiments, the liposomal trans-crocetin is administered once a day (e.g., every 24 hours (+/−9 hours). In some embodiments, the liposomal trans-crocetin is administered to a subject (e.g., human) experiencing ARDS and/or having a PaO2/FiO2 ratio of less than 200 mm Hg. In other particular embodiments, the liposomal trans-crocetin is administered to a subject in order to increase the patients PaO2/FiO2 ratio. In some embodiments, administration of the liposomal trans-crocetin increases the patient's PaO2/FiO2 ratio by 5%-75%, or any range therein between. In some embodiments, administration of the liposomal trans-crocetin increases the patient's PaO2/FiO2 ratio by 10%-50%, or any range therein between, after 4, 3, 2, or 1 day(s) of trans-crocetin treatment. In some embodiments, administration of the liposomal trans-crocetin increases the patient's PaO2/FiO2 ratio by 10%-50%, or any range therein between, after 4, 3, 2, or 1 day(s) of trans-crocetin treatment. In further embodiments, the administration of the liposomal trans-crocetin increases the patient's PaO2/FiO2 ratio by at least 5%, 10%, 15%, 20%, 25%, 30% 40% or 50% after 4, 3, 2, or 1 day(s) of trans-crocetin treatment.

In particular embodiments, liposomal trans-crocetin is administered at a dosage of about 5 mg/kg 3 times a day, 2 times a day, once a day, once every other day, once every 3 days, once every 4 days, once every 5 days, once every 6 days, twice a weekly, once weekly, once every other week, or once a month. In a particular embodiment, the liposome encapsulated trans-crocetin is administered once or twice a day (e.g., every 24 hours (+/−9 hours)), once every other day, or once a week. In some embodiments, the liposome encapsulated trans-crocetin is administered once a day. In some embodiments, the liposome encapsulated trans-crocetin is administered twice a week. In some embodiments, the liposome encapsulated trans-crocetin is administered once every three days. In some embodiments, the liposome encapsulated trans-crocetin is administered once a month. In particular embodiments, the liposomal trans-crocetin is administered to a subject (e.g., human) experiencing acute lung distress (e.g., presenting symptoms such as having difficulty breathing, tachypnea, mental confusion due to low oxygen levels) and/or having a PaO2/FiO2 ratio of less than 300 mm Hg or less than 250 mm Hg. In other particular embodiments, the liposomal trans-crocetin is administered to a subject (e.g., human) experiencing ARDS and/or having a PaO2/FiO2 ratio of less than 200 mm Hg. In other particular embodiments, the liposomal trans-crocetin is administered to a subject in order to increase the patients PaO2/FiO2 ratio. In some embodiments, administration of the liposomal trans-crocetin increases the patient's PaO2/FiO2 ratio by 5%-75%, or any range therein between or any range therein between, after 4, 3, 2, or 1 day(s) of trans-crocetin treatment. In some embodiments, administration of the liposomal trans-crocetin increases the patient's PaO2/FiO2 ratio by 10%-50%, or any range therein between, after 4, 3, 2, or 1 day(s) of trans-crocetin treatment. In further embodiments, the administration of the liposomal trans-crocetin increases the patient's PaO2/FiO2 ratio by at least 5%, 10%, 15%, 20%, 25%, 30% 40% or 50%. after 4, 3, 2, or 1 day(s) of trans-crocetin treatment.

In particular embodiments, liposomal trans-crocetin is administered at a dosage of about 7.5 mg/kg, 15, or 20 days, or more. 3 times a day, 2 times a day, once a day, once every other day, once every 3 days, once every 4 days, once every 5 days, once every 6 days, twice a weekly, once weekly, once every other week, or once a month. In a particular embodiment, the liposome encapsulated trans-crocetin is administered once or twice a day (e.g., every 24 hours (+/−9 hours)), once every other day, or once a week. In some embodiments, the liposome encapsulated trans-crocetin is administered once a day. In some embodiments, the liposome encapsulated trans-crocetin is administered twice a week. In some embodiments, the liposome encapsulated trans-crocetin is administered once every three days. In some embodiments, the liposome encapsulated trans-crocetin is administered once a month. In particular embodiments, the liposomal trans-crocetin is administered to a subject (e.g., human) experiencing acute lung distress (e.g., presenting symptoms such as having difficulty breathing, tachypnea, mental confusion due to low oxygen levels) and/or having a PaO2/FiO2 ratio of less than 300 mm Hg or less than 250 mm Hg. In other particular embodiments, the liposomal trans-crocetin is administered to a subject (e.g., human) experiencing ARDS and/or having a PaO2/FiO2 ratio of less than 200 mm Hg. In other particular embodiments, the liposomal trans-crocetin is administered to a subject in order to increase the patients PaO2/FiO2 ratio. In some embodiments, administration of the liposomal trans-crocetin increases the patient's PaO2/FiO2 ratio by 5%-75%, or any range therein between, after 4, 3, 2, or 1 day(s) of trans-crocetin treatment.

In further embodiments, the administration of the liposomal trans-crocetin increases the patient's PaO2/FiO2 ratio by 20%-50%, or any range therein between, after 3, 2, or 1 day of trans-crocetin treatment. In some embodiments, administration of the liposomal trans-crocetin increases the patient's PaO2/FiO2 ratio by at least 25%, after 4, 3, 2, or 1 day(s) of trans-crocetin treatment. In further particular embodiments, the administration of the liposomal trans-crocetin increases the patient's PaO2/FiO2 ratio by at least 30% after 4, 3, 2, or 1 day(s) of trans-crocetin treatment.

In particular embodiments, liposomal trans-crocetin is administered at a dosage of about 7.5 mg/kg three times a day, 2 times a day, once a day, once every other day, once every 3 days, once every 4 days, once every 5 days, once every 6 days, twice a week, once weekly, once every other week, or once a month. In a particular embodiment, the liposomal trans-crocetin is administered once a day (e.g., every 24 hours (+/−9 hours)), or twice a day (e.g., every 12 hours (+/−3 hours)), once every other day, or once a week. In some embodiments, the liposomal trans-crocetin is administered once a day. In some embodiments, the liposomal trans-crocetin is administered twice a week. In some embodiments, the liposomal trans-crocetin is administered once every three days. In some embodiments, the liposomal trans-crocetin is administered once a month. In particular embodiments, liposomal trans-crocetin is administered at a dosage of about 5 mg/kg once a day. In particular embodiments, liposomal trans-crocetin is administered at a dosage of about 5 mg/kg once a day for 1, 2, 3, 4, 5, 6, 7, 8, 9, 10, 15, or 20 days, or more. In some embodiments, administration of the liposomal trans-crocetin increases the patient's PaO2/FiO2 ratio by 5%-75%, or any range therein between, after 4, 3, 2, or 1 day(s) of trans-crocetin treatment. In particular embodiments, the administration of the liposomal trans-crocetin increases the patient's PaO2/FiO2 ratio by at least 20% after 4, 3, 2, or 1 day(s) of trans-crocetin treatment. In further particular embodiments, the administration of the liposomal trans-crocetin increases the patient's PaO2/FiO2 ratio by at least 25% after 4, 3, 2, or 1 day(s) of trans-crocetin treatment. In further particular embodiments, the administration of the liposomal trans-crocetin increases the patient's PaO2/FiO2 ratio by at least 30% after 4, 3, 2, or 1 day(s) of trans-crocetin treatment.

Where a series of constant doses are administered, for example, approximately once a day, twice a day, three times a day, four times a day, every other day, 2 times a week, three times a week, every week, approximately every 2 weeks, approximately every 3 weeks or approximately every 4 weeks, preferably once a day (e.g., every 24 hours+/−9 hours)). Doses of trans-crocetin may continue to be administered until, for example, alleviation of symptoms or as otherwise determined by a physician. For example, from about 2, 3, 4, 5, 6, 7, 8, 9, 10, 15, or more doses of trans-crocetin may be administered.

In one embodiment, the administration of one or more loading dose(s) of trans-crocetin is followed by one or more maintenance dose(s) of trans-crocetin. In other embodiments, multiple identical maintenance doses of trans-crocetin are administered to the patient in succession. In one embodiment, a loading dose of about 5 mg/kg to about 7.5 mg/kg (e.g., about 5.0 mg/kg or about 7.5 mg/kg) of liposomal trans-crocetin is administrated to a patient followed by one or more maintenance doses of about 2.5 mg/kg to about 5.0 mg/kg (e.g., about 2.5 mg/kg, or about 5.0 mg/kg) of trans-crocetin. In particular embodiments, two loading dose of trans-crocetin are administered within 24 hours apart. In particular embodiments, a total of one loading dose of trans-crocetin is administered to the patient followed by a maintenance dose of trans-crocetin 24 hours (+/−9 hours) later. In some embodiments, maintenance doses of trans-crocetin are administered once, twice, three times a day, or once, twice or three times a week, for a total of 2 to 20 doses, or more. In particular embodiments, two maintenance doses of liposomal trans-crocetin are administered twice a day, for a total of 2 to 20 days, or more. In other particular embodiments, two maintenance doses of liposomal trans-crocetin are administered once a day, for a total of 2 to 20 days, or more.

In another preferred embodiment, one or more loading dose(s) of liposomal trans-crocetin is followed by one or more maintenance dose(s) of liposomal trans-crocetin.

In one embodiment, one or more loading dose(s) of liposomal trans-crocetin is followed by one or more maintenance dose(s) of liposomal trans-crocetin. In other embodiments, multiple identical doses of liposomal trans-crocetin at about 2.5 mg/kg are administered to the patient. In one embodiment, a dose (loading dose) 4 mg/kg to 7.5 mg/kg (e.g., 5 mg/kg), or any range therein between, of liposomal trans-crocetin is followed by one or more doses (maintenance dose) 2.0 mg/kg to 5 mg/kg (e.g., 2.5 mg/kg), or any range therein between, of liposomal trans-crocetin. In some embodiments, two loading dose of liposomal trans-crocetin (e.g., 4 mg/kg to 7.5 mg/kg (e.g., 5 mg/kg), or any range therein between) are administered within 24 hours of each other. In some embodiments, two or more maintenance doses (e.g., 2.0 mg/kg to 5 mg/kg (e.g., 2.5 mg/kg), or any range therein between) of liposomal trans-crocetin are administered once, twice, three times a day, or once, twice or three times a week, for a total of 2 to 20 doses, or more. In particular embodiments, two maintenance doses of liposomal trans-crocetin are administered once a day, for a total of at least 2 to 20 days, or more.

In one embodiment, a dose (loading dose) of approximately 5 mg/kg of liposomal trans-crocetin is followed by one or more doses of approximately 2.5 mg/kg) (maintenance dose) of liposomal trans-crocetin. In particular embodiments, two loading dose of liposomal trans-crocetin are administered within 24 hours of each other. In some embodiments, the maintenance doses of liposomal trans-crocetin are administered once, twice, three times a day, or once, twice or three times a week, for a total of 2 to 20 doses, or more In particular embodiments, two maintenance doses of liposomal trans-crocetin are administered twice a day, for a total of 2 to 20 days, or more. In other particular embodiments, two maintenance doses of liposomal trans-crocetin are administered once a day, for a total of 2 to 20 days, or more.

In one embodiment, a dose (loading dose) of approximately 7.5 mg/kg of liposomal trans-crocetin is followed by one or more doses of approximately 2.5 mg/kg)(maintenance dose) of liposomal trans-crocetin. In particular embodiments, two loading dose of liposomal trans-crocetin are administered within 24 hours of each other. In some embodiments, the maintenance doses of liposomal trans-crocetin are administered once, twice, three times a day, or once, twice or three times a week, for a total of 2 to 20 doses, or more In particular embodiments, two maintenance doses of liposomal trans-crocetin are administered twice a day, for a total of 2 to 20 days, or more. In other particular embodiments, two maintenance doses of liposomal trans-crocetin are administered once a day, for a total of 2 to 20 days, or more.

In another embodiment, a dose of about 5 mg/kg to about 7.5 mg/kg (e.g., about 5.0 mg/kg or about 7.5 mg/kg) of liposomal trans-crocetin is administered as a loading dose, followed by one or more maintenance doses of about 2.5 mg/kg to about 5.0 mg/kg (e.g., about 2.5 mg/kg, or about 5.0 mg/kg) of liposomal trans-crocetin, once, twice, three times a day, or once, twice or three times a week, for a total of 2 to 20 doses, or more. In particular embodiments, two maintenance doses of liposomal trans-crocetin are administered twice a day, for a total of 2 to 20 days, or more. In other particular embodiments, two maintenance doses of liposomal trans-crocetin are administered once a day, for a total of 2 to 20 days, or more.

Suitably, the maintenance doses maintain a relatively constant therapeutic level of the trans-crocetin in a subject throughout the maintenance phase. Suitably, the administered maintenance doses of trans-crocetin (e.g., liposomal trans-crocetin) maintain a steady state in the subject throughout the maintenance phase.

The period during which maintenance doses are provided will depend on the length of time in which it is desired to maintain therapeutic levels of the trans-crocetin (e.g., liposomal trans-crocetin). In some embodiments, the total number of maintenance doses is at least 2, 3, 4, 5, 6, 7, 8, 9, 10, 15, or 20, or more. In some embodiments, the total number of maintenance doses is 2-50, 4-26, or 5-16, or any range therein between. Suitably the maintenance doses are distributed at regular intervals over the duration of treatment. In a suitable embodiment the time intervals between the maintenance doses may be longer than time intervals between the loading doses.

In one embodiment, the time intervals between the loading doses may be the same as the time intervals between the maintenance doses. In particular embodiments the time intervals between two or more loading doses and two or more the maintenance doses is 12 hours (+/−3 hours). In another particular embodiment, the time interval between two or more loading doses and two or more the maintenance doses is administered once a day, (e.g., every 24 hours (+/−9 hours).

In one embodiment, the concentration of a maintenance dose of trans-crocetin pharmaceutical compositions provided herein is between 1 mg/kg to 10 mg/kg or between 2.5 mg/kg to 7.5 mg/kg or between 2.5 mg/kg to 5 mg/kg, or any range therein between, and the time interval between the maintenance doses is 6-24 hours (+/−2 hours). In another embodiment, the concentration of a maintenance dose of trans-crocetin is 2.5 mg/kg or 5 mg/kg, and the time interval between the maintenance doses is 1s2 hours (+/−3 hours). However, it will be appreciated that the time interval between the maintenance doses may depend on the concentration and formulation of the trans-crocetin contained in the doses. Thus, if the concentration of a maintenance dose is increased, the time interval between doses may be increased. By the same token, if the concentration of a maintenance dose is decreases, the time interval between doses may be decreased. In particular embodiments the concentration trans-crocetin administered during the loading phase is higher than the concentration of one or more of the maintenance doses.

Methods of Treatment and Use

The trans-crocetin pharmaceutical compositions provided herein such as liposomal trans-crocetin compositions, have uses that provide advances over prior treatments of disorders and conditions that include without limitation, infection and infectious diseases such as HIV/AIDS: human immunodeficiency virus-1 (HIV-1), tuberculosis, malaria and its complications such as cerebral malaria, severe anemia, acidosis, acute kidney failure and ARDS, sepsis, inflammation (e.g., chronic inflammatory diseases), ischemia, (including an ischemic condition such as ischemic stroke, coronary artery disease, peripheral vascular disease, cerebral vascular disease, ischemia associated renal pathologies, and ischemia associated with wounds); shock (e.g., hemorrhagic shock), stroke, cardiovascular disease, renal pathologies, wound healing, metabolic disease, hyperproliferative diseases such as cancer, and disorders of the immune system, cardiovascular system, digestive, nervous, respiratory, and endocrine system. In some embodiments, the disclosure provides liposomal trans-crocetin compositions and dosing regimens for treating or preventing a disorder or condition in a subject needing such treatment or prevention, the method comprising administering an effective amount of a pharmaceutical composition provided herein (e.g., one or more doses of trans-crocetin in a dose and/or dosing regimen administered according to the method of any one of [1], [2], [26]-[131] and [172]-[182]) to the subject.

Use of a pharmaceutical composition provided herein (e.g., the pharmaceutical composition of any of one or more doses of trans-crocetin (e.g., a trans-crocetin dose(s) and/or dosing regimen(s) administered according to the method of any one of [1], [2], [26]-[131] and [172]-[182]), in the manufacture of a medicament for the treatment of a disorder or condition in a subject is also provided herein. As are, pharmaceutical compositions of any of one or more doses of trans-crocetin (e.g., a trans-crocetin dose(s) and/or dosing regimen(s) administered according to the method of any one of [1], [2], [26]-[131] and [172]-[182]) for use in a medical medicament.

In one embodiment, the disclosure provides trans-crocetin pharmaceutical compositions and dosing regimens for use in treating an ischemic or hypoxic condition in a subject that comprises administering to the subject an effective amount of a liposomal trans-crocetin pharmaceutical composition and/or dosing regimen provided herein (e.g., dosing regimen for a dose of liposomal trans-crocetin, thereby treating an ischemic or hypoxic condition in the subject. In a particular embodiment, the trans-crocetin composition is administered in an amount sufficient to achieve a serum trans-crocetin concentration of 0.4 ug/ml to 50 ug/ml, 1 ug/ml to 50 ug/ml, 10 ug/ml to 50 ug/ml, or 15 ug/ml to 50 ug/ml, or any range therein between. In a particular embodiment, the trans-crocetin composition is administered in an amount sufficient to achieve a serum trans-crocetin concentration of at least 0.4 ug/ml (e.g., at least 0.75 ug/ml, 1.0 ug/ml, 5 ug/ml, 10 ug/ml. 15 ug/ml, or 20 ug/ml).

In one embodiment, the disclosure provides a method of treating an ischemic or hypoxic condition in a subject, that comprises administering to a subject one or more doses of liposomal trans-crocetin in an amount of 2.5 mg/kg to 7.5 mg/kg, or 2.5 mg/kg to 5 mg/kg (e.g., 2.5 mg/kg, 5 mg/kg, or 7.5 mg/kg), or any range therein between, In one embodiment, the disclosure provides a method of treating an ischemic or hypoxic condition in a subject, that comprises administering to a subject one or more doses of liposomal trans-crocetin in an amount of 1 mg/kg to 4 mg/kg (e.g., 2 mg/kg to 4 mg/kg, and 2.5 mg/kg), or any range therein between. In some embodiments, the subject is administered 1-30, 1-20, 1-15, 1-12, 1-10, or 1-5 doses of trans-crocetin. In further embodiments, the subject is administered 2-30, 2-20, 2-15, 2-12, 2-10, or 2-5 doses of trans-crocetin. In particular embodiments, two or more doses of trans-crocetin are administered to the subject 3 hours, 6 hours, 12 hours (+/−3 hours), or 24 hours (+/−6 hours) apart.

In one embodiment, the disclosure provides a method of treating an ischemic or hypoxic condition in a subject, that comprises administering to the subject one or more loading doses of liposomal trans-crocetin followed by administering one or more maintenance doses of liposomal trans-crocetin. In another embodiment, the disclosure provides a method of treating an ischemic or hypoxic condition in a subject, that comprises administering to the subject one or more loading doses liposomal trans-crocetin followed by administering one or more maintenance doses of liposomal trans-crocetin.

In one embodiment, liposomal trans-crocetin is first administered in a loading phase, during which the subject is administered 1, 2, 3, or more loading doses of liposomal trans-crocetin in an amount of a dose of 2.5 mg/kg to 7.5 mg/kg, or 2.5 mg/kg to 5 mg/kg (e.g., 2.5 mg/kg, 5 mg/kg, or 7.5 mg/kg), or any range therein between, and wherein liposomal trans-crocetin is then further administered to the subject in a maintenance phase, during which the subject is administered one or more maintenance doses of liposomal trans-crocetin. In some embodiments, the subject is administered one or more maintenance doses of liposomal trans-crocetin in an amount of 1 mg/kg to 4 mg/kg (e.g., 2 mg/kg to 4 mg/kg, and 2.5 mg/kg), or any range therein between. In some embodiments, two or more loading doses of liposomal trans-crocetin are administered to the subject 12 hours (+/−3 hours) or 24 hours (+/−6 hours) apart or any range therein between. In some embodiments, 2, 3, 4, 5, or more doses of liposomal trans-crocetin are administered to the subject 2-8 hours, 6-12 hours, 8-24 hours, 24-48 hours, or 48-168 hours apart, or any range therein between.

In one embodiment, the disclosure provides liposomal trans-crocetin compositions and dosing regimens for use in treating an ischemic or hypoxic condition in a subject, wherein the trans-crocetin is first provided in a loading phase, during which the subject receives 1, 2, 3, or more loading doses of liposomal trans-crocetin in an amount of 2.5 mg/kg to 5 mg/kg or 2.5 mg/kg to 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in an amount of 2.5 mg/kg to 5 mg/kg or 2.5 mg/kg to 7.5 mg/kg and wherein the time interval between 1, 2, 3, 4, 5, or more, or all maintenance doses is 2-8 hours, 6-12 hours, 8-24 hours, 24-48 hours, or 48-168 hours, or any range therein between.

In one embodiment, the disclosure provides liposomal trans-crocetin compositions and dosing regimens for use in treating an ischemic or hypoxic condition in a subject, wherein the liposomal trans-crocetin is first provided in a loading phase, during which the subject receives 1, 2, 3, or more loading doses of liposomal trans-crocetin in an amount of 5 mg/kg to 7.5 mg/kg and wherein all loading doses are administered within 12 hours (+/−3 hours) or 24 hours (+/−9 hours), and wherein liposomal trans-crocetin is then further provided to the subject in a maintenance phase, during which the subject receives a plurality of maintenance doses of liposomal trans-crocetin in an amount of 2 mg/kg to 5 mg/kg (e.g., 2.5 mg/kg) mg/kg and wherein the time interval between 1, 2, 3, 4, 5, or more, or all maintenance doses is 2-8 hours, 6-12 hours, 8-24 hours, 24-48 hours, 48-168 hours.

In one embodiment, the disclosure provides liposomal trans-crocetin compositions and dosing regimens for use in treating an ischemic or hypoxic condition in a subject, wherein the liposomal trans-crocetin is first provided in a loading phase, during which the subject receives 1, 2, 3, or more loading doses of liposomal trans-crocetin in an amount of 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in an amount of 5 mg/kg and wherein the time interval between 1, 2, 3, 4, 5, or more, or all maintenance doses is 2-8 hours, 6-12 hours, 8-24 hours, 24-48 hours, or 48-168 hours, or any range therein between.

In one embodiment, the disclosure provides liposomal trans-crocetin compositions and dosing regimens for use in treating an ischemic or hypoxic condition in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of 0.4 ug/ml to 50 ug/ml, or any range therein between, and wherein liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of 0.4 ug/ml to 50 ug/ml or any range therein between. In some embodiments, the time interval between 1, 2, 3, 4, 5, or more, or all maintenance doses is 2-8 hours, 6-12 hours, 8-24 hours, 24-48 hours, or 48-168 hours.

In one embodiment, the disclosure provides liposomal trans-crocetin compositions and dosing regimens for use in treating an ischemic or hypoxic condition in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of 1 ug/ml to 50 ug/ml (e.g., 10 ug/ml to 50 ug/ml, or 15 ug/ml to 50 ug/ml, or any range therein between) and wherein liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of 1 ug/ml to 50 ug/ml (e.g., 10 ug/ml to 50 ug/ml, or 15 ug/ml to 50 ug/ml, or any range therein between). In some embodiments, the time interval between 1, 2, 3, 4, 5, or more, or all maintenance doses is 2-8 hours, 6-12 hours, 8-24 hours, 24-48 hours, or 48-168 hours.

In one embodiment, the disclosure provides liposomal trans-crocetin compositions and dosing regimens for use in treating an ischemic or hypoxic condition in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of at least 0.4 ug/ml (e.g., at least 0.75 ug/ml, 1.0 ug/ml, 5 ug/ml, 10 ug/ml, 15 ug/ml, or 20 ug/ml), and wherein liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of at least 0.4 ug/ml (e.g., at least 0.75 ug/ml, 1.0 ug/ml, 5 ug/ml, 10 ug/ml. 15 ug/ml, or 20 ug/ml). In some embodiments, the time interval between 1, 2, 3, 4, 5, or more, or all maintenance doses is 2-8 hours, 6-12 hours, 8-24 hours, 24-48 hours, or 48-168 hours.

In one embodiment, the disclosure provides a liposomal trans-crocetin pharmaceutical composition for use in treating acute respiratory distress syndrome (ARDS) in a subject that comprises administering to the subject an effective amount of a liposomal trans-crocetin pharmaceutical composition and/or dosing regimen provided herein, such as a liposomal composition, thereby treating ARDS in the subject. In a particular embodiment, the trans-crocetin composition is administered in an amount sufficient to achieve a serum trans-crocetin concentration of 0.4 ug/ml to 50 ug/ml or 1 ug/ml to 50 ug/ml (e.g., 10 ug/ml to 50 ug/ml, or 15 ug/ml to 50 ug/ml, or any range therein between). In a particular embodiment, the trans-crocetin composition is administered in an amount sufficient to achieve a serum trans-crocetin concentration of at least 0.4 ug/ml 0.4 ug/ml (e.g., at least 0.75 ug/ml, 1.0 ug/ml, 5 ug/ml, 10 ug/ml, 15 ug/ml, or 20 ug/ml).

In one embodiment, the disclosure provides a method of treating ARDS in a subject, that comprises administering to the subject one or more doses of liposomal trans-crocetin in an amount of 2.5 mg/kg to 7.5 mg/kg, or 2.5 mg/kg to 5 mg/kg (e.g., 2.5 mg/kg, 5 mg/kg, or 7.5 mg/kg), or any range therein between, In one embodiment, the disclosure provides a method of treating ARDS in a subject, that comprises administering to the subject one or more doses of liposomal trans-crocetin in an amount of 1 mg/kg to 4 mg/kg (e.g., 2 mg/kg to 4 mg/kg, and 2.5 mg/kg), or any range therein between. In some embodiments, the subject is administered 1-30, 1-20, 1-15, 1-12, 1-10, or 1-5 doses of trans-crocetin. In further embodiments, the subject is administered 2-30, 2-20, 2-15, 2-12, 2-10, or 2-5 doses of trans-crocetin. In particular embodiments, two or more doses of trans-crocetin are administered to the subject 3 hours, 6 hours, 12 hours (+/−3 hours), or 24 hours (+/−6 hours) apart.

In one embodiment, the disclosure provides a method of treating ARDS in a subject, that comprises administering to the subject one or more loading doses of liposomal trans-crocetin followed by administering one or more maintenance doses of liposomal trans-crocetin. In another embodiment, the disclosure provides a method of treating ARDS in a subject, that comprises administering to the subject one or more loading doses liposomal trans-crocetin followed by administering one or more maintenance doses of liposomal trans-crocetin. In one embodiment, liposomal trans-crocetin is first administered in a loading phase, during which the subject is administered 1, 2, 3, or more loading doses of liposomal trans-crocetin in an amount of a dose of 2.5 mg/kg to 7.5 mg/kg, or 2.5 mg/kg to 5 mg/kg (e.g., 2.5 mg/kg, 5 mg/kg, or 7.5 mg/kg), or any range therein between, and wherein liposomal trans-crocetin is then further administered to the subject in a maintenance phase, during which the subject is administered one or more maintenance doses of liposomal trans-crocetin. In some embodiments, the subject is administered one or more maintenance doses of liposomal trans-crocetin in an amount of 1 mg/kg to 4 mg/kg (e.g., 2 mg/kg to 4 mg/kg, and 2.5 mg/kg), or any range therein between. In some embodiments, two or more loading doses of liposomal trans-crocetin are administered to the subject 12 hours (+/−3 hours) or 24 hours (+/−6 hours) apart or any range therein between. In some embodiments, 2, 3, 4, 5, or more doses of liposomal trans-crocetin are administered to the subject 2-8 hours, 6-12 hours, 8-24 hours, 24-48 hours, or 48-168 hours apart, or any range therein between.

In one embodiment, the disclosure provides liposomal trans-crocetin compositions and dosing regimens for use in treating ARDS in a subject, wherein the liposomal trans-crocetin is first provided in a loading phase, during which the subject receives 1, 2, 3, or more loading doses of liposomal trans-crocetin in an amount of 2.5 mg/kg to 5 mg/kg or 2.5 mg/kg to 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in an amount of 2.5 mg/kg to 5 mg/kg or 2.5 mg/kg to 7.5 mg/kg and wherein the time interval between 1, 2, 3, 4, 5, or more, or all maintenance doses is 2-8 hours, 6-12 hours, 8-24 hours, 24-48 hours, or 48-168 hours, or any range therein between.

In one embodiment, the disclosure provides liposomal trans-crocetin compositions and dosing regimens for use in treating ARDS in a subject, wherein the liposomal trans-crocetin is first provided in a loading phase, during which the subject receives 1, 2, 3, or more loading doses of liposomal trans-crocetin in an amount of 5 mg/kg to 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in amount of 5 mg/kg to 7.5 mg/kg and wherein the time interval between 1, 2, 3, 4, 5, or more, or all maintenance doses is 2-8 hours, 6-12 hours, 8-24 hours, 24-48 hours, 48-168 hours.

In one embodiment, the disclosure provides liposomal trans-crocetin compositions and dosing regimens for use in treating ARDS in a subject, wherein the liposomal trans-crocetin is first provided in a loading phase, during which the subject receives 1, 2, 3, or more loading doses of liposomal trans-crocetin in an amount of 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in an amount of 5 mg/kg and wherein the time interval between 1, 2, 3, 4, 5, or more, or all maintenance doses is 2-8 hours, 6-12 hours, 8-24 hours, 24-48 hours, or 48-168 hours, or any range therein between.

In one embodiment, the disclosure provides liposomal trans-crocetin compositions and dosing regimens for use in treating ARDS in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of 0.4 ug/ml to 50 ug/ml, or any range therein between, and wherein liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of 0.4 ug/ml to 50 ug/ml or any range therein between. In some embodiments, the time interval between 1, 2, 3, 4, 5, or more, or all maintenance doses is 2-8 hours, 6-12 hours, 8-24 hours, 24-48 hours, or 48-168 hours.

In one embodiment, the disclosure provides liposomal trans-crocetin compositions and dosing regimens for use in treating ARDS in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of 1 ug/ml to 50 ug/ml (e.g., 10 ug/ml to 50 ug/ml, or 15 ug/ml to 50 ug/ml, or any range therein between) and wherein liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of 1 ug/ml to 50 ug/ml (e.g., 10 ug/ml to 50 ug/ml, or 15 ug/ml to 50 ug/ml, or any range therein between). In some embodiments, the time interval between 1, 2, 3, 4, 5, or more, or all maintenance doses is 2-8 hours, 6-12 hours, 8-24 hours, 24-48 hours, or 48-168 hours.

In one embodiment, the disclosure provides liposomal trans-crocetin compositions and dosing regimens for use in treating ARDS in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of at least 0.4 ug/ml (e.g., at least 0.75 ug/ml, 1.0 ug/ml, 5 ug/ml, 10 ug/ml, 15 ug/ml, or 20 ug/ml) trans-crocetin is then further provided to the subject in a maintenance phase, during which the subject receives a plurality of maintenance doses of liposomal trans-crocetin in an amount and over a time interval sufficient to maintain a serum trans-crocetin concentration of at least 0.4 ug/ml (e.g., at least 0.75 ug/ml, 1.0 ug/ml, 5 ug/ml, 10 ug/ml. 15 ug/ml, or 20 ug/ml). In some embodiments, the time interval between 1, 2, 3, 4, 5, or more, or all maintenance doses is 2-8 hours, 6-12 hours, 8-24 hours, 24-48 hours, or 48-168 hours.

In one embodiment, the disclosure provides a dosing regimen for trans-crocetin pharmaceutical compositions for use in treating sepsis in a subject that comprises administering to the subject an effective amount of a liposomal trans-crocetin pharmaceutical composition and/or dosing regimen provided herein, such as a liposomal composition, thereby treating sepsis in the subject. In a particular embodiment, the trans-crocetin composition is administered in an amount sufficient to achieve a serum trans-crocetin concentration of 0.4 ug/ml to 50 ug/ml, 1 ug/ml to 50 ug/ml, 10 ug/ml to 50 ug/ml, or 15 ug/ml to 50 ug/ml, or any range therein between. In a particular embodiment, the trans-crocetin composition is administered in an amount sufficient to achieve a serum trans-crocetin concentration of at least 0.4 ug/ml (e.g., at least 0.75 ug/ml, 1.0 ug/ml, 5 ug/ml, 10 ug/ml. 15 ug/ml, or 20 ug/ml).

In one embodiment, the disclosure provides a method of treating sepsis in a subject, that comprises administering to the subject one or more doses of liposomal trans-crocetin in an amount of 2.5 mg/kg to 7.5 mg/kg, or 2.5 mg/kg to 5 mg/kg (e.g., 2.5 mg/kg, 5 mg/kg, or 7.5 mg/kg), or any range therein between, In one embodiment, the disclosure provides a method of treating sepsis in a subject, that comprises administering to the subject one or more doses of liposomal trans-crocetin in an amount of 1 mg/kg to 4 mg/kg (e.g., 2 mg/kg to 4 mg/kg, and 2.5 mg/kg), or any range therein between. In some embodiments, the subject is administered 1-30, 1-20, 1-15, 1-12, 1-10, or 1-5 doses of trans-crocetin. In further embodiments, the subject is administered 2-30, 2-20, 2-15, 2-12, 2-10, or 2-5 doses of trans-crocetin. In particular embodiments, two or more doses of trans-crocetin are administered to the subject 3 hours, 6 hours, 12 hours (+/−3 hours), or 24 hours (+/−6 hours) apart.

In one embodiment, the disclosure provides a method of treating sepsis in a subject, that comprises administering to the subject one or more loading doses of liposomal trans-crocetin followed by administering one or more maintenance doses of liposomal trans-crocetin. In another embodiment, the disclosure provides a method of treating sepsis in a subject, that comprises administering to the subject one or more loading doses liposomal trans-crocetin followed by administering one or more maintenance doses of liposomal trans-crocetin. In one embodiment, liposomal trans-crocetin is first administered in a loading phase, during which the subject is administered 1, 2, 3, or more loading doses of liposomal trans-crocetin in an amount of a dose of 2.5 mg/kg to 7.5 mg/kg, or 2.5 mg/kg to 5 mg/kg (e.g., 2.5 mg/kg, 5 mg/kg, or 7.5 mg/kg), or any range therein between, and wherein liposomal trans-crocetin is then further administered to the subject in a maintenance phase, during which the subject is administered one or more maintenance doses of liposomal trans-crocetin. In some embodiments, the subject is administered one or more maintenance doses of liposomal trans-crocetin in an amount of 1 mg/kg to 4 mg/kg (e.g., 2 mg/kg to 4 mg/kg, and 2.5 mg/kg), or any range therein between. In some embodiments, two or more loading doses of liposomal trans-crocetin are administered to the subject 12 hours (+/−3 hours) or 24 hours (+/−6 hours) apart or any range therein between. In some embodiments, 2, 3, 4, 5, or more doses of liposomal trans-crocetin are administered to the subject 2-8 hours, 6-12 hours, 8-24 hours, 24-48 hours, or 48-168 hours apart, or any range therein between.

In one embodiment, the disclosure provides liposomal trans-crocetin compositions and dosing regimens for use in treating sepsis in a subject, wherein the liposomal trans-crocetin is first provided in a loading phase, during which the subject receives 1, 2, 3, or more loading doses of trans-crocetin in an amount of 2.5 mg/kg to 5 mg/kg or 2.5 mg/kg to 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in an amount of 2.5 mg/kg to 5 mg/kg or 2.5 mg/kg to 7.5 mg/kg and wherein the time interval between 1, 2, 3, 4, 5, or more, or all maintenance doses is 2-8 hours, 6-12 hours, 8-24 hours, 24-48 hours, or 48-168 hours, or any range therein between.

In one embodiment, the disclosure provides liposomal trans-crocetin compositions and dosing regimens for use in treating sepsis in a subject, wherein the liposomal trans-crocetin is first provided in a loading phase, during which the subject receives 1, 2, 3, or more loading doses of liposomal trans-crocetin in an amount of e.g 5 mg/kg to 7.5 mg/kg and wherein all loading doses are administered within 12 hours (+/−3 hours) or 24 hours (+/−9 hours), and wherein liposomal trans-crocetin is then further provided to the subject in a maintenance phase, during which the subject receives a plurality of maintenance doses of liposomal trans-crocetin in an amount of 5 mg/kg to 7.5 mg/kg, and wherein the time interval between 1, 2, 3, 4, 5, or more, or all maintenance doses is 2-8 hours, 6-12 hours, 8-24 hours, 24-48 hours, 48-168 hours.

In one embodiment, the disclosure provides liposomal trans-crocetin compositions and dosing regimens for use in treating sepsis in a subject, wherein the trans-crocetin composition is first provided in a loading phase, during which the subject receives 1, 2, 3, or more loading doses of liposomal trans-crocetin in an amount of 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in an amount of 5 mg/kg and wherein the time interval between 1, 2, 3, 4, 5, or more, or all maintenance doses is 2-8 hours, 6-12 hours, 8-24 hours, 24-48 hours, or 48-168 hours, or any range therein between.

In one embodiment, the disclosure provides liposomal trans-crocetin compositions and dosing regimens for use in treating sepsis in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of 0.4 ug/ml to 50 ug/ml (e.g., 1 ug/mi to 50 ug/ml, 10 ug/ml to 50 ug/ml, or 15 ug/ml to 50 ug/ml, or any range therein between), and wherein liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of 0.4 ug/ml to 50 ug/ml (e.g., 1 ug/ml to 50 ug/ml, 10 ug/ml to 50 ug/ml, or 15 ug/ml to 50 ug/ml, or any range therein between). In some embodiments, the time interval between 1, 2, 3, 4, 5, or more, or all maintenance doses is 2-8 hours, 6-12 hours, 8-24 hours, 24-48 hours, or 48-168 hours.

In one embodiment, the disclosure provides liposomal trans-crocetin compositions and dosing regimens for use in treating sepsis in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of 1 ug/ml to 50 ug/ml (e.g., 10 ug/ml to 50 ug/ml, or 15 ug/ml to 50 ug/ml, or any range therein between), and wherein liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of 1 ug/ml to 50 ug/ml (e.g., 10 ug/ml to 50 ug/ml, or 15 ug/ml to 50 ug/ml, or any range therein between). In some embodiments, the time interval between 1, 2, 3, 4, 5, or more, or all maintenance doses is 2-8 hours, 6-12 hours, 8-24 hours, 24-48 hours, 48-168 hours.

In one embodiment, the disclosure provides liposomal trans-crocetin compositions and dosing regimens for use in treating sepsis in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of at least 0.4 ug/ml 0.4 ug/ml (e.g., at least 0.75 ug/ml, 1.0 ug/ml, 5 ug/ml, 10 ug/ml, 15 ug/ml, or 20 ug/ml). Liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of at least 0.4 ug/ml 0.4 ug/ml (e.g., at least 0.75 ug/ml, 1.0 ug/ml, 5 ug/ml, 10 ug/ml, 15 ug/ml, or 20 ug/ml). In some embodiments, the time interval between 1, 2, 3, 4, 5, or more, or all maintenance doses is 2-8 hours, 6-12 hours, 8-24 hours, 24-48 hours, 48-168 hours.

In one embodiment, the disclosure provides a liposomal trans-crocetin pharmaceutical composition for use in treating pneumonia in a subject that comprises administering to the subject an effective amount of a liposomal trans-crocetin pharmaceutical composition and/or dosing regimen provided herein, such as a liposomal composition, thereby treating pneumonia in the subject. In a particular embodiment, the trans-crocetin composition is administered in an amount sufficient to achieve a serum trans-crocetin concentration of 0.4 ug/ml to 50 ug/ml or 1 ug/ml to 50 ug/ml (e.g., 10 ug/ml to 50 ug/ml, or 15 ug/ml to 50 ug/ml, or any range therein between). In a particular embodiment, the trans-crocetin composition is administered in an amount sufficient to achieve a serum trans-crocetin concentration of at least 0.4 ug/ml (e.g., at least 0.75 ug/ml, 1.0 ug/ml, 5 ug/ml, 10 ug/ml. 15 ug/ml, or 20 ug/ml).

In one embodiment, the disclosure provides a method of treating pneumonia in a subject, that comprises administering to the subject one or more doses of liposomal trans-crocetin in an amount of 2.5 mg/kg to 7.5 mg/kg, or 2.5 mg/kg to 5 mg/kg (e.g., 2.5 mg/kg, 5 mg/kg, or 7.5 mg/kg), or any range therein between, in one embodiment, the disclosure provides a method of treating pneumonia in a subject, that comprises administering to the subject one or more doses of liposomal trans-crocetin in an amount of 1 mg/kg to 4 mg/kg (e.g., 2 mg/kg to 4 mg/kg, and 2.5 mg/kg), or any range therein between. In some embodiments, the subject is administered 1-30, 1-20, 1-15, 1-12, 1-10, or 1-5 doses of trans-crocetin. In further embodiments, the subject is administered 2-30, 2-20, 2-15, 2-12, 2-10, or 2-5 doses of trans-crocetin. In particular embodiments, two or more doses of trans-crocetin are administered to the subject 3 hours, 6 hours, 12 hours (+/−3 hours), or 24 hours (+/−6 hours) apart.

In one embodiment, the disclosure provides a method of treating pneumonia in a subject, that comprises administering to the subject one or more loading doses of liposomal trans-crocetin followed by administering one or more maintenance doses of liposomal trans-crocetin. In another embodiment, the disclosure provides a method of treating pneumonia in a subject, that comprises administering to the subject one or more loading doses liposomal trans-crocetin followed by administering one or more maintenance doses of liposomal trans-crocetin. In one embodiment, liposomal trans-crocetin is first administered in a loading phase, during which the subject is administered 1, 2, 3, or more loading doses of liposomal trans-crocetin in an amount of a dose of 2.5 mg/kg to 7.5 mg/kg, or 2.5 mg/kg to 5 mg/kg (e.g., 2.5 mg/kg, 5 mg/kg, or 7.5 mg/kg), or any range therein between, and wherein liposomal trans-crocetin is then further administered to the subject in a maintenance phase, during which the subject is administered one or more maintenance doses of liposomal trans-crocetin. In some embodiments, the subject is administered one or more maintenance doses of liposomal trans-crocetin in an amount of 1 mg/kg to 4 mg/kg (e.g., 2 mg/kg to 4 mg/kg, and 2.5 mg/kg), or any range therein between. In some embodiments, two or more loading doses of liposomal trans-crocetin are administered to the subject 12 hours (+/−3 hours) or 24 hours (+/−6 hours) apart or any range therein between. In some embodiments, 2, 3, 4, 5, or more doses of liposomal trans-crocetin are administered to the subject 2-8 hours, 6-12 hours, 8-24 hours, 24-48 hours, or 48-168 hours apart, or any range therein between.

In one embodiment, the disclosure provides liposomal trans-crocetin compositions and dosing regimens for use in treating pneumonia in a subject, wherein the liposomal trans-crocetin is first provided in a loading phase, during which the subject receives 1, 2, 3, or more loading doses of liposomal trans-crocetin in an amount of 2.5 mg/kg to 5 mg/kg or 2.5 mg/kg to 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in a dose of 100 mg-200 mg, 120 mg-160 mg (e.g., 140 mg), or (b) an amount of 2.5 mg/kg to 5 mg/kg or 2.5 mg/kg to 7.5 mg/kg and wherein the time interval between 1, 2, 3, 4, 5, or more, or all maintenance doses is 2-8 hours, 6-12 hours, 8-24 hours, 24-48 hours, or 48-168 hours, or any range therein between.

In one embodiment, the disclosure provides liposomal trans-crocetin compositions and dosing regimens for use in treating pneumonia in a subject, wherein the liposomal trans-crocetin is first provided in a loading phase, during which the subject receives 1, 2, 3, or more loading doses of liposomal trans-crocetin in an amount of e.g., 5 mg/kg to 7.5 mg/kg, and wherein all loading doses are administered within 12 hours (+/−3 hours) or 24 hours (+/−9 hours), and wherein liposomal trans-crocetin is then further provided to the subject in a maintenance phase, during which the subject receives a plurality of maintenance doses of liposomal trans-crocetin in an amount of 5 mg/kg to 7.5 mg/kg and wherein the time interval between 1, 2, 3, 4, 5, or more, or all maintenance doses is 2-8 hours, 6-12 hours, 8-24 hours, 24-48 hours, 48-168 hours.

In one embodiment, the disclosure provides liposomal trans-crocetin compositions and dosing regimens for use in treating pneumonia in a subject, wherein the liposomal trans-crocetin is first provided in a loading phase, during which the subject receives 1, 2, 3, or more loading doses of liposomal trans-crocetin in an amount of 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in an amount of 5 mg/kg and wherein the time interval between 1, 2, 3, 4, 5, or more, or all maintenance doses is 2-8 hours, 6-12 hours, 8-24 hours, 24-48 hours, or 48-168 hours, or any range therein between.

In one embodiment, the disclosure provides liposomal trans-crocetin compositions and dosing regimens for use in treating pneumonia in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of 0.4 ug/ml to 50 ug/ml (e.g., 1 ug/ml to 50 ug/ml, 10 ug/ml to 50 ug/ml, or 15 ug/ml to 50 ug/ml, or any range therein between), and wherein liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of 0.4 ug/ml to 50 ug/ml (e.g., 1 ug/ml to 50 ug/ml, 10 ug/ml to 50 ug/ml, or 15 ug/ml to 50 ug/ml, or any range therein between). In some embodiments, the time interval between 1, 2, 3, 4, 5, or more, or all maintenance doses is 2-8 hours, 6-12 hours, 8-24 hours, 24-48 hours, or 48-168 hours.

In one embodiment, the disclosure provides liposomal trans-crocetin compositions and dosing regimens for use in treating pneumonia in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of 1 ug/ml to 50 ug/ml (e.g., 10 ug/ml to 50 ug/ml, or 15 ug/ml to 50 ug/ml, or any range therein between) and wherein liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of 1 ug/ml to 50 ug/ml (e.g., 10 ug/ml to 50 ug/ml, or 15 ug/ml to 50 ug/ml, or any range therein between). In some embodiments, the time interval between 1, 2, 3, 4, 5, or more, or all maintenance doses is 2-8 hours, 6-12 hours, 8-24 hours, 24-48 hours, or 48-168 hours.

In one embodiment, the disclosure provides liposomal trans-crocetin compositions and dosing regimens for use in treating pneumonia in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of at least 0.4 ug/ml (e.g., at least 0.75 ug/ml, 1.0 ug/ml, 5 ug/ml, 10 ug/ml, 15 ug/ml, or 20 ug/ml), and wherein liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of at least 0.4 ug/ml (e.g., at least 0.75 ug/ml, 1.0 ug/ml, 5 ug/ml, 10 ug/ml, 15 ug/ml, or 20 ug/ml). In some embodiments, the time interval between 1, 2, 3, 4, 5, or more, or all maintenance doses is 2-8 hours, 6-12 hours, 8-24 hours, 24-48 hours, or 48-168 hours.

In one embodiment, the disclosure provides a liposomal trans-crocetin pharmaceutical composition for use in treating infection in a subject that comprises administering to the subject an effective amount of a liposomal trans-crocetin pharmaceutical composition and/or dosing regimen provided herein, such as a liposomal composition, thereby treating infection in the subject. In a particular embodiment, the trans-crocetin composition is administered in an amount sufficient to achieve a serum trans-crocetin concentration of 0.4 ug/ml to 50 ug/ml (e.g., 1 ug/ml to 50 ug/ml, 10 ug/ml to 50 ug/ml, or 15 ug/ml to 50 ug/ml, or any range therein between). In a particular embodiment, the trans-crocetin composition is administered in an amount sufficient to achieve a serum trans-crocetin concentration of at least 0.4 ug/ml (e.g., at least 0.75 ug/ml, 1.0 ug/ml, 5 ug/ml, 10 ug/ml. 15 ug/ml, or 20 ug/ml).

In one embodiment, the disclosure provides a method of treating infection in a subject, that comprises administering to the subject one or more doses of liposomal trans-crocetin in an amount of 2.5 mg/kg to 7.5 mg/kg, or 2.5 mg/kg to 5 mg/kg (e.g., 2.5 mg/kg, 5 mg/kg, or 7.5 mg/kg), or any range therein between, In one embodiment, the disclosure provides a method of treating infection in a subject, that comprises administering to the subject one or more doses of liposomal trans-crocetin in an amount of 1 mg/kg to 4 mg/kg (e.g., 2 mg/kg to 4 mg/kg, and 2.5 mg/kg), or any range therein between. In some embodiments, the subject is administered 1-30, 1-20, 1-15, 1-12, 1-10, or 1-5 doses of trans-crocetin. In further embodiments, the subject is administered 2-30, 2-20, 2-15, 2-12, 2-10, or 2-5 doses of trans-crocetin. In particular embodiments, two or more doses of trans-crocetin are administered to the subject 3 hours, 6 hours, 12 hours (+/−3 hours), or 24 hours (+/−6 hours) apart. In some embodiments the infection is a bacterial infection (e.g., an infection caused by Enterobacteriaceae species (spp.), *Streptococcus pneumoniae, Staphylococcus aureus, Haemophilus influenzae, Klebsiella pneumoniae, Escherichia coli*, or *Pseudomonas aeruginosa*), a viral infection (e.g., an infection caused by an influenza virus, or a coronavirus such as COVID-19), or a fungal infection. In particular embodiments the infection is caused by a virus (e.g., COVID-19).

In one embodiment, the disclosure provides a method of treating infection in a subject, that comprises administering to the subject one or more loading doses of liposomal trans-crocetin followed by administering one or more maintenance doses of liposomal trans-crocetin. In another embodiment, the disclosure provides a method of treating infection in a subject, that comprises administering to the subject one or more loading doses liposomal trans-crocetin followed by administering one or more maintenance doses of liposomal trans-crocetin. In one embodiment, liposomal trans-crocetin is first administered in a loading phase, during which the subject is administered 1, 2, 3, or more loading doses of liposomal trans-crocetin in an amount of a dose of 2.5 mg/kg to 7.5 mg/kg, or 2.5 mg/kg to 5 mg/kg (e.g., 2.5 mg/kg, 5 mg/kg, or 7.5 mg/kg), or any range therein between, and wherein liposomal trans-crocetin is then further administered to the subject in a maintenance phase, during which the subject is administered one or more maintenance doses of liposomal trans-crocetin. In some embodiments, the subject is administered one or more maintenance doses of liposomal trans-crocetin in an amount of 1 mg/kg to 4 mg/kg (e.g., 2 mg/kg to 4 mg/kg, and 2.5 mg/kg), or any range therein between. In some embodiments, two or more loading doses of liposomal trans-crocetin are administered to the subject 12 hours (+/−3 hours) or 24 hours (+/−6 hours) apart or any range therein between. In some embodiments, 2, 3, 4, 5, or more doses of liposomal trans-crocetin are administered to the subject 2-8 hours, 6-12 hours, 8-24 hours, 24-48 hours, or 48-168 hours apart, or any range therein between. In some embodiments the infection is a bacterial infection (e.g., an infection caused by Enterobacteriaceae species (spp.), *Streptococcus pneumoniae, Staphylococcus aureus, Haemophilus influenzae, Klebsiella pneumoniae, Escherichia coli*, or *Pseudomonas aeruginosa*), a viral infection (e.g., an infection caused by an influenza virus, or a coronavirus such as COVID-19), or a fungal infection. In particular embodiments the infection is caused by a virus (e.g., COVID-19).

In one embodiment, the disclosure provides liposomal trans-crocetin compositions and dosing regimens for use in treating an infection in a subject, wherein the liposomal trans-crocetin is first provided in a loading phase, during which the subject receives 1, 2, 3, or more loading doses of liposomal trans-crocetin in an amount of 2.5 mg/kg to 5 mg/kg or 2.5 mg/kg to 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in an amount of 2.5 mg/kg to 5 mg/kg or 2.5 mg/kg to 7.5 mg/kg and wherein the time interval between 1, 2, 3, 4, 5, or more, or all maintenance doses is 2-8 hours, 6-12 hours, 8-24 hours, 24-48 hours, or 48-168 hours, or any range therein between. In some embodiments, the infection is a bacterial infection (e.g., an infection caused by Enterobacteriaceae species (spp.), *Streptococcus pneumoniae, Staphylococcus aureus, Haemophilus influenzae, Klebsiella pneumoniae, Escherichia coli*, or *Pseudomonas aeruginosa*), a viral infection (e.g., an infection caused by an influenza virus, or a coronavirus such as COVID-19), or a fungal infection. In particular embodiments the infection is caused by a virus (e.g., COVID-19).

In one embodiment, the disclosure provides liposomal trans-crocetin compositions and dosing regimens for use in treating an infection in a subject, wherein the liposomal trans-crocetin is first provided in a loading phase, during which the subject receives 1, 2, 3, or more loading doses of liposomal trans-crocetin in an amount of an amount of 4 mg/kg to 7.5 mg/kg (e.g., 5 mg/kg) and wherein all loading doses are administered within 12 hours (+/−3 hours) or 24 hours (+/−9 hours), and wherein liposomal trans-crocetin is then further provided to the subject in a maintenance phase, during which the subject receives a plurality of maintenance doses of liposomal trans-crocetin in an amount of 2 mg/kg to 4 mg/kg (e.g., 2.5 mg/kg) and wherein the time interval between 1, 2, 3, 4, 5, or more, or all maintenance doses is 2-8 hours, 6-12 hours, 8-24 hours, 24-48 hours, 48-168 hours. In some embodiments, the infection is a bacterial infection (e.g., an infection caused by Enterobacteriaceae species (spp.), *Streptococcus pneumoniae, Staphylococcus aureus, Haemophilus influenzae, Klebsiella pneumoniae, Escherichia coli*, or *Pseudomonas aeruginosa*), a viral infection (e.g., an infection caused by an influenza virus, or a coronavirus such as COVID-19), or a fungal infection. In particular embodiments the infection is caused by a virus (e.g., COVID-19).

In one embodiment, the disclosure provides liposomal trans-crocetin compositions and dosing regimens for use in treating an infection in a subject, wherein the liposomal trans-crocetin is first provided in a loading phase, during which the subject receives 1, 2, 3, or more loading doses of liposomal trans-crocetin in an amount of 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in an amount of 5 mg/kg and wherein the time interval between 1, 2, 3, 4, 5, or more, or all maintenance doses is 2-8 hours, 6-12 hours, 8-24 hours, 24-48 hours, or 48-168 hours, or any range therein between. In some embodiments, the infection is a bacterial infection (e.g., an infection caused by Enterobacteriaceae species (spp.), *Streptococcus pneumoniae, Staphylococcus aureus, Haemophilus influenzae, Klebsiella pneumoniae, Escherichia coli*, or *Pseudomonas aeruginosa*), a viral infection (e.g., an infection caused by an influenza virus, or a coronavirus such as COVID-19), or a fungal infection. In particular embodiments the infection is caused by a virus (e.g., COVID-19).

In one embodiment, the disclosure provides liposomal trans-crocetin compositions and dosing regimens for use in treating an infection in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of 0.4 ug/ml to 50 ug/ml (e.g., 1 ug/ml to 50 ug/ml, 10 ug/ml to 50 ug/ml, or 15 ug/ml to 50 ug/ml, or any range therein between), and wherein liposomal trans-crocetin is then further provided to the subject in a maintenance, phase, during which the subject receives a plurality of maintenance doses of liposomal trans-crocetin in an amount and over a time interval sufficient to maintain a serum trans-crocetin concentration of 0.4 ug/ml to 50 ug/ml (e.g., 1 ug/ml to 50 ug/ml, 10 ug/ml to 50 ug/ml, or 15 ug/ml to 50 ug/ml, or any range therein between). In some embodiments, the time interval between 1, 2, 3, 4, 5, or more, or all maintenance doses is 2-8 hours, 6-12 hours, 8-24 hours, 24-48 hours, 48-168 hours. In some embodiments, the infection is a bacterial infection (e.g., an infection caused by Enterobacteriaceae species (spp.), *Streptococcus pneumoniae, Staphylococcus aureus, Haemophilus influenzae, Klebsiella pneumoniae, Escherichia coli*, or *Pseudomonas aeruginosa*), a viral infection (e.g., an infection caused by an influenza virus, or a coronavirus such as COVID-19), or a fungal infection. In particular embodiments the infection is caused by a virus (e.g., COVID-19).

In one embodiment, the disclosure provides liposomal trans-crocetin compositions and dosing regimens for use in treating infection in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of 1 ug/ml to 50 ug/ml (e.g., 10 ug/ml to 50 ug/ml, or 15 ug/ml to 50 ug/ml, or any range therein between), and wherein liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of 1 ug/ml to 50 ug/ml (e.g., 10 ug/ml to 50 ug/ml, or 15 ug/ml to 50 ug/ml, or any range therein between). In some embodiments, the time interval between 1, 2, 3, 4, 5, or more, or all maintenance doses is 2-8 hours, 6-12 hours, 8-24 hours, 24-48 hours, 48-168 hours. In some embodiments, the infection is a bacterial infection (e.g., an infection caused by Enterobacteriaceae species (spp.), *Streptococcus pneumoniae, Staphylococcus aureus, Haemophilus influenzae, Klebsiella pneumoniae, Escherichia coli,* or *Pseudomonas aeruginosa*), a viral infection (e.g., an infection caused by an influenza virus, or a coronavirus such as COVID-19), or a fungal infection. In particular embodiments the infection is caused by a virus (e.g., COVID-19).

In one embodiment, the disclosure provides liposomal trans-crocetin compositions and dosing regimens for use in treating an infection in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of at least 0.4 ug/ml (e.g., at least 0.75 ug/ml, 1.0 ug/ml, 5 ug/ml, 10 ug/ml, 15 ug/ml, or 20 ug/ml), and wherein liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of at least 0.4 ug/ml (e.g., at least 0.75 ug/ml, 1.0 ug/ml, 5 ug/ml, 10 ug/ml, 15 ug/ml, or 20 ug/ml). In some embodiments, the time interval between 1, 2, 3, 4, 5, or more, or all maintenance doses is 2-8 hours, 6-12 hours, 8-24 hours, 24-48 hours, 48-168 hours, or any range therein between. In some embodiments, the infection is a bacterial infection (e.g., an infection caused by Enterobacteriaceae species (spp.), *Streptococcus pneumoniae, Staphylococcus aureus, Haemophilus influenzae, Klebsiella pneumoniae, Escherichia coli,* or *Pseudomonas aeruginosa*), a viral infection (e.g., an infection caused by an influenza virus, or a coronavirus such as COVID-19), or a fungal infection. In particular embodiments the infection is caused by a virus (e.g., COVID-19).

In an additional embodiment, the disclosure provides liposomal trans-crocetin compositions and dosing regimens for increasing the delivery of oxygen in a subject that comprises administering to the subject an effective amount of a liposomal trans-crocetin pharmaceutical composition and/or dosing regimen provided herein, such as a liposomal trans-crocetin composition) thereby increasing the delivery of oxygen to the tissues and/or organs in the subject. In a particular embodiment, the trans-crocetin composition is administered in an amount sufficient to achieve a serum trans-crocetin concentration of 0.4 ug/ml to 50 ug/ml (e.g., 1 ug/ml to 50 ug/ml, 10 ug/ml to 50 ug/ml, or 15 ug/ml to 50 ug/ml, or any range therein between). In a particular embodiment, the trans-crocetin composition is administered in an amount sufficient to achieve a serum trans-crocetin concentration of at least 0.4 ug/ml (e.g., at least 0.75 ug/ml, 1.0 ug/ml, 5 ug/ml, 10 ug/ml, 15 ug/ml, or 20 ug/ml) or 1 ug/ml to 50 ug/ml, or any range therein between.

In some embodiments, the trans-crocetin composition dosing regimen provided herein in administered in combination therapy with oxygen, hemoglobin, erythropoietin, and/or fluorocarbons.

In one embodiment, the disclosure provides a method for increasing the delivery of oxygen in a subject that comprises administering to the subject one or more doses of liposomal trans-crocetin in an amount of 2.5 mg/kg to 7.5 mg/kg, or 2.5 mg/kg to 5 mg/kg (e.g., 2.5 mg/kg, 5 mg/kg, or 7.5 mg/kg), or any range therein between, In one embodiment, the disclosure provides a method increasing the delivery of oxygen in a subject, that comprises administering to the subject one or more doses of liposomal trans-crocetin in an amount of 1 mg/kg to 4 mg/kg (e.g., 2 mg/kg to 4 mg/kg, and 2.5 mg/kg), or any range therein between. In some embodiments, the subject is administered 1-30, 1-20, 1-15, 1-12, 1-10, or 1-5 doses of trans-crocetin. In further embodiments, the subject is administered 2-30, 2-20, 2-15, 2-12, 2-10, or 2-5 doses of trans-crocetin. In particular embodiments, two or more doses of trans-crocetin are administered to the subject 3 hours, 6 hours, 12 hours (+/−3 hours), or 24 hours (+/−6 hours) apart.

In one embodiment, the disclosure provides a method for increasing the delivery of oxygen in a subject, that comprises administering to the subject one or more loading doses of liposomal trans-crocetin followed by administering one or more maintenance doses of liposomal trans-crocetin. In another embodiment, the disclosure provides a method for increasing the delivery of oxygen in a subject, that comprises administering to the subject one or more loading doses liposomal trans-crocetin followed by administering one or more maintenance doses of liposomal trans-crocetin. In one embodiment, liposomal trans-crocetin is first administered in a loading phase, during which the subject is administered 1, 2, 3, or more loading doses of liposomal trans-crocetin in an amount of a dose of 2.5 mg/kg to 7.5 mg/kg, or 2.5 mg/kg to 5 mg/kg (e.g., 2.5 mg/kg, 5 mg/kg, or 7.5 mg/kg), or any range therein between, and wherein liposomal trans-crocetin is then further administered to the subject in a maintenance phase, during which the subject is administered one or more maintenance doses of liposomal trans-crocetin. In some embodiments, the subject is administered one or more maintenance doses of liposomal trans-crocetin in an amount of 1 mg/kg to 4 mg/kg (e.g., 2 mg/kg to 4 mg/kg, and 2.5 mg/kg), or any range therein between. In some embodiments, two or more loading doses of liposomal trans-crocetin are administered to the subject 12 hours (+/−3 hours) or 24 hours (+/−6 hours) apart or any range therein between. In some embodiments, 2, 3, 4, 5, or more doses of liposomal trans-crocetin are administered to the subject 2-8 hours, 6-12 hours, 8-24 hours, 24-48 hours, or 48-168 hours apart, or any range therein between.

In one embodiment, the disclosure provides trans-crocetin pharmaceutical compositions and dosing regimens for use in increasing the delivery of oxygen in a subject, wherein the liposomal trans-crocetin composition is first provided in a loading phase, during which the subject receives 1, 2, 3, or more loading doses of liposomal trans-crocetin in an amount of 2.5 mg/kg to 5 mg/kg or 2.5 mg/kg to 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in an amount of 2.5 mg/kg to 5 mg/kg or 2.5 mg/kg to 7.5 mg/kg and wherein the time interval between 1, 2, 3, 4, 5, or more, or all maintenance doses is 2-8 hours, 6-12 hours, 8-24 hours, 24-48 hours, or 48-168 hours, or any range therein between.

In one embodiment, the disclosure provides a dosing regimen for liposomal trans-crocetin pharmaceutical compositions for use in increasing the delivery of oxygen in a subject wherein the liposomal trans-crocetin is first provided in a loading phase, during which the subject receives 1, 2, 3, or more loading doses of liposomal trans-crocetin in an amount of e.g., 5 mg/kg to 7.5 mg/kg and wherein all loading doses are administered within 12 hours (+/−3 hours) or 24 hours (+/−9 hours), and wherein liposomal trans-crocetin is then further provided to the subject in a maintenance phase, during which the subject receives a plurality of maintenance doses of liposomal trans-crocetin in an amount of 5 mg/kg to 7.5 mg/kg and wherein the time interval between 1, 2, 3, 4, 5, or more, or all maintenance doses is 2-8 hours, 6-12 hours, 8-24 hours, 24-48 hours, 48-168 hours.

In one embodiment, the disclosure provides a dosing regimen for liposomal trans-crocetin pharmaceutical compositions for use in increasing the delivery of oxygen in a subject, wherein the liposomal trans-crocetin is first provided in a loading phase, during which the subject receives 1, 2, 3, or more loading doses of liposomal trans-crocetin in an amount of 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in an amount of 5 mg/kg and wherein the time interval between 1, 2, 3, 4, 5, or more, or all maintenance doses is 2-8 hours, 6-12 hours, 8-24 hours, 24-48 hours, or 48-168 hours, or any range therein between.

In one embodiment, the disclosure provides a dosing regimen for liposomal trans-crocetin pharmaceutical compositions for use in increasing the delivery of oxygen in a subject wherein the liposomal trans-crocetin is first provided in a loading phase, during which the subject receives 1, 2, 3, or more loading doses of liposomal trans-crocetin in an amount sufficient to achieve a serum trans-crocetin concentration of 0.4 ug/ml to 50 ug/ml, or any range therein between, and wherein liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of 0.4 ug/ml to 50 ug/ml, or any range therein between. In some embodiments, the time interval between 1, 2, 3, 4, 5, or more, or all maintenance doses is 2-8 hours, 6-12 hours, 8-24 hours, 24-48 hours, 48-168 hours.

In one embodiment, the disclosure provides a dosing regimen for liposomal trans-crocetin pharmaceutical compositions for use in increasing the delivery of oxygen in a subject wherein the liposomal trans-crocetin is first provided in a loading phase, during which the subject receives 1, 2, 3, or more loading doses of liposomal trans-crocetin in an amount sufficient to achieve a serum trans-crocetin concentration of 1 ug/ml to 50 ug/ml (e.g., 10 ug/ml to 50 ug/ml, or 15 ug/ml to 50 ug/ml, or any range therein between) and wherein liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of 1 ug/ml to 50 ug/ml (e.g., 10 ug/ml to 50 ug/ml, or 15 ug/ml to 50 ug/ml, or any range therein between). In some embodiments, the time interval between 1, 2, 3, 4, 5, or more, or all maintenance doses is 2-8 hours, 6-12 hours, 8-24 hours, 24-48 hours, 48-168 hours.

In one embodiment, the disclosure provides a dosing regimen for liposomal trans-crocetin pharmaceutical compositions for use in increasing the delivery of oxygen in a subject, wherein the liposomal trans-crocetin is first provided in a loading phase, during which the subject receives 1, 2, 3, or more loading doses of liposomal trans-crocetin in an amount sufficient to achieve a serum trans-crocetin concentration of at least 0.4 ug/ml (e.g., at least 0.75 ug/ml, 1.0 ug/ml, 5 ug/ml, 10 ug/ml, 15 ug/ml, or 20 ug/ml), and wherein liposomal trans-crocetin is then further provided to the subject in a maintenance phase, during which the subject receives a plurality of maintenance doses of liposomal trans-crocetin in an amount and over a time interval sufficient to maintain a serum trans-crocetin concentration of at least 0.4 ug/ml (e.g., at least 0.75 ug/ml, 1.0 ug/ml, 5 ug/ml, 10 ug/ml, 15 ug/ml, or 20 ug/ml). In some embodiments, the time interval between 1, 2, 3, 4, 5, or more, or all maintenance doses is 2-8 hours, 6-12 hours, 8-24 hours, 24-48 hours, or 48-168 hours, or any range therein between.

In additional embodiments, the disclosure provides liposomal trans-crocetin compositions and dosing regimens for increasing the delivery of oxygen in a subject who has or is at risk for developing ischemia, that comprises administering to the subject an effective amount of a liposomal trans-crocetin pharmaceutical composition provided herein, such as a liposomal trans-crocetin composition, thereby increasing the delivery of oxygen to the tissues and/or organs in the subject. In some embodiments, the subject has or is at risk for developing ischemia. In some embodiments, an effective amount of the pharmaceutical composition is administered to the subject before, during or following surgery (e.g., transplantation; reattachment of severed extremities, body parts or soft tissues; graft surgery, and vascular surgery). In some embodiments, an effective amount of the pharmaceutical composition is administered to a subject who has or is at risk for developing a wound, a burn injury, an electrical injury, or exposure to ionizing radiation. In some embodiments, an effective amount of the pharmaceutical composition is administered to a subject who has or is at risk for developing peripheral vascular disease, coronary artery disease, stroke, thrombosis, a clot, chronic vascular obstruction or vasculopathy (e.g., secondary to diabetes, hypertension, or peripheral vascular disease), or cerebral ischemia, pulmonary hypertension (adult or neonate); sickle cell disease; neointimal hyperplasia or restenosis (following angioplasty or stenting). In some embodiments, an effective amount of the pharmaceutical composition is administered to a subject who has or is at risk for developing a myopathy, kidney disease; asthma or adult respiratory distress syndrome; Alzheimer's and other dementias secondary to compromised cranial blood flow. In some embodiments, the method comprises administering a liposomal trans-crocetin pharmaceutical composition in a dosing regimen according to the method of any one of [1]-[187] to the subject. Use of a liposomal trans-crocetin composition, in the manufacture of a medicament for increasing the delivery of oxygen in a subject is also provided herein. As are, pharmaceutical compositions of one or more doses of trans-crocetin (e.g., a trans-crocetin dose(s) and/or dosing regimen(s) administered according to the method of any one of [1]-[187] for use in a medical medicament. In some embodiments, the administered pharmaceutical composition comprises a surface active copolymer. In further embodiments, the liposomal composition comprises a poloxamer such as P188, P124, P182, P188, or P234. In yet further embodiments, the liposomal composition comprises the poloxamer P188.

Methods are also disclosed herein for increasing the delivery of oxygen in a neonate subject or a subject who is elderly that comprises administering to the subject a pharmaceutical composition provided herein, such as a dose of a liposomal trans-crocetin composition, thereby increasing the delivery of oxygen to the tissues and/or organs of the subject. In some embodiments, the subject is elderly (e.g., a human subject that is more than 65, more than 70, more than 75, or more than 80 years of age). In some embodiments, the subject has or is at risk for developing a respiratory condition or disease (e.g., COPD, respiratory distress syndrome or adult respiratory distress syndrome). In some embodiments, the subject has or is at risk for developing a degenerative disorder, such as dementia or Alzheimer's disease. In some embodiments, the method comprises administering one or more doses of trans-crocetin (e.g., a trans-crocetin dose(s) and/or dosing regimen(s) administered according to the method of any one of [1]-[187] to the subject. Use of a liposomal trans-crocetin composition in the manufacture of a medicament for increasing the delivery of oxygen in an elderly subject is also provided herein. As are, liposomal trans-crocetin compositions for use in a medical medicament.

In additional embodiments, the disclosure provides liposomal trans-crocetin compositions and dosing regimens for increasing the delivery of oxygen in a subject who has or is at risk for developing ischemia/reperfusion injury, that comprises administering to the subject an effective amount of a pharmaceutical composition pharmaceutical composition provided herein, such as a liposomal trans-crocetin composition, thereby increasing the delivery of oxygen to the tissues and/or organs in the subject. In some embodiments, an effective amount of the pharmaceutical composition is administered to the subject before, during or following surgery (e.g., transplantation; reattachment of severed extremities, body parts or soft tissues; graft surgery, and vascular surgery). In some embodiments, the ischemia/reperfusion injury is due to a condition selected from infarction, atherosclerosis, thrombosis, thromboembolism, lipid-embolism, bleeding, stent, surgery, angioplasty, end of bypass during surgery, organ transplantation, total ischemia, and combinations thereof. In some embodiments, the ischemia/reperfusion injury is produced in an organ or a tissue selected from the group: heart, liver, kidney, brain, intestine, pancreas, lung, skeletal muscle and combinations thereof. In some embodiments, the ischemia/reperfusion injury is selected from the group: organ dysfunction, infarct, inflammation, oxidative damage, mitochondrial membrane potential damage, apoptosis, reperfusion-related arrhythmia, cardiac stunning, cardiac lipotoxicity, ischemia-derived scar formation, and combinations thereof. In particular embodiments, the ischemia/reperfusion injury is due to myocardial infarction. In some embodiments, an effective amount of the pharmaceutical composition is administered to a subject who has or is at risk for developing peripheral vascular disease, coronary artery disease, stroke, thrombosis, a clot, chronic vascular obstruction or vasculopathy (e.g., secondary to diabetes, hypertension, or peripheral vascular disease), or cerebral ischemia, pulmonary hypertension (adult or neonate); sickle cell disease; neointimal hyperplasia or restenosis (following angioplasty or stenting). In some embodiments, an effective amount of the pharmaceutical composition is administered to a subject who has or is at risk for developing a myopathy, kidney disease; asthma or adult respiratory distress syndrome; Alzheimer's and other dementias secondary to compromised cranial blood flow. In some embodiments, the method comprises administering a liposomal trans-crocetin pharmaceutical composition in a dosing regimen according to the method of any one of [1]-[187] to the subject. Use of a liposomal trans-crocetin composition in the manufacture of a medicament for increasing the delivery of oxygen in a subject is also provided herein. As are, one or more doses of trans-crocetin (e.g., a trans-crocetin dose(s) and/or dosing regimen(s) administered according to the method of any one of [1]-[187] for use in a medical medicament.

In one embodiment, the disclosure provides a dosing regimen for liposomal trans-crocetin pharmaceutical compositions for use in increasing the efficacy of a therapeutic agent in a subject that comprises administering to the subject an effective amount of a liposomal trans-crocetin pharmaceutical composition and/or dosing regimen provided herein, such as a liposomal composition, thereby increasing the delivery of oxygen to the tissues and/or organs in the subject. In a particular embodiment, the trans-crocetin composition is administered in an amount sufficient to achieve a serum trans-crocetin concentration of 0.4 ug/ml to 50 ug/ml or 1 ug/ml to 50 ug/ml, or any range therein between. In a particular embodiment, the trans-crocetin composition is administered in an amount sufficient to achieve a serum trans-crocetin concentration of 10 ug/ml to 50 ug/ml, or 15 ug/ml to 50 ug/ml, or any range therein between. In a particular embodiment, the trans-crocetin composition is administered in an amount sufficient to achieve a serum trans-crocetin concentration of at least 0.4 ug/ml (e.g., at least 0.75 ug/ml, 1.0 ug/ml, 5 ug/ml, 10 ug/ml, 15 ug/ml, or 20 ug/ml).

In an additional embodiment, the disclosure provides a liposomal trans-crocetin composition for use in increasing the efficacy of a therapeutic agent in a subject, that comprises administering to a subject who is receiving, will receive, or has received treatment with the therapeutic agent, the trans-crocetin composition in a loading phase during which the subject receives 1, 2, 3, or more loading doses of liposomal trans-crocetin in an amount of 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in an amount of 5 mg/kg and wherein the time interval between 1, 2, 3, 4, 5, or more, or all maintenance doses is 2-8 hours, 6-12 hours, 8-24 hours, 24-48 hours, or 48-168 hours, or any range therein between.

In additional embodiments, the disclosure provides liposomal trans-crocetin compositions and dosing regimens for increasing the efficacy of a therapeutic agent in a subject, that comprises administering to a subject who is receiving, will receive, or has received treatment with the therapeutic agent, an effective amount of a liposomal trans-crocetin composition, thereby increasing the efficacy of the therapeutic agent in the subject. In a particular embodiment, the trans-crocetin composition is administered in an amount sufficient to achieve a serum trans-crocetin concentration of at least 0.4 ug/ml (e.g., at least 0.75 ug/ml, 1.0 ug/ml, 5 ug/ml, 10 ug/ml, 15 ug/ml, or 20 ug/ml).

In one embodiment, the disclosure provides a dosing regimen for liposomal trans-crocetin pharmaceutical compositions for use in increasing the efficacy of a therapeutic agent in a subject, that comprises administering to a subject who is receiving, will receive, or has received treatment with the therapeutic agent, liposomal trans-crocetin in a loading phase during which the subject receives 1, 2, 3, or more loading doses of liposomal trans-crocetin in an amount of 2.5 mg/kg to 5 mg/kg or 2.5 mg/kg to 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in an amount of 2.5 mg/kg to 5 mg/kg or 2.5 mg/kg to 7.5 mg/kg and wherein the time interval between 1, 2, 3, 4, 5, or more, or all maintenance doses is 2-8 hours, 6-12 hours, 8-24 hours, 24-48 hours, or 48-168 hours, or any range therein between.

In one embodiment, the disclosure provides a dosing regimen for liposomal trans-crocetin pharmaceutical compositions for use in increasing the efficacy of a therapeutic agent in a subject, which comprises administering to a subject who is receiving, will receive, or has received treatment with the therapeutic agent, liposomal trans-crocetin in a loading phase, during which the subject receives 1, 2, 3, or more loading doses of liposomal trans-crocetin in an amount of 2.5 mg/kg to 5 mg/kg or 2.5 mg/kg to 7.5 mg/kg and wherein all loading doses are administered within 3 hours, and wherein liposomal trans-crocetin is then further provided to the subject in a maintenance phase, during which the subject receives a plurality of maintenance doses of liposomal trans-crocetin in an amount of 2.5 mg/kg to 5 mg/kg or 2.5 mg/kg to 7.5 mg/kg and wherein the time interval between 1, 2, 3, 4, 5, or more, or all maintenance doses is 2-8 hours, 6-12 hours, 8-24 hours, 24-48 hours, or 48-168 hours, or any range therein between.

In some embodiments, the disclosure provides liposomal trans-crocetin compositions and dosing regimens for treating or preventing a disorder or condition associated with endotoxemia in a subject needing such treatment or prevention, the method comprising administering a liposomal trans-crocetin pharmaceutical composition in a dosing regimen according to the method of any one of [1]-[187] to the subject.

In some embodiments, the disclosure provides liposomal trans-crocetin compositions and dosing regimens for treating or preventing a disorder or condition associated with sepsis in a subject needing such treatment or prevention, the method comprising administering a liposomal trans-crocetin pharmaceutical composition in a dosing regimen according to the method of any one of [1]-[187] to the subject. In some embodiments, the subject has a low grade endotoxemic disease.

In some embodiments, the disclosure provides liposomal trans-crocetin compositions and dosing regimens for treating or preventing a subject at risk of developing sepsis, the method comprising administering a liposomal trans-crocetin pharmaceutical composition in a dosing regimen according to the method of any one of [1]-[187] to the subject. In some embodiments, the subject is immunocompromised or immunosuppressed. In some embodiments, the subject is critically ill. In some embodiments, the subject elderly or neonatal. In some embodiments, the subject has febrile neutropenia. In some embodiments, the subject has an infection.

In some embodiments, the disclosure provides liposomal trans-crocetin compositions and dosing regimens for treating or preventing a disorder or condition associated with burn injury in a subject that is a burn victim, the method comprising administering a liposomal trans-crocetin pharmaceutical composition in a dosing regimen according to the method of any one of [1]-[187] to the subject.

In some embodiments, the disclosure provides liposomal trans-crocetin compositions and dosing regimens for treating or preventing a disorder or condition associated with infection in a subject needing such treatment or prevention, the method comprising administering a liposomal trans-crocetin pharmaceutical composition in a dosing regimen according to the method of any one of [1]-[187] to the subject. In some embodiments, the infection is a bacterial infection (e.g., a *P. aeruginosa* infection, an *S. aureus* infection (e.g., MRSA), *Mycobacterium tuberculosis* infection, an enterococcal infection (e.g., VRE), or a condition associated therewith. In some embodiments, the infection is a fungal infection (e.g., a candidiasis infection such as invasive candidiasis) or a condition associated therewith. In some embodiments, the infection is a parasitic infection (e.g., Schistosomiasis, and human African trypanosomiasis), or a condition associated therewith. In some embodiments, the infection is malaria or a condition associated therewith, such as cerebral malaria, severe anemia, acidosis, acute kidney failure and ARDS. In some embodiments, the infection is a viral infection (e.g., COVID-19, Ebola, Dengue and Marburg) or a condition associated therewith, such as ARDS, influenza, measles, and a viral hemorrhagic fever.

In some embodiments, the disclosure provides liposomal trans-crocetin compositions and dosing regimens for treating anemia in a subject which comprises administering to a subject who has experienced, is experiencing, will experience, or is at risk of experiencing anemia, a liposomal trans-crocetin pharmaceutical composition in a dosing regimen according to the method of any one of [1]-[187]. In some embodiments, trans-crocetin is administered to a subject having acute blood loss anemia (e.g., anemia caused by rapid massive hemorrhage) or an associated condition. In some embodiments, trans-crocetin is administered to a subject having chronic blood loss anemia (e.g., anemia caused by prolonged moderate blood loss or blood deficiency) or an associated condition.

In some embodiments, the disclosure provides liposomal trans-crocetin compositions and dosing regimens for treating blood loss in a subject which comprises administering to a subject who has experienced, is experiencing, will experience, or is at risk of experiencing blood loss, a liposomal trans-crocetin pharmaceutical composition in a dosing regimen according to the method of any one of [1]-[187]. In some embodiments, trans-crocetin is administered to a subject that displays one or more symptoms associated with acute blood loss including, but not limited to, faintness, dizziness, thirst, sweating, weak and rapid pulse, rapid respiration, hypoxia, and tissue necrosis. In other embodiments, trans-crocetin is administered to a subject that appears to be clinically free of symptoms that are associated with acute blood loss. In some embodiments, the subject suffers from blood loss caused by an illness, surgery, or trauma. In some embodiments, the subject suffers from severe blood loss, or blood loss greater than 33%, or one-third, of blood volume. In some embodiments, the subject suffers from moderate blood loss, or blood loss between 20% to 33% of blood volume. In some embodiments, the subject suffers from mild blood loss, or blood loss less than 20% of blood volume. Normal blood volume is about 8% of body weight, or about 5 liter, for a human subject. In some embodiments, the subject is receiving or has received one or more types of therapy against blood loss including, but not limited to, blood transfusion, saline or dextrose infusions, or erythropoietin injection.

In some embodiments, the disclosure provides liposomal trans-crocetin compositions and dosing regimens for treating or preventing a disorder or condition associated with ischemia or hypoxia in a subject needing such treatment or prevention, the method comprising administering a liposomal trans-crocetin pharmaceutical composition in a dosing regimen according to the method of any one of [1]-[187] to the subject. In some embodiments, the disease or condition associated with ischemia or hypoxia is associated with surgery or traumatic injury. In some embodiments, the disease or condition is ischemic-reperfusion injury, transient cerebral ischemia, cerebral ischemia-reperfusion, ischemic stroke, hemorrhagic stroke, traumatic brain injury, ischemic heart disease, migraine (e.g., a chronic migraine or severe migraine disorder), gastrointestinal ischemia, kidney disease, pulmonary embolism, acute respiratory failure, neonatal respiratory distress syndrome, obstetric emergencies to reduce perinatal comorbidity (such as, pre/eclampsia and conditions that lead to cerebral palsy), myocardial infarction, acute limb or mesenteric ischemia, cardiac cirrhosis, chronic peripheral vascular disease, congestive heart failure, atherosclerotic stenosis, anemia, thrombosis, embolism, macular degeneration, a neurodegenerative disease (e.g., Alzheimer's disease, Parkinson's disease, and Amyotrophic Lateral Sclerosis (ALS)), sleep apnea, and surgery or traumatic injury. In some embodiments, the disease or condition associated with ischemia or hypoxia is myocardial infarction, or congestive heart failure with or without cardiac cirrhosis. In some embodiments, the disease or condition is pulmonary embolism, acute respiratory failure, chronic peripheral vascular disease, atherosclerotic stenosis, anemia, thrombosis, or embolism. In some embodiments, the disease or condition associated with ischemia or hypoxia is macular degeneration or an oncologic condition associated with hypoxia. In some embodiments, the disease or condition is kidney disease. In some embodiments, the disease or condition is lipopolysaccharide medication or toxin induced acute kidney injury (AKI) or end stage kidney disease. In some embodiments, the administration of the provided trans-crocetin compositions and dosing regimens reduce hypoxia in the subject by 5%, 10%, 20%, 50%, 100%, or more. Hypoxia can be measured using methods known in the art. For example, hypoxia can be measured using tissue oxygenation level as a proxy.

In some embodiments, the disclosure provides liposomal trans-crocetin compositions and dosing regimens for treating or preventing a disorder or condition associated with shock in a subject needing such treatment or prevention, the method comprising administering a liposomal trans-crocetin pharmaceutical composition in a dosing regimen according to the method of any one of [1]-[187] to the subject. In some embodiments, the disease or condition is associated with cardiogenic shock. In some embodiments, the disease or condition is associated with, hypovolemic shock. In some embodiments, the disease or condition is associated with septic shock or other forms of distributive shock. In some embodiments, the disease or condition is associated with neurogenic shock. In some embodiments, the disease or condition is associated with anaphylactic shock. In particular embodiments, the administration of the trans-crocetin is associated with a reduction in heart rate, blood acidosis, and/or organ damage in the subject. In particular embodiments, trans-crocetin is administered within 1 hour or within 4, 12, 18 or 24 hours, or 48 hours of the onset of shock or a condition associated with shock.

In some embodiments, the disclosure provides liposomal trans-crocetin compositions and dosing regimens for treating or preventing a disorder or condition associated with nitric oxide deficiency in a subject needing such treatment or prevention, the method comprising administering a liposomal trans-crocetin pharmaceutical composition in a dosing regimen according to the method of any one of [1]-[187] to the subject. In some embodiments, the disease or disorder is sickle cell disease, paroxysmal nocturnal hemoglobinuria (PNH), a hemolytic anemia, a thalassemia, another red blood cell disorder, or a condition associated therewith. In some embodiments, the disease or disorder is a purpura such as thrombotic thrombocytic purpura (TTP), hemolytic uremic syndrome (HUS), idiopathic thrombocytopenia (ITP), or and another platelet disorder, or a condition associated therewith. In some embodiment, the disease or disorder is a coagulation abnormality such as disseminated intravascular coagulopathy (DIC), purpura fulminans, heparin induced thrombocytopenia (HIT), hyperleukocytosis, hyper viscosity syndrome, or a condition associated therewith.

In some embodiments, the disclosure provides liposomal trans-crocetin compositions and dosing regimens for treating or preventing a disorder or condition associated with inflammation in a subject needing such treatment or prevention, the method comprising administering a liposomal trans-crocetin pharmaceutical composition in a dosing regimen according to the method of any one of [1]-[187] to the subject. In some embodiments, the disease or condition associated with inflammation is low-grade inflammation. In some embodiments, the disease or condition associated with inflammation is systemic inflammation. In some embodiments, the disease or condition associated with inflammation is acute inflammation or a chronic inflammatory disease.

In some embodiments, the disclosure provides liposomal trans-crocetin compositions and dosing regimens for treating or preventing a disorder or condition associated with a cardiovascular disease or condition in a subject needing such treatment or prevention, the method comprising administering a liposomal trans-crocetin pharmaceutical composition in a dosing regimen according to the method of any one of [1]-[187] to the subject. In some embodiments, cardiovascular disease or condition is coronary artery disease. In some embodiments, the cardiovascular disease or condition is myocardial infarction, sudden cardiac death, cardiorespiratory arrest, hypertension, pulmonary arterial hypertension, atherosclerosis, occlusive arterial disease, Raynaud's disease, peripheral vascular disease, other vasculopathies such as Buerger's disease, Takayasu's arthritis, and post-cardiac arrest syndrome (PCAS), chronic venous insufficiency, heart disease, congestive heart failure, or a chronic skin ulcer. Methods and biomarkers for evaluating cardiovascular health (e.g., levels of conventional troponins (cTnI and cTnT), Ischemia-Modified Albumin (IMA), B-type Natriuretic Peptide and N-terminal proBNP, whole blood choline, and unesterified free fatty acid (FFAu)) and cardiovascular injury and disease, and the efficacy of treatment regimens are known in the art In some embodiments, the disclosure provides liposomal trans-crocetin compositions and dosing regimens for treating or preventing a disorder or condition associated with a liver disease, injury or condition in a subject needing such treatment or prevention, the method comprising administering a liposomal trans-crocetin pharmaceutical composition in a dosing regimen according to the method of any one of [1]-[187] to the subject. In some embodiments, the liver disease or condition is hepatic ischemia/reperfusion injury. In some embodiments, the liver disease or condition is a hepatic resection or liver transplantation. In some embodiments, the liver disease or condition is cirrhosis. In some embodiments, the liver disease or condition is nonalcoholic fatty liver disease (NAFLD), non-alcoholic steatohepatitis (NASH). In some embodiments, the liver disease or condition is alcoholic liver disease. In some embodiments, the liver disease or condition is acute liver injury. Methods and biomarkers for evaluating liver health (e.g., levels of liver enzymes ALT, AST, ALP, and LDH), as well as liver injury and disease and the efficacy of treatment regimens are known in the art.

In some embodiments, the disclosure provides liposomal trans-crocetin compositions and dosing regimens for treating or preventing a disorder or condition associated with a lung disease or condition in a subject needing such treatment or prevention, the method comprising administering a liposomal trans-crocetin pharmaceutical composition in a dosing regimen according to the method of any one of [1]-[187] to the subject. In some embodiments, the lung disease or condition is acute respiratory distress syndrome (ARDS). In some embodiments, the lung disease or condition is chronic obstructive pulmonary disease (COPD). In some embodiments, the lung disease or condition is pulmonary fibrosis. In some embodiments, the lung disease or condition is emphysema. In some embodiments, the lung disease or condition is asthma. In some embodiments, the lung disease or condition is pulmonary hemorrhage. In some embodiments, the lung disease or condition is asthma. In some embodiments, the lung disease or condition is lung injury (e.g., acute lung injury (ALT). In some embodiments, the lung disease or condition is lung cancer. In some embodiments, the condition is cystic fibrosis.

In some embodiments, an effective amount of trans-crocetin (e.g., one or more doses of trans-crocetin and/or trans-crocetin dosing regimen according to any one of [1]-[187] is administered to a subject (e.g., a human) experiencing acute lung distress (e.g., presenting symptoms such as having difficulty breathing, tachypnea, mental confusion due to low oxygen levels) and/or having a PaO2/FiO2 ratio of less than 300 mm Hg or less than 250 mm Hg. In additional embodiments, the pharmaceutical composition is administered to a subject having a PaO2/FiO2 ratio of <300 mm Hg to ≥200 mm Hg. In additional embodiments, the pharmaceutical composition is administered to a subject having a PaO2/FiO2 ratio of <300 mm Hg to ≥250 mm Hg. In further embodiments the pharmaceutical composition comprises liposomal trans-crocetin.

In some embodiments, an effective amount of trans-crocetin (e.g., one or more doses of trans-crocetin and/or trans-crocetin dosing regimen according to any one of [1]-[187] is administered to a subject (e.g., a human) experiencing Acute Respiratory ARDS and/or having a PaO2/FiO2 ratio of less than 200 mm Hg. In further embodiments the pharmaceutical composition comprises liposomal trans-crocetin.

In some embodiments, a liposomal trans-crocetin composition provided herein (e.g., one or more doses of trans-crocetin in a trans-crocetin dose and/or dosing regimen provided herein) is administered according to the method of any one of [1]-[187] to a subject (e.g., a human) in order to increase the patient's PaO2/FiO2 ratio. In some embodiments, administration of the pharmaceutical composition increases the patient's PaO2/FiO2 ratio by at 5%-75%, or any range therein between. In further embodiments, the administration of the pharmaceutical composition increases the patient's PaO2/FiO2 ratio by at least 5%, 10%, 15%, 20%, 25%, 30% 40% or 50%. In further embodiments the pharmaceutical composition comprises liposomal trans-crocetin. In further embodiments, the administration of the trans-crocetin increases the patient's PaO2/FiO2 ratio by 5%-75%, or any range therein between, after 4, 3, 2, or 1 day(s) of trans-crocetin treatment. In further embodiments, the administration of the trans-crocetin increases the patient's PaO2/FiO2 ratio by 10%-50%, or any range therein between, after 4, 3, 2, or 1 day(s) of trans-crocetin treatment. In further embodiments, the administration of the trans-crocetin increases the patient's PaO2/FiO2 ratio by at least 5%, 10%, 15%, 20%, 25%, 30%40% or 50%, after 4, 3, 2, or 1 day(s) of trans-crocetin treatment.

In some embodiments, the disclosure provides liposomal trans-crocetin compositions and dosing regimens for treating or preventing a disorder or condition associated with a kidney disease or condition in a subject needing such treatment or prevention, the method comprising administering a liposomal trans-crocetin pharmaceutical composition in a dosing regimen according to the method of any one of [1]-[187] to the subject. In some embodiments, the kidney disease or condition is lipopolysaccharide-induced acute kidney injury (AKI). In some embodiments, the kidney disease or condition is chronic renal failure with or without end stage kidney disease. Methods and biomarkers for evaluating renal health (e.g., levels of N-acetyl-β-glucosaminidase (NAG), α1-microglobulin (α1M), Cystatin-C (Cys-C), Retinol binding protein (RBP), microalbumin, Kidney injury molecule-1 (KIM-1), Clusterin, Interleukin-18 (IL18), Cysteine-rich protein (Cyr61), osteopontin (OPN), Fatty acid-binding protein (FABP), Fetuin-A, and neutrophil gelatinase-associated lipocalin (NGAL)), as well as renal injury and disease and the efficacy of treatment regimens are known in the art.

In some embodiments, the disclosure provides liposomal trans-crocetin compositions and dosing regimens for treating or preventing a disorder or condition associated with a vascular disease in a subject needing such treatment or prevention, the method comprising administering a liposomal trans-crocetin pharmaceutical composition in a dosing regimen according to the method of any one of [1]-[187] to the subject. In some embodiments, the disease or condition is coronary artery disease. In some embodiments, the disease or condition is hypertension. In some embodiments, the disease or condition is atherosclerosis. In some embodiments, the disease or condition is post-cardiac arrest syndrome (PCAS). In some embodiments, the disease or condition is occlusive arterial disease, peripheral vascular disease, chronic venous insufficiency, chronic skin ulcers, or Raynaud's disease. In some embodiments, the disorder or condition associated with a vascular disease is heart disease. In further embodiments, the disorder or condition is congestive heart failure. In some embodiments, the disorder or condition associated with vascular disease is ischemic bowel disease.

In some embodiments, the disclosure provides liposomal trans-crocetin compositions and dosing regimens for treating or preventing a disorder or condition associated with a heart attack or stroke in a subject needing such treatment or prevention and/or at risk of having a heart attack or stroke, the method comprising administering a liposomal trans-crocetin pharmaceutical composition in a dosing regimen according to the method of any one of [1]-[187] to the subject. In some embodiments, the disorder or condition is ischemic stroke. In some embodiments, the disorder or condition is hemorrhagic stroke. Methods and biomarkers for evaluating heart attack and stroke (e.g., levels of blood B-type natriuretic peptide (BNP), C-reactive protein (CRP), GlycA, CK-MB, Cardiac troponin, myoglobin, low-density lipoprotein-cholesterol and hemoglobin A1c (HgA1c), lipoprotein-associated phospholipase A2, glial fibrillary acidic protein, S100b, neuron-specific enolase, myelin basic protein, interleukin-6, matrix metalloproteinase (MMP)-9, D-dimer, and fibrinogen)), and the efficacy of treatment regimens are known in the art.

In some embodiments, the disclosure provides liposomal trans-crocetin compositions and dosing regimens for treating or preventing a disorder or condition associated with nervous system in a subject needing such treatment or prevention, the method comprising administering a liposomal trans-crocetin pharmaceutical composition in a dosing regimen according to the method of any one of [1]-[187] to the subject. In some embodiments, the disease or condition is pain (e.g., chronic pain). In some embodiments, the disease or condition is a neurodegenerative disease (e.g., Alzheimer's disease or Parkinson's disease). In some embodiments, the disorder or condition associated with nervous system is neural injury.

In some embodiments, the disclosure provides liposomal trans-crocetin compositions and dosing regimens for treating or preventing a disorder or condition associated with inflammatory bowel disease in a subject needing such treatment or prevention, the method comprising administering an effective amount of a liposomal trans-crocetin pharmaceutical composition provided herein (e.g., one or more doses of trans-crocetin and/or trans-crocetin dosing regimens according to the method of any one of [1]-[187]) to the subject. In some embodiments, the disorder or condition is Crohn's disease. In some embodiments, the disorder or condition is ulcerative colitis.

In some embodiments, the disclosure provides liposomal trans-crocetin compositions and dosing regimens for treating or preventing a disorder or condition associated with type 2 diabetes or predisposition for diabetes in a subject needing such treatment or prevention, the method comprising administering a liposomal trans-crocetin pharmaceutical composition in a dosing regimen according to the method of any one of [1]-[187] to the subject. In some embodiments, the disorder or condition is metabolic disease. In some embodiments, the disorder or condition is insulin resistance. In some embodiments, the disorder or condition is a diabetic vascular disease (e.g., a microvascular disease such as retinopathy and nephropathy). In some embodiments, the disorder or condition is diabetic neuropathy. In some embodiments, the disorder or condition is ulcers, diabetic necrosis, or gangrene.

In some embodiments, the disclosure provides liposomal trans-crocetin compositions and dosing regimens for treating or preventing a myopathy, chronic microvascular disease, or microangiopathy, or a disorder associated with microvascular dysfunction such as age-related macular degeneration (AMD) in a subject needing such treatment or prevention, the method comprising administering a liposomal trans-crocetin pharmaceutical composition in a dosing regimen according to the method of any one of [1]-[187] to the subject.

In some embodiments, the disclosure provides liposomal trans-crocetin compositions and dosing regimens for treating or preventing a disorder or condition associated with sclerosis in a subject needing such treatment or prevention, the method comprising administering a liposomal trans-crocetin pharmaceutical composition in a dosing regimen according to the method of any one of [1]-[187] to the subject. In some embodiments, the disorder or condition associated with sclerosis is systemic sclerosis.

In some embodiments, the disclosure provides liposomal trans-crocetin compositions and dosing regimens for treating endotoxemia in a subject needing such treatment, the method comprising administering a liposomal trans-crocetin pharmaceutical composition in a dosing regimen according to the method of any one of [1]-[187] to the subject. In some embodiments, the endotoxemia is associated with a condition such as periodontal disease (e.g., periodontitis or inflammation of the gums), chronic alcoholism, chronic smoking, transplantation, or neonatal necrotizing enterocolitis, or neonatal ear infection.

In some embodiments, the disclosure provides a method of reducing systemic levels of LPS, endotoxin and/or another trigger of systemic inflammation in a subject in need thereof, the method comprising administering a liposomal trans-crocetin pharmaceutical composition in a dosing regimen according to the method of any one of [1]-[187] to the subject.

Combination Therapy

The liposomal trans-crocetin compositions and dosing regimens provided herein can be administered alone or in combination therapy with one or more additional therapeutic agents. In some embodiments, The liposomal trans-crocetin composition is administered in combination therapy with another therapeutic agent. Combinations may be administered either concomitantly, e.g., combined in the same liposomal composition, delivery vehicle (e.g., liposome), as an admixture, separately but simultaneously or concurrently; or sequentially. This includes presentations in which the combined therapeutic agents are administered together as a therapeutic mixture, and also procedures in which the combined agents are administered separately but simultaneously, e.g., as through separate intravenous lines into the same subject. Administration "in combination" further includes the separate administration of the liposomal trans-crocetin composition before or after the additional therapeutic agent (s). Methods of treatment using the combination therapy are also provided. In some embodiments, one or more doses of trans-crocetin is administered to the subject before the subject is administered the additional therapeutic agent (e.g., 5 minutes to 72 hours, 15 minutes to 48 hours, or 30 minutes to 24 hours before administration of the additional therapeutic agent, or within 12 hours, 9 hours, 6 hours, 4 hours, 2 hours, or within 1 hour before the administration of the additional therapeutic agent). In further embodiments, the additional therapeutic agent is radiation, a chemotherapeutic agent, an immunotherapeutic agent, or oxygen therapy.

In some embodiments, a liposomal trans-crocetin pharmaceutical composition and/or dosing regimen provided herein (e.g., one or more doses of trans-crocetin and/or dosing regimens administered according to the method of any one of [1]-[187] is administered to the subject in combination with another therapeutic agent.

In some embodiments, a liposomal trans-crocetin pharmaceutical composition and/or dosing regimens provided herein is administered in combination therapy with another ionizable carotenoid or a carotenoid comprising at least one polar group or monocyclic group. In some embodiments, the trans-crocetin salt is a multivalent salt (i.e., a trans-crocetin salt containing divalent, trivalent or tetravalent counterion). In one embodiment, the carotenoid comprising at least one polar group or monocyclic group polar group is symmetric. In another embodiment, a trans-crocetin salt is administered in combination therapy with at least one carotenoid selected from: zeanthin, astaxanthin, lutein, and xanthophyll. In another embodiment, the trans-crocetin salt is administered in combination therapy with astaxanthin. In another embodiment, the trans-crocetin salt composition is administered in combination with abscisic acid (ABA).

In some embodiments, a liposomal trans-crocetin pharmaceutical composition and/or dosing regimen provided herein (e.g., a liposomal trans-crocetin composition and/or dosing regimen administered according to the method of any one of [1]-[187] is administered in combination therapy with a standard of care treatment for the disorder or condition to be treated.

In some embodiments, a liposomal trans-crocetin pharmaceutical composition and/or dosing regimen provided herein is administered in combination therapy with an antimicrobial agent. In some embodiments, the antimicrobial agent is an antiviral agent. In particular embodiments, the antiviral agent is remdesivir. In some embodiments, the antimicrobial agent is an anti-bacterial agent. In some embodiments, the antibacterial agent is selected from, but not limited to, ertapenem, piperacillin-tazobactam, cefepime, aztreonam, metronidazole, meropenem, ceftriaxone, ciprofloxacin, vancomycin, linezolid, tobramycin, levofloxacin, azithromycin, cefazolin, and ampicillin. In some embodiments, the antibacterial agent is selected from, but not limited to, ceftriaxone, levofloxacin, ciprofloxacin, cefazolin, piperacillin-tazobactam, meropenem, metronidazole, vancomycin, and ampicillin. In other embodiments, the antimicrobial agent is an anti-fungal agent. In further embodiments, the anti-fungal agent is caspofungin or another antifungal drug. In other embodiments, the antimicrobial agent is an anti-malarial agent. In further embodiments, the anti-malarial agent is selected from, but not limited to, artemisinin and its analogs, chloroquin and its analogs, atovaquone, a quinine derivative, proguanil or another anti-malarial drug.

In some embodiments, a liposomal trans-crocetin pharmaceutical composition and/or dosing regimen provided herein is administered in combination therapy with activated protein C (e.g., rhAPC), or drotrecogin alfa (activated) (DAA).

In some embodiments, a liposomal trans-crocetin pharmaceutical composition and/or dosing regimen provided herein is administered in combination therapy with a corticosteroid (e.g., a glucocorticoid or mineralocorticoid such as fludrocortisonel). In some embodiments, the corticosteroid is a glucocorticoid. In further embodiments, the glucocorticoid is selected from cortisone, ethamethasoneb, prednisone, prednisolone, triamcinolone, dexamethasone and methylprednisolone.

In some embodiments, a liposomal trans-crocetin pharmaceutical composition and/or dosing regimen provided herein is administered in combination therapy with intravenous administration of a vitamin. In some embodiments, the vitamin is vitamin C (ascorbic acid).

In some embodiments, a liposomal trans-crocetin pharmaceutical composition and/or dosing regimen provided herein is administered in combination therapy with a glucocorticoid and vitamin C (e.g., intravenous vitamin C administration). In some embodiments, the glucocorticoid is selected from cortisone, ethamethasoneb, prednisone, prednisolone, triamcinolone, dexamethasone and methylprednisolone. In further embodiments, the glucocorticoid is hydrocortisone. In additional embodiments, a liposomal trans-crocetin composition provided herein is administered in combination therapy with a glucocorticoid, vitamin C, and/or thiamine.

In some embodiments, a liposomal trans-crocetin pharmaceutical composition and/or dosing regimen provided herein is administered in combination therapy with a vasopressor therapeutic agent. In some embodiments, the vasopressor therapeutic agent is norepinephrine or similar drugs, or angiotensin II (e.g., GIAPREZA™). In some embodiments, the vasopressor therapeutic agent is epinephrine, phenylnephrine, dopamine, or vasopressin. In some embodiments, the vasopressor therapeutic agent is ephedrine, milrinone, isoproterenol, dobutamine, isoproterenol, or dopamine.

In some embodiments, a liposomal trans-crocetin pharmaceutical composition and/or dosing regimen provided herein is administered in combination therapy with a thrombolytic therapeutic agent. In some embodiments, the thrombolytic therapeutic agent tissue plasminogen activator (tPA).

In additional embodiments, a liposomal trans-crocetin pharmaceutical composition and/or dosing regimen provided herein is administered in combination therapy with an anesthetic agent. In some embodiments, the anesthetic agent is administered before the pharmaceutical composition (e.g., as an anesthetic preconditioning (APC) regimen, prior to surgery). In some embodiments, the anesthetic agent is administered after the pharmaceutical composition (e.g., post-surgery). In some embodiments, anesthetic agent is isoflurane, sevoflurane, or propofol. In some embodiments, anesthetic agent is cystathionine-β-synthase (CBS), cystathionine-γ-lyase (CSE), or 3-mercapto-pyruvate-sulfurtransferase (MST).

In some embodiments, a liposomal trans-crocetin pharmaceutical composition and/or dosing regimen provided herein is administered in combination therapy with a therapeutic agent selected from: heparin, vasopressin, antidiuretic hormone (ADH), and a 3-Hydroxy-3-methylglutaryl coenzyme A reductase inhibitor (statin).

In some embodiments, a liposomal trans-crocetin pharmaceutical composition and/or dosing regimen provided herein is administered in combination therapy with an anti-inflammatory therapeutic agent.

In some embodiments, a liposomal trans-crocetin pharmaceutical composition and/or dosing regimen provided herein is administered in combination therapy with oxygen and/or intravenous fluids to maintain/increase blood oxygen levels and/or blood pressure or hyperbaric therapy.

In some embodiments, a liposomal trans-crocetin pharmaceutical composition and/or dosing regimen provided herein is administered in combination therapy with an antioxidant. In some embodiments, the trans-crocetin salt provided herein is administered in combination therapy with at least one of alpha-tocopherol, melatonin, ascorbic acid (AA), alpha lipoic acid, desferoxamine, and trimetazidine (TMZ). In some embodiments, the trans-crocetin salt provided herein is administered in combination therapy with at least one of glutathione, N-Acetylcysteine (NAC), Bucillamine (N-(2-mercapto-2-methylpropionyl)-1-cysteine), a superoxide dismutase (SOD) or derivative thereof, catalase (CAT), and allopurinol, idebenone.

The liposomal trans-crocetin pharmaceutical compositions and dosing regimens provided herein have applications in cancer therapy both as mono and combination therapy. In some embodiments, a liposomal trans-crocetin pharmaceutical composition and/or dosing regimen provided herein is administered in combination therapy with one or more chemotherapeutic agents (e.g., to enhance the effect of chemotherapy on cancer cells and mitigate the effects of chemotherapy-induced myelosuppression and anemia). The combination therapy may include, for example, coadministration or concurrent administration, using separate formulations or a single pharmaceutical formulation, and consecutive administration in either order, wherein preferably there is a time period while both (or all) active agents simultaneously exert their biological activities. Thus, the chemotherapeutic agent may be administered prior to, or following, administration of the trans-crocetin. In this embodiment, the timing between at least one administration of the chemotherapeutic agent and at least one administration of the trans-crocetin is preferably approximately 1 week, 3 days, 24 hours, 12 hours, 6 hours or less. In some embodiments, the liposomal trans-crocetin composition is administered to the subject before the chemotherapeutic agent (e.g., 5 minutes to 72 hours, 15 minutes to 48 hours, or 30 minutes to 24 hours before administration of the chemotherapeutic agent, or within 12 hours, 9 hours, 6 hours, 4 hours, 2 hours, or within 1 hour before the administration of the chemotherapeutic agent.

Alternatively, the chemotherapeutic agent and the liposomal trans-crocetin are administered concurrently to the patient, in a single formulation or separate formulations. Treatment with the combination of the chemotherapeutic agent and the trans-crocetin (may result in a synergistic, or greater than additive, therapeutic benefit to the subject.

In some embodiments, a liposomal trans-crocetin pharmaceutical composition and/or dosing regimen provided herein is administered in combination therapy with a chemotherapeutic agent (e.g., to enhance the effect of chemotherapy on cancer cells and mitigate the effects of chemotherapy-induced myelosuppression and anemia).

Examples of chemotherapeutic agents that can be administered in combination therapy with the trans-crocetin compositions provided herein include but are not limited to an alkylating agent such as thiotepa and cyclosphosphamide (Cytoxan™); an alkyl sulfonate such as busulfan, improsulfan and piposulfan; an aziridine such as benzodopa, carboquone, meturedopa, and uredopa; an ethylenimine or methylamelamine such as altretamine, triethylenemelamine, trietylenephosphoramide, triethylenethiophos-phaoramide and trimethylolomelamine; a nitrogen mustard such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; a nitrosurea such as carmustine, chlorozotocin, fotemustine, lomustine, nimustine, ranimustine; an antibiotic such as an aclacinomysin, actinomycin, authramycin, azaserine, a bleomycin, cactinomycin, calicheamicin, carabicin, carminomycin, carzinophilin, a chromomycin, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; an antimetabolite such as methotrexate and 5-fluorouracil (5-FU); a folic acid analogue such as denopterin, methotrexate, pemetrexed, pteropterin, trimetrexate; a purine analog such as fludarabine, 6-mercaptopurine, thiamiprine, thioguanine; a pyrimidine analog such as ancitabine, azacitidine, 6-azauridine, carmofur, cytarabine, dideoxyuridine, doxifluridine, enocitabine, floxuridine, 5-FU; an androgen such as calusterone, dromostanolone propionate, epitiostanol, mepitiostane, testolactone; an anti-adrenal such as aminoglutethimide, mitotane, trilostane; a folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidaniine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2.2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol®, Bristol-Myers Squibb Oncology, Princeton, N.J.) and docetaxel (Taxotere®, Rhône-Poulenc Rorer, Antony, France); chlorambucil; gemcitabine; 6-thioguanine; mercaptopurine; methotrexate; a platinum analog such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamicins; capecitabine; and pharmaceutically acceptable salts, acids or derivatives of any of the above.

Also included as chemotherapeutic agents are anti-hormonal agents that act to regulate or inhibit hormone action on tumors such as anti-estrogens including for example, tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, a liposomal trans-crocetin composition is administered in combination therapy with a chemotherapeutic agent that is less effective under hypoxic conditions. In some embodiments, the chemotherapeutic agent is an alkylating agent. In further embodiments, the chemotherapeutic agent is a member selected from carboplatin, cisplatin, melphalan, oxaliplatin, procarbazine, temozolomide, and thiotepa. In some embodiments, the chemotherapeutic agent is an antimetabolite agent. In further embodiments, the chemotherapeutic agent is a member selected from 5-Fluorouracil, gemcitabine, methotrexate, and pemetrexed. In some embodiments, the chemotherapeutic agent is an antibiotic. In further embodiments, the chemotherapeutic agent is a member selected from actinomycin D, bleomycin, doxorubicin, and streptonigrin. In some embodiments, the chemotherapeutic agent is a plant alkaloid. In further embodiments, the chemotherapeutic agent is a plant alkaloid selected from docetaxel, etoposide, vincristine, irinotecan, and VP-16. In some embodiments, the chemotherapeutic agent is a multikinase inhibitor. In further embodiments, the chemotherapeutic agent is sorafenib.

In some embodiments, a liposomal trans-crocetin pharmaceutical composition and/or dosing regimen provided herein is administered in combination therapy with an immunotherapy. In some embodiments, one or more provided trans-crocetin compositions are administered to a subject before the administration of an immunotherapeutic agent (e.g., 5 minutes to 72 hours, 15 minutes to 48 hours, or 30 minutes to 24 hours before, or within 12 hours, 9 hours, 6 hours, 4 hours, 2 hours, or 1 hour before the administration of the immunotherapeutic agent.

In some embodiments, a liposomal trans-crocetin pharmaceutical composition and/or dosing regimen provided herein is administered in combination therapy with a checkpoint inhibitor. In some embodiments, the checkpoint inhibitor is a monoclonal antibody (e.g., a humanized antibody, chimeric antibody, or a fully human antibody), a fusion protein or other binding protein, a biologic therapeutic, or a small molecule, that binds to blocks or inhibits the activity of the checkpoint inhibitor.

In some embodiments, a liposomal trans-crocetin pharmaceutical composition and/or dosing regimen provided herein is administered is administered in combination therapy with a checkpoint inhibitor that inhibits a checkpoint protein selected from PD1, PDL1, CTLA4, PDL2, LAG3, TIM3, 2B4, A2aR, ID02, B7-H3, B7-H4, BTLA, CD2, CD20, CD27, CD28, CD30, CD33, CD40, CD52, CD70, CD80, CD86, CD112, CD137, CD160, CD226, CD276, DR3, OX-40, GAL9, GITR, HVEM, IDO1, ICOS, KIR, LAIR, LIGHT, MARCO, PS, SLAM, TIGIT, VISTA, and VTCN1, or a combination thereof. In some embodiments, the liposomal trans-crocetin pharmaceutical composition is administered in combination therapy with a checkpoint inhibitor that inhibits a checkpoint protein selected from PD1, PDL1, CTLA4, PDL2, LAG3, TIM3, 2B4, A2aR, B7-H3, B7-H4, BTLA, HVEM, GAL9, VISTA, TIGIT, KIR, CD160, CGEN-15049, CHK1, CHK2, and a B-7 family ligand, or a combination thereof.

In some embodiments, the checkpoint inhibitor disrupts binding of PD1 to PDL1. In some embodiments, the checkpoint inhibitor inhibits PD1. In some embodiments, the checkpoint inhibitor is an anti-PD1 antibody. In some embodiments, the checkpoint inhibitor is AMP-224 (Amplimmune, GSK), MEDI0680 (MedImmune), lambrolizumab (e.g., MK-3475), pidilizumab (e.g., CT-011; CureTech, Ltd.), or REGN2810 (Regeneron). In particular embodiments, the checkpoint inhibitor is nivolimumab (e.g., BMS-936558 or MDX1106; Bristol-Myers Squibb). In particular embodiments, the checkpoint inhibitor is pembrolizumab (e.g., Keytruda®; Merck).

In some embodiments, the checkpoint inhibitor inhibits PDL1. In some embodiments, the checkpoint inhibitor is an anti-PDL1 antibody. In particular embodiments, the checkpoint inhibitor is BMS-936559, durvalumab (e.g., Imfinzi®, AstraZeneca MEDI4736) AstraZeneca), atezolizumab (e.g., Tecentriq®, Genentech, Roche), avelumab (Merck, Pfizer), aezolizumab (e.g., MPDL3280A), avelumab (e.g., MSB0010718C), or MDX1105-01 (Bristol-Myers Squibb)).

In some embodiments, the checkpoint inhibitor inhibits CTLA4. In some embodiments, the checkpoint inhibitor is a CTLA4 antibody. In some embodiments, CTLA4 inhibitor is ipilimumab CTLA4 (e.g., Yervoy® (Bristol-Myers Squibb), or tremelimumab (CTLA4).

In some embodiments, the checkpoint inhibitor inhibits Lymphocyte Activation Gene-3 (LAG3). In some embodiments, the checkpoint inhibitor is an anti-LAG3 antibody. In particular embodiments, the LAG3 inhibitor is relatlimab (e.g., BMS-986016 (Bristol-Myers Squibb), MK4280 (Merck & Co.), REGN3767 (Regeneron), GSK2831781 (GSK), LAG525 (Novartis), TSR-033 (Tesaro), EOC202, INCAGN02385, FS118 (F-star), MGD013 (MacroGenics), Sym-022 (Symphogen), B1754111 (Bohringer Ingelheim), or IMP321 (Immutep S.A.).

In some embodiments, the checkpoint inhibitor inhibits T-cell immunoglobulin mucin containing protein-3 (TIM3). In some embodiments, the checkpoint inhibitor is an anti-TIM3 antibody. In particular embodiments, the TIM3 inhibitor is TSR-022 (Tesaro), LY3321367 (Eli Lilly), Sym023 (Symphogen), INCAGN2390 (Incyte), MBG453 (Novartis), BMS-986258 (BMS), SHR-1702 (Jiangsu HengRui), or R07121661 (Roche).

In some embodiments, the checkpoint inhibitor inhibits TIGIT. In some embodiments, the checkpoint inhibitor is an anti-TIGIT antibody. In particular embodiments, the TIGIT inhibitor is tiragolumab (e.g., RG6058, MTIG7192A (Genentech)), MK-7684 (Merck), BMS-986207 (Bristol-Myers Squibb), etigilimab (OMP-313M32; Oncomed), ASP8374 (Astellas Pharma/Potenza), AB154 (Arcus Biosciences), BGB-A1217 (Beigene), AGEN1307 (Agenus), COM902 (Compugen), IBI-939 (Innovent), E0S884448 (Iteos Therapeutics), CASC-674 (Seattle Genetics), MTIG7192A (Genentech), or NCT03119428. In particular embodiments, the TIGIT inhibitor is Tiragolumab (RG6058), MK-7684, or BMS-986207.

In some embodiments, the checkpoint inhibitor inhibits VISTA. In some embodiments, the checkpoint inhibitor is an anti-VISTA antibody. In particular embodiments, the VISTA inhibitor is JNJ-61610588 (Johnson & Johnson) or CA-170 (Curis).

In some embodiments, the checkpoint inhibitor inhibits B7-H3. In some embodiments, the checkpoint inhibitor is an anti-B7-H3 antibody. In particular embodiments, the B7-H3 inhibitor is enoblituzumab (e.g., MGA271 (MacroGenics)), MGD009e (MacroGenics), 131I-8H9/omburtamab, or 124I-8H9/omburtamab.

In some embodiments, the checkpoint inhibitor is selected from the group: lirlumab KIRD2, IPH2101, and KIRD2.

In some embodiments, a liposomal trans-crocetin pharmaceutical composition and/or dosing regimen provided herein is administered in combination therapy with an antibody selected from: simtuzumab, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, nannatumab, naptumomab, necitumumab, nimotuzumab, nofetumomab, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49, and 3F8.

In some embodiments, the immunotherapy activates or increases the activity of a costimulatory receptor. In some embodiments, the immunotherapy is a monoclonal antibody (e.g., a humanized antibody, chimeric antibody, or a fully human antibody), a fusion protein or other binding protein, a biologic therapeutic, or a small molecule, that binds to and activates or increases the activity of the costimulatory receptor.

In some embodiments, the immunotherapy activates or increases the activity of CD27. In some embodiments, the immunotherapy is a CD27 agonist. In particular embodiments, the CD27 agonist is varlilumab (e.g., CDX-1127, Celldex Therapeutics).

In some embodiments, the immunotherapy activates or increases the activity of inducible T-cell co-stimulator (ICOS, also known as CD278). In some embodiments, the immunotherapy is an ICOS agonist. In some embodiments, the immunotherapy activates or increases the activity of glucocorticoid-induced tumor necrosis factor receptor (GITR).

In some embodiments, the immunotherapy activates or increases the activity of CD137 (called 4-1BB). In some embodiments, the immunotherapy is a 4-1BB agonist. In particular embodiments, the 4-1BB agonist is utomilumab (e.g., PF-05082566, Pfizer) or urelumab (e.g., BMS-663513, Bristol-Myers Squibb).

In some embodiments, the immunotherapy activates or increases the activity of OX40. In particular embodiments, the OX40 agonist is an antibody selected from: PF-04518600/PF-8600 (Pfizer), GSK3174998 (Merck); MEDI0562 (Medimmune/AstraZeneca), MEDI6469 (Medimmune/AstraZeneca); and BMS-986178 (Bristol-Myers Squibb).

In some embodiments, a liposomal trans-crocetin pharmaceutical composition and/or dosing regimen provided herein is administered in combination with radiation therapy. In some embodiments, the radiation therapy is intraoperative radiation therapy ("IORT"). In some embodiments, the radiation is localized to a tumor site. In some embodiments, the subject is subjected to intraoperative radiation prior to resection of the tumor or following resection of the tumor. The tumor site may comprise different types of cells including cancerous and benign cells. In some embodiments, the radiation therapy is stereotactic body radiotherapy ("SBRT") or stereotactic radiosurgery ("SRS"). In some embodiments, a liposomal trans-crocetin pharmaceutical composition and/or dosing regimen provided herein is administered in combination therapy with radiation therapy to treat, stomach cancer, lung cancer, cervical cancer, brain cancer, pancreatic cancer, cancer of the head or neck, breast cancer, or cancer of the oral cavity.

In some embodiments, the radiation may be ionizing radiation such as particle beam radiation. In some embodiments, the particle beam radiation is from electrons, protons, neutrons, heavy ions such as carbon ions, or pions. In some embodiments, the ionizing radiation is from x-rays, UV-light. γ-rays, or microwaves. In some embodiments, more than one type of radiation therapy is administered to the subject.

In some embodiments, the radiation is administered to the subject with a mobile electron beam therapy system. The radiation may be delivered before, during or after a surgical procedure. In some embodiments, the patient is administered a radiation sensitizer (e.g., an electron-affinic nitroimidazole, such as a molecule comprising 2-nitroimidazole (e.g. Etanidazole or doranidazole). In further embodiments, the patient is administered a radiation sensitizer and subjected to radiation therapy within a short time thereafter, such as within about 2 hours of each other, such as within about 1 hour of each other, e.g., within about 40 minutes of each other.

In some embodiments, one or more provided trans-crocetin compositions are administered to a subject before the administration of radiation (e.g., 5 minutes to 72 hours, 15 minutes to 48 hours, or 30 minutes to 24 hours before, or within 12 hours, 9 hours, 6 hours, 4 hours, 2 hours, or 1 hour before the administration of the radiation.

Kits for Administration of Active Agents

In another embodiment, the disclosure provides a kit for administering liposomal trans-crocetin to a subject for treating a disorder, or condition. In some embodiments, the disclosure provides a kit for delivering a therapeutic agent to a subject, the kit comprising: (a) a first composition comprising a provided liposomal trans-crocetin composition; and a (b) second composition containing for example, reagents, buffers, excipients, or another therapeutic agent that is stored separately prior to administration to the subject. Such kits typically include two or more components necessary for treating a disease state, such as hypoxia or inflammation related condition. In some embodiments, the kits include for example, a provided liposomal trans-crocetin composition, along with reagents, buffers, containers and/or equipment. The liposomal trans-crocetin compositions and formulations can be in lyophilized form and then reconstituted prior to administration. In some embodiments, the kits include a packaging assembly that include one or more components used for treating the disease state of a patient. For example, a packaging assembly may include separate containers that house the therapeutic trans-crocetin compositions and other excipients or therapeutic agents that can be mixed with the compositions prior to administration to a patient. In some embodiments, a physician may select and match certain components and/or packaging assemblies depending on the treatment or diagnosis needed for a particular patient.

EXAMPLES

Example 1—Production of Calcium Trans-Crocetin Liposomes

Two different variants of trans-crocetin were used to produce trans-crocetin liposomes, namely: trans-crocetin free acid (TC) and its sodium salt, sodium trans-crocetin (STC). Trans-crocetin was encapsulated in liposomes by the following procedures.

Multiple Bilayer (Multilamellar) Vesicle (MLV) Production:

First, the lipid components of the liposome lipid membrane were weighed out and combined as a concentrated solution in ethanol at a temperature of around 65° C. In one preparation, the lipids used were hydrogenated soy phosphatidylcholine, cholesterol, and DSPE-PEG-2000 (1,2-distearoyl-sn-glycero-3-phosphoethan-olamine-N-[methoxy (polyethylene glycol)-2000]). The molar ratio of HSPC: cholesterol:PEG-DSPE was approximately 3:2:0.15. In another preparation, the lipids used were HSPC, cholesterol, PEG-DSPE-2000, and 1-palmitoyl-2-glutaryl-sn-glycero-3-phosphocholine (PGPC). The molar ratio of HSPC:cholesterol:PEG-DSPE:PGPC was approximately 2.7:2:0.15:0.3. Next, calcium acetate was dissolved in an aqueous buffer at a concentration of 125 mM, or 250 mM, with a pH of 7.0. The calcium acetate solution was heated up to 65° C.

The ethanolic lipid solution was added into the calcium acetate solution using a pipet. During this step the solution was well stirred using a magnetic stirrer. The mixing was performed at an elevated temperature (63° C.-72° C.) to ensure that the lipids were in a liquid crystalline state (as opposed to the gel state that they would attain at temperatures below the lipid transition temperature (Tm=51° C.-54° C.)). As a result, the lipids were hydrated and formed multiple bilayer (multilamellar) vesicles (MLVs) containing calcium acetate in the interior space.

Downsizing of MLVs Using Filter Extrusion:

The MLVs were fragmented into unilamellar (single bilayer) vesicles of the desired size by high-pressure extrusion using two passes through stacked (track-etched polycarbonate) membranes. The stacked membranes had two layers with a pore size of 200 nm and six layers with a pore size of 100 nm. During extrusion, the temperature was maintained above the Tm to ensure plasticity of the lipid membranes. As a result of the extrusion, large and heterogeneous in size and lamellarity MLVs were turned into small, homogenous (100-120 nm) unilamellar vesicles (ULVs) that sequestered calcium acetate in their interior space. A Malvern Zetasizer Nano ZS instrument (Southborough, MA) with back scattering detector (90°) was used for measuring the hydrodynamic size (diameter) of the vesicles at 25° C. in a plastic micro cuvette. The samples were diluted 50-fold in formulation matrix before analysis.

After ULVs containing calcium acetate had been produced, the extra-liposomal calcium acetate was removed using SEC (size exclusion chromatography, with PD10 columns) or TFF (tangential flow diafiltration). Tonicity reagent was added to the liposomes to balance the osmolality (final concentration: 5% dextrose for 125 mM calcium acetate liposomes and 10% dextrose in for 250 mM calcium acetate liposomes). Once the calcium acetate gradient was generated, the trans-crocetin loading procedure is preferably performed within 24 hours. The lipid content of the prepared liposome solution was determined by phosphate assay.

1 mg/mL trans-crocetin solution was prepared in 10% dextrose (for 250 mM calcium acetate liposomes) and pH was adjusted to 8. The trans-crocetin solution was mixed with calcium acetate liposome solution at different Drug/ Lipid ratios (100 g/mM, 80 g/mM, 60 g/mM or 40 g/mM). The mixture was then thoroughly stirred and heated to 65° C. for 30 minutes, followed by quick cool down to room temperature using an ice water bath. This step can be replaced by stirring the mixture at room temperature overnight.

The movement of trans-crocetin molecule (charge-free, neutral form) across the liposome lipid bilayer was driven by the gradient generated with calcium acetate (in other words, acetic acid diffused out, trans-crocetin diffused in). Trans-crocetin was then trapped inside of the liposomes by ionizing and then forming a precipitate with calcium (as a calcium salt form (calcium trans-crocetin, CTC)).

Purification of Liposomes:

The extra-liposomal trans-crocetin was removed using SEC (PD10 columns) or TFF. In this example, the buffer used in SEC was HBS (HEPES buffered saline, pH 6.5). Upon completion of purification, filter sterilization was performed using a 0.22 micron filter. A Malvern Zetasizer Nano ZS instrument (Southborough, MA) with back scattering detector (90°) was used for measuring the hydrodynamic size (diameter) of the vesicles at 25° C. in a plastic micro cuvette. The samples were diluted before analysis.

into microfluidic channel and mixed while flowing through it with Precision NanoSystems' NanoAssemblr® device. The mixing was performed at an elevated temperature (63° C.-72° C.) to ensure that the lipids were in the liquid crystalline state (as opposed to the gel state that they would attain at temperatures below the lipid transition temperature (Tm=51° C.-54° C.)). The size of liposome can be controlled by ratio between lipid solution and aqueous solution, as well as the mixing flow rate.

Example 3—MTC Liposome Generation and Characterization

Production of Trans-Crocetin Liposomes with Magnesium Acetate Gradient:

To produce magnesium trans-crocetin liposomes, two different variants of the molecule can be used namely: trans-crocetin free acid (TC) and its sodium salt, sodium trans-crocetinate (STC).

Liposome with magnesium acetate is prepared by the following procedure. First, the lipid components of the liposome membrane were weighed out and combined as a concentrated solution in ethanol at a temperature of around 65° C. In one example, the lipids used were hydrogenated

TABLE 1

Physical characteristics of representative CTC loaded nanoparticles

| | Starting concentration | Encapsulation efficiency | Final concentration | Drug/Lipid Ratio | Diameter | PDI | Zeta potential |
|---|---|---|---|---|---|---|---|
| CTC LPs | 1 mg/ml trans-crocetin disodium | 96.9% | 0.24 mg/ml | 78.6 g/mM lipids | 105.7 nm | 0.056 | −2.88 mV |
| CTC Lps | 0.75 mg/ml trans-crocetin disodium | 98.32% | 3.92 mg/ml | 68.23 g/mM lipids | 103.8 nm | 0.041 | −2.71 mV |
| CTC Lps | 0.75 mg/mL trans-crocetin disodium | 99.47% | 3.90 mg/mL | 66.23 g/mM lipids | 100.8 nm | 0.031 | −3.67 mV |
| CTC Lps | 0.75 mg/ml trans-crocetin disodium | 92.59% | 2.49 mg/mL | 34.74 g/mM lipids | 101.9 nm | 0.038 | −3.83 mV |
| PGPC CTC Lp2 | 0.75 mg/ml trans-crocetin disodium | 98.30% | 5.34 mg/mL | 85.74 g/mM lipids | 95.9 nm | 0.043 | −3.66 mV |

Example 2—Preparation of Calcium Acetate Liposomes with Nanoassemblr®

Calcium acetate loaded liposomes were prepared by the following procedure. First, the lipid components of the liposome lipid membrane were weighed out and combined as a concentrated solution in ethanol at a temperature of around 65° C. In one example, the lipids used were hydrogenated soy phosphatidylcholine, cholesterol, and DSPE-PEG-2000 (1,2-distearoyl-sn-glycero-3-phosphoethanolamine-N-[methoxy-(polyethylene glycol)-2000]).

The molar ratio of HSPC:cholesterol:PEG-DSPE was approximately 3:2:0.15. In another example, the lipids used were HSPC, cholesterol, PEG-DSPE-2000, and 1-palmitoyl-2-glutaryl-sn-glycero-3-phosphocholine (PGPC). The molar ratio of HSPC:cholesterol:PEG-DSPE:PGPC was approximately 2.7:2:0.15:0.3.

Next, calcium acetate was dissolved in an aqueous buffer at a concentration of 125 or 250 mM, with a pH of 7.0. The calcium acetate solution was heated to 65° C. The ethanolic lipid solution and the calcium acetate solution were separately transferred to syringes. Two solutions were injected soy phosphatidylcholine, cholesterol, and DSPE-PEG-2000 (1,2-distearoyl-sn-glycero-3-phosphoethanolamine-N-[methoxy(polyethylene Gly-col)-2000]). The molar ratio of HSPC:cholesterol:PEG-DSPE was approximately 3:2:0.15. In another example, the lipids used were HSPC, cholesterol, PEG-DSPE-2000, and 1-palmitoyl-2-glutaryl-sn-glycero-3-phosphocholine (PGPC). The molar ratio of HSPC:Cholesterol:PEG-DSPE:PGPC was approximately 2.7:2:0.15:0.3. Next, magnesium acetate was dissolved in an aqueous buffer at a concentration of 125 or 250 mM with a pH of 7.0. The magnesium acetate solution was heated up to 65° C. The ethanolic lipid solution was added into the magnesium acetate solution using a pipette. During this step the solution was well stirred using a magnetic stirrer. The mixing was performed at an elevated temperature (63° C.-72° C.) to ensure that the lipids were in a liquid crystalline state (as opposed to the gel state that they attain at temperatures below the lipid transition temperature Tm=51° C.-54° C.)). As a result, the lipids were hydrated and form multilamellar vesicles (MLVs) containing magnesium acetate in their interior space (internal solution).

Downsizing of MLVs Using Filter Extrusion:

The MLVs are fragmented into unilamellar (single bilayer) vesicles of the desired size by high-pressure extrusion using two passes through stacked (track-etched polycarbonate) membranes. The stacked membranes have two layers with a pore size of 200 nm and six layers with a pore size of 100 nm. During extrusion, the temperature was maintained above the Tm. As a result of the extrusion, large and heterogeneous in size and lamellarity MLVs were turned into small, homogenous (100-120 nm) unilamellar vesicles (ULVs) that sequestered the calcium acetate in their interior space. A Malvern Zetasizer Nano ZS instrument (Southborough, MA) with back scattering detector (90°) was used for measuring the hydrodynamic size (diameter) of the vesicles at 25° C. in a plastic micro cuvette. The samples were diluted 50-fold in formulation matrix before analysis.

Gradient Generation:

After ULVs containing magnesium acetate were produced, the extra-liposomal magnesium acetate was removed using SEC (size exclusion chromatography, with PD10 columns) or TFF (tangential flow diafiltration). Tonicity reagent solutions (such as 50% dextrose) were added to the liposomes to balance the osmolality (final concentration: 5% dextrose for 125 mM magnesium acetate liposomes and 10% dextrose for 250 mM magnesium acetate liposomes). The lipid content of the prepared liposome solution was determined by phosphate assay.

Trans-Crocetin Loading into Magnesium Acetate Liposomes:

1 mg/mL trans-crocetin or trans-crocetin sodium solution was prepared in 10% dextrose (for 250 mM magnesium acetate liposomes) and pH was adjusted to 8-8.5 with sodium hydroxide. Trans-crocetin sodium solution was mixed with magnesium acetate liposome solution at different Drug/lipid ratio (100 g/mol, 80 g/mol, 60 g/mol or 40 g/mol). The mixture was then thoroughly stirred and heated up to 65° C. for 30 minutes, followed by quick cool down to room temperature using an ice water bath. This step can be replaced by stirring the mixture at room temperature overnight.

Purification of Liposomes:

The extra-liposomal trans-crocetin was removed using SEC (PD10 columns) or TFF. In this example, the buffer used in SEC was HBS (HEPES buffered saline, pH 6.5). Upon completion of purification, filter sterilization was performed using a 0.2-0.22 micron filter. A Malvern Zetasizer Nano ZS instrument (Southborough, MA) with back scattering detector (90°) was used for measuring the hydrodynamic size (diameter) at 25° C. in a plastic micro cuvette. The samples were diluted before analysis.

TABLE 3

| Liposomal CTC and MTC PK result summary | | | | |
| --- | --- | --- | --- | --- |
| Test article | T$_{1/2}$ (h) | AUC (mg/ml*h) | C$_{max}$ (mg/ml) | Plasma Exposure (fold increase compared to free drug STC) NCA analysis |
| STC free drug | 0.35 | 0.21 | 0.36 | NA |
| STC free drug | 0.47 | 0.26 | NA | NA |
| CTC-LP-80 | 5.12 | 8.36 | 1.26 | 40 |
| CTC-LP-60 | 4.52 | 6.4 | 1.1 | 35 |
| CTC-LP-40 | 5.8 | 10.75 | 1.44 | 56 |
| MTC-LP-80 | 2.88 | 5.29 | 1.29 | 25 |
| MTC-LP-60 | 2.9 | 6.01 | 1.44 | 29 |
| MTC-LP-40 | 2.67 | 5.25 | 1.37 | 25 |
| Fluorescent Dye Labeled Liposome | 12.2 | NA | NA | NA |

Balb/c mice (3 mice/group) were treated with a single dose of STC free drug, CTC/MTC-LPs (D/L ratio 80, 60, 40), and fluorescent dye labeled liposome via a slow intravenous bolus in order to collect serial blood samples at various timepoints over 24 hour period (typically, 5 min, 1 hr., 2 hr., 4 hr., 8 hr., and 24 hr.).

5 µL of each plasma sample was mixed with 395 µL methanol containing 1% formic acid. Sample mixtures were well mixed by vortexing. Samples were incubated at −20° C. for 1 hr. and then equilibrated at room temperature for 15 min. Samples were vortexed and then centrifuged at 10000 RPM for 10 m0 at room temperature. 200 µL of supernatant was removed from each sample without disturbing pellet and analyzed by HPLC. If the amount of plasma permitted, this analysis was duplicated.

The concentration of STC in the plasma samples was quantified by standard curve constructed by analyzing plasma samples containing known amount of STC. PK profiles were analyzed.

TABLE 2

| Physical characteristics of representative MTC loaded nanoparticles | | | | | | |
| --- | --- | --- | --- | --- | --- | --- |
| | Starting concentration | Encapsulation efficiency | Final concentration | Drug/Lipid Ratio | Diameter | PDI | Zeta potential |
| MTC LP (D/L-80) | 0.75 mg/mL Trans-crocetin disodium | 99.98% | 5.03 mg/ml | 77.22 g/mol lipids | 102.1 nm | 0.046 | −2.32 mV |
| MTC LP (D/L-60) | 0.75 mg/mL Trans-crocetin disodium | 98.82% | 4.00 mg/mL | 58.83 g/mol lipids | 103.4 nm | 0.034 | −3.23 mV |
| MTC LP (D/L-40) | 0.75 mg/mL Trans-crocetin disodium | 98.90% | 2.25 mg/mL | 35.13 g/mol lipids | 103.7 nm | 0.039 | −3.23 mV |

TABLE 4

| | | Particle | | Zeta | Lipid | Crocetin | |
| | Analysis | size | | potential | Conc. | Conc. | Resulting |
| Test article | date | (nm) | PDI | (mV) | (mM) | (mg/mL) | D/L |
|---|---|---|---|---|---|---|---|
| CTC-LP-80 1st | Initial | 101.1 | 0.039 | −3.09 | 63.88 | 5.01 | 78.47 |
| CTC-LP-80 1st | 1 Month | 100.3 | 0.046 | −1.56 | 1.64 | 0.13 | 77.73 |
| CTC-LP-80 1st | 2 Months | 99.33 | 0.049 | −3.44 | 1.25 | 0.10 | 76.46 |
| CTC-LP-80 1st | 5 Months | 99.56 | 0.046 | −2.49 | 2.03 | 0.16 | 78.37 |
| CTC-LP-80 1st | 6 Months | 103.3 | 0.06 | −2.21 | 1.73 | 0.14 | 78.66 |
| CTC-LP-80 2nd | Initial | 97.3 | 0.049 | −3.44 | 71.09 | 5.44 | 76.57 |
| CTC-LP-80 2nd | 3 Months | 99.6 | 0.037 | −2.21 | 2.22 | 0.17 | 78.83 |
| CTC-LP-80 2nd | 4 Months | 99.8 | 0.038 | −3.27 | 2.14 | 0.17 | 79.91 |
| CTC-LP-80 2nd | 5 Months | 99.7 | 0.05 | −4.55 | 1.31 | 0.10 | 78.73 |
| CTC-LP-80 3rd | Initial | 102.3 | 0.042 | −0.80 | 70.57 | 5.48 | 77.64 |
| CTC-LP-80 3rd | 2 Months | 102.9 | 0.038 | −2.11 | 2.04 | 0.16 | 77.72 |
| CTC-LP-80 3rd | 3 Months | 102.3 | 0.042 | −2.74 | 2.01 | 0.15 | 76.22 |
| CTC-LP-80 3rd | 4 Moths | 104.2 | 0.090 | −2.17 | 1.12 | 0.09 | 77.10 |
| CTC-LP-80 4th | Initial | 99.6 | 0.037 | −2.21 | 70.57 | 5.58 | 79.11 |
| CTC-LP-80 4th | 1 Month | 101.6 | 0.054 | −2.00 | 2.52 | 0.20 | 80.76 |
| CTC-LP-80 4th | 2 Months | 100.8 | 0.042 | −3.22 | 2.05 | 0.16 | 77.11 |
| CTC-LP-80 4th | 3 Months | 102.8 | 0.073 | −5.01 | 1.36 | 0.11 | 79.06 |
| CTC-LP-60 | Initial | 100.8 | 0.0 | −3.7 | 58.91 | 3.90 | 66.23 |
| CTC-LP-60 | 4 Months | 104.0 | 0.0 | −1.9 | 2.12 | 0.14 | 68.12 |
| CTC-LP-60 | 5 Months | 103.2 | 0.037 | −2.63 | 1.70 | 0.12 | 68.89 |
| CTC-LP-40 | Initial | 101.9 | 0.0 | −3.8 | 71.54 | 2.49 | 34.74 |
| CTC-LP-40 | 4 Months | 106.1 | 0.0 | −2.1 | 2.54 | 0.09 | 36.58 |
| CTC-LP-40 | 5 Months | 103.1 | 0.038 | −2.28 | 2.21 | 0.08 | 36.41 |

CTC liposome stability was further assessed by characterizing liposome solution after the liposomes were purified from potentially leached our drug by size exclusion column after certain storage duration (up to 6 months). The characterization methods were same as previously described.

The CTC liposomes showed almost the same drug/lipid ratio within error range. Therefore, negligible drug leaching over 6 months at the storage condition (4° C.) was confirmed.

TABLE 5

Evaluation of liposome batch reproducibility and stability

| D/L of BC samples | March | April | May | June | July | August | September | October |
|---|---|---|---|---|---|---|---|---|
| CTC-LP-80 (1st) | 76.57 | 76.37 | 75.81 | | | 75.36 | 78.10 | |
| CTC-LP-80 (2nd) | | | 76.57 | | | 76.41 | 82.12 | 77.12 |
| CTC-LP-80 (3rd) | | | | 77.64 | | 78.13 | 77.81 | 76.54 |
| CTC-LP-80 (4th) | | | | | 79.11 | 82.93 | 78.92 | 80.77 |

Liposome batch reproducibility and stability were evaluated by characterizing the D/L.

CTC liposomes showed negligible change in this evaluation. Thus, CTC liposomes showed stability at least 6 months.

TABLE 6

MTC liposome stability

| | | Particle | | Zeta | Lipid | Drug | |
| | Analysis | size | | Potential | Conc. | Conc. | D/L |
| Test article | date | (nm) | PDI | (mV) | (mM) | (mg/mL) | (g/mol) |
|---|---|---|---|---|---|---|---|
| MTC-LP-80 | Initial | 102.1 | 0.046 | −2.32 | 65.2 | 5.03 | 77.22 |
| MTC-LP-80 | 1 Month | 104.4 | 0.038 | −2.84 | 19.70 | 1.53 | 77.72 |
| MTC-LP-80 | 2 Months | 105.5 | 0.051 | −4.78 | 18.29 | 1.41 | 77.22 |
| MTC-LP-60 | Initial | 103.4 | 0.034 | −3.23 | 57.96 | 3.27 | 56.39 |
| MTC-LP-60 | 10 days | 105.2 | 0.05 | −2.46 | 23.14 | 1.38 | 59.67 |
| MTC-LP-60 | 1 Month | 105.4 | 0.056 | −4.45 | 23.31 | 1.39 | 59.85 |
| MTC-LP-40 | Initial | 103.7 | 0.039 | −3.23 | 64.04 | 2.25 | 35.13 |
| MTC-LP-40 | 10 days | 104 | 0.03 | −2 | 24.39 | 0.87 | 35.76 |
| MTC-LP-40 | 1 Month | 106.5 | 0.058 | −5.74 | 23.21 | 0.84 | 36.27 |

Determination procedures were the same as previously described.

MTC liposomes showed almost the same drug/lipid ratio within error range. Therefore, liposome is stable at least 2 months period at storage condition (4° C.) was confirmed.

Example 4—Reoxygenation Properties of L4L-121 In Vitro

The reoxygenation properties of L4L-121 was evaluated in vitro in endothelial cells (HUVECs). The IC50 of L4L-121 in HUVECs was determined after 72 h of treatment by viability assays (CellTiter-Glob, Promega). No toxicity was observed for concentrations up to 1 mg/mL, with an IC50 of 1136±21 μg/mL (FIG. 2E). HUVEC cells were next incubated in hypoxic conditions (1% PO2) for 24 h before treatment with either free TC or various concentrations of L4L-121. The cells under continuous hypoxic conditions that were treated with free TC demonstrated a rapid reoxygenation effect at 30 min post-treatment (up to 15% PO2 with 5 μg/mL TC) (FIGS. 2F and 2G) by flow cytometry, a rapid loss of efficacy of free TC over time (back to 5% PO2 at 3 h after treatment) (FIGS. 2F and 2G). In contrast, with L4L-121 treatment over time (FIG. 2H), the liposomal formulation increased oxygen levels as quickly as treatment using free TC. Without being bound by theory, this rapid oxygenation effect of L4L-121 is likely attributed to a biphasic release of TC from the liposomes that includes an initial fast release (approx. 25% in the first 6 h) of some of the payload followed by a more sustained release of TC from the liposomes over a prolonged period.

Materials and Methods

HUVECs (passages 3 and 4) were plated at ~80% confluence for 24 h under hypoxic conditions (1% 02, 37° C.). For quantification of the hypoxia levels, cells were then incubated for 1 h with 1.5 μM BioTracker 520 Green Hypoxia Dye (Sigma-Aldrich) before being washed and stored in the hypoxia chamber for 1 h. Finally, the cells were treated with either PBS or L4L-121 at various concentrations and times. Hypoxia levels were quantified with a BD Accuri™ C6 cell analyzer with a direct read-out of the BioTracker probe. The results were analyzed with FlowJo software version 10 (TreeStar).

Example 5—Pharmacokinetics and Toxicity of L4L-121 of L4L-121 in Mice

The PK properties of L4L-121 were evaluated in healthy mice. This study was designed to compare the PK characteristics of L4L-121 to its counterpart free TC after one intravenous injection at equal doses of 2.5 mg/kg (normalized to TC). The half-life increased ~6-fold (3.718 vs 0.619 h), while the exposure (AUC) increased ~12-fold (32.4 vs 2.7 h*μg/ml) compared to that of the free TC (data not shown). The toxicity of L4L-121 has been studied in healthy mouse models at doses up to 50 mg/kg. The objective of this study was to evaluate the toxicity of L4L-121 compared to saline. For this study, forty male mice with ages ranging from 9 to 10 weeks were treated for 5 days with different daily doses of L4L-121 and monitored for AEs. No signs of toxicity were observed, with a stable body weight post-treatment, for doses up to 25 mg/kg (data not shown). Importantly, while F4/80 staining confirmed the high level of L4L-121 in the liver, as shown by the increased amount of positive staining of Kupffer cells (data not shown), hematoxylin and eosin (H&E)-stained slides of the liver (data not shown) confirmed that no macroscopic changes were observed 5 days post-treatment at the highest tested concentrations (25 mg/kg).

Example 6—Liposomal CTC Efficacy Studies in Mice (Study 1)

The objective of this study was to evaluate the efficacy of liposome encapsulated calcium trans-crocetinate (L4L-121) plus standard of care when compared to saline plus standard of care, in a CLP model used to induce severe grade sepsis. For this study, ten male mice per group with ages ranging from 8-10 weeks were treated for 5 days. The mice in the control group received a day administration of 0.9% saline via IP injection at a volume of 0.25 mL for 5 days in conjunction with 12.5 mg/kg of imipenem twice a day. The other mice were treated with 50 mg/kg of L4L-121 once a day in conjunction with 12.5 mg/kg of imipenem twice a day.

The study duration was 6 days. The following efficacy parameters were evaluated for all groups: Blood was collected on all animals following euthanasia. Following blood collection, heart, spleen, liver, lungs, kidneys and cecum were collected. Survival was assessed by enumeration of mortality over 5 days following CLP surgery.

Results

As shown in FIG. 5, although L4L-121 in combination with imipenem demonstrated a reduction in mortality when compared to the saline plus imipenem control group. Thirty percent mortality was observed in the L4L-121 with imipenem group, compared to 50% mortality in the saline with imipenem group.

L4L-121 Efficacy Study 2: Study Design and Results

Study Design

This study was performed to evaluate the efficacy of L4L-121 plus standard of care when compared to saline plus standard of care, in a CLP model used to induce severe grade sepsis. For this study, ten male mice in each group with ages ranging from 8-10 weeks were treated for 5 days. The mice in the control group received a day administration of 0.9% saline via IP injection at a volume of 0.3 mL for 5 days in conjunction with 12.5 mg/kg of imipenem twice a day. The other mice were treated with 50 mg/kg of L4L-121 with a drug to lipid ratio of 60 gm/mol of lipid (D/L 60) once a day in conjunction with 12.5 mg/kg of imipenem twice a day, or 50 mg/kg of L4L-121 with a drug to lipid ratio of 80 gm/mol of lipid (D/L 80) once a day in conjunction with 12.5 mg/kg of imipenem twice a day.

The study duration was 6 days. The following efficacy parameters were evaluated for all groups: Survival was assessed by enumeration of mortality over 5 days following CLP surgery. Animals which were found dead had half of each tissue collected (lungs, kidneys, heart, spleen and liver) collected. Animals that were euthanized prior to study end had blood and tissue collected. Blood was collected on all animals following euthanasia for both moribund mice and those remaining at Day 5 and a full chemistry panel was performed which included assessment of albumin, alkaline phosphatase (ALP), alanine aminotransferase (ALT), aspartate aminotransferase (AST), blood urea nitrogen (BUN), calcium, cholesterol, creatine kinase, creatinine, glucose, total bilirubin, total protein, triglycerides).

Results

As shown in FIG. 6, L4L-121 D/L 80 in combination with imipenem demonstrated a reduction in mortality when compared to the imipenem-treated control group. Fifty percent mortality was observed in the LAL-121 D/L 80 group, compared to 60% in the D/L 60 and the saline plus imipenem groups. None of the deaths recorded in the L4L-121 D/L 80 group were attributed to euthanasia while two of the six deaths recorded in the saline group were a result of euthanasia.

At the time of euthanasia, blood samples, lungs, kidneys, heart, spleen and liver were harvested from the mice. In order to evaluate if any toxicity was present following treatment with L4L-121, a histopathological review of the tissues was performed, and a complete serum chemistry was analyzed. As indicated in FIG. 7, when compared to the saline control group, there were no clinically meaningful changes in creatinine, blood urea nitrogen, alanine aminotransferase, total bilirubin and alkaline phosphatase levels following a day treatment with L4L-121 at the dose level of 50 mg/kg. There was a slight decrease in albumin levels following treatment with L4L-121 and a numerically greater decrease in the saline group.

The overlapping UV absorption between trans-crocetin and other components of serum such as, bilirubin (~450 nm), can lead to errant measurements of trans-crocetin and these other components (e.g., bilirubin). For instance, the inventors have observed that the use of vanadate mediated oxidation method-Randox assays to quantitate bilirubin levels in the serum of patients that have been administered liposomal trans-crocetin leads to high levels of interference that results in a falsely elevated measurement for total bilirubin. In contrast, the inventors have determined that diazo methods such as the sulfanilic acid-based method that uses the BioVision™ kit and the DPD-based method using the Beckman Coulter AU680 Clinical Analyzer display only minimal interference in the presence of for example, liposome encapsulated trans-crocetin. Accordingly, in some embodiments, the disclosure provides a method of determining the level of bilirubin in serum of a patient treated with liposomal trans-crocetin and/or complexed/conjugated trans-crocetin that involves assaying a biological sample obtained from the patient (e.g., serum or plasma) using an acid- or DPD-based diazo method to assay bilirubin content in the sle.

L4L-121 Efficacy Study 3: Study Design and Results
Study Design

The objective of this study was to evaluate the efficacy of L4L-121 plus standard of care when compared to saline plus standard of care, in a CLP model used to induce severe grade sepsis. For this study, ten female mice per group with ages ranging from 11-12 weeks were treated for 5 days. The mice in the control group received a day administration of 0.9% saline via IP injection at a volume of 0.3 mL for 5 days in conjunction with 12.5 mg/kg of imipenem twice a day. The other mice were treated with 50 mg/kg of L4L-121 once a day in conjunction with 12.5 mg/kg of imipenem twice a day.

The study duration was 6 days. The efficacy parameters were evaluated for all groups as follows:

Survival was assessed by enumeration of mortality over 5 days following CLP surgery.

Animals which were found dead had half of each tissue collected (lungs, kidneys, heart, spleen and liver) collected.

Animals that were euthanized prior to study end had blood and tissue collected.

Blood was collected on all animals following euthanasia for both moribund mice and those remaining at Day 5 and a full chemistry panel was performed (albumin, ALP, ALT, AST, BUN, calcium, cholesterol, creatine kinase, creatinine, glucose, total bilirubin, total Protein and triglycerides).

Results

All mice in all treatment groups received all five doses of a day treatment. As seen in FIG. 8, mice treated with L4L-121 and imipenem showed 30% mortality, with two of the three deaths attributed to euthanasia. By contrast, animals treated with saline vehicle and imipenem demonstrated 70% death and one of the seven deaths was a result of euthanasia.

Liver indices were obtained from mice treated with L4L-121 plus imipenem as well as mice treated with saline plus imipenem. As can be seen in FIG. 9, there were no appreciable differences in creatinine, glucose and ALP levels between both groups. Albumin levels were lower than the normal range, both in mice treated with L4L-121 plus imipenem and those treated with saline plus imipenem. There was an increase in blood urea nitrogen and total bilirubin in both groups of mice, and calcium was higher in mice treated with L4L-121 plus imipenem.

L4L-121 Efficacy Study 4: Study Design and Results
Study Design

Based on observations from the prior 3 studies, the Sponsor decided to perform a dose ranging study to optimize the L4L-121 dose. The objective of this study was to evaluate the efficacy of varying doses of L4L-121 plus standard of care when compared to saline and standard of care, in a CLP model used to induce severe grade sepsis. For this study, ten female mice per arm, with ages ranging from 9-10 weeks, were treated for 5 days. The mice in the control group received a day administration of 0.9% saline via IP injection at a volume of 0.3 mL for 5 days in conjunction with 12.5 mg/kg of imipenem twice a day. The other mice were treated with four different doses of L4L-121 once a day (1 mg/kg, 5 mg/kg, 25 mg/kg and 50 mg/kg) in conjunction with 12.5 mg/kg of imipenem twice a day.

The study duration was 6 days. The efficacy parameters were evaluated for all groups as follows:

Survival was assessed by enumeration of mortality over 5 days following CLP surgery.

Animals which were found dead had half of each tissue collected (lungs, kidneys, heart, spleen and liver) collected.

Animals that were euthanized prior to study end had blood and tissue collected.

Blood was collected on all animals following euthanasia for both moribund mice and those remaining at Day 5 and a full chemistry panel was performed (albumin, ALP, ALT, AST, BUN, calcium, cholesterol, creatine kinase, creatinine, glucose, total bilirubin, total protein, triglycerides).

Results

Data from this study showed that there was a significant improvement in survival following treatment with a 5 mg/kg dose of L4L-121 plus imipenem compared to saline plus imipenem treated animals.

As seen in FIG. 10, mice treated with a 50 mg/kg dose of L4L-121 and imipenem demonstrated 70% mortality. Three of the seven deaths were a result of euthanasia. Mice which received a 25 mg/kg dose of L4L-121 and imipenem had 40% mortality. Two of the four deaths were due to euthanasia. Mice treated with a 5 mg/kg dose of L4L-121 and imipenem had 20% death. None of the deaths were due to euthanasia. Animals treated with saline vehicle and imipenem demonstrated 70% death. Treatment with 5 mg/kg dose of L4L-121 demonstrated a statistically significant decrease in mortality when compared to the vehicle control group (P=0.0321). Mice which received a 1 mg/kg dose of L4L-121 and imipenem had 60% mortality. None of the deaths were attributed to euthanasia.

Liver function indices shown below were obtained from mice treated at 1, 5, 25 and 50 mg/kg, as well as from the untreated controls. As can be seen in FIG. 11, there was an apparent elevation in calcium levels with the 50 mg/kg dose. Further, at 50 mg/kg there was an elevation in alanine aminotransferase. Creatinine levels were within normal range for mice treated with 1 and 5 mg/kg of L4L-121 as well as mice treated with saline plus imipenem. Only one mouse was outside of normal range in the each of the 25 and 50 mg/kg treatment groups. Bilirubin and blood urea nitrogen levels were within normal range for mice treated with 1 mg/kg of L4L-121 and mice treated with saline plus imipenem. With increasing doses of L4L-121, a trend towards increase in these indices was noted, although the mean bilirubin levels in both the 5 and 25 mg/kg treatment groups remained within the normal range for mice, as did the mean blood urea nitrogen levels in the 5 mg/kg treatment group. The mean albumin levels were within normal range for the 1 and 5 mg/kg treatment groups and decreased albumin levels were observed in the 50 and 25 mg/kg treatment groups, as well as in the saline plus imipenem group.

Example 6—Pharmacokinetics

A pharmacokinetic study was performed in mice where a dose of 50 mg/kg of L4L-121 was administered as a single agent and compared to a 50 mg/kg single dose of free drug trans sodium crocetinate. Blood was collected following treatment administration, per the schedule described below.

TABLE 7

| L4L-121 pharmacokinetic study: Treatment assignment | | | | | |
|---|---|---|---|---|---|
| Group | Sex | Number of Mice | Treatment | Route of Administration | Dose mg/kg | Blood Collection Timepoint |
| 1 | F | 3 | Free Drug TSC | Intravenous | 50 | 5 min, 30 min, 1 hr, 2 hr, 6 hr. |
| 2 | F | 3 | Free Drug TSC | Intravenous | 50 | 15 min, 1 hr, 2 hr, 4 hr, 8 hr. |
| 3 | F | 3 | L4L-121 | Intravenous | 50 | 5 min, 1 hr, 2 hr, 4 hr, 8 hr, 24 hr. |

The following pharmacokinetic parameters were then estimated:

Half-life that determines the length of the treatment effect

Area under the curve (AUC) that reflects the actual body exposure to treatment after administration of a dose of the treatment Cmax

TABLE 8

| L4L-121 pharmacokinetic parameters | | | | |
|---|---|---|---|---|
| Group | Treatment | T½ (h) | AUC (mg/ml*h) | $C_{max}$ (mg/ml) | Plasma Exposure (fold increase compared to free drug TSC) NCA analysis |
| 1 | Free Drug TSC | 0.35 | 0.21 | 0.36 | NA |
| 2 | Free Drug TSC | 0.47 | 0.26 | NA | NA |
| 3 | L4L-121 | 5.12 | 8.36 | 1.26 | 40 |

As can be seen from the table above, L4L-121 formulation results in a significant improvement of half-life over free drug TSC (5-hours vs less than 0.5 hours) and approximately 40-fold improvement in exposure (AUC) of total plasma trans crocetin levels.

Example 7—Clinical Study of Liposomal Trans-Crocetin in Patients with Acute Respiratory Distress Syndrome Due to COVID-19

A phase 2 clinical study was initiated to assess the safety and efficacy of liposomal trans-crocetin in patients with acute respiratory distress syndrome due to COVID-19 disease. This was an open label phase II study of treatment with liposomal trans-crocetin in patients who experience severe acute respiratory distress syndrome (ARDS) and were receiving artificial respiratory support due to COVID-19. The purpose of this study was to evaluate the improvement in PaO2/FiO2 by more than 25% in two cohorts of patients treated liposomal trans-crocetin. In the first cohort, patients received trans-crocetin at a dose of 0.25 mg/kg administered as intravenous (IV) bolus every 3 hours. The second cohort was treated by a liposomal formulation containing trans-crocetin. The liposomal formulation allowed for a gradual release of the free drug, to study the feasibility of once a day or less frequent dosing. Pharmacokinetic assessment was carried out to identify an optimal dose and schedule. Primary outcome measures included proportion of patients showing an increase of at least 25% of PaO2/FiO2 ratio (Time Frame: 24 hours). Secondary outcome measures included (1) proportion of patients with a PaO2/FiO2 ratio above 200 mm Hg (Time Frame: 24, 48 and 72 hours), and (2) all cause mortality (Time Frame: 28 days).

Data obtained from the first patients is disclosed herein. An additional 8-10 patients will be enrolled at the Cohort 4 dose to further demonstrate safety and efficacy.

The drug substance and active moiety tested was trans-crocetin and the drug product was liposomal trans-crocetin injection. Trans-crocetin, a carotenoid, has been shown to possess the capabilities to increase the diffusion of oxygen in plasma or water across a diffusion gradient. Gainer, Expert Opin. Investig. Drugs, 17(6):917-924 (2008); Gainer et al., Circ. Shock, 41(1):1-7 (1993); Roy et al., Shock, 10(3):213-217 (1998); Dhar et al., Mol. Cell. Biochem., 278(1-2):139-146 (2005).

Crocetins, as a class of natural products, have been recognized as having multiple clinically beneficial properties, including but not limited to, oxygen transport in hypoxic conditions and management of endotoxemia associated clinical conditions. Crocetins, in particular the sub-group of trans-crocetin salts and the one previously investigated, sodium trans-crocetin, which is also referred to as trans sodium crocetinate (TSC), have a unique property whereby they alter the structure of water in blood plasma by causing additional hydrogen bonds to form among the water molecules1. As a consequence of this 'order-making' effect of trans-crocetin, also referred to as kosmotropic effect, trans-crocetin improves the diffusion of oxygen as well as other small molecules such as glucose, in plasma, as shown in FIG. 12. Gainer, Expert Opin. Investig. Drugs, 17(6):917-924 (2008); Stennett et al., J. Phys. Chem. B., 110(37):18078-18080 (2006). As can be seen, there is a 30% improvement in diffusion capacity, up to approximately 1.3 to 150 μmol/L (equivalent to 0.4 to 49 μg/mL).

The clinical development of trans-crocetin has been problematic because its oxygen diffusion enhancing effect is transient, due to two key factors: (a) poor solubility-trans-crocetinate monovalent metal salts such as TSC, as free drugs were designed presumably to overcome the solubility issue associated with crocetin (free acid), and (b) short half-life—TSC half-life is approximately 30 minutes, which in a clinical setting leads to transient effect on oxygen diffusion enhancement, as seen in FIG. 13. The liposomal encapsulation of trans-crocetin generated a stable formulation with remarkably increased half-life (tin, 2 to 6 hours compared to half an hour for TSC in a mouse PK study).

Patients with severe COVID-19 frequently present with features of acute respiratory distress syndrome (ARDS). The pathophysiology of ARDS includes pulmonary edema due to alveolar injury followed by an inflammatory/infectious process, as observed in SARS-CoV-2 infection, leading to acute hypoxemia with bilateral pulmonary infiltrates. These patients usually require respiratory support with a ventilator. However, many patients present early on with severe hypoxia without extensive lung damage. Patients with this hypoxia, also termed "silent hypoxia", may not necessarily show classic ARDS. Such patients compensate for hypoxia by breathing faster until they experience respiratory fatigue and collapse suddenly. In such patients, mechanical ventilation may not be as helpful, as has been evidenced by a relatively high mortality rate reported in patients receiving mechanical ventilation in the setting of COVID-19.

Without being bound by a specific theory, liposome encapsulated trans-crocetin could improve hypoxia in the body primarily in the following two ways: (1) Increase the rate of oxygen diffusion at the alveolar-capillary interface by increasing the diffusivity of oxygen across a gradient in conditions such as ARDS, and (2) Increase the rate of oxygen diffusion at the point where oxygen leaves the red blood cells and travels through plasma and interstitium to reach the tissues and individual cells. When this biological process of oxygen diffusion at this level is compromised, silent hypoxia could occur.

The primary purpose of this study was to determine a safe dosing regimen of liposome encapsulated trans-crocetin and to assess preliminary efficacy as measured by improvement in PaO2/FiO2 by more than 25% in patients treated with liposome encapsulated trans-crocetin, as well as safety and the pharmacokinetic profile of liposome encapsulated trans-crocetin.

Three dosing schedules have been studied so far in four cohorts of patients, as described in the table below. All doses were administered over 90 minutes, as an infusion intravenously.

TABLE 9

Dosing Cohorts

| Cohort | No. of Patients | Dose | Schedule | Renal Function |
|---|---|---|---|---|
| 1 | 6 | 2.5 mg/kg | Daily | Normal |
| 2 | 6 | Day 1: 5 mg/kg loading dose Day 2 onwards: 2.5 mg/kg | Daily | Normal |
| 3 | 4 | Day 1: 5 mg/kg loading dose Day 2 onwards: 2.5 mg/kg | Daily | Impaired; patients on dialysis |

TABLE 9-continued

Dosing Cohorts

| Cohort | No. of Patients | Dose | Schedule | Renal Function |
|---|---|---|---|---|
| 4 | 2 | Day 1: 7.5 mg/kg loading dose, followed by 5 mg/kg after 12 hours Day 2 onwards: 5 mg/kg | Every 12 hours | Normal |

While trans sodium crocetinate (TSC) was investigated in clinical trials with no safety concerns, the present study was the first clinical study to investigate a liposomal form of trans-crocetin.

In the first cohort treated with liposome encapsulated trans-crocetin, 6 patients were enrolled at the selected dosage of 2.5 mg/kg/day to determine if the dosing regimen was safe and whether it provided the required exposure for efficacy. Based on preclinical assessments, the target therapeutic range of free trans-crocetin should be between 0.4 and 49 μg/mL. Since 2 mg/kg/day was the dose safely administered in human for the primary ingredient, a 2.5 mg/kg/day dosage for liposomal trans-crocetin was selected on the fact that the encapsulated form is expected to release 90% of the overall free drug amount over time.

In the first cohort, six patients were treated with liposomal trans-crocetin at 2.5 mg/kg/day by an infusion of 90 minutes. Among the 30 cycles of administration no adverse event was observed. The PK of the total drug pointed out the need of 3 cycles to reach the point of balance suggesting the potential desirability of a loading dosage (FIG. 14).

A second cohort of 6 patients was subsequently treated with a loading dose at Day 1 of 5 mg/kg followed by the 2.5 mg/kg/day (Table 9). The loading dosage allowed a target therapeutic range of free TC released from liposomes (0.4 to 49 μg/mL) to be achieved from Day 1 and maintain the PK parameters in accordance with the previous findings from cohort 1 (Table 10). Again, no safety concern was observed. A stronger signal of activity emerged with the 5 mg/kg loading dose, as shown in FIG. 15.

TABLE 10

PK parameters for Cohorts 1, 2 and 3.

| | | Cohort 1 | Cohort 2 | Cohort 3 |
|---|---|---|---|---|
| Cycle 1 Cmax | μg/mL | 21 | 39 | 45 |
| Cycle 1 Ctrough | μg/mL | 4.6 | 9.6 | 7.7 |
| Cycle > 1 Cmax | μg/mL | 30.5 | 35 | 44 |
| Cycle > 1 Ctrough | μg/mL | 6.4 | 9.8 | 10.6 |
| Tmax | Hour | 1.5 | 1.5 | 1.5 |
| T½ | Hour | 15 | 15 | 15 |
| AUC 0-inf | μg · h/mL | 300 | 580 | 980 |
| VD | ml/kg | 200 | 140 | 61 |

A subset of 4 patients with renal dysfunction who required dialysis were included in a third cohort. A different pharmacokinetic profile was observed in this subset of patients. PK for the total drug demonstrated a decrease in the volume of distribution in patients in Cohort 3. This was most likely attributable to a re-balance of drug between the patient plasma and the dialysate (Table 10).

The PK of the free drug from Day 1 in patients from Cohort 2 indicated that free drug concentrations were at their lower concentration at H16 and H24 (ranged between 0.3-5.2 μg/mL) (FIG. 16). PK simulations suggested that administration of liposomal trans-crocetin every 12 hours would be more appropriate. Moreover, the maintenance dose of 2.5 mg/kg/day from Day 2 onwards showed free drug concentration below the threshold of activity in half of the cases at H24 (median 0.58 µg/mL ranged from 0 to 1.44). Collectively, these results supported the decision to increase the loading dose to 7.5 mg/kg, followed by a dose of 5 mg/kg every 12 hours thereafter.

Two patients in cohort 4 were treated with the revised dosing schedule of 7.5 mg/kg loading dose followed by 5 mg/kg every 12 hours thereafter. The 2 patients from the cohort 4 experienced adverse events: grade II increase of total bilirubin without any hepatic biological disturbance. This suggests a possible interference between the color of trans-crocetin and the colorimetric method used to measure bilirubin could be the explanation and a measurement artefact. With respect to efficacy, both patients showed improvement of PaO2/FiO2 ratio and a decrease in the level and aggressiveness of artificial ventilation (as reflected by a decrease in positive expiratory pressure (PEP; cmH2O), and F102) in Cohort 2 over time (FIGS. 17A-D).

Safety Study of L4L-121

After additional investigation based on various methods of assessment of bilirubin quantification, we concluded that the observed elevation of bilirubin was artefactual due to the interference between TC and the assay and protocols used for the quantification of bilirubin levels. No other AEs related to the administration of L4L-121 were reported (data not shown).

In cohort 4, the PK profile of the total drug was in accordance with the previous findings. The free drug concentration between doses appeared to remain within the boundaries of biological activity at H8 and H12 (ranged from 8.6 to 4.6 µg/mL>0.49 µg/mL). The Cmax following the loading dose were beyond the upper margin of activity (59 and 88 µg/mL>49 µg/mL) while the Cmax following the maintenance dosage were within the margins (34.7-44 µg/mL<49 µg/mL). Contamination by the liposome form may over-estimate the value of free drug concentration and may need to be taken into consideration.

In summary, the dosing of humans at the following doses is reported:

Cohort 1: 2.5 mg/kg once a day;

Cohort 2 and Cohort 3: 5 mg/kg loading dose followed by 2.5 mg/kg once a day from Day 2 onwards; and Cohort 4: 7.5 mg/kg followed by 5 mg/kg every 12 hours.

No adverse events or safety concerns were reported in Cohorts 1, 2 and 3. A Grade 2 elevation of bilirubin levels, without other corresponding hepatic abnormalities, was seen in both patients in Cohort 4. This raises the possibility that this might be artefactual and due to a possible interference between the color of trans-crocetin and the colorimetric method used to measure bilirubin.

With a day dosing, exposures observed revealed that the free trans-crocetin levels were undetectable in many patients at 8 hours for doses of 2.5 mg/kg, and at 12 hours for the loading dose of 5 mg/kg dose followed by 2.5 mg/kg a day. This suggested that, with a once a day dosing strategy used in Cohort 1, 2 and 3, many patients were being exposed to sub-therapeutic drug levels for at least half, if not most, of the treatment period.

PK exposure seen in patients with renal impairment suggested that such patients may require dose modifications specific to their clinical condition.

With a 7.5 mg/kg loading dose followed by 5 mg/kg every 12 hours thereafter studied in Cohort 4, preliminary data suggested that patients were being exposed to drug levels that decreased over time but remained within the therapeutic range during the course of treatment.

TABLE 11

Pharmacokinetic properties of L4L-121 in 18 patients with COVID-19. Total drug concentration in the blood, (bottom) released trans-crocetin (free drug) in the blood. Table 11 summarizes the main PK parameters of the study. Overall, AUC and Cmax increased in a dose-dependent manner for both the free drug and total L4L-121.

| | Cohort | N | Type | Dose (mg/kg) | Kel (24 h) | $R_{24h}$ | $T_{1/2}$ (h) | $C_{trough}$ (µg/mL) | $C_{max}$ (µg/mL) | $C_{maxlast}$ (µg/mL) | $AUC_{0-t}$ (h·µg/mL) | $AUC_{last}$ (h·µg/mL) | Vss (L) | CI (L/h) |
|---|---|---|---|---|---|---|---|---|---|---|---|---|---|---|
| TOTAL DRUG | 1 | 6 | Multiple Dose | 2.50 | 0.08 | 0.92 | 9.44 | 4.70 | 36.13 | 38.02 | 263.78 | 566.67 | 7.78 | 0.08 |
| | 2 | 6 | Loading Dose | 5.00 | 0.07 | 0.88 | 10.35 | 12.51 | 75.37 | | 635.46 | | 7.50 | 0.62 |
| | 2 | 6 | Multiple Dose | 2.50 | 0.05 | 0.82 | 14.48 | 13.95 | | 55.72 | | 699.00 | 10.35 | 0.14 |
| | 3 | 4 | Loading Dose | 5.00 | 0.10 | 0.99 | 6.74 | 10.92 | 77.10 | | 717.00 | | 10.89 | 0.65 |
| | 3 | 4 | Multiple Dose | 2.50 | 0.05 | 0.85 | 16.34 | 12.08 | | 46.33 | | 1117.81 | 21.21 | 0.23 |
| | 4 | 2 | Loading Dose | 7.50 | 0.13 | 0.93 | 5.69 | 41.57 | 141.51 | | 1551.95 | | 3.81 | 0.29 |
| | 4 | 2 | Multiple Dose | 5.00 | 0.04 | 0.64 | 24.37 | 54.45 | 233.04 | 242.00 | 15082.33 | 1618.55 | 1.59 | 0.02 |

| | Cohort | N | Type | Dose (mg/kg) | Kel (24 h) | $R_{24h}$ | $T_{1/2}$ (h) | $C_{trough}$ (µg/mL) | $C_{max}$ (µg/mL) | $C_{maxlast}$ (µg/mL) | $AUC_{0-t}$ (h·µg/mL) | $AUC_{last}$ (h·µg/mL) | Vss (L) | CI (L/h) |
|---|---|---|---|---|---|---|---|---|---|---|---|---|---|---|
| FREE DRUG | 1 | 6 | Multiple Dose | 2.50 | 0.11 | 0.62 | 7.53 | 2.38 | 18.68 | 62.43 | 132.20 | 167.80 | 15.66 | 1.93 |
| | 2 | 6 | Loading Dose | 5.00 | 0.09 | 0.83 | 8.43 | 4.88 | 47.12 | | 311.59 | | 13.52 | 1.51 |
| | 2 | 6 | Multiple Dose | 2.50 | 0.10 | 0.78 | 9.17 | 3.64 | | 29.25 | | 287.88 | 41.94 | 0.60 |
| | 3 | 4 | Loading Dose | 5.00 | 0.11 | 0.77 | 8.35 | 3.00 | 28.25 | | 217.72 | | 15.27 | 1.46 |
| | 3 | 4 | Multiple Dose | 2.50 | 0.10 | 0.77 | 7.33 | 0.90 | | 21.58 | | 198.31 | 16.41 | 0.27 |
| | 4 | 2 | Loading Dose | 7.50 | 0.25 | 0.89 | 2.89 | 6.24 | 73.78 | | 346.84 | | 4.33 | 1.48 |
| | 4 | 2 | Multiple Dose | 5.00 | 0.21 | 0.92 | 3.44 | 9.95 | | 41.77 | | 251.00 | 11.28 | 0.18 |

Despite the low exposures in Cohort 1, 2 and 3 patients, encouraging activity was noted with responses at 24 hours and beyond documented in all cohorts. Of note, in Cohort 2, all patients had a >25% improvement in PaO2/FiO2 ratio by 96 hours. These responses were staggered over time, perhaps likely due to the suboptimal PK exposure described above. In contrast, in Cohort 4, with a higher and sustained therapeutic drug exposure, >25% increase in PaO2/FiO2 ratio was observed at 24 hours in both patients enrolled in this cohort.

Efficacy in COVID-19 Patients

The primary objective of this study was to demonstrate that treatment with L4L-121 leads to an improvement of 25% or more in PaO2/FiO2 in patients with ARDS under artificial respiratory support. Overall, 39% of the patients had an increase of >25% during the first 24 h of treatment with L4L-121. All patients in cohorts 2 and 3 and 50% of patients in cohorts 1 and 4 had a >25% improvement in their PaO2/FiO2 ratio anytime during the treatment period. Collectively, 78% of the patients had a >25% improvement in their PaO2/FiO2 ratio at any time during the treatment period (FIG. 17A).

For secondary indicators of efficacy, an overall 28-day survival rate of 83% was observed (FIG. 17A). During the 5 days of treatment with L4L-121, 2 (11%) patients were extubated.

Although 1 patient had died by day 8, the number of patients requiring the most aggressive form of ventilatory support decreased from 13 (72%) patients at baseline to 8 (44%) patients by day 8, as did the requirement for paralytics and sedatives, in general. A strategy used to improve the ventilation of patients with ARDS is to place them in a prone position to increase oxygen diffusion. A total of 4 patients were prone at the start of treatment; however, by the end of the treatment at day 5, all patients were switched back to the supine position, improving their overall comfort (FIG. 17B).

Of interest, addressing parameters of oxygenation, the PaO2/FiO2 ratio tended to increase over time after treatment with L4L-121, with a more evident increase after day 2 post-treatment (FIG. 17B). The number of patients requiring noradrenaline decreased from 13 patients (72.2% of the patients) at baseline to 5 (27.8%) by day 3 of treatment with L4L-121.

Overall, following treatment with L4L-121, a trend was observed where the mean total sequential organ failure assessment (SOFA) scores decreased by more than 2 points from baseline to day 8 (FIG. 17C). The decrease in SOFA scores with treatment helps explain the clinical observations of an overall improvement in patient clinical status, suggesting that treatment with L4L-121 may improve perfusion of other organs in addition to the benefits observed in the respiratory system. A clinically promising outcome is reflected by the decrease observed over time in the mean cardiovascular SOFA subscore following treatment with L4L-121 (FIG. 17C). This decrease in cardiovascular SOFA subscore suggests an overall improvement in cardiovascular function and an improved ability to perfuse the patient's body overall.

In conditions such as COVID-19 and sepsis, ARDS leading to systemic oxygen deprivation or hypoxia has been identified as the primary cause of death, especially in severe cases. Hypoxia has been linked to a sequence of self-enhancing poor prognostic factors for clinical outcome in COVID-19 patients and other ARDS-related conditions, such as sepsis.

Treatment options for patients with severe COVID-19 are currently limited to mechanical ventilation and supportive care, with a poor survival outcome.

In vitro results and preclinical therapeutic assessment in a mouse model of sepsis demonstrated the reoxygenation activity of TC, indicating the enhancement of oxygen diffusion and the exposure optimization provided by the L4L-121 formulation. These preclinical data enabled us to perform a fast-track approved clinical study to evaluate this novel liposomal platform.

The patients enrolled in the study were on average hospitalized in the ICU for-12 days prior to treatment with underlying comorbidities that have been associated with worsened outcome by SARS-CoV-2 infection. Moreover, 100% of the patients included in the study demonstrated increased clotting activity, further emphasizing that the patient population treated was sick and would be expected to have challenges with organ perfusion.

Thirty-nine percent of the patients met the primary endpoint of a >25% improvement in the PaO2/FiO2 ratio at 24 h. In addition, up to 78% of the patients attained a >25% PaO2/FiO2 ratio during the treatment period. Beyond this ratio, additional markers of improvement in respiratory function during treatment included a general decrease in the FiO2 requirement and a slight decrease in PaCO2, a decrease in aggressive ventilation, a decrease in the use of sedatives and paralytic agents, and a decrease in the number of patients requiring placement in a prone position. Furthermore, the observed improvement in total SOFA score and subscores indicated that treatment with L4L-121 may improve microcirculation and thus perfusion of other organs, thereby enhancing multiorgan function in addition to the benefits observed in the respiratory system. Together, these observations suggest the potential clinical benefit of L4L-121 in treating patients with COVID-19 and, more broadly, in other high-unmet medical need settings with a similar underlying pathophysiology, such as sepsis, where multiorgan dysfunction is an important contributor to morbidity and mortality.

In this study, a 28-day survival rate of 83% was observed, which is particularly promising. Of note, in a similar patient population, survival rates of 57% and 69% were observed following treatment with standard care without and with dexamethasone, respectively (RECOVERY trial) 15. To date, no related AEs have been identified with the clinical use of L4L-121 at doses up to 12.5 mg/kg administered in a 24 h period. In conclusion, the overall risk/benefit profile of L4L-121 for the treatment of patients with ARDS due to COVID-19 requiring mechanical ventilation appears to be favorable in this high-risk patient population, which currently has no approved medications. The findings of this ongoing study, though promising, are preliminary and coupled with a small sample size. Nevertheless, given the urgent need in the context of the pandemic situation, a temporary authorization for routine use has been established in France for this compound since Nov. 17, 2020.

While the disclosed methods have been described in connection with what is presently considered to be the most practical and preferred embodiments, it is to be understood that the methods encompassed by the disclosure are not to be limited to the disclosed embodiments, but on the contrary, is intended to cover various modifications and equivalent arrangements included within the spirit and scope of the appended claims.

The disclosure of each of U.S. Appl. No. 62/666,699, filed May 3, 2018, U.S. Appl. No. 63/007,884, filed Apr. 9, 2020, U.S. Appl. No. 63/007,777, filed Apr. 9, 2020, U.S. Appl.

No. 63/007,878, filed Apr. 9, 2020, U.S. Appl. No. 63/029, 362, filed May 22, 2020, U.S. Appl. No. 63/029,362, filed May 24, 2020, and Intl. Appl. No. PCT/US2019/030625, filed May 3, 2019, is herein incorporated by reference in its entirety.

The disclosure of each of U.S. Appl. No. 63/057,208, filed Jul. 27, 2020, U.S. Appl. No. 63/057,203, filed Jul. 27, 2020, U.S. Appl. No. 63/063,809, filed Aug. 10, 2020, U.S. Appl. No. 63/064,281, filed Aug. 11, 2020, U.S. Appl. No. 63/064, 300, filed Aug. 11, 2020, U.S. Appl. No. 63/071,312, filed Aug. 27, 2020, and U.S. Appl. No. 63/071,338, filed Aug. 27, 2020, is herein incorporated by reference in its entirety.

The disclosure of each of U.S. Appl. No. 63/077,989, filed Jul. 27, 2020, U.S. Appl. No. 63/057,203, filed Sep. 14, 2020, U.S. Appl. No. 63/007,884, filed Apr. 9, 2020, U.S. Appl. No. 63/029,362, filed May 22, 2020, U.S. Appl. No. 63/029,536, filed May 24, 2020, U.S. Appl. No. 63/057,208, filed Jul. 27, 2020, U.S. Appl. No. 63/063,809, filed Aug. 10, 2020, U.S. Appl. No. 63/064,281, filed Aug. 11, 2020, U.S. Appl. No. 63/077,986, filed Sep. 14, 2020, and U.S. Appl. No. 63/125,908, filed Dec. 15, 2020, is herein incorporated by reference in its entirety.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

What is claimed is:

1. A method of increasing the delivery of oxygen in a subject comprising administering an effective amount of one or more dose(s) of 2 mg/kg to 10 mg/kg liposomal trans-crocetin, or any range therein between, to a subject in need thereof, wherein the administered liposomal trans-crocetin comprises a pegylated liposome encapsulating trans-crocetin having the formula: Q-trans-crocetin-Q, wherein, Q is at least one multivalent cation selected from $Ca^{2+}$, $Mg^{2+}$, $Zn^{2+}$, $Cu^{2+}$, $Co^{2+}$, $Fe^{2+}$, a divalent organic cation, and a trivalent cation; and wherein the diameter of the liposome is 20 nm to 200 nm.

2. The method of claim 1, wherein one or more doses of liposomal trans-crocetin is administered to the subject in an amount of 2 mg/kg to 8 mg/kg, or any range therein between.

3. The method of claim 1, wherein one or more doses of liposomal trans-crocetin is administered to the subject in an amount of 2.5 mg/kg to 7.5 mg/kg, 2.5 mg/kg to 5 mg/kg (e.g., 2.5 mg/kg or 5 mg/kg), or any range therein between.

4. The method of claim 1, wherein the subject is administered 1 to 50, 1 to 40, 1 to 30, 1 to 25, 1 to 20, 1 to 15, 1 to 10, or 1 to 5 doses of liposomal trans-crocetin in an amount of 2 mg/kg to 10 mg/kg, or any range therein between.

5. The method of claim 2, wherein the subject is administered 1 to 50, 1 to 40, 1 to 30, 1 to 25, 1 to 20, 1 to 15, 1 to 10, or 1 to 5 doses of liposomal trans-crocetin in an amount of 2 mg/kg to 8 mg/kg, or any range therein between.

6. The method of claim 2, wherein the subject is administered 1 to 50, 1 to 40, 1 to 30, 1 to 25, 1 to 20, 1 to 15, 1 to 10, or 1 to 5 doses of liposomal trans-crocetin in an amount of 2.5 mg/kg to 7.5 mg/kg, or any range therein between.

7. The method of claim 2, wherein the subject is administered 1 to 50, 1 to 40, 1 to 30, 1 to 25, 1 to 20, 1 to 15, 1 to 10, or 1 to 5 doses of liposomal trans-crocetin in an amount of 2 mg/kg to 5.5 mg/kg, or any range therein between.

8. The method of claim 1, wherein one or more doses of the administered liposomal trans-crocetin is 2.5 mg/kg, 5.0 mg/kg, or 7.5 mg/kg.

9. The method of claim 1, wherein one or more doses of the administered liposomal trans-crocetin comprises liposomes encapsulating calcium trans-crocetinate or magnesium trans-crocetinate having a zeta potential of −25 to 0 mV, or any range therein between.

10. The method of claim 1, wherein one or more doses of the administered liposomal trans-crocetin comprises liposomes having a diameter of 80 nm to 120 nm, or any range therein between.

11. The method of claim 1, wherein one or more doses of the administered liposomal trans-crocetin comprises liposomes having a diameter of 80 nm to 120 nm or any range therein between and a zeta potential of −25 to 0 mV or any range therein between.

12. The method of claim 1, wherein the subject is administered two or more doses of liposomal trans-crocetin 1 hour to 48 hours, 1.5 hours to 24 hours, 2 hours to 18 hours, 4 hours to 16 hours, or 1 hour to 8 hours apart, or any range therein between, or one dose of liposomal trans-crocetin five times a day, four times a day, three times a day, twice a day, once a day, or once every other day.

13. The method of claim 12, wherein the subject is administered one dose of liposomal trans-crocetin in an amount of 2 mg/kg to 8 mg/kg, or any range therein between, five times a day, four times a day, three times a day, twice a day, once a day, or once every other day.

14. The method of claim 1, wherein the subject is administered one or more loading dose(s) of liposomal trans-crocetin at 2 mg/kg to 10 mg/kg, 2.5 mg/kg to 7.5 mg/kg, or 2.5 mg/kg to 5 mg/kg, or any range therein between, and wherein when more than one loading dose is administered, the doses are administered 1 hour to 48 hours, 1.5 hours to 24 hours, 2 hours to 18 hours, 4 hours to 16 hours, or 1 hour to 8 hours (e.g., 3 hours) apart, or any range therein between, or wherein the subject is administered a maintenance dose of liposomal trans-crocetin four times a day, three times a day, two times a day, once a day, or once every other day.

15. The method of claim 14, wherein the subject is further administered two or more maintenance dose(s) of liposomal trans-crocetin at 2 mg/kg to 10 mg/kg, 2.5 mg/kg to 7.5 mg/kg, or 2.5 mg/kg to 5 mg/kg, or any range therein between, of trans-crocetin.

16. The method of claim 15, wherein the subject is administered 1 to 50, 1 to 40, 1 to 30, 1 to 25, 1 to 20, 1 to 15, 1 to 10, or 1 to 5, or any range therein between, maintenance doses of liposomal trans-crocetin.

17. The method of claim 16, wherein the subject is administered 1 to 50, 1 to 40, 1 to 30, 1 to 25, 1 to 20, 1 to 15, 1 to 10, or 1 to 5, or any range therein between, maintenance doses of liposomal trans-crocetin at a concentration of 2 mg/kg to 5.5 mg/kg, or any range therein between.

18. The method of claim 15, wherein the subject is administered two or more maintenance dose(s) of liposomal trans-crocetin 1 hour to 48 hours, 1.5 hours to 24 hours, 2 hours to 18 hours, 4 hours to 16 hours, or 1 hour to 8 hours apart, or any range therein between, or the subject is administered one maintenance dose of liposomal trans-crocetin four times a day, three times a day, two times a day, once a day, or once every other day.

19. The method of claim 1, wherein the method treats ischemia or hypoxia in the subject.

20. The method of claim 1, wherein (1) the subject is in need of increased oxygen delivery; (2) the pharmaceutical composition is administered to increase the physical or mental performance of the subject; (3) the age of the subject is 50 or older; (4) the subject is immunocompromised; (5) the subject receives chemotherapy and/or is immune-suppressed; (6) the subject is a burn victim; and/or (7) the subject is critically ill.

21. The method of claim 1, wherein three times a day, twice a day, once a day, one or more administered dose(s) of liposomal trans-crocetin comprises:

[a] anionic, cationic, or neutral liposomes composed of at least one selected from: DSPE; DSPE-PEG; DSPE-PEG-FITC; DSPE-PEG-maleimide; HSPC; HSPC-PEG; cholesterol; cholesterol-PEG; and cholesterol-maleimide,

[b] a buffer and has a pH of 5-8, or any range therein between,

[c] and a tonicity agent.

22. The method of claim 1, wherein the subject is administered a dose of liposomal trans-crocetin three times a day, twice a day, or once a day.

23. The method of claim 21, wherein the subject is administered a dose of liposomal trans-crocetin three times a day, twice a day, or once a day.

24. The method of claim 1, wherein one or more administered dose(s) of liposomal trans-crocetin has a trans-crocetin/lipid ratio of about 10 to 150 g/mol or about 20 to 100 g/mol, or any range therein between.

25. The method of claim 1, wherein one or more administered dose(s) of liposomal trans-crocetin comprises liposomes encapsulating calcium trans-crocetinate, wherein the liposomes have a diameter of 80 nm to 120 nm, or any range therein between and a zeta potential of −25 to 0 mV, and wherein the trans-crocetin/lipid ratio is 20 to 120 g/mM, or any range therein between.

26. The method of claim 1, wherein the subject has acute respiratory distress syndrome (ARDS).

\* \* \* \* \*